United States Patent
Lampe et al.

(10) Patent No.: US 12,344,653 B2
(45) Date of Patent: Jul. 1, 2025

(54) ANTIGEN BINDING MOLECULES FOR SMALL CELL LUNG CANCER

(71) Applicant: FRED HUTCHINSON CANCER CENTER, Seattle, WA (US)

(72) Inventors: Paul Lampe, Seattle, WA (US); Ashley McGarry Houghton, Seattle, WA (US); Kristin Lastwika, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 78 days.

(21) Appl. No.: 17/025,991

(22) Filed: Sep. 18, 2020

(65) Prior Publication Data
US 2021/0085716 A1 Mar. 25, 2021

Related U.S. Application Data

(60) Provisional application No. 62/903,546, filed on Sep. 20, 2019.

(51) Int. Cl.
*C07K 14/725* (2006.01)
*A61K 40/11* (2025.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
CPC ..... A61K 35/17; A61P 35/00; C07K 14/7051; C07K 16/2896; C07K 2317/21; C07K 16/3023; C12N 5/0638; C12N 2510/00
See application file for complete search history.

(56) References Cited

U.S. PATENT DOCUMENTS

| | | | |
|---|---|---|---|
| 2011/0091454 A1* | 4/2011 | Diber | G16B 25/00 424/139.1 |
| 2015/0355177 A1 | 12/2015 | Komorowski | |

(Continued)

FOREIGN PATENT DOCUMENTS

| | | |
|---|---|---|
| WO | 2009/102960 | 8/2009 |
| WO | 2017/205832 | 11/2017 |

OTHER PUBLICATIONS

Lu, H., and Z. Jiang (2018) Advances in antibody therapeutics targeting small-cell lung cancer Adv Clin Exp Med 27(9); 1317-1323 (Year: 2018).*

(Continued)

*Primary Examiner* — Joanne Hama
*Assistant Examiner* — Audrey L Buttice
(74) *Attorney, Agent, or Firm* — Schwabe, Williamson & Wyatt PC

(57) ABSTRACT

Small cell lung cancer specific chimeric antigen receptor comprising: an antigen-binding domain capable of specifically binding an antigen selected from Tables 1A, 1B, 2A, 2B and 4 and/or that specifically binds to or interacts GAD65, PTPRU, TFRC and GABA-b. A method for treating a subject suffering from SCLC comprising, introducing into the subject a therapeutically effective amount of a T lymphocyte comprising a chimeric antigen receptor. An antigen binding molecule, comprising: an antigen-binding domain capable of specifically binding an antigen selected from Tables 1A, 1B, 2A, 2B and 4 and/or that specifically binds to or interacts GAD65, PTPRU, TFRC and GABA-b. A method of detecting an SCLC tumor in a subject.

18 Claims, 23 Drawing Sheets

(51) Int. Cl.
*A61K 40/31* (2025.01)
*A61K 40/42* (2025.01)
*A61P 35/00* (2006.01)
*C07K 16/28* (2006.01)
*C12N 5/0783* (2010.01)

(52) U.S. Cl.
CPC .......... *A61K 40/4202* (2025.01); *A61P 35/00* (2018.01); *C07K 16/2896* (2013.01); *C12N 5/0638* (2013.01)

(56) References Cited

U.S. PATENT DOCUMENTS

2018/0364228 A1 12/2018 Stoecker
2018/0371052 A1* 12/2018 Ma .................. C07K 14/70517

OTHER PUBLICATIONS

Kazarian, M., and I.A. Laird-Offringa (2011) Small-cell lung cancer-associated autoantibodies: potential applications to cancer diagnosis, early detection, and therapy Molecular Cancer 10(33); 2-19 (Year: 2011).*
Aluicio-Sarduy, E., et al (2018) PET radiometals for antibody labeling J Labelled Comp Radiopharm 61(9); 636-651 (Year: 2018).*
Hampe, C.S., et al (2001) A novel monoclonal antibody specific for the N-terminal end of GAD65 Journal of Neuroimmunology 113; 63-71 (Year: 2001).*
Byers, L.A., et al (2019) Phase 1 study of AMG 119, a chimeric antigen receptor (CAR) T cell therapy targeting DLL3, in patients with relapsed/refractory small cell lung cancer Journal of Clinical Oncology 2019 ASCO Annual Meeting I, Meeting Abstract, 1-4 (Year: 2019).*
Corte, C.M.D., et al (2019) Beyond Chemotherapy: Emerging Biomarkers and Therapies as Small Cell Lung Cancer Enters the Immune Checkpoint Era Cancer 125(4); 496-498 (Year: 2019).*
Deneka, A., et al.(2019) Tumor-Targeted Drug Conjugates as an Emerging Novel Therapeutic Approach in Small Cell Lung Cancer (SCLC) Cancers 11; 1-23 (Year: 2019).*
Brezina, S., et al (2015) Immune-Signatures for Lung Cancer Diagnostics: Evaluation of Protein Microarray Data Normalization Strategies Microarrays 4; 162-187 (Year: 2015).*
Zhou, R., et al (2015) Tumor invasion and metastasis regulated by microRNA-184 and microRNA-574-5p in small-cell lung cancer Oncotarget 6(42); 44609-44622 (Year: 2015).*
Doria, M.I., et al (1988) Immunophenotype of small cell lung cancer Cancer (62); 1939-1945 (Year: 1988).*
Karachaliou, N., et al (2016) Cellular and molecular biology of small cell lung cancer: an overview Transl Lung Cancer Res 5(1); 2-15 (Year: 2016).*
Rho, J.h. and P.D. Lampe (2013) High-throughput screening for native autoantigen-autoantibody complexes using antibody microarrays J. Proteome Res 12(5) 2311-2320 (Year: 2013).*
Huang, R. (2015) Associated links among smoking, chronic obstructive pulmonary disease, and small cell lung cancer: A pooled analysis in the international lung cancer consortium EBioMEdicine 2; 1677-1685 (Year: 2015).*
Shembekar, N., et al (2018) Single-cell droplet microfluidic screening for antibodies specifically binding to target cells CellPress 22; 2206-2215 and attached supplemental materials (Year: 2018).*
Almquist, D., et al (2016) Multimodal therapy for limited-stage small-cell lung cancer American Society of Clinical Oncology 12(2); 111-118 (Year: 2016).*
Zhu, Z., et al (2014) Protein tyrosine phosphatase receptor U (PTPRU) is required for glioma growth and motility Carcinogenesis 35 (8); 1901-1910 (Year: 2014).*
Chapman, CJ et al, Immuno-Biomarkers in Small Cell Lung Cancer: Potential Early Cancer Signals. Clinical Cancer Research. Dec. 7, 2010; vol. 17, No. 6; pp. 1-25; abstract; p. 8, paragraph 2, p. 9, paragraph 4; DOI: 10.1158/1078-0432.CCR-10-1363.
Pan, J. et al. Identification fo Serological Biomarkers for Early Diagnosis of Lung Cancer Using a Protein Array-Based Approach. Molecular Cell Proteomics. Oct. 11, 2017; vol. 16, No. 12; pp. 2069-2078; p. 2070, col. 1, paragraph 2; p. 2073, col. 1, paragraph 1, p. 2073, col. 2, paragraph 2, DOI: 10.1074/mcp.RA117.000212.
Pellkofer et al., Modelling paraneoplastic CNS disease: T-cells specific for onconeuronal antigang PNMA1 mediate autoimmune encephalomyelitis in the rat, Brain, 2004, 127, pp. 1822-1830. (2004).

* cited by examiner

|  | AUC | Sens | Spec | PPV | NPV | LR | Delong |
|---|---|---|---|---|---|---|---|
| AAb | 0.779 | 0.917 | 0.571 | 0.647 | 0.889 | - | - |
| Mayo | 0.731 | 0.639 | 0.786 | 0.719 | 0.717 | 0.0011 | 0.0336 |
| Mayo + AAb | 0.835 | 0.917 | 0.690 | 0.717 | 0.906 | | |
| Brock | 0.770 | 0.722 | 0.762 | 0.722 | 0.762 | 0.0013 | 0.0179 |
| Brock + AAb | 0.869 | 0.917 | 0.738 | 0.75 | 0.912 | | |
| Gould | 0.663 | 0.806 | 0.548 | 0.604 | 0.767 | 0.0001 | 0.0087 |
| Gould + AAb | 0.824 | 0.917 | 0.643 | 0.688 | 0.900 | | |

Figure 5K

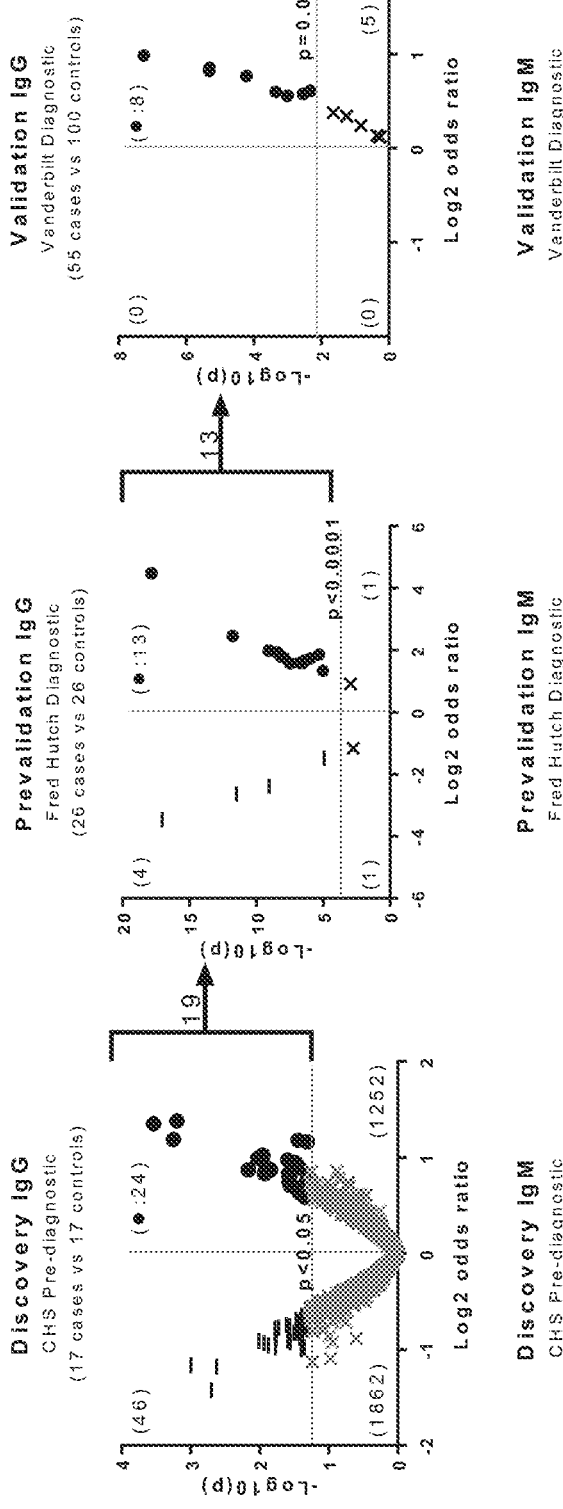
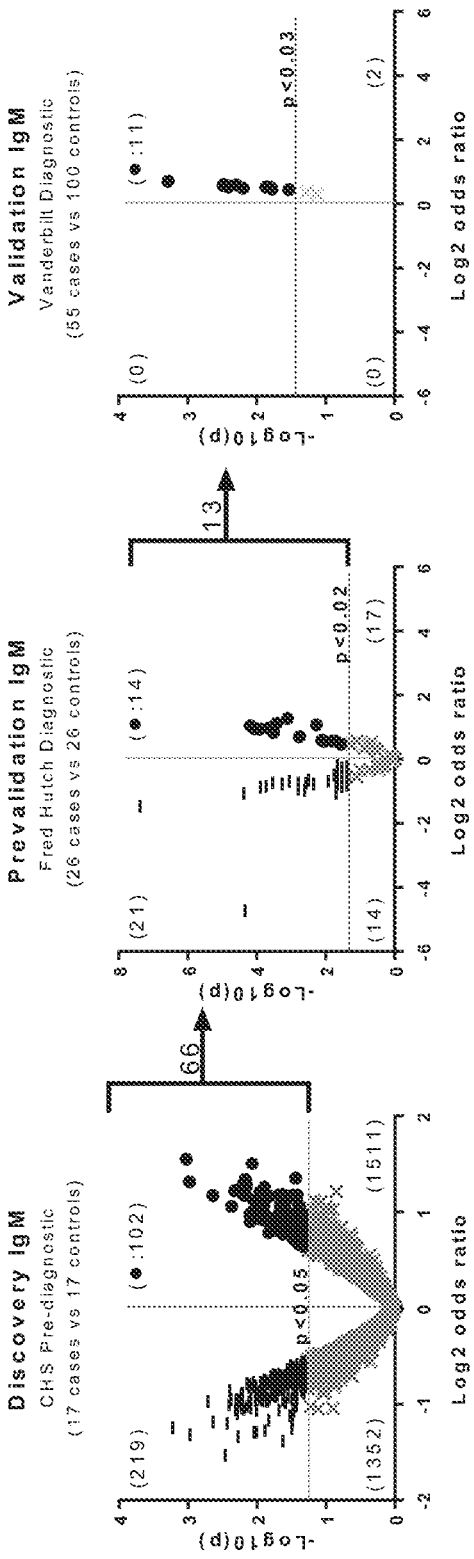
Figure 7A Figure 7B Figure 7C

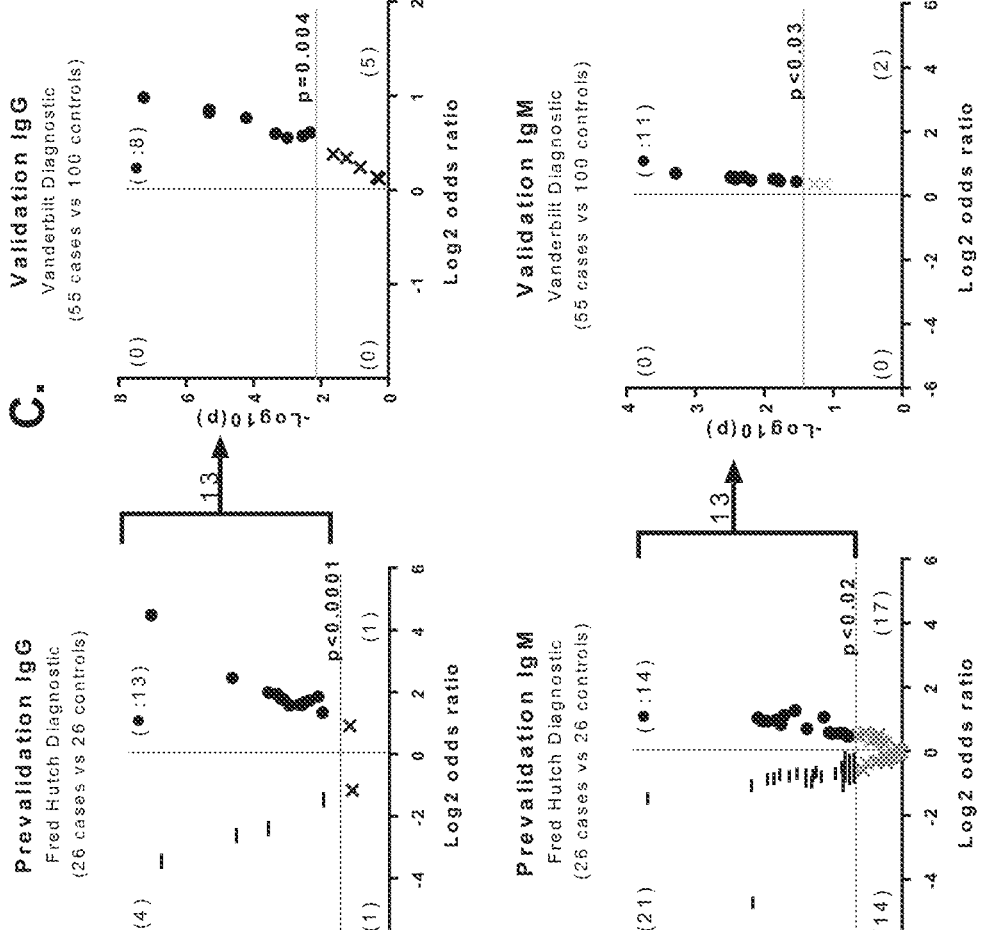
FIGURE 12A FIGURE 12B FIGURE 12C

ANTIGEN BINDING MOLECULES FOR SMALL CELL LUNG CANCER

CROSS REFERENCE TO RELATED APPLICATION

This application claims the benefit under 35 USC § 119(e) of U.S. Provisional Application No. 62/903,546, filed Sep. 20, 2019. This application is also related to International Application No: PCT/US19/23741, filed on Mar. 22, 2019. Each of these applications is incorporated herein by reference in its entirety for all purposes.

ACKNOWLEDGMENT OF GOVERNMENT SUPPORT

This invention was made with government support under CA185097 and CA186157 awarded by the National Institutes of Health. The government has certain rights in the invention.

FIELD

This disclosure relates to the field of small cell lung cancer (SCLC) and in particular, to autoantibodies and autoantibody-autoantigen complexes as biomarkers of SCLC, methods of detection of small cell lung cancer using antigen binding molecules derived from autoantibodies identified as biomarkers of SCLC, chimeric antigen receptors (CAR) derived from autoantibodies identified as biomarkers of SCLC, and engineered cells comprising such CARs, and methods of use thereof, platforms and methods of use thereof.

BACKGROUND

Small cell lung cancer (SCLC) kills 30,000 Americans each year with five-year survival rates of just ~7% Small cell lung cancer (SCLC) accounts for approximately 10-15% of lung cancers and shares one very important characteristic with essentially all solid tumor malignancies. However, patients diagnosed early (limited stage) display far superior survival metrics with a significant cure rate. Unfortunately, few cases are identified at limited stage and computerized tomography (CT) screening is ineffective for SCLC. This is likely a result of the aggressive nature and mediastinal location of SCLC, such that annual imaging is not sufficient. There currently is no blood test recommended for lung cancer early detection. Since the majority of SCLC patients are diagnosed at extensive stage—where current treatment options offer limited benefit—many investigators have not appreciated the fact that nearly approximately 20% of limited stage SCLC patients can be cured with conventional cytotoxic chemotherapy. Furthermore, surgical resection— generally not considered for SCLC—can be curative when combined with chemotherapy for highly selected and very early stage patients. The low-dose CT screening protocols that have proven effective for NSCLC have not displayed benefit in SCLC. This is likely a result of the aggressive nature and mediastinal location of SCLC, such that annual imaging is not sufficient. As such, assays and methods for identifying SCLC in the early stage are needed.

Adoptive immunotherapy, which involves the transfer of autologous antigen-specific T cells generated ex vivo, is a promising strategy to treat cancer. Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy chain variable fragments of a monoclonal antibody joined by a flexible linker. The signaling domains for first generation CARs are derived from the cytoplasmic region of the CD3zeta or the Fc receptor gamma chains. Engineered cells expressing chimeric antigen receptors that target SCLC would be useful in therapeutic settings in which specific targeting and T cell-mediated killing of SCLC cells is desired.

BRIEF DESCRIPTION OF THE DRAWINGS

FIG. 5A, B-cell content from N=75 NSCLC tumor specimens. FIG. 5B, CD20 IHC depicting B-cell clusters within lymphoid aggregates in a lung adenocarcinoma. FIGS. 5C-5D, B-cells following column purification by flow cytometry and Ig isolation. FIG. 5E, HuProt Arrays identified 13 antibodies present in tumor-derived B-cell extract and paired plasma, but not in control plasma. FIG. 5F, 10/13 free autoantibodies are also present as antigen-complexed autoantibodies at higher levels in cases (N=10) verses controls (N=10). 4/10 autoantibodies reach statistical significance (unpaired t test). Five autoantibodies are significantly higher in plasma from NSCLC nodules (n=126) compared to benign nodules (n=126) patients (unpaired t test).

FIGS. 5G-5K Tumor-derived B-cells produce tumor-specific autoantibodies. (FIG. 5G) Flow cytometry quantification of CD19+ B cells in CD45+ leukocytes by stage of non small cell lung cancer. Tumors have significantly more CD19+ B cells in all stages of NSCLC compared to NAL. Stage 1 n=47, stage 2 n=13, stage 3 n=9 (mean±s.e.m.) p-values via Welch's t test. (FIG. 5H) Quantification of fluorescent intensity of top autoantibodies with ≥50% sensitivity and ≥70% specificity (n=10/group) (mean±s.e.m., unpaired student's t-test *=p<0.02, =p<0.0002, *=p<0.00001). (FIG. 5I) 5 autoantibodies are significantly higher in plasma from NCSLC nodule (n=125) compared to benign nodules (n=125) patients (unpaired t-test). (FIG. 5J) ROC curves of 4-autoantibody panel (AAb) alone, Mayo model alone, Brock model alone, Gould model alone and the combinations of AAb panel and each model in indeterminate pulmonary nodules (IPNs) with the largest diameter between 8 mm and 20 mm (n=42 cases, 36 controls). (FIG. 5K) Adding the AAb panel to a malignancy risk prediction model significantly improved the ability to detect malignant IPNs. Sens=sensitivity, Spec=specificity, PPV=positive predictive value, NPV=negative predictive value, LR=likelihood ratio for malignancy detection, Delong=two-sided Delong's t test.

FIG. 7A-7C illustrates sequential discovery and validation of SCLC Autoantibodies IgG and IgM autoantibodies (FIG. 7A) discovered in the CHS pre-diagnostic cohort (FIG. 7B) pre-validated in the Fred Hutch diagnostic cohort and (FIG. 7C) validated in a third cohort from Vanderbilt. Expression in cases: (solid circles, increased); (dash, decreased); (x, insignificant).

FIG. 10 SCLC panel autoantibodies are upregulated at least 1 year prior to diagnosis. *=p<0.05. The CHS specimens (N=17) utilized to generate preliminary data were drawn either 0-1 or 1-2 years prior to diagnosis. Data from FIG. 8 was re-analyzed as a function of the time of blood draw. The data show that most of the markers were similarly effective when the plasma was drawn 1-2 years prior to diagnosis as when drawn less than one year prior to diagnosis. These data indicate that autoantibody-antigen complex markers can be effective at least 2 years prior to clinical diagnosis.

FIGS. 12A-12C are graphs showing the sequential discovery and validation of SCLC autoantibodies. IgG and IgM autoantibodies (FIG. 12A) discovered in the CHS pre-diagnostic cohort (FIG. 12B) prevalidated in the Fred Hutch diagnostic cohort and (FIG. 12C) validated in a third cohort from Vanderbilt. Expression in cases: • increased; – decreased; x insignificant.

(FIG. 13A) GAD65, PTPRU, TFRC and GABA-b IgG antoantibody-antigen complex signal are significantly (p<0.03) higher in SCLC cases vs. controls in the FH cohort (N=52). (FIG. 13B) Representative immunohistochemical staining of GAD65, PTPRU, TFRC, and GABA-b on positive control tissues, SCLC PDX tumors and a lack of staining on secondary antibody alone controls. (FIG. 13C) Representative immunohistochemical staining of PLD3, SPINT2, CD133, TFRC, CA9, PTPRU, and GAD65 on positive control tissues, SCLC PDX tumors and SCLC tumor biopsies, and a lack of staining on secondary antibody alone controls.

(FIG. 14A) CD133 autoantibodies analyzed as a function of time of blood draw in the CHS and FHCRC. (FIG. 14B) Analysis of CD133 cell surface expression by flow cytometry for two SCLC cell lines (H82 and H69) and a negative control fibroblast line (p3T3). (FIG. 14C) Representative immunohistochemical staining of CD133 in normal human lung tissue and primary SCLC tumor cells. (FIG. 14D) Graphs showing percent lysis of SCLC tumor cell lines (H82 and H69) by CAR T cell constructs targeting CD133, as compared to untransfected T cells and an unrelated CAR T cell target not expressed in the SCLC cell lines.

DETAILED DESCRIPTION OF SEVERAL EMBODIMENTS

Terms

Figure 1:
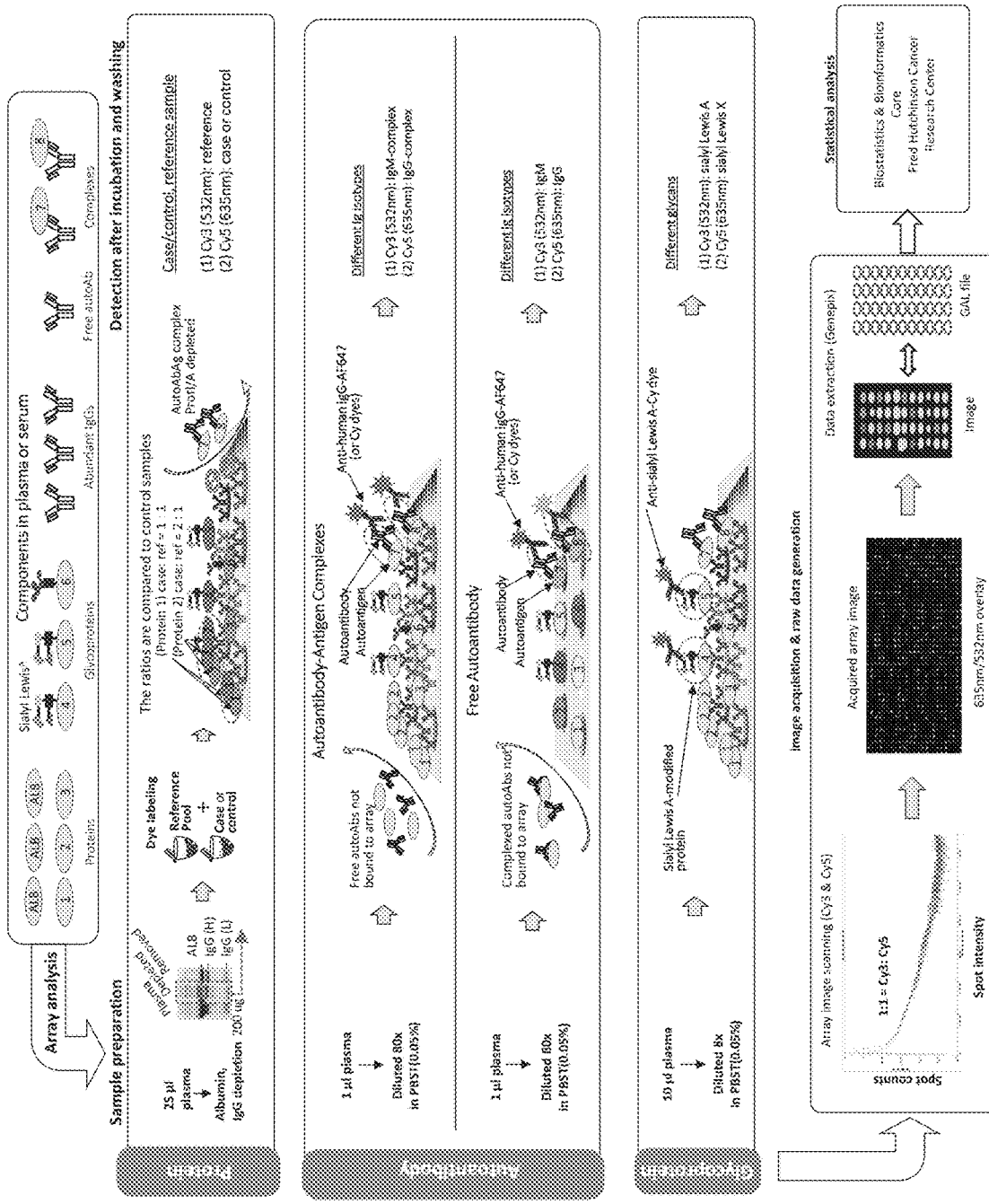
FIG. 1 Hybrid marker array schematic. Schematic showing how the array platform can be used to obtain proteomic, autoantibody-antigen complexes, free autoantibody, or glycomic levels using distinct probing strategies in accordance with embodiments disclosed herein. For proteomics, the samples (case or control) are labeled with Cy5 and a reference plasma pool with Cy3 to obtain the level of each protein relative to the reference. For free and complexed autoantibodies the antibody to the human IgG and IgM are directly labeled, an anti SleX and SleA detect the presence of cancer specific glycan moieties.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

All publications, patent applications, patents, and other references mentioned herein are incorporated by reference in their entirety. All sequences provided in the disclosed Genbank Accession numbers are incorporated herein by reference as available on Mar. 22, 2018. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administration: To provide or give a subject an agent by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes or any combination of techniques thereof.

The disclosed compositions or other therapeutic agents of the present disclosure can be formulated into therapeutically-active pharmaceutical compositions that can be administered to a subject parenterally or orally. Parenteral administration routes include, but are not limited to epidermal, intraarterial, intramuscular (IM, and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

The disclosed compositions or other therapeutic agent can be mixed or combined with a suitable pharmaceutically acceptable excipients to prepare pharmaceutical compositions. Pharmaceutically acceptable excipients include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example. Liposomal suspensions may also be suitable as pharmaceutically acceptable carriers.

Upon mixing or addition of a disclosed composition, or other therapeutic agent, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier.

Pharmaceutical carriers suitable for administration of the disclosed compositions or other therapeutic agent include any such carriers known to be suitable for the particular mode of administration. In addition, the disclosed composition or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, DE).

The disclosed compositions or other therapeutic agent can be prepared with carriers that protect them against rapid elimination from the body, such as coatings or time-release formulations. Such carriers include controlled release formulations, such as, but not limited to, microencapsulated delivery systems. The disclosed compositions or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, an acceptable SCLC animal model may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates; chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

If a disclosed composition or other therapeutic agent is administered orally as a suspension, the pharmaceutical compositions can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/ flavoring agents. Oral liquid preparations can contain conventional additives such as suspending agents, e.g., gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these compositions can contain dicalcium phosphate, lactose, magnesium stearate, microcrystalline cellulose, and starch and/or other binders, diluents, disintegrants, excipients, extenders, and lubricants.

If oral administration is desired, a disclosed composition, or other therapeutic substance can be provided in a composition that protects it from the acidic environment of the stomach. For example, a disclosed composition, or other therapeutic agent can be formulated with an enteric coating that maintains its integrity in the stomach and releases the active compound in the intestine. A disclosed composition or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, the disclosed composition or other therapeutic substance can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. The disclosed composition or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need to be administered less frequently.

Agent: Any protein, nucleic acid molecule (including chemically modified nucleic acids), compound, antibody, small molecule, organic compound, inorganic compound, cell, such as T-cell, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including treating a subject with or at-risk of acquiring SCLC).

In some examples, an agent can act directly or indirectly to alter the activity and/or expression of SCLC associated molecule, such as a SCLC early detection molecule. In a particular example, a therapeutic agent (such as an antisense compound or antibody) significantly alters the expression and/or activity of a SCLC associated molecule. An example of a therapeutic agent is one that can decrease the activity of a gene or gene product associated with SCLC, for example as measured by a clinical response (such as an increase survival time or a decrease in one or more signs or symptoms associated with SCLC). Therapeutically agents also include organic or other chemical compounds that mimic the effects of the therapeutically effective peptide, antibody, or nucleic acid molecule.

A "pharmaceutical agent" is a chemical compound or composition capable of inducing a desired therapeutic or prophylactic effect when administered to a subject, alone or in combination with another therapeutic agent(s) or pharmaceutically acceptable carriers. In a particular example, a pharmaceutical agent significantly reduces the expression and/or activity of a SCLC associated molecule thereby increasing a subject's survival time, reducing a sign or symptom associated with the disease, prolonging the onset of SCLC signs or symptoms.

Antibody: The term "antibody", as used herein, means any antigen-binding molecule or molecular complex comprising at least one complementarity determining region (CDR) that specifically binds to or interacts with a particular antigen, such as one of the antigens shown in Tables 1A, 1B, 2A, 2B and 4, an antibody shown in Table 3 and/or that specifically binds to or interacts GAD65, PTPRU, TFRC and GABA-b. The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-BCMA antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e g, by disulfide bond(s)).

In certain embodiments, the antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al.

(1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The antibodies may comprise variants of any of the HCVR, LCVR, and/or CDR amino acid sequences disclosed herein having one or more conservative substitutions. For example, the anti-BCMA antibodies may have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

An "autoantibody" is an antibody produced by the immune system that is directed against one or more of the individual's own proteins.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2)

aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, the terms "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "chimeric antigen receptor" (CAR) refers to molecules that combine a binding domain against a component present on the target cell, for example an antibody-based specificity for a desired antigen (e.g., a tumor antigen, such as BCMA) with a T cell receptor-activating intracellular domain to generate a chimeric protein that exhibits a specific anti-target cellular immune activity. Generally, CARs consist of an extracellular single chain antibody-binding domain (scFv) fused to the intracellular signaling domain of the T cell antigen receptor complex zeta chain, and have the ability, when expressed in T cells, to redirect antigen recognition based on the monoclonal antibody's specificity.

The term "vector," as used herein, includes, but is not limited to, a viral vector, a plasmid, an RNA vector or a linear or circular DNA or RNA molecule which may consists of chromosomal, non-chromosomal, semi-synthetic or synthetic nucleic acids. In some cases, the vectors are those capable of autonomous replication (episomal vector) and/or expression of nucleic acids to which they are linked (expression vectors). Large numbers of suitable vectors are known to those of skill in the art and are commercially available. Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, and lentivirus.

A "costimulatory domain" or "costimulatory molecule" refers to the cognate binding partner on a T-cell that specifically binds with a costimulatory ligand, thereby mediating a costimulatory response by the cell, such as, but not limited to proliferation. Costimulatory molecules include, but are not limited to, an MHC class I molecule, BTLA and Toll ligand receptor. Examples of costimulatory molecules include CD27, CD28, CD8, 4-1BB (CD137) (SEQ ID NO: 99), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. A costimulatory molecule is a cell surface molecule other than an antigen receptor or their ligands that is required for an efficient immune response.

A "costimulatory ligand" refers to a molecule on an antigen presenting cell that specifically binds a cognate costimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A costimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3.

A "costimulatory signal" refers to a signal, which in combination with a primary signal, such as TCR/CD3 ligation, leads to T cell proliferation and/or upregulation or downregulation of key molecules.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The term "subject" or "patient" as used herein includes all members of the animal kingdom including non-human primates and humans. In one embodiment, patients are humans with a cancer (e.g., multiple myeloma).

A "signal transducing domain" or "signaling domain" of a CAR, as used herein, is responsible for intracellular signaling following the binding of an extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector function signal and directs the cell to perform a specialized function. Examples of signal transducing domains for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. In some cases, signaling domains comprise two distinct classes of cytoplasmic signaling sequences, those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Exemplary ITAMs include those derived from TCRzeta, FcRgamma, FcRbeta, FcRepsilon, CD3gamma, CD3delta, CD3epsilon, CD5, CD22, CD79a, CD79b and CD66d. In some embodiments, the signal transducing domain of the CAR can comprise the CD3zeta signaling domain Alteration or modulation in expression: An alteration in expression of a gene, gene product or modulator thereof, such as one or more SCLC associated molecules disclosed herein, refers to a change or difference, such as an increase or decrease, in the level of the gene, gene product, or modulators thereof that is detectable in a biological sample (such as a sample from a subject at-risk or having SCLC) relative to a control (such as a sample from a subject without a SCLC) or a reference value known to be indicative of the level of the gene, gene product or modulator thereof in the absence of the disease. An "alteration" in expression includes an increase in expression (up-regulation) or a decrease in expression (down-regulation).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe or antibody) will occur on the array a plurality of times (such as twice), for instance to provide internal controls. The number of addressable locations on the array can vary, for example from at least two, to at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 2-100 addressable locations, such as 2-40 addressable locations. In particular examples, an array consists essentially of probes or primers or antibodies (such as those that permit amplification or detection) specific for SCLC as disclosed herein, such as the molecules disclosed in Tables 1-3 and in some examples, also 1 to 10 or 1 to 6 control molecules (such as housekeeping genes or proteins).

In particular examples, an array includes nucleic acid molecules, such as oligonucleotides that are at least 15 nucleotides in length, at least 30 nucleotides, at least 40 nucleotides, or at least 50 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to SCLC-associated molecules, such as those disclosed in Tables 1-3 and in some examples also 1 to 10 controls.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of the target complex. For example, binding can be detected functionally by determining whether binding has an observable effect upon a biosynthetic process such as expression of a gene, DNA replication, transcription, translation, and the like. Methods of detecting binding of an antibody to a protein are disclosed herein and also can include known methods of protein detection, such as Western blotting.

Biological activity: The beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, the agent significantly reduces the biological activity of the one or more SCLC associated molecules disclosed herein which reduces one or more signs or symptoms associated with the SCLC.

Biomarker: Molecular, biological or physical attributes that characterize a physiological state and can be objectively measured to detect or define disease progression or predict or quantify therapeutic responses. For instance, a substance used as an indicator of a biologic state. It is a characteristic that is objectively measured and evaluated as an indicator of normal biologic processes, pathogenic processes, or pharmacologic responses to a therapeutic intervention. In one example, a biomarker is a protein or nucleic acid sequence of a corresponding gene that is indicator of SCLC.

Clinical outcome: Refers to the health status of a patient following treatment for a disease or disorder, such as SCLC, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Contacting: Placement in direct physical association, including both a solid and liquid form. Contacting an agent with a cell can occur in vitro by adding the agent to isolated cells or in vivo by administering the agent to a subject.

Control: A sample or standard used for comparison with a test sample, such as a biological sample obtained from a patient (or plurality of patients) without a particular disease or condition, such as SCLC. In some embodiments, the control is a sample obtained from a healthy patient (or plurality of patients) (also referred to herein as a "normal" control), such as a normal biological sample or from a non-cancerous biological sample from the patient that has particular disease or condition, such as SCLC. In some embodiments, the control is a historical control or standard value (e.g., a previously tested control sample or group of samples that represent baseline or normal values (e.g., expression values), such as baseline or normal values of a particular gene, gene product in a subject without SCLC). In some examples, the control is a standard value representing the average value (or average range of values) obtained from a plurality of patient samples (such as an average value or range of values of the gene or gene products in the subjects without SCLC).

Consists essentially of: In the context of the present disclosure, "consists essentially of" indicates that the expression of additional SCLC-associated molecules can be evaluated, but not more than ten additional SCLC-associated molecules. In some examples, "consist essentially of" indicates that no more than 5 other molecules are evaluated, such as no more than 4, 3, 2, or 1 other molecules. In some examples, fewer than the recited molecules are evaluated, but not less than 5, 4, 3, 2 or 1 fewer molecules. In some examples, the expression of one or more controls is evaluated. In this context "consist of" indicates that only the expression of the stated molecules are evaluated; the expression of additional molecules is not evaluated.

CRMP5 (Collapsin response-mediator protein-5): One of the five intracellular phosphoproteins of the CRMP family which are predominantly expressed in the nervous system during development and play important roles in axon formation from neurites and in growth cone guidance and collapse through their interactions with microtubules. Cleaved forms of CRMPs have also been linked to neuron degeneration after trauma induced injury. CRMP5 is only 50-51% homologous with each of the other CRMPs.

Decrease: To reduce the quality, amount, or strength of something. In one example, a therapy decreases one or more symptoms associated with SCLC, for example as compared to the response in the absence of the therapy. In a particular example, a therapy decreases (also known as down-regulates) the expression of a SCLC-associated molecule, such as a decrease of at least 10%, at least 20%, at least 25%, at least 30%, at least 40%, at least 50%, or even at least 90% in a SCLC associated molecule expression. A gene product can be RNA (such as mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression or protein expression in a biological sample taken from a subject who does not have SCLC. Such decreases can be measured using the methods disclosed herein. For example, "detecting or measuring expression of a gene product" includes quantifying the amount of the gene, gene product or modulator thereof present in a sample. Quantification can be either numerical or relative. Detecting expression of the gene, gene product or modulators thereof can be achieved using any method known in the art or described herein, such as by measuring nucleic acids by PCR (such as RT-PCR) and proteins by ELISA. In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have SCLC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

In other embodiments of the methods, the increase or decrease is of a diagnostically significant amount, which refers to a change of a sufficient magnitude to provide a statistical probability of the diagnosis.

The level of expression in either a qualitative or quantitative manner can detect nucleic acid or protein. Exemplary methods include microarray analysis, RT-PCR, Northern blot, Western blot, and mass spectrometry.

Detecting: Identifying the presence, absence or relative or absolute amount of the object to be detected.

Diagnosis: The process of identifying a disease, such as SCLC, by its signs, symptoms and results of various tests. The conclusion reached through that process is also called "a diagnosis." Forms of testing commonly performed include blood tests, medical imaging, urinalysis, and biopsy.

Effective amount: An amount of agent that is sufficient to generate a desired response, such as reducing lessening, ameliorating, eliminating, preventing, or inhibiting one or more signs or symptoms associated with a condition or disease treated and may be empirically determined. When administered to a subject, a dosage will generally be used that will achieve target tissue/cell concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example anti-pathogenic agents), induces the desired response such as treatment of SCLC.

In particular examples, it is an amount of an agent capable of modulating one or more of the disclosed genes, gene products or modulators thereof associated with SCLC by least 20%, at least 50%, at least 60%, at least 70%, at least 80%, at least 90%, at least 95%, at least 98%, or even at least 100% (elimination of the disease to a point beyond detection) by the agent.

In some examples, an effective amount is an amount of a pharmaceutical preparation that alone, or together with a pharmaceutically acceptable carrier or one or more additional therapeutic agents, induces the desired response.

In one example, a desired response is to increase the subject's survival time by slowing the progression of the disease. The disease does not need to be completely inhibited for the pharmaceutical preparation to be effective. For example, a pharmaceutical preparation can decrease the progression of the disease by a desired amount, for example by at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the SCLC within the subject. Treatment can involve only slowing the progression of the disease temporarily, but can also include halting or reversing the progression of the disease permanently.

Effective amounts of the agents described herein can be determined in many different ways, such as assaying for a reduction in of one or more signs or symptoms associated with the SCLC in the subject or measuring the expression level of one or more molecules known to be associated with the SCLC. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied (for example a nucleic acid molecule isolated from a cellular extract versus a chemically synthesized and purified nucleic acid), the subject being treated, the severity and type of the condition being treated, and the manner of administration.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have SCLC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

GAD65 (Glutamic Acid Decarboxylase isoform): An isoform of glutamic acid decarboxylase or glutamate decarboxylase which encodes GAD2 gene. GAD65 is expressed in the brain where GABA is used as a neurotransmitter. GAD65 also expressed in the insulin-producing I3-cells of the pancreas, in varying ratios depending upon the species. This enzyme maintains the only physiological supply of GABA in mammals.

Inhibiting a disease or condition: A phrase referring to inhibiting the development of a disease or condition, such as reducing, decreasing or delaying a sign or symptom associated with the disease or condition, for example, in a subject who is at-risk of acquiring the disease/condition or has the particular disease/condition. Particular methods of the present disclosure provide methods for inhibiting SCLC.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Label or Detectable Moiety: A composition detectable by spectroscopic, photochemical, biochemical, immunochemical, electromagnetic, or chemical means. For example, useful labels include radiolabels such as $^{32}P$, $^{35}S$, or $^{125}I$; heavy isotopes such as $^{15}N$ or $^{13}C$ or heavy atoms such as selenium or metals; fluorescent dyes; chromophores, electron-dense reagents; enzymes that generate a detectable signal (e.g., alkaline phosphatase or peroxidase, as commonly used in an ELISA); or spin labels. The label or detectable moiety has or generates a measurable signal, such as a radioactive, chromogenic, or fluorescent signal, that can be used to quantify the amount of bound detectable moiety in a sample. The detectable moiety can be incorporated in or attached to a molecule (such as a protein, for example, an antibody) either covalently, or through ionic, van der Waals or hydrogen bonds, e.g., or by incorporation of labeled precursors. The label or detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin, which can be linked to a directly detectable label. The binding partner may itself be directly detectable, for example, an antibody may be itself labeled with a fluorescent molecule. The binding partner also may be indirectly detectable, for example, it may be bound by another moiety that comprises a label. Quantitation of the signal is achieved by any appropriate means, e.g., fluorescence detection, spectrophotometric detection (e.g., absorption at a particular wavelength), scintillation counting, mass spectrometry, densitometry, or flow cytometry. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998). In particular examples, a label or detectable moiety is conjugated to a binding agent that specifically binds to one or more of the SCLC-associated molecules.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

Measure: To detect, quantify or qualify the amount (including molar amount), concentration or mass of a physical entity or chemical composition either in absolute terms in the case of quantifying, or in terms relative to a comparable physical entity or chemical composition.

PNMA1 (paraneoplastic Ma antigen 1) and/or PNMA2 (paraneoplastic Ma antigen 2): Proteins encoded by the PNMA1 or PNMA2 genes, respectively.

Prognosis: A prediction of the course of a disease, such as SCLC. The prediction can include determining the likelihood of a subject to develop aggressive, recurrent disease, to survive a particular amount of time (e.g. determine the likelihood that a subject will survive 1, 2, 3 or 5 years), to respond to a particular therapy or combinations thereof.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified mRNA preparation is one in which the mRNA is more pure than in an environment including a complex mixture of nucleic acid molecules.

Sample (or biological sample): A biological specimen containing genomic DNA, RNA (including mRNA), protein, cells (such as T-cells) or combinations thereof, obtained from a subject. Examples include, but are not limited to, peripheral blood, urine, saliva, tissue biopsy, surgical specimen, and autopsy material.

Screening: As used herein, "screening" refers to the process used to evaluate and identify candidate agents that can be used to identify SCLC, such as early stage SCLC. In some cases, screening involves contacting a candidate agent (such as an antibody, small molecule or cytokine) with SCLC cells and testing the effect of the agent on expression of SCLC associated molecules. Expression of a microRNA can be quantified using any one of a number of techniques known in the art and described herein, such as by microarray analysis or by qRT-PCR.

Sensitivity: The percent of diseased individuals (individuals with prostate cancer) in which the biomarker of interest is detected (true positive number/total number of diseased× 100). Nondiseased individuals diagnosed by the test as diseased are "false positives".

In some examples, sensitivity of an assay describes the ability of the assay to accurately predict whether one has SCLC using the disclosed SCLC associated molecules, such as those provided in Tables 1-3, as compared to another assay method. For example, a marker with a sensitivity of at least 70%, including 75%, 80%, 90%, 95% or greater sensitivity is one that is capable of accurately predicting SCLC.

Specificity: The percent of nondiseased individuals for which the biomarker of interest is not detected (true negative/total number without disease×100). Diseased individuals not detected by the assay are "false negatives." Subjects who are not diseased and who test negative in the assay, are termed "true negatives."

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Queries searched with the blastn program are filtered with DUST (Hancock and Armstrong, 1994, *Comput. Appl. Biosci.* 10:67-70). Other programs may use SEG. In addition, a manual alignment can be performed. Proteins with even greater similarity will show increasing percentage identities when assessed by this method. Thus, in some examples, expression of a SCLC-associated protein having at least 80%, at least 85%, at least 90%, at least 95%, at least 98%, or at least 99% sequence identity to a native SCLC protein sequence, while retaining the biological function of the protein, can be examined using the disclosed methods. One of skill in the art will appreciate that the particular sequence identity ranges are provided for guidance only.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease.

Small Cell Lung Cancer or Carcinoma: A type of highly malignant cancer within the lung. Compared to non-small cell carcinoma, small cell lung carcinoma has a shorter doubling time, higher growth fraction, and earlier development of metastases. Small-cell lung carcinoma usually presents in the central airways and infiltrates the submucosa leading to narrowing of bronchial airways. Common symptoms include cough, dyspnea, weight loss, and debility. Smoking is a significant risk factor. Over 70% of patients with small-cell lung carcinoma present with metastatic disease; common sites include liver, adrenals, bone, and brain. Due to its high grade neuroendocrine nature, small-cell carcinomas can produce ectopic hormones, including adrenocorticotropic hormone (ACTH) and anti-diuretic hormone (ADH). Ectopic production of large amounts of ADH leads to syndrome of inappropriate antidiuretic hormone hypersecretion (SIADH). Lambert-Eaton myasthenic syndrome (LEMS) is a well-known paraneoplastic condition linked to small-cell carcinoma. SCLC is also referred to as "oat cell carcinoma" due to the flat cell shape and scanty cytoplasm.

SCLC is thought to originate from neuroendocrine cells (APUD cells) in the bronchus called Feyrter cells. Hence, they express a variety of neuroendocrine markers, and may lead to ectopic production of hormones like ADH and ACTH that may result in paraneoplastic syndromes and Cushing's syndrome. Approximately half of all individuals diagnosed with Lambert-Eaton myasthenic syndrome (LEMS) will eventually be found to have a small-cell carcinoma of the lung.

Combined small-cell lung carcinoma can occur in combination with a wide variety of other histological variants of lung cancer, including extremely complex malignant tissue admixtures. When it is found with one or more differentiated forms of lung cancer, such as squamous cell carcinoma or adenocarcinoma, the malignant tumor is then diagnosed and classified as a combined small cell lung carcinoma (c-SCLC). C-SCLC is the only currently recognized subtype of SCLC.

Standard: A substance or solution of a substance of known amount, purity or concentration. A standard can be compared (such as by spectrometric, chromatographic, or spectrophotometric analysis) to an unknown sample (of the same or similar substance) to determine the presence of the substance in the sample and/or determine the amount, purity or concentration of the unknown sample. In one embodiment, a standard is a peptide standard. An internal standard is a compound that is added in a known amount to a sample prior to sample preparation and/or analysis and serves as a reference for calculating the concentrations of the components of the sample. In one example, nucleic acid standards serve as reference values for tumor or non-tumor expression levels of specific nucleic acids. In some examples, peptide standards serve as reference values for tumor or non-tumor expression levels of specific peptides. Isotopically-labeled peptides are particularly useful as internal standards for peptide analysis since the chemical properties of the labeled peptide standards are almost identical to their non-labeled counterparts. Thus, during chemical sample preparation steps (such as chromatography, for example, HPLC) any loss of the non-labeled peptides is reflected in a similar loss of the labeled peptides.

Tissue: A plurality of functionally related cells. A tissue can be a suspension, a semi-solid, or solid. Tissue includes cells collected from a subject, such as from the lung.

Treating a disease: A therapeutic intervention that ameliorates a sign or symptom of a disease or pathological condition related to a SCLC, such as a sign or symptom of SCLC. Treatment can induce remission or cure of a condition or slow progression, for example, in some instances can include inhibiting the full development of a disease, for example preventing development of a SCLC. Prevention of a disease does not require a total absence of disease. For example, a decrease of at least 10%, such as at least 20%, at least 25%, at least 30%, at least 40%, at least 50%, decrease in a sign or symptom associated with the condition or disease, such as SCLC, can be sufficient. As used herein, the term "ameliorating," with reference to a disease or condition, refers to any observable beneficial effect of the treatment. The beneficial effect can be evidenced, for example, by a delayed onset of clinical symptoms of the disease or condition in a susceptible subject, a reduction in severity of some or all clinical symptoms of the disease or condition, a slower progression of the disease or condition, a reduction in the number of relapses of the disease or condition, an improvement in the overall health or well-being of the subject, by other parameters well known in the art that are specific to the particular disease or condition, and combinations of such factors.

PTPRU—An enzyme that is encoded by the PTPRU gene which is a member of the protein tyrosine phosphatase (PTP) family. PTPRU is also known as PTP-pi, PTP lambda, hPTP-J, PTPRO and PTP psi. PTPs are known to be signaling molecules that regulate a variety of cellular processes including cell growth, differentiation, mitotic cycle, and oncogenic transformation. This PTP possesses an extracellular region, a single transmembrane region, and two tandem intracellular catalytic tyrosine phosphatase domains, and thus represents a receptor-type PTP (RPTP). RPTPs are able to remove phosphate moieties from tyrosine residues.

TFRC (transferrin receptor)—Transferrin receptor also known as Cluster of Differentiation 71 (CD71), is a protein that in humans is encoded by the TFRC gene.

GABA-b (gamma-Aminobutyric acid)—Metabotropic transmembrane receptors for gamma-aminobutyric acid (GABA) that are linked via G-proteins to potassium channels. They can stimulate the opening of K+ channels which brings the neuron closer to the equilibrium potential of K+. This reduces the frequency of action potentials which reduces neurotransmitter release. Thus GABA-b receptors are inhibitory receptors. GABA-b receptors also reduces the activity of adenylyl cyclase and Ca2+ channels by using G-proteins with Gi/GO a subunits. GABA-b receptors are involved in behavioral actions of ethanol, gamma-Hydroxybutyric acid (GHB), and possibly in pain.

Introduction

Our group has developed a novel large format antibody array containing >3200 different antibodies (see below and Example 1) to interrogate pre-diagnostic plasma sample sets for the purpose of cancer early detection. We can utilize the same antibody array platform for proteomic, glycomic, and autoantibody-antigen complex interrogation by implementing three distinct probing strategies. Together, our triple hybrid platform is highly sensitive (picogram level) and reproducible (coefficient of variation, CV<10%). We have identified viable biomarker candidates in ovarian, breast, pancreas, and colon cancer, and have recently developed panels capable of non-small cell lung cancer (NSCLC) early detection with ROC curve (AUC) values of ~0.90 (12).

The ability of our antibody arrays to detect autoantibodies is particularly relevant to SCLC early detection. SCLC can be complicated by a number of paraneoplastic syndromes (PNS) driven by autoantibodies typically targeting central nervous system (CNS) proteins aberrantly expressed by the SCLC lesion. Many of these "free" autoantibodies can be found in the plasma of 10% or more of SCLC patients, most of which do not display evidence of the PNS. The existence of such autoantibodies serves as a key proof of concept that disease specific autoantibodies exist in SCLC. In addition, we have found other highly specific autoantibodies for SCLC not associated with PNS. Furthermore, we have found that by determining both the free autoantibody and autoantibody complexed to its corresponding autoantigen (e.g., the PNS proteins), we get much greater sensitivity for SCLC detection. Many of these autoantigens appear to be tumor specific. We state that the identification of tumor specific autoantigens could be useful for 2 specific purposes that could be tailored to each specific patient; (1) Antibodies to these markers can be used as antibody-based positron emission tomography (immunoPET) probes to identify tumors not apparent via CT or other imaging methods (i.e., too small or present in difficult to image locations). (2) As immunotherapy targets—specifically as chimeric antigen receptor (CAR) T-cell targets.

Chimeric Antigen Receptors (CARs)

Chimeric antigen receptors (CARs) redirect T cell specificity toward antibody-recognized antigens expressed on the surface of cells (e.g., cancer cells), while T cell receptors (TCRs) extend the range of targets to include intracellular antigens (e.g., tumor antigens).

One aspect of the present invention includes a chimeric antigen receptor (CAR) which is specific for antigens expressed on the surface of SCLC tumor cells. The CARs as described herein can included an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, 4-1BB. The CAR can include a hinge or spacer region between the extracellular binding domain and the transmembrane domain, such as a CD8alpha hinge.

The binding domain or the extracellular domain of the CAR provides the CAR with the ability to bind to the target antigen of interest. A binding domain (e.g., a ligand-binding domain or antigen-binding domain) can be any protein, polypeptide, oligopeptide, or peptide that possesses the ability to specifically recognize and bind to a biological molecule (e.g., a cell surface receptor or tumor protein, or a component thereof), such as the antigen binding domain of an auto antigen described and/or detected using the methods described here. A binding domain includes any naturally occurring, synthetic, semi-synthetic, or recombinantly produced binding partner for a biological molecule of interest. For example, a binding domain may be antibody light chain and heavy chain variable regions, or the light and heavy chain variable regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE analysis). The target may be an antigen of clinical interest against which it would be desirable to trigger an effector immune response that results in SCLC tumor killing. In one embodiment, the target antigen of the binding domain of the chimeric antigen receptor is a protein on the surface of SCLC tumor cells as shown in Tables 1A, 1B, 2A, 2B and 4. In one embodiment, the target antigen of the binding domain of the chimeric antigen receptor is a GAD65, PTPRU, TFRC or GABA-b protein on the surface of SCLC tumor cells.

Illustrative ligand-binding domains include antigen binding proteins, such as antigen binding fragments of an antibody, such as scFv, scTCR, extracellular domains of receptors, ligands for cell surface molecules/receptors, or receptor binding domains thereof, and tumor binding proteins. In certain embodiments, the antigen binding domains included in a CAR can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is a single chain antibody (scFv), and may be a murine, human or humanized scFv. Single chain antibodies may be cloned from the V region genes of a hybridoma specific for a desired target. A technique which can be used for cloning the variable region heavy chain (VH) and variable region light chain (VL) has been described, for example, in Orlandi et al., *PNAS*, 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs can include a linker(s) between the various domains, added for appropriate spacing and conformation of the molecule. For example, in one embodiment, there may be a linker between the binding domain VH or VL which may be between 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long.

In certain embodiments, linkers suitable for use in the CAR are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure.

The binding domain of the CAR can be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are typically insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the invention include those derived from TCRzeta, FcRgamma, FcRbeta, CD3gamma, CD3delta, CD3epsilon, CD5, CD22, CD79a, CD79b and CD66d. In one particular embodiment, the intracellular signaling domain of the anti-BCMA CARs described herein are derived from CD3zeta.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1BB, other costimulatory domains are contemplated for use with the CARs described herein. The inclusion of one or more co-stimulatory signaling domains may enhance the efficacy and expansion of T cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy*, 2009; 17: 1453-1464; Zhong et al., *Molecular Therapy*, 2010; 18: 413-420; Carpenito et al., *PNAS*, 2009; 106:3360-3365).

In certain embodiments, the polynucleotide encoding the CAR described herein is inserted into a vector. The vector is a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine, c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

In various embodiments, the vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontech), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR are provided in a viral vector. A viral vector can be that derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immnodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.*, 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The CARs are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the CAR is introduced and expressed in immune effector cells so as to redirect their specificity to a target antigen of interest, e.g., an SCLC cell.

Methods for making the immune effector cells which express the CAR are provided. In one embodiment, the method comprises transfecting or transducing immune effector cells isolated from a subject, such as a subject having a SCSL tumor cell, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium, and may lack magnesium or may lack many, if not all, divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention. PBMCs may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+T helper cells can be sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The invention provides a population of modified immune effector cells for the treatment of a patient having a SCLC.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

Thus, provided are methods of treating an individual diagnosed with or suspected of having, or at risk of developing a hematopoietic malignancy characterized in part by the abnormal accumulation of immunoglobulin-producing plasma cells in the bone marrow, such as in multiple myeloma, comprising administering to the individual a therapeutically effective amount of the CAR-expressing immune effector cells as described herein.

In one embodiment, the invention provides a method of treating a subject diagnosed with SCLC comprising removing immune effector cells from a subject diagnosed with SCLC, genetically modifying said immune effector cells with a vector comprising a nucleic acid encoding a chimeric antigen receptor of the instant invention, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the invention in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the invention and returning the transduced cells into the subject.

Disclosed are methods of preparing immune cells for immunotherapy comprising introducing, ex vivo, into such immune cells the polynucleotides or vectors encoding one of the chimeric antigen receptors described herein.

The present invention also encompasses immune cells comprising a polynucleotide or lentiviral vector encoding one of the chimeric antigen receptors discussed herein. In some embodiments, these immune cells are used for immunotherapy (e.g., treatment of cancer).

The present invention also encompasses methods of genetically modifying immune cells to make them more suitable for allogeneic transplantation. According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced. According to further aspect of the invention, the immune cells can be further manipulated to make them more active or limit exhaustion, by inactivating genes encoding proteins that act as "immune checkpoints" that act as regulators of T-cells activation, such as PD1 or CTLA-4.

Engineered Immune Cells

Immune cells comprising a chimeric antigen receptor of the invention (or engineered immune cells) are another object of the present invention. In some cases, the immune cell is an immune effector cell. In some cases, the immune cell is a T cell. In some cases, the immune cell is a T lymphocyte selected from an inflammatory T lymphocyte, a cytotoxic T lymphocyte, a regulatory T lymphocyte, or a helper T lymphocyte. In some cases, the immune cell is a CD8+ cytotoxic T lymphocyte.

Activation and Expansion of Engineered Immune Cells

Whether prior to or after genetic modification of the engineered cells (e.g., T cells), even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Therapeutic Applications

The present invention includes compositions comprising an engineered cell (e.g., a T cell) expressing a chimeric antigen receptor of the invention and a pharmaceutically acceptable vehicle. In some cases, the engineered cells form a medicament, particularly for immunotherapy. In some cases, the engineered cells are used for the treatment of cancer (e.g., multiple myeloma). In some cases, the engineered cells are used in the manufacture of a medicament for immunotherapy and/or the treatment of SCLC.

The present invention includes methods comprising administering to a subject in need thereof a therapeutic composition comprising an engineered cell (e.g., a T cell) expressing a chimeric antigen receptor as discussed herein. The therapeutic composition can comprise a cell expressing any chimeric antigen receptor as disclosed herein and a pharmaceutically acceptable carrier, diluent or vehicle. As used herein, the expression "a subject in need thereof" means a human or non-human animal that exhibits one or more symptoms or indicia of cancer (e.g., a subject expressing a tumor or suffering from any of the cancers mentioned herein), or who otherwise would benefit from an inhibition or reduction or a depletion of SCLC cells.

The engineered cells of the present invention are useful, inter alia, for treating any disease or disorder in which stimulation, activation and/or targeting of an immune response would be beneficial.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating SCLC comprising administering a population of engineered cells described elsewhere herein to a subject after the subject has been determined to have SCLC. For example, the present invention includes methods for treating SCLC comprising administering engineered immune cells to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

The treatments discussed herein can be ameliorating, curative or prophylactic. Treatments may be either part of an autologous immunotherapy or part of an allogeneic immunotherapy. By autologous, it is meant that the cells, cell line or population of cells used for treating patients are originating from the patient or from a Human Leucocyte Antigen (HLA) compatible donor. By allogeneic is meant that the cells, cell line or population of cells used for treating patients are not originating from the patient but from a donor.

Cells that can be used with the disclosed methods are described herein. The treatments can be used to treat patients diagnosed with a pre-malignant or malignant SCLC. The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In some embodiments, the effective amount of cells is administered as a single dose. In some embodiments, the effective amount of cells is administered as more than one dose over a period time Timing of administration is within the judgment of managing physician and depends on the clinical condition of the patient. The cells or population of cells may be obtained from any source, such as a blood bank or a donor. While individual needs vary, determination of ranges of effective amounts of a given cell type for a particular disease or condition are within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In one embodiment, the effective amount of cells or composition comprising those cells is administered parenterally. This administration can be an intravenous administration. In some cases, administration can be directly done by injection within a tumor.

In certain embodiments of the present invention, cells are administered to a patient in conjunction with (e.g., before, simultaneously or following) any number of relevant treatment modalities.

Administration Regimens

According to certain embodiments of the present invention, multiple doses of the engineered cells may be administered to a subject over a defined time course. The methods according to this aspect of the invention comprise sequentially administering to a subject multiple doses of the cells. As used herein, "sequentially administering" means that each dose is administered to the subject at a different point in time, e.g., on different days separated by a predetermined interval (e.g., hours, days, weeks or months). The present invention includes methods which comprise sequentially administering to the patient a single initial dose, followed by one or more secondary doses, and optionally followed by one or more tertiary doses.

The terms "initial dose," "secondary doses," and "tertiary doses," refer to the temporal sequence of administration of the engineered cells of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of engineered cells, but generally may differ from one another in terms of frequency of administration. In certain embodiments, however, the amount of engineered cells contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose which is administered to a patient prior to the administration of the very next dose in the sequence with no intervening doses.

The methods according to this aspect of the invention may comprise administering to a patient any number of secondary and/or tertiary doses. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Antigen Binding Molecules

Disclosed are antigen binding molecules, such as antibodies and fragments thereof, isolated, detected and/or characterized by the methods and/or platforms disclosed herein, which can be used for therapeutic and/or diagnostic methods. In one aspect, antibodies isolated, detected and/or characterized by the methods and/or platforms disclosed herein may be conjugated with any label moiety, toxic moiety or the like, which can be covalently attached to the antibody through a reactive moiety, an activated moiety, or a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation are be toxic to the cell expressing the antigen.

Labelled antigen binding molecules may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

Radioisotopes (radionuclides), such as 3H, 11C, 14C, 18F, 32P, 35S, 64Cu, 68Ga, 86Y, 99Tc, 111In, 123I, 124I, 125I, 131I, 133Xe, 177Lu, 211At, or 213Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9): 1137-1146).

Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Metal-chelate complexes suitable as antibody labels for imaging experiments are disclosed: U.S. Pat. Nos. 5,342, 606; 5,428,155; 5,316,757; 5,480,990; 5,462,725; 5,428, 139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazindiones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) β-D-galactosidase β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. Nos. 4,275,149 and 4,318,980.

A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372, 907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antigen binding molecules are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Hybrid Plasma Marker Panel, Assay and Methods of Use Thereof

Disclosed herein is a hybrid plasma marker panel. The disclosed hybrid biomarker platform measures four different protein types—SCLC autoantibody-antigen complexes, SCLC uncomplexed autoantibodies, SCLC associated proteins and SCLC glycoproteins. These new discovery methods allow the antibody arrays to perform not only proteomics, but also to determine whether the specific proteins that were bound also have cancer-specific glycosylation differences or were bound to the array as a complex with human IgG or IgM (i.e., autoantibody-antigen complexes), as illustrated in FIG. 1. In essence, the array fractionates and purifies the proteins to localize them to the specific spots on the array, which can then probe the bound protein with either a fluorescently labeled antibody specific for the cancer modified carbohydrate (most clinically used cancer biomarkers are glycosylated proteins, CA-125, PSA, CA19-9, etc.) such as sialyl Lewis A or sialyl Lewis X or a fluorescently labeled antibody to human IgG or IgM for autoantibody-antigen complex detection. Both methods are highly sensitive and combined with proteomic analysis allow the level of protein, modified carbohydrate and the presence of autoantibody for any protein for which a specific antibody is present on the array to be determined. Methods for the discovery of either glycomic or autoantibody-antigen complexes as biomarkers are quite novel as separate techniques and certainly unprecedented in combination. The disclosed assay measures both "free" autoantibody that binds SCLC associated molecules as well the autoantibody-antigen (SCLC associated molecule) complex.

In some embodiments, a hybrid plasma marker panel for detecting SCLC associated molecules is disclosed. A biomarker detection panel disclosed herein comprises a plurality of molecules, such as a plurality of autoantibody molecules not bound to their cognate autoantigen and/or bound to their cognate autoantigen (i.e., an autoantigen-autoantibody complex), for example, 2 or more, 3 or more, 4 or more, 5 or more, 6 or more, 7 or more, 10 or more, 20 or more, 50 or more, 100 or more, 200 or more, 500 or more, 1,000 or more, 2,000 or more, 5,000 or more, or 10,000 or more, of which at least two of the autoantibody molecules are from Tables 1A-4 and/or those shown in FIGS. 5E-5K. In some embodiments, the disclosed panel includes detecting molecules for one or more of the disclosed SCLC associated molecules, such as those provided in Tables 1A-4. In some examples, a disclosed panel includes at least two autoantibody molecules listed or capable of detecting molecules in Tables 1B, 2A, 2B, 3 or 4, such as two, three, four, five, six, seven, eight, nine, ten, eleven, twelve, thirteen or more. In some examples, a disclosed panel includes at least two autoantibody molecules from Table 3 or 4, such as two, three, four, five, six, seven, eight, nine, ten, eleven, twelve or thirteen molecules listed in Table 3 or 4. In some examples, a disclosed panel includes two or four autoantibodies disclosed in Table 3, including autoantibody molecules for PNMA1 and/or PNMA2. In some examples, a disclosed panel includes at least autoantibody molecules to PNMA1 and PNMA2. In some examples, a disclosed panel includes at least autoantibody molecules capable of detecting PNMA1, PNMA2 and GAD65 autoantibodies and/or autoantibody-autoantigen complexes. In some examples, a disclosed panel includes at least autoantibody molecules for detecting PNMA1, PNMA2 and CRMP5 autoantibodies and/or autoantibody-autoantigen complexes. In some examples, a disclosed panel includes at least autoantibody molecules to PNMA1, PNMA2, GAD65 and CRMP5 autoantibodies. In some embodiments, the disclosed panel further includes controls or standards. In some examples, a disclosed panel includes or consists essentially of autoantibody molecules to PNMA1 and PNMA2. In some examples, a disclosed panel includes or consists essentially of autoantibody molecules to PNMA1, PNMA2 and GAD65. In some examples, a disclosed panel includes or consists essentially of autoantibody molecules to PNMA1, PNMA2 and CRMP5 autoantibodies. In some examples, a disclosed panel includes or consists essentially of autoantibody molecules to PNMA1, PNMA2, GAD65 and CRMP5 autoantibodies.

An autoantibody molecule can be a target antibody, target antigen and/or a target autoantibody-antigen complex. A target antigen can be an entire protein, such as a protein referred to as a target antigen, or can be a variant, processed, unprocessed, or modified form of the designated protein, or can be or comprise an epitope-containing fragment of the protein designated. An autoantibody molecule that is a target antibody is an antibody that can detect an autoantibody in a sample that is complexed to an autoantigen. An autoantibody molecule in certain embodiments is at least 70%, 75%, 80%, 85%, 90%, 95%, or 100% identical to an at least 25, 50, 75, 100 or the entire amino acid segment of the native autoantibody. The autoantibody molecule in certain illustrative embodiments binds to an autoantibody provided in Tables 2A-4 and/or FIGS. 5E-5K.

The biomarker detection panel in some embodiments has a specificity of 80% or greater, 85% or greater, 90% or greater, 96% or greater, or 98% or greater, and/or a sensitivity of 80% or greater, 90% or greater, 96% or greater, 98% or greater, or 100%, for diagnosing SCLC.

Methods of using a disclosed hybrid marker antibody array methods of detecting SCLC, methods of diagnosing a subject with SCLC and methods of identifying SCLC associated molecules. In some examples, a disclosed method include providing a biological sample, such as a plasma or serum sample, to a disclosed panel, such as a panel array, for analysis. In some examples, the sample biological sample used in the assays and detection and diagnosis methods is a saliva sample or a blood sample, or a fraction thereof, such as plasma or serum. In some embodiments, the sample is blood or a fraction thereof, such as, for example, serum. In other embodiments, the sample is a non-fluid sample, such as a tissue sample. In some examples, the method includes obtaining a sample from a subject that is either at-risk of acquiring or having a specific condition. For example, a sample is obtained from a subject at-risk of acquiring SCLC, such as a chronic smoker or an individual that used to be a chronic smoker, such as an individual that previously smoked for 30 pack years.

The method further includes analyzing purified biological samples for SCLC associated markers by first preparing protein samples, autoantibody samples (which include free autoantigen, free autoantibody and autoantigen-autoantibody complexes) and glycoprotein samples for analysis, such as purifying the samples by techniques known to one of skill in the art. The various SCLC associated molecules, such as one or more disclosed in Tables 1A-4 and/or FIGS. 5E-5K, are then detected in the four types of prepared samples (protein samples, autoantigen antibody samples, autoantibody samples and glycoprotein samples) by incubating the four sample types with the panel including molecules of interest under the appropriate conditions sufficient for promoting interaction/binding and then removing any excess substances by washing. Results can then be visualized by methods known to those of skill in the art such as by protein arrays. FIG. 1 provides a representative schematic illustrating an exemplary method of detection.

While ELISAs remain the "gold standard" for proteomic validation studies, high dimensional analyses have become popular choices for discovery-based methods. Antibodies typically have nano- to sub-nanomolar affinities and can therefore be used to detect proteins even when present at low abundance (e.g., PSA), and the number of commercially available antibodies easily exceeds the number of proteins that have been identified in blood. (1) When used in a microarray format, antibodies represent a cost-effective advance in precision, throughput, and protein coverage (2) and offer a direct route to validation and clinical application. Antibody array technology has been developing for over a decade, and has been applied successfully by many groups for the discovery and validation of potential biomarkers. (3-11) Commercial antibody arrays containing tens to a few hundred antibodies are available from several companies (e.g., R&D, Millipore, Hypromatrix, RayBiotech, Lab Vision, Sigma, etc.), but the defined size and inflexibility of content limits their utility. Disclosed herein are arrays that are much larger and currently contain approximately 3,200 antibodies that are printed in triplicate (10,800 total spots/slide). In addition to simply being ten times larger (antibody number) than most other available antibody arrays, the disclosed hybrid biomarker platform can measure three distinctly different types of biomarkers: proteomics, glycomics or autoantibodies. In essence, the array fractionates and purifies the proteins to localize them to the specific spots on the array, and we can then probe the bound protein with either a fluorescently labeled antibody specific for the cancer modified carbohydrate such as sialyl Lewis A (the CA19-9 antigen) or sialyl Lewis X or a fluorescently labeled antibody to human IgG or IgM for autoantibody-antigen complex (AAb:AAg) detection. Together, the triple hybrid platform is highly sensitive (picogram level)(12) and reproducible (coefficient of variation, CV<10%). (12-14) Using it, viable proteomic biomarker candidates in ovarian (12, 15, 16), breast (17), pancreas (18, 19), colon cancer (13, 14), and lung cancer are disclosed.

In particular, FIG. 1 provides a schematic showing how the array platform can be used to obtain proteomic, autoantibody-antigen complexes, free autoantibody, or glycomic levels using distinct probing strategies. For proteomics, the samples (case or control) are labeled with Cy5 and a reference plasma pool with Cy3 to obtain the level of each protein relative to the reference. For free and complexed autoantibodies the antibody to the human IgG and IgM are directly labeled, an anti SleX and SleA detect the presence of cancer specific glycan moieties.

Figure 2:
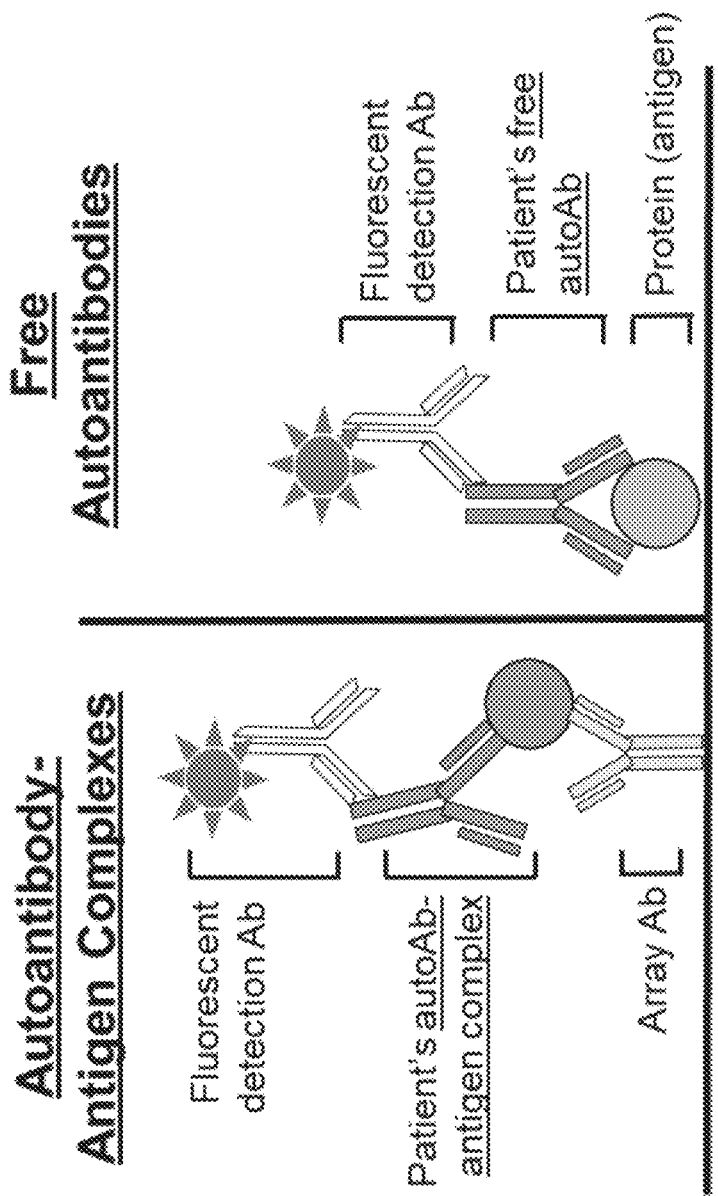
FIG. 2 Autoantibody Detection Platforms for SCLC Early Detection. Antibody (Ab) arrays have antibodies covalently linked to the array surface to detect autoantibody-antigen complexes. Proteins covalently linked to a surface can detect free autoantibodies. This approach is used to diagnose paraneoplastic syndromes associated with SCLC in the clinic.

Additionally, FIG. 2 provides a representative schematic illustrating autoantibody detection platforms for SCLC Early Detection disclosed herein. The inventors have developed a novel large format antibody array containing >3200 different antibodies to interrogate pre-diagnostic plasma sample sets for the purpose of cancer early detection. The antibody arrays are used for both proteomic and autoantibody-antigen complex interrogation which is highly sensitive (picogram level) and reproducible (coefficient of variation, CV<10%) (12-14). Viable biomarker candidates in ovarian (12, 15, 16), breast (20), pancreas (18, 19), colon cancer (13, 14), and NSCLC (21) are disclosed. In some embodiments, the disclosed panel is used to detect SCLC in the early stages including months, as well as years such as one year, two years or three years prior to clinical symptoms of the disease, such as lesions in the lung. In some cases, detection of SCLC associated molecules, such as those disclosed in any one of Tables 1A-4, is followed up with periodic monitoring, such as CT screening and/or additional plasma screening. For examples, a high-risk signature that is not associated with a detectable lesion by CT imaging, possible preventive treatments could be administered such as targeting one or more of the molecules associated with SCLC or known to be involved in the onset. In some examples, identification of SCLC associated molecules would be followed by serial CT imaging, such as on a monthly, every other month, every six months basis. In one example, serial CT imaging is done every two months initially to ensure that if a microscopic SCLC lesion existed, it would be identified while still at limited stage. In some examples, complementary diagnostic markers based on tagged antibody imaging may be used.

In particular examples, the method includes detecting expression of one or more disclosed SCLC associated molecules/biomarkers, such as two or more SCLC biomarkers, wherein the SCLC biomarkers include, consist essentially of, or consist of those disclosed in Tables 1A-4 and/or FIGS. 5E-5K, by the panel disclosed herein. In some examples, controls are also detected, such as 1 to 10, 1 to five, or one to two controls. In some embodiments of the method, an alteration in expression of two or more SCLC biomarkers in the patients sample relative to the control indicates a diagnosis of the subject with early stage SCLC.

In some embodiments of the method, following identifying a subject with early stage SCLC additional methods of diagnosis are performed such as CT scans of the patient's lungs to determine if lesions are present. In some embodiments, the method is repeated over time for the individual. In some embodiments, the individual is monitored at regular or irregular intervals after cancer treatment by determining immune reactivity of samples of the patient to a biomarker detection panel of the disclosure. The immune reactivity of a sample tested at a later date can be compared with the immune reactivity of a sample taken at an earlier date.

In some embodiments, the biomarker detection panel is provided bound to one or more solid or semi-solid supports, such as, for example, a gel or matrix, beads, particles, fibers, rods, filaments, or a filter, strip, sheet, membrane, plate (for example, a multiwell plate), dish, chip or array. In some embodiments, at least 50% of the human proteins bound to the solid support are test antigens of the biomarker detection panel. In some preferred embodiments, at least 55%, at least 60%, at least 65%, at least 70%, at least 75%, at least 80%, at least 85%, at least 90%, or at least 95% of the human proteins bound to the solid support are test antigens of the biomarker detection panel. In some embodiments, the biomarker detection panel is provided in or on a protein array. In some embodiments, antibodies and/or affinity reagents are provided on the solid supports.

Also disclosed are kits that include one or more biomarker detection panels as provided herein. The kits can include one or more reagents for detecting binding of an antibody, or an antigen-antibody complex, from a sample. Detection reagents can include one or more antibodies, labels, labeling reagents, or buffers. In some embodiments, the one or more autoantibody molecules of a biomarker panel of a kit are provided bound to a solid support. In some embodiments of kits, the kit provides a biomarker detection panel in which the target antigens of the detection panel are bound to a chip or array. In some embodiments, a disclosed kit includes two or more autoantibody molecules of Tables 1A-4 and/or FIGS. 5E-5K associated with different vessels and/or solid supports.

The disclosure is further illustrated by the following non-limiting Examples.

EXAMPLES

Example 1

Small cell lung cancer (SCLC) shares one very important characteristic with essentially all solid tumor malignancies: early detection of the cancer leads to improved survival metrics. Since the majority of SCLC patients are diagnosed at extensive stage—where current treatment options offer limited benefit—many investigators have not appreciated the fact that nearly approximately 20% of limited stage SCLC patients can be cured with conventional cytotoxic chemotherapy. Furthermore, surgical resection—generally not considered for SCLC—can be curative when combined with chemotherapy for highly selected and very early stage patients. This example describes the discovery and validation of a novel hybrid plasma marker panel capable of reliably detecting SCLC while still at an early, limited stage.

One of the major reasons that SCLC early detection could prove successful is that there exists a clearly defined high-risk population: heavy cigarette smokers. The lack of at-risk populations for many cancer types has been the greatest obstacle preventing development and implementation of early detection methodologies. In general populations, diagnostic tests need to display nearly perfect sensitivity and specificity to keep false positives and subsequent follow up harms to a minimum. The existence of an at-risk population for non-small cell lung cancer (NSCLC) is one of major reasons why CT screening has proven successful. However, it is important to note that the patient population currently approved for CT screening—age 55-80, >30 pack years smoking, quit smoking<15 years ago—reportedly represents just 45% of NSCLC cases. Although NSCLC has a very clear association with cigarette smoking, many patients (mostly adenocarcinoma) report only modest pack-year consumption and are diagnosed decades removed from active cigarette smoking. In this respect, SCLC provides a much more uniform at-risk population, since essentially all SCLC patients have a substantial cigarette smoking history. Ultimately, we believe that the addition of a blood test capable of SCLC early detection could be added to annual low-dose CT screening protocols, as the at-risk SCLC population resides within the at-risk NSCLC cohort. Our scientific premise is clear: that a hybrid plasma marker panel based on molecular features unique to SCLC (i.e. autoantibody production) is capable of identifying SCLC at the microscopic stage, prior to clinical detection. Identification of SCLC at such an early stage will undoubtedly improve survival rates for this deadly disease.

Since SCLC and NSCLC share overlapping at-risk populations, consideration of what has proved successful and unsuccessful for NSCLC early detection is relevant here. Several groups have attempted to identify blood borne early detection markers for lung and other cancers. Unfortunately, most have failed to identify reliable biomarkers for a variety of reasons, including: a) poorly matched cases and controls, b) discovery techniques that have high dimensionality but low throughput, c) use of late stage cases that identify markers of disease burden, not early detection, d) failure to include discovery and validation cohorts within the study design, and e) slow translation of discovery results into tests that can be utilized in validation trials. No lung cancer biomarkers have progressed past formal validation trials, much less FDA approval. The one exception to this is the Percepta Bronchial Genomic Classifier (Veracyte) though this assay has not been implemented into routine clinical practice given the requirement for a bronchoscopy and bronchial brush biopsy. Carcinoembryonic antigen (CEA), an oncofetal protein not typically expressed in adults, is the most established blood marker, but its primary utility is as an indicator of treatment response. Unfortunately, it is not useful for early detection because it is frequently found in the blood of "healthy" smokers and people with many other types of cancer. CYFRA-21-2, a fragment of cytokeratin is probably the second most widely used, but, in addition to NSCLC, it also detects other epithelial cancers and has shown a broad range of sensitivities in different studies. No marker or panel has sufficient sensitivity and specificity to be recommended for use even in a recurrence or response to treatment setting. Given the genetic and molecular heterogeneity inherent to cigarette smoke related cancers, it remains unclear if a single biomarker approach is feasible. Accordingly, our group has developed a hybrid marker approach, capable of identifying markers related to distinct molecular features of the cancer (e.g. excessive glycosylation of proteins).

Technological advances in the detection and separation of biomolecules, coupled with an increasing capacity to analyze enormous volumes of the resultant data, have allowed investigators to take an objective approach to biomarker discovery. While ELISAs remain the "gold standard" for validation studies, high dimensional analyses have become popular choices for discovery-based methods. Although the components of the blood proteome span 10 or more orders of magnitude of concentration, conventional mass spectrometry and other analytical techniques typically span 3-4 orders of protein concentration and are more susceptible to the obscuring effects of highly abundant plasma proteins (e.g. albumin) requiring extensive upfront purification and reduced throughput. Antibodies typically have nano- to sub-nanomolar affinities and can therefore be used to detect proteins even when present at low abundance (e.g., PSA), and the number of commercially available antibodies easily exceeds the number of proteins that have been identified in blood. When used in a microarray format, antibodies represent a cost-effective advance in precision, throughput, and protein coverage and offer a direct route to validation and clinical application. We have addressed the above common pitfalls by employing a novel hybrid plasma marker panel based on antibody mediated detection methods and by employing numerous distinct SCLC cohorts for purposes of discovery and validation to avoid the "over-fitting" of the data frequently encountered in such efforts.

TABLE 1A

Paraneoplastic syndrome-associated antibodies in SCLC
Table 1A. Paraneoplastic Syndrome (PNS)-Associated Antibodies in SCLC

| Antibody | Antigen | UniProt Accession | GenBank Protein Accession | PNS | ~Antibody frequency in SCLC patient without PNS symptoms (%) |
|---|---|---|---|---|---|
| Anti-Hu | HuB, HuC, HuD | Q12926;; Q14576;; P26378 | EAW58581; XP_005251452; XP_011516079; XP_011516088; XP_016869903; XP_016869906; XP_016869909; NP_001338391; NP_001338396; NP_001338397; NP_001338398; NP_001338399; NP_001338403; BAD92531; XP_006716799; XP_011516076; XP_011516086; XP_016869898; XP_016869915; NP_001338392; XP_005251451; XP_016869902; XP_016869905; XP_016869907; XP_016869908; XP_016869912; EAW58582; XP_011516081; XP_016869897; | Encephalomyelitis | 15-25 |

TABLE 1A-continued

Paraneoplastic syndrome-associated antibodies in SCLC
Table 1A. Paraneoplastic Syndrome (PNS)-Associated Antibodies in SCLC

| Antibody | Antigen | UniProt Accession | GenBank Protein Accession | PNS | ~Antibody frequency in SCLC patient without PNS symptoms (%) |
|---|---|---|---|---|---|
| | | | XP_016869900; NP_001338389; NP_001338400; NP_001338402; NP_001338404; NP_004423; EAW58586; Q12926; AAA69537; XP_005251450; XP_011516080; XP_011516082; XP_011516087; XP_016869901; NP_001338385; NP_001338393; NP_001338401; NP_001338405; NP_001338406; ; EAW58583; EAW58584; EAW58585; XP_016869899; XP_016869904; XP_016869910; XP_016869914; NP_001338386; NP_001338388; NP_001338390; NP_001338395; NP_001338407; AAH30692; XP_006716797; XP_006716798; XP_011516078; XP_011516085; XP_016869911; XP_016869913; NP_001164668; NP_001338384; NP_001338387; NP_001164666; NP_001338394 ;; ; CAC21655; BAA21838; AAA58677; EAW84221; NP_001411; CCQ43760; AAK57545; AAK67714; AAH11875; NP_115657; EAW84220; XP_011526080; Q14576 ;; EAX06844; BAH12553; AAK57538; AAK57540; AAK57541; XP_011539195; NP_001311138; NP_001311145; NP_001138248; NP_001138249; NP_001311141; BAH12899; NP_001281277; NP_001311142; NP_001311143; NP_001311146; NP_068771; ; P26378; BAH12876; AAK57539; AAA58396; XP_011539192; XP_016856029; AAH36071; AAD14142; XP_011539196; EAX06841; XP_016856031; | | |

TABLE 1A-continued

Paraneoplastic syndrome-associated antibodies in SCLC
Table 1A. Paraneoplastic Syndrome (PNS)-Associated Antibodies in SCLC

| Antibody | Antigen | UniProt Accession | GenBank Protein Accession | PNS | ~Antibody frequency in SCLC patient without PNS symptoms (%) |
|---|---|---|---|---|---|
| | | | NP_001138246; NP_001311137; NP_001311144; EAX06842; XP_011539197; XP_016856027; EAX06843; EAX06845; XP_006710474; XP_011539191; XP_016856028; XP_016856030; NP_001138247 | | |
| Anti-CRMP5 | Collapsin response mediator protein (CRMP-5) | Q9BPU6 | AAK16830; CAT03392; CAD28503; EAX00668; Q9BPU6; EAX00667; AAY14652; NP_064519; CAR95653; AAF80348; AAP35517; AAX93268; CAB95124; AAH02874; NP_001240652; NP_001240653 | Encephalomyelitis | 10 |
| Anti-ZIC | ZIC2 (derived from zinc fingers of cerebellum) | O95409 | EAX09030; XP_011519412; EAX09031; AAG38995; AAG28409; NP_009060; O95409; ; AAC96325 | Encephalomyelitis | 15 |
| Anti-Ma | Paraneoplastic Ma protein-1 (PNMA-1) | Q8ND90 | CAG33393; NP_006020; AAN05100; BAF83669; CAD38995; Q8ND90; EAW81126; AAH39577 | Encephalomyelitis | Unknown |
| Anti-Ta | PNMA-2 | Q9UL42 | BAG51501; AAH47515; AAF05626; EAW63575; BAA74906; NP_009188; AAH36489; AAD02098; AAH62301; XP_011542667; AAF05625; Q9UL42 | Encephalomyelitis | Unknown |
| Anti-VGCC | Voltage-gated calcium channel (VGCC) | O00555; Q00975 | ; AAB33068; AAB64179; EAW84365; ABV80232; NP_001120693; NP_001120694; ; EAW84364; BAA94766; AAB49676; AAB49678; EAW84361; O00555; AAB61612; AAB61613; AAF03935; EAW84363; EAW84366; CAA68172; AAC77460; AAB49674; AAC26839; AAD38386; EAW84362; NP_001167551; NP_075461; BAA94765; AAB49675; AAB49677; NP_000059 ;; AAG13643; AAG14397; EAW88417; AAA51898; XP_016870606; XP_016870608; XP_016870609; NP_001230741; AAG13646; AAG14396; EAW88418; XP_011517295; AAG13649; AAA51897; XP_011517296; XP_016870605; AAG13645; AAG13648; AAG14398; CAJ41866; XP_016870607; AAC51138; AAG13647; | Lambert-Eaton | 5 |

TABLE 1A-continued

Paraneoplastic syndrome-associated antibodies in SCLC
Table 1A. Paraneoplastic Syndrome (PNS)-Associated Antibodies in SCLC

| Antibody | Antigen | UniProt Accession | GenBank Protein Accession | PNS | ~Antibody frequency in SCLC patient without PNS symptoms (%) |
|---|---|---|---|---|---|
| | | | AAG13650; EAW88415; NP_000709; ; EAW88416; Q00975; XP_011517293; XP_011517294; XP_016870604; AAG13642; AAG13644; BAD92704 | | |
| Anti-SOX | Sry-like high mobility group box (SOX) | O00570 | CAA73847; NP_005977; EAX09158; O00570 | Lambert-Eaton | 25-35 |
| Anti-GAD65 | Glutamic acid decarboxylase-2 | Q05329 | EAW86101; EAW86104; EAW86103; CAB62572; AAA62367; Q05329; AAH29517; AAA58491; EAW86102; NP_000809; AAP88040; NP_001127838; AAI26328; AAI26330; BAC86947 | Lambert-Eaton | 15 |
| Anti-IA2 | Protein tyrosine phosphatase receptor type N (PTPRN) | Q16849 | BAG57712; AAA90974; BAD92605; BAF84158; XP_011509868; AAP35621; NP_001186693; ; BAG59024; XP_016860101; NP_001186692; EAW70725; Q16849; AAH07713; XP_016860098; XP_016860100; BAG53662; AAH70053; CAA44688; XP_016860099; NP_002837; AAY24038; EAW70724; EAW70726 | Lambert-Eaton | 10 |
| Anti-Rc | Recoverin | P35243 | P35243; BAG36819; AAB23163; AAB23392; AAB26894; AAP88840; NP_002894; EAW90014; BAJ84088; BAA19460; AAH01720 | CAR | 10-15 |
| Anti-Ri | Neuro-oncological ventral antigen (Nova) | P51513 | EAW65994; AAA16022; XP_011535102; XP_016876832; XP_016876836; P51513; BAF82328; XP_016876833; NP_006480; ; EAW65990; EAW65993; EAW65995; AAH75038; AAH75039; CAA94810; XP_016876834; NP_002506; BAH13506; XP_016876837; XP_016876838; BAF83711; BAF84157; XP_016876835; EAW65991; EAW65992; XP_016876831; NP_006482 | Opsoclonus-myoclonus | 5 |

Since data from the National Lung Screening Trial does not support the use of CT screening of SCLC early detection, novel approaches must be considered. SCLC has a unique cell of origin, the pulmonary neuroendocrine cell (PNEC), which represents just 0.4% of lung airway cells, but accounts for nearly 15% of lung cancers. Likely as a function of its unique cell of origin, antibodies against CNS antigens are frequently encountered in SCLC patients, which occasionally give rise to paraneoplastic syndromes (PNS). This serves as a key proof of concept that specific autoantibodies exist in some SCLC patients that can be leveraged for diagnostic purposes. There are several PNS associated with SCLC, though four of them occur more commonly: limbic encephalitis (paraneoplastic encephalomyelitis), Lambert-Eaton Myasthenic syndrome (LEMS), cancer-associated retinopathy (CAR), and opsoclonus-myoclonus syndrome (OMS). Although these syndromes are admittedly rare, the key principle highlighted by these syndromes is that there exist circulating antibodies against auto-antigens in these subjects, and that these antibodies are frequently identified in SCLC patients who do not display evidence of the PNS (see Table 1A). We present data demonstrating the ability to use such markers for the purpose of SCLC early detection (Table 3).

Identification of SCLC Specific Autoantibodies

SCLCs also generate highly glycosylated proteins that could potentially mark the presence of the cancer. For example, a recent report highlighted glycosylation differences in serum alpha-1 antitrypsin in SCLC patients. The ability of our hybrid plasma marker panel to identify glycosylation differences allows us to assay for these modifications using the same base assays and specimen set.

Novel Highly Multiplexed Antibody Array

Disclosed herein is a novel hybrid biomarker platform to generate a highly sensitive and specific plasma-based early detection panel for SCLC. Our hybrid biomarker platform measures three distinctly different types of biomarkers (see FIG. 1), in addition to simply being ten times larger (antibody number) than most other available antibody arrays. These new discovery methods have allowed us to use the antibody arrays to perform not only proteomics but also to determine whether the specific proteins that were bound also have cancer-specific glycosylation differences or were bound to the array as a complex with human IgG or IgM (i.e., autoantibody-antigen complexes), as illustrated in the figure. In essence, the array fractionates and purifies the proteins to localize them to the specific spots on the array, and we can then probe the bound protein with either a fluorescently labeled antibody specific for the cancer modified carbohydrate (most clinically used cancer biomarkers are glycosylated proteins, CA-125, PSA, CA19-9, etc.) such as sialyl Lewis A or sialyl Lewis X or a fluorescently labeled antibody to human IgG or IgM for autoantibody-antigen complex detection. Protein arrays can also be used to determine the levels of uncomplexed or "free" autoantibody present in a subjects plasma. Both methods are highly sensitive and combined with proteomic analysis have allowed us to determine the level of protein, modified carbohydrate and the presence of autoantibody for any protein for which we have a specific antibody on the array. Methods for the discovery of either glycomic or autoantibody-antigen complexes as biomarkers are quite novel as separate techniques and certainly unprecedented in combination. Both the glycosylation marks and autoantibody marks are highly relevant to SCLC, as discussed above. Lastly, the hybrid nature of our panels enables us to choose a set of markers that all display high specificity but need not display high sensitivity on an individual basis, so long as the set cumulatively provides the necessary sensitivity.

SCLC Specific Antibody Discovery

Another innovative aspect of this disclosure is the performance of an unbiased screen to identify SCLC-specific circulating antibodies. The ideal biomarker would represent a tumor-specific process, and therefore carry a high specificity. Because tumors can express unique mutant, oncofetal, CNS site-privileged, or cleaved proteins, the possibility exists that infiltrating lymphocytes would recognize this new epitope as "foreign," and generate an autoantibody against it. Some autoantibodies may be relatively uncommon (low sensitivity) but should be highly specific. Using this strategy, we have been able to develop a set of markers that cumulatively have a high sensitivity, while maintaining high specificity. We have recently employed a similar strategy using tumor-derived B cells to discover novel autoantibodies that effectively mark NSCLC. As a proof of concept, we have identified 28 distinct autoantibody-antigen complexes (Table 1B) that distinguish SCLC cases from controls in a discovery set.

TABLE 1B

Autoantibody-antigen complexes
Table 1B. CHS Discovery SCLC Antigen-Complexed Autoantibodies

| Gene | UniProt Accession | GenBank Protein Accession |
| --- | --- | --- |
| GPLD1 | P80108 | AAH20748; CAC14844; EAW55451; P80108; XP_016866243; EAW55450; AAH07614; AAH93645; AAI12002; AAA36444; EAW55448; AAG16627; AAA36445; XP_011512811; XP_016866242; CAC87068; NP_001494; EAW55449 |
| PTPRU | Q92729 | EAX07652; BAG52941; XP_016855484; AAC51938; XP_016855482; NP_573439; AAB07074; BAD92092; AAI46656; ; Q92729; CAA65832; XP_006710332; XP_016855481; XP_016855483; CAA65016; NP_573438; EAX07650; EAX07651; NP_005695; CCQ43332; AAB51343; NP_001181930 |
| NUDT5 | Q9UKK9 | ; EAW86320; CAG33476; NP_001308576; NP_054861; EAW86322; AAF25479; EAW86321; AAF29079; BAF83820; NP_001308577; Q9UKK9; AAF06734; AAH00025 |
| INHA | P05111 | EAW70774; ACI28454; AAH06391; CAA01158; CAA28040; AAP35600; AAA59166; AAA59167; ; P05111; NP_002182 |
| INHBC | P55103 | EAW97011; BAG37366; NP_005529; ; P55103; AAI30325; AAI30327 |
| ANAPC2 | Q9UJX6 | BAG58931; ; AAF05751; AAH01579; Q9UJX6; AAH32503; NP_037498; AAH09487; EAW88361; BAA92644; BAG57788 |
| PLD3 | Q8IV08 | EAW56954; EAW56956; XP_005258761; EAW56951; AAH00553; AAH36327; AAH96820; XP_005258766; EAW56957; XP_005258764; EAW56953; EAW56955; Q8IV08; AAB16799; XP_016882037; NP_036400; ; EAW56958; XP_005258767; XP_011524995; XP_016882035; NP_001278240; EAW56950; EAW56952; CAD57504; EAW56959; XP_011524994; BAG57127; XP_005258765; XP_006723185; XP_016882036; XP_016882038; NP_001026866 |

TABLE 1B-continued

Autoantibody-antigen complexes
Table 1B. CHS Discovery SCLC Antigen-Complexed Autoantibodies

| Gene | UniProt Accession | GenBank Protein Accession |
|---|---|---|
| PTEN | P60484 | AAD13528; AMQ76358; EAW50172; AAC51182; AAD38372; CCF23296; ADM26755; ADM26756; AEZ67429; AEZ67430; AMQ76357; CCV19970; DAA64601; NP_001291646; ADM26753; AEZ67432; AEZ67435; AEZ67436; AEZ67437; CAG29302; AHW56562; NP_001291647; AAC08699; AEZ67438; CDI44160; EAW50173; ADZ48535; ARB02560; ADM26759; AEZ67434; AMQ76359; CCV66764; P60484; AAC51183; NP_000305; AAY57327; ADM26754; AEZ67431; BAA24090; EAW50174; EAW50175; AAH05821; AAB66902; ; ADM26749; EAZ67433; BAG36351 |
| CTSB | P07858 | AAL99369; EAW65631; EAW65632; CAI46053; NP_680093; EAW65633; CAA77178; XP_006716308; XP_016868588; EAW65634; BAG52127; BAG59411; XP_016868586; P07858; BAG52477; XP_011542114; XP_016868590; EAW65630; EAW65635; XP_006716307; XP_016868587; XP_016868589; ; AAL99368; NP_680090; EAW65636; BAF82928; AAH95408; AAC37547; AAA52125; NP_001899; NP_680092; BAG53460; BAG60046; AAH10240; AAA52129; NP_001304166; NP_680091 |
| SSRP1 | Q08945 | CCQ43203; EAW73734; XP_016873669; AAH05116; NP_003137; Q08945; AAA58660; ; BAD92369; EAW73735; AAH91486; XP_016873670 |
| MMP15 | P51511 | ; AAP35361; EAW82966; P51511; BAA13071; CAA88373; NP_002419; EAW82965; AAH55428; ABJ53423; BAA22225; AAH36495 |
| B3GNT6 | Q6ZMB0 | BAB88882; BAD18819; BAG36432; ; AAI03909; AAI03910; BAC87028; AAI03911; EAW75013; AAH25357; NP_619651; Q6ZMB0; BAF85462 |
| ACP1 | P24666 | CAA76416; NP_004291; AAB59628; BAF82623; AAI06012; AAP35800; AAB59355; AAC52067; EAX01115; EAX01116; AAH07422; AAY14958; EAX01111; BAD93075; AAB27085; NP_001035739; EAX01112; P24666; AEE61174; AAB59354; NP_009030; ; EAX01113; EAX01114; BAF84550 |
| NLRP7 | Q8WX94 | AAL69963; XP_006723138; EAW72313; BAG63894; DAA01246; ; NP_996611; BAG60806; XP_006723139; XP_011524898; XP_011524903; EAW72315; EAW72316; AAO18158; AAI09125; AAI09126; XP_011524901; EAW72314; Q8WX94; NP_001120727; NP_631915 |
| CDH5 | P33151 | AAI17521; P33151; BAG62180; BAG62074; ; BAD93145; AAH96364; XP_011521103; BAA87418; CAA42468; AAH96363; AAH96365; EAW83009; BAG62052; AAB41796; CAA56306; NP_001786 |
| HSPG2 | P98160 | AAB95116; P98160; AAI09205; AAA52700; XP_016856611; NP_001278789; EAW94994; EAW94995; EAW94996; CAA44373; CAC18534; EAW94997; BAD93088; XP_011539620; XP_016856609; NP_005520; AAL79552; AAB21121; ; AAA52699; XP_016856610 |
| SPINK1 | P00995 | ABH06584; AAA36521; CAA68697; P00995; ; AAG00531; NP_001341895; ABH06583; EAW61817; NP_003113; AAH25790; AAA36522 |
| CD34 | P28906 | CAJ01226; EAW93459; AAN15135; BAF85719; BAG57638; BAG62486; AAH39146; AAB25223; BAE46748; AAA03181; NP_001764; AAA03659; CAD98000; ; P28906; AAF14634; AAM82157; AAB25222; EAW93458; BAF84218; NP_001020280 |
| MAPRE1 | Q15691 | AAI06069; AAC09471; EAW76349; BAG59745; AAI28443; NP_036457; ; Q15691; AAI09282; EAW76348; BAG35484; XP_011526998 |
| NADSYN1 | Q6IA69 | BAC65148; Q6IA69; EAW74792; BAB14034; CAG33567; BAA91722; BAG53556; AAH03638; AAH03666; NP_060631; ; EAW74793 |
| SPINT2 | O43291 | ; BAA25024; AAV38918; AAC02781; EAW56766; AAB84031; AAV38919; CAG28532; NP_001159575; EAW56767; AAH11951; O43291; BAG59653; CAE06264; AAH11955; BAF84221; AAH12868; NP_066925; AAH07705; AAV38920; AEE61093; AAH01668 |
| CA9 | Q16790 | CBL94025; CAB82444; NP_001207; ; Q16790; ABL67717; ALQ33410; ALQ33411; EAW58359; CAA47315; AAH14950 |
| HIF1A | Q16665 | ; AAF20139; AAG43026; BAG35314; EAW80807; EAW80808; AAF20140; BAG59438; NP_001521; AAF20149; BAG65259; ACN88547; AAC68568; BAB70608; BAI49183; BAM28632; BAG61496; EAW80806; AAP88778; AAC50152; BAG65167; AAC51210; NP_001230013; NP_851397; EAW80809; Q16665; AAH12527 |
| TFRC | P02786 | AAH01188; CAD97930; NP_001121620; NP_001300895; NP_003225; EAW53670; EAW53672; AAF04564; EAW53671; EAW53673; AAA61153; BAF84412; BAD92491; CAA25527; ABF47088; P02786; NP_001300894; ; BAH11872 |
| PROM1 | O43490 | AAM33415; BAF98780; AAS19705; XP_011512192; NP_001139323; NP_006008; CAE90442; AAB92514; AAS19706; AAS19707; AER93377; XP_016864288; EAW92750; EAW92752; BAG51317; AAS19709; XP_011512205; XP_016864289; XP_016864290; |

TABLE 1B-continued

Autoantibody-antigen complexes
Table 1B. CHS Discovery SCLC Antigen-Complexed Autoantibodies

| Gene | UniProt Accession | GenBank Protein Accession |
|---|---|---|
| | | XP_016864293; NP_001139320; NP_001139324; O43490; XP_011512195; XP_011512199; XP_016864291; BAG51316; BAG52133; AAH12089; XP_005248253; XP_011512196; XP_011512201; XP_011512202; XP_016864292; NP_001139319; EAW92751; AAS19708; XP_011512194; XP_016864294; NP_001139321; CAE83895; AER93376; XP_011512204; ; AAO15307; XP_005248252; XP_006714037; XP_011512197; XP_011512198; XP_011512200; NP_001139322 |
| CDH23 | Q9H251 | BAB47441; AAG48303; CAB59256; AAT72162; AAI08255; XP_011538346; EAW54429; BAB61902; AAG27034; AAT72166; AAH65284; AAI39904; XP_006718003; NP_001165403; NP_001165405; NP_443068; AAT72165; AAI36977; XP_011538348; XP_011538351; XP_011538353; NP_001165404; EAW54428; AAH11570; AAI36978; XP_006718005; XP_011538345; XP_011538354; XP_016871995; NP_001165406; NP_001165407; ; EAW54432; BAC04231; AAH32581; XP_011538350; XP_016871988; XP_016871997; NP_001165401; NP_071407; EAW54430; AAQ88980; XP_011538341; XP_011538344; XP_016871990; XP_016871992; XP_016871994; NP_001165402; CCQ43681; EAW54427; BAB84986; XP_011538349; XP_016871989; XP_016871991; XP_016871993; EAW54426; EAW54431; Q9H251; AAT72161; XP_011538347; XP_016871996 |
| SLMO2 | Q9Y3B1 | Q9Y3B1; ; NP_057129; AAH13969; AAD34102; NP_001243332; EAW75443; BAG60414; AAH10649; EAW75442; BAA92114 |
| GRAP2 | O75791 | AAC69273; AAF60319; NP_001278755; EAW60357; EAW60360; AAF31758; AAD41782; BAH14008; CAG46647; AAD13027; CAA09757; BAH13929; XP_006724439; EAW60356; BAH13978; NP_001278753; NP_001278754; NP_001278757; O75791; AAD04926; AAL58573; AAH26002; CAG30384; NP_004801; ; CAG38761; EAW60358; EAW60359; EAW60361; AAF60320; BAH13944; BAH13969; BAG35685; AAH25692; CAA77021 |

Multiple Dataset Discovery/Validation

One of the major shortcomings of the early detection biomarker field has been the lack of appropriate validation efforts. Unbiased screens can routinely generate markers that distinguish between case and control within any given dataset, as a function of "over-fitting" the data. Such markers frequently fail when tested in independent datasets. It is essential that all early detection studies have validation efforts integrated into the project from the outset, as is the case here. With respect to SCLC, this is easier said than done. Biorepositories for SCLC specimens are in short supply. This is largely related to the fact that SCLCs are rarely resected, such that tissue banks, for the most part, don't exist. Since translational research programs have been rare in SCLC, even plasma specimens are difficult to obtain. Through our involvement with early detection networks and collaborators, we have accumulated>250 SCLC specimens for this project allowing us to validate our biomarker panel in several distinct cohorts minimizing the likelihood that we are developing cohort specific markers.

Validation and Performance of the Antibody Array for Plasma Biomarkers

Figure 3B:
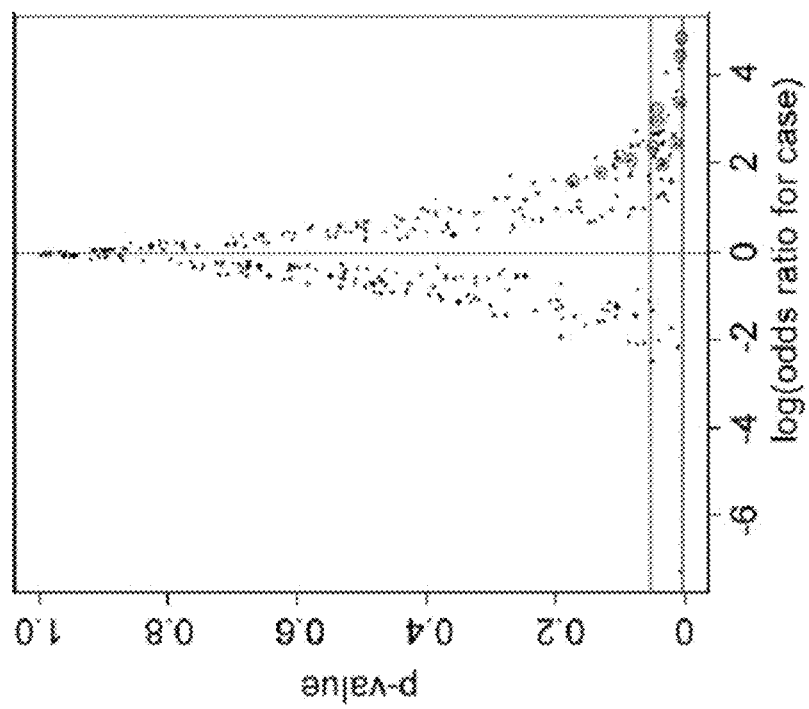
FIG. 3B Antibody Array Accuracy Proof of Principle in Ovarian Cancer. Scatter plot with the p-value of each antibody displayed as a function of the log of the odds ratio for case. Those data points between the horizontal aqua lines indicate discriminating antibodies (p<0.05); data points to the right of the vertical aqua line indicate case>control, left control>case. All antibodies to known biomarkers preferentially recognized case sera, 8/12 with p<0.05 (red circles=CA125, green=mesothelin, and blue=HE4).
Figure 3A:
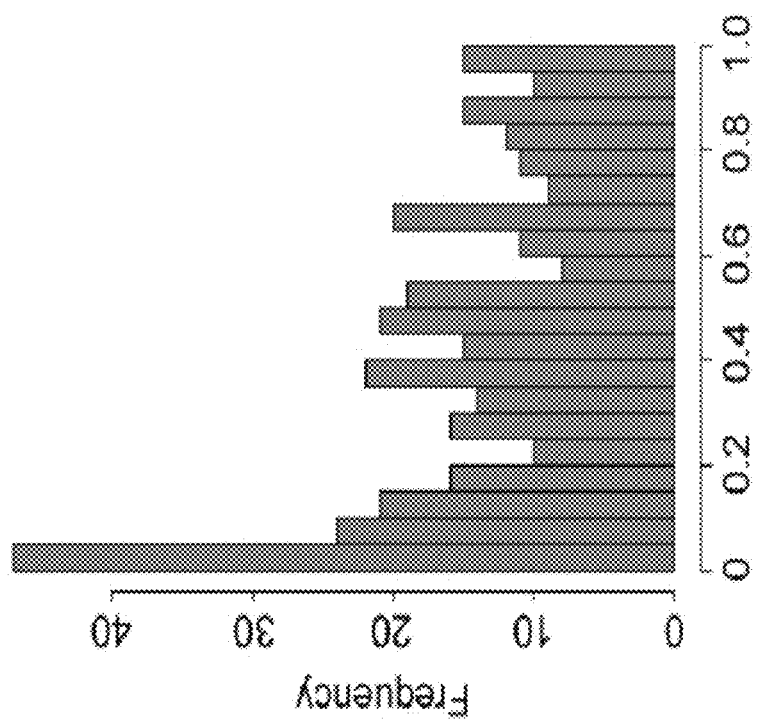
FIG. 3A Antibody Array Accuracy Proof of Principle in Ovarian Cancer. Histogram of p-values from antibody array using ovarian cancer plasma specimens. Logistic regression was used to estimate each antibody's ability to predict disease. The probability score for each antibody (p-value by Wilcoxon sign-rank testing) is displayed as a function of the number of antibodies with that score. The leftward skew indicates that this array was enriched for antibodies capable of identifying case/control status with high probability.

We demonstrated our ability to successfully immobilize 320 unique full-length and 4800 recombinant antibodies on a high density microarray with functionality suitable for biomarker discovery and validation. Among the top-performing array features were 10 of the 10 antibodies to the known ovarian cancer biomarkers CA125 and mesothelin (FIGS. 3A and 3B). These markers were significant classifiers of disease status on their own based on their low false discovery rate (FDR or q-value) and p-value and also, as a group had a mean CV value of 3.67% (the vast majority of array features have CV's under 10% in multiple studies). Our fractionation/concentration procedures yield detectable protein for even low-abundance proteins such as IL1β which we could readily detect at endogenous levels as well as when 2 and 5 pg of IL1β were spiked-in. Taken together, these data indicate our platform is reproducible, efficient and reliable for high-throughput analysis of human plasma proteins for utility as biomarkers of disease.

Lung Cancer Biomarkers Identified Using Pre-Diagnostic Plasma Specimens

Figure 4:
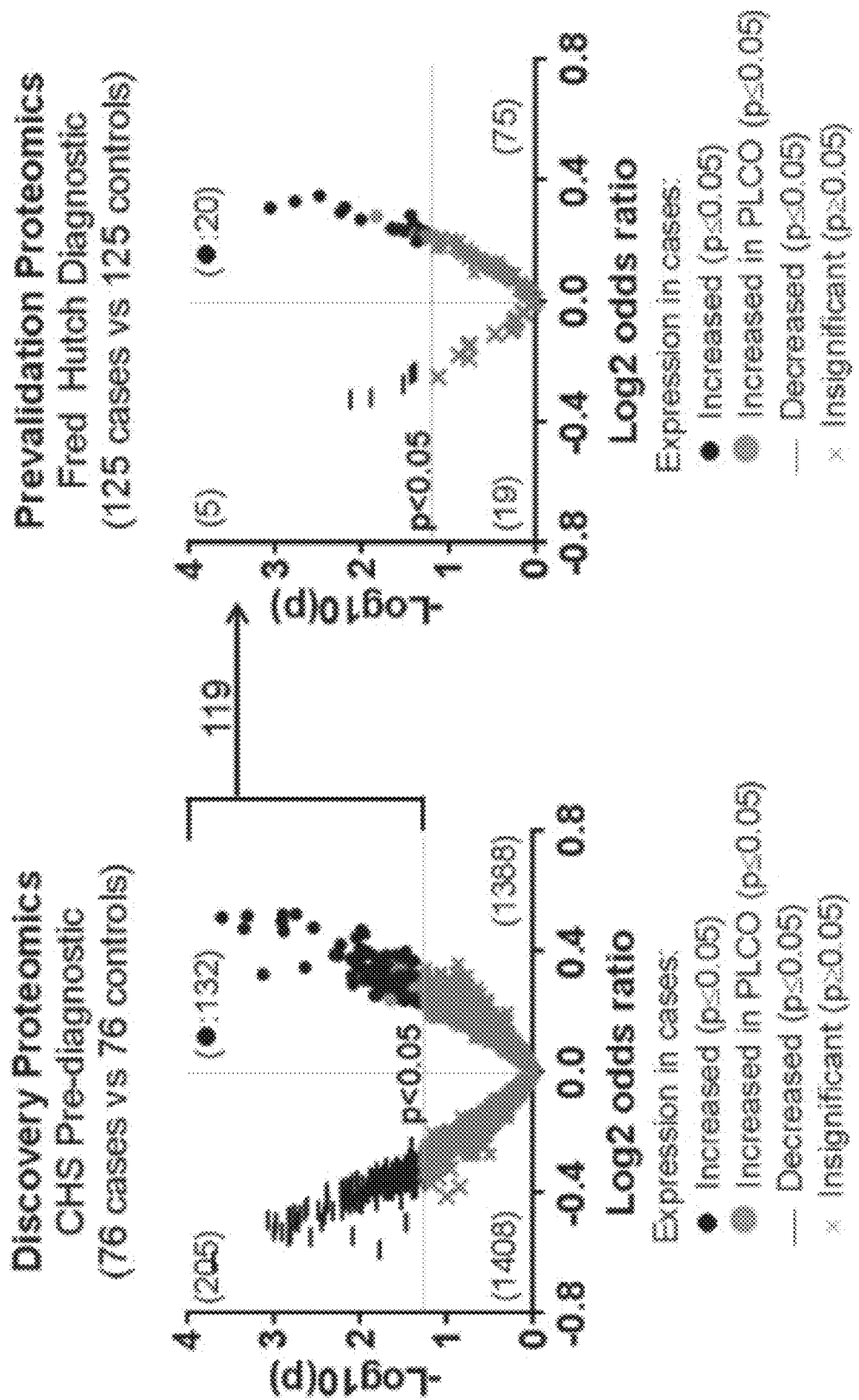
FIG. 4 Validated Proteomic Markers in NSCLC. Volcano plot of proteomic antibody array for N=76 cases/controls from CHS identified several markers significantly up- or down-regulated compared to control. A total of 25 markers validated in the Fred Hutch cohort (N=125) of which 20 were up-regulated and 5 down-regulated. Notably, 3 of these upregulated markers also validated in the PLCO cohort (N=265), indicating significant validation in the PLCO cohort (N=265), indicating significant validation.

We have performed proteomic analysis of Cardiovascular Health Study (CHS) study participants that were diagnosed with NSCLC<2 years since their last study blood draw (i.e., pre-diagnostic samples) comparing 76 cases to 76 matched cancer-free controls. Cases and controls were matched on age, gender and smoking status (never, past, current). We typically focus on upregulated biomarkers as they intuitively might be more likely to be directly related to the presence of the cancer. N=132 proteins showed significant (p<0.05) differences in people that were subsequently diagnosed with NSCLC. We have also performed analysis on samples from the Fred Hutch Lung Cancer Early Detection and Prevention Clinic (LCEDPC) cohort of ~500 subjects that were referred to our center for pulmonary nodule evaluation. For this reason, this cohort has a high number of both benign and malignant pulmonary nodules and a higher proportion of later stage cancers than a typical screening cohort. Chest CT, plasma specimens, pathology reports and a detailed clinical history were also available for all subjects as part of an annotated database. N=125 subjects with nodules that were later determined to be cancerous were matched 1:1 with subjects with benign nodules (as determined by >2 year follow-up CT showing regression or no change or definitive follow-up testing) first based on gender (exact match), then age (±2 yr), and finally pack years of smoking (best available match). Of the cancers, 63% were lung adenocarcinoma (LUAD) and 19% were lung squamous cell carcinoma (LUSQ). Of the N=119 upregulated proteins discovered in the CHS samples, N=20 were validated as upregulated at p<0.05 in the LCEDPC study—(7× what would be expected by chance). We have also completed proteomic analysis of N=265 Prostate, Lung, Colorectal, and Ovarian Cancer Screening Study (PLCO) participants that were diagnosed with NSCLC up to 2 years after the blood draw and N=265 controls matched on BMI, gender, smoking status, age, race and family history of lung cancer. We found 3 of the 20 significantly upregulated proteins in the CHS and LCEDPC cohorts were also up in the PLCO samples (FIG. 4). The fact that 3 proteomic markers were significant in 3 separate studies, two from pre-diagnostic (i.e., similar to NLST and models for screening/early detection) sample sets and the third being a nodule diagnostic cohort indicates significant validation. Furthermore, 20 more biomarkers overlap between the different sample sets but do not quite reach as high significance in the third and some markers are significant in all groups for different subtypes of lung cancer (i.e., squamous cell carcinoma (LUSQ) or adenocarcinoma (LUAD) specific).

Our array approach can also be used to measure glycomic and autoantibody-autoantigen complex differences. Examination of proteins with significant increases in sialyl Lewis-A and -X content in the CHS samples showed N=14 proteins with increased sialyl Lewis-A (p<0.043) and N=16 with sialyl Lewis-X (p<0.025) modifications. The LCEDPC samples showed validation of 4/14 and 2/16 of the glycomic markers at p<0.006. In terms of autoantibody-autoantigen complexes, we found 51 IgG (p<0.01) and 33 IgM (p<0.023) complexes significantly increased in the CHS samples (not shown). In LCEDPC samples, 15/51 IgG and 2/33 IgM markers validate at p<0.02. Currently, we are finishing the glycomic and autoantibody testing of the PLCO samples. Thus, we have 5 proteomic, 6 glycomic and 17 autoantibodies that have been discovered and then validated in at least one additional NSCLC sample set. In terms of sensitivity and specificity, 23 of the 28 markers have individual AUC values>0.60 for the CHS samples. Most markers are expressed in the plasma membrane, secreted or both. Several are WNT-related, some associated with immune function, cell-cell adhesion and fetal or pregnancy associated indicating potential reactivation of developmental programs Interestingly, multiple proteins from the same family are upregulated at the protein level or have cancer-specific glycosylation. When the top 4 markers are combined they yield an area under the curve (AUC)=0.82 (45% sensitivity at 90% specificity). When we tested this 4-marker combination rule in the LCEDPC samples, we obtained an AUC=0.83 (50% sensitivity at 90% specificity). Given these are quite different sample sets (i.e., one from participants up to 2 years prior to diagnosis—and one from patients at a nodule evaluation clinic), this level of validation is exciting. In fact, an optimal AUC for the LCEDPC samples for the best 4 markers (all different than the 4 above) was 0.93 (87% sensitivity at 90% specificity).

Tumor-Derived B Cells Produce Tumor Specific Autoantibodies

Figure 5B:
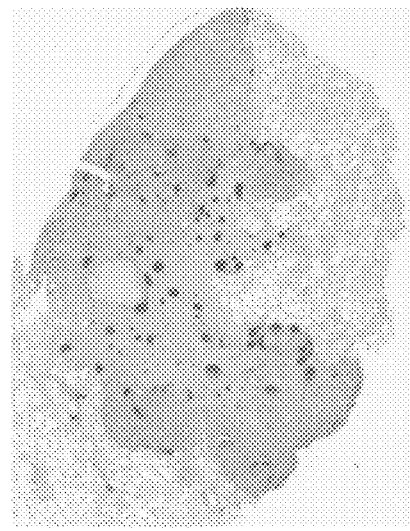
FIGS. 5A-5F Tumor-derived B cells produce tumor-specific autoantibodies.
Figure 5A:
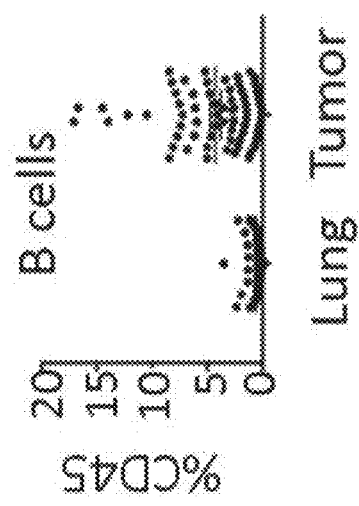
Figure 5D:
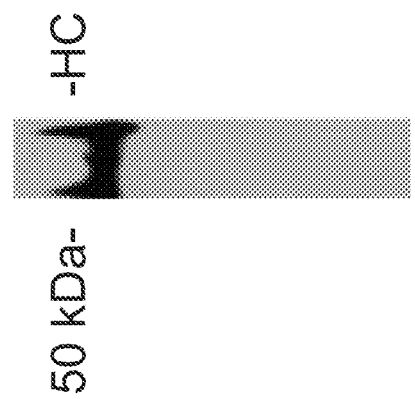
Figure 5C:
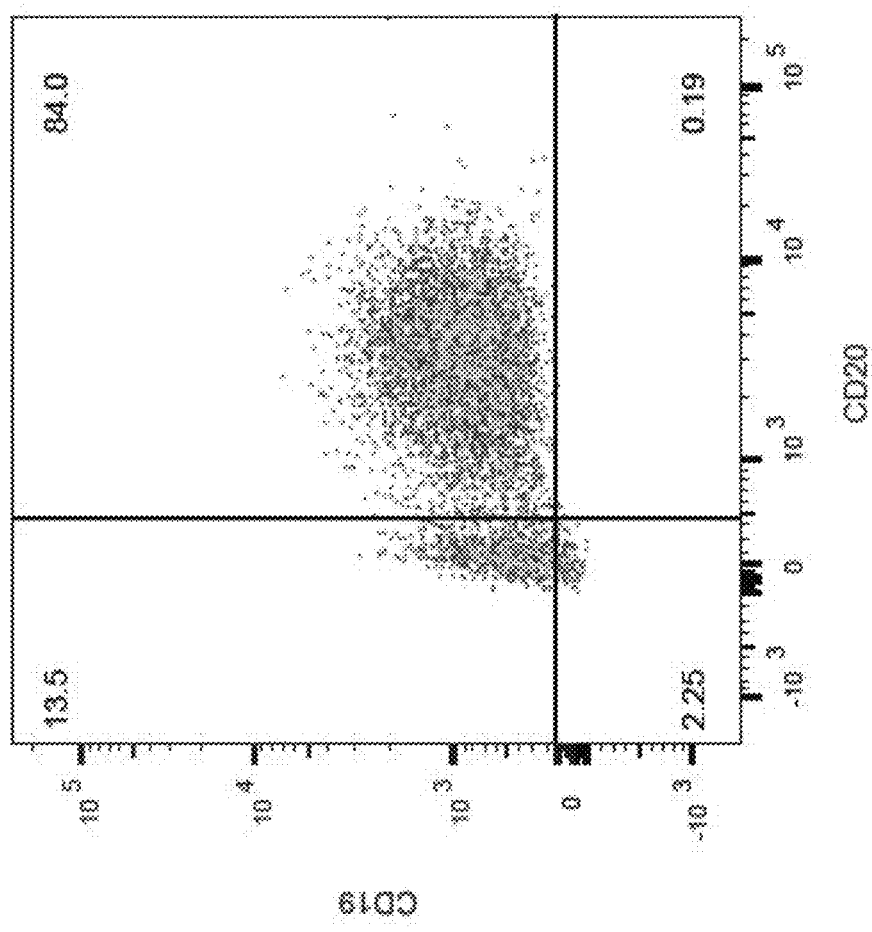
Figure 5E:
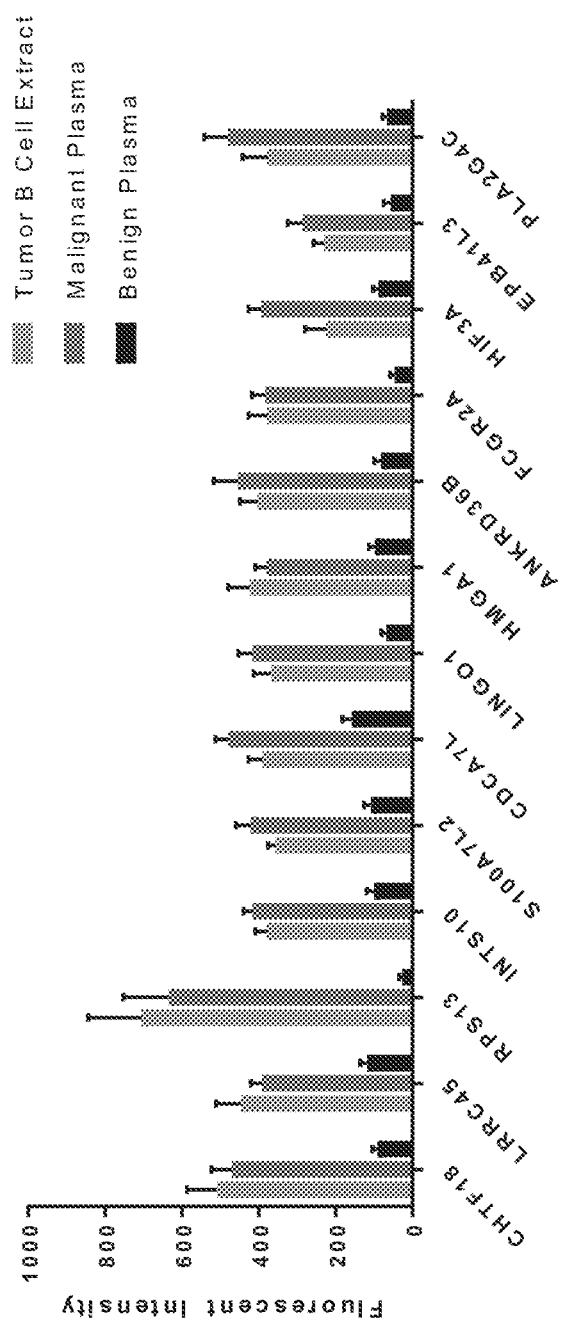
Figure 5F:
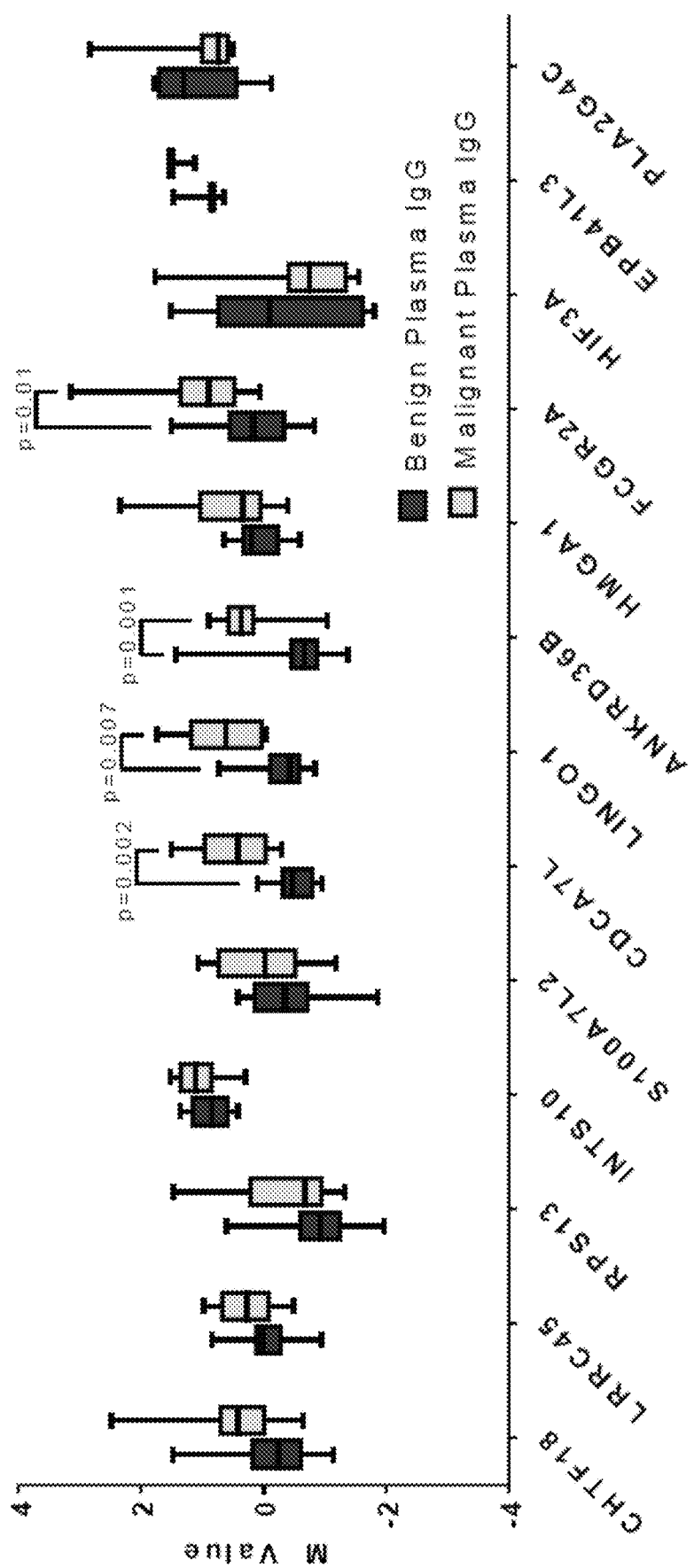
Figure 5G:
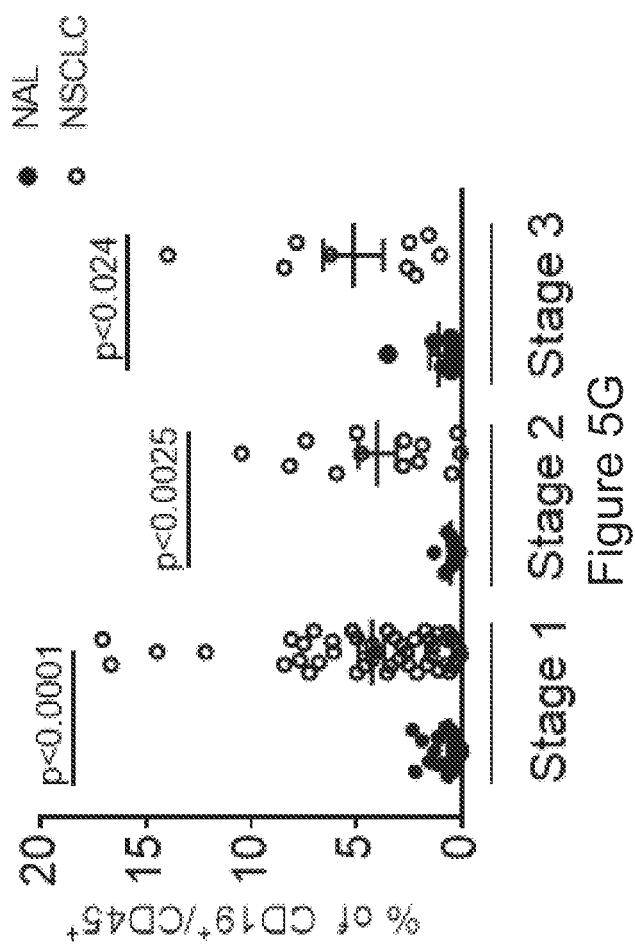
Figure 5H:
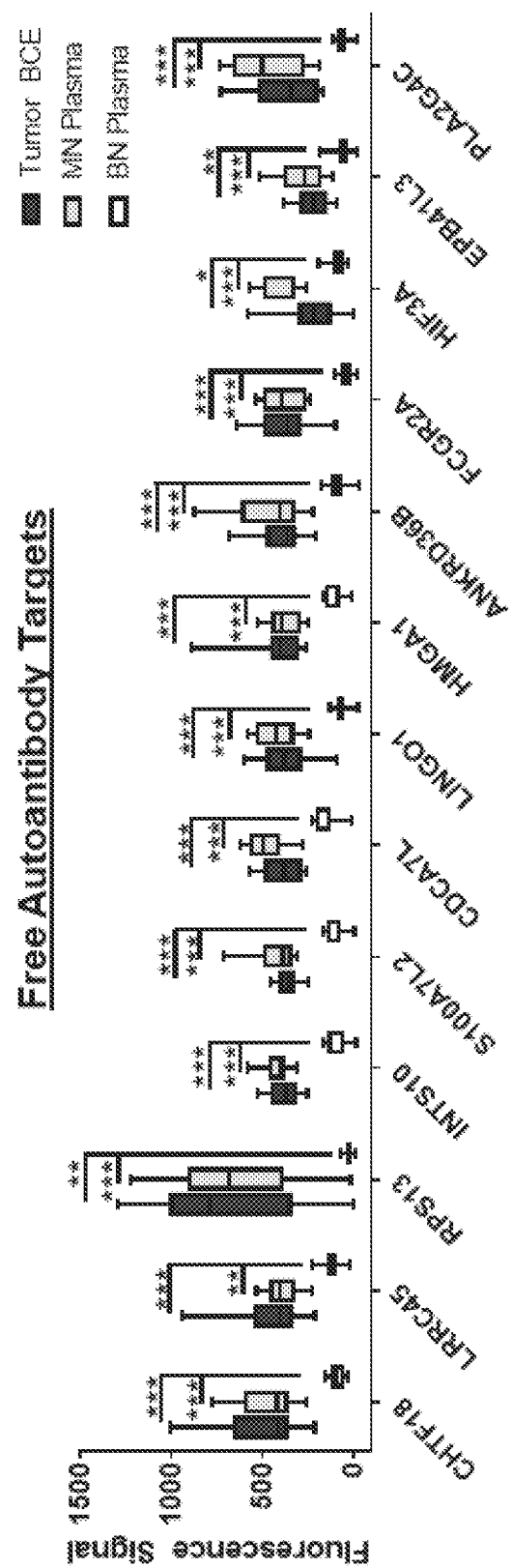
Figure 5J:
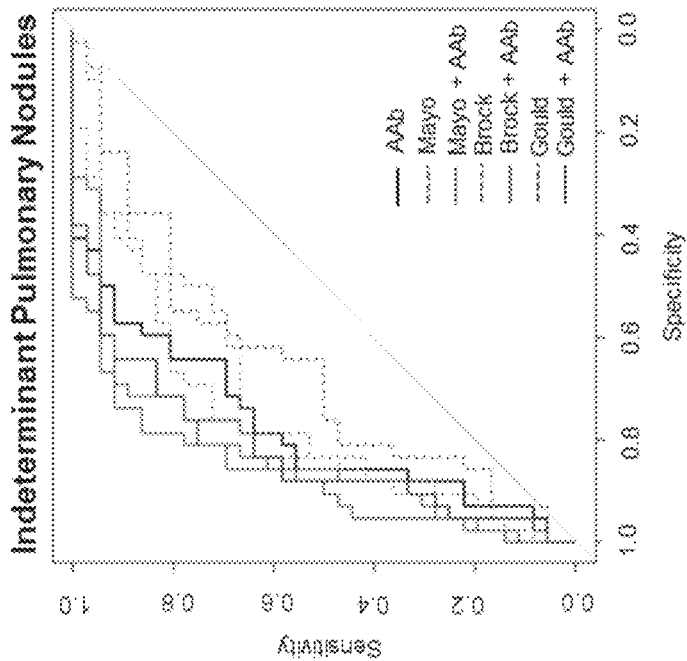
Figure 5I:
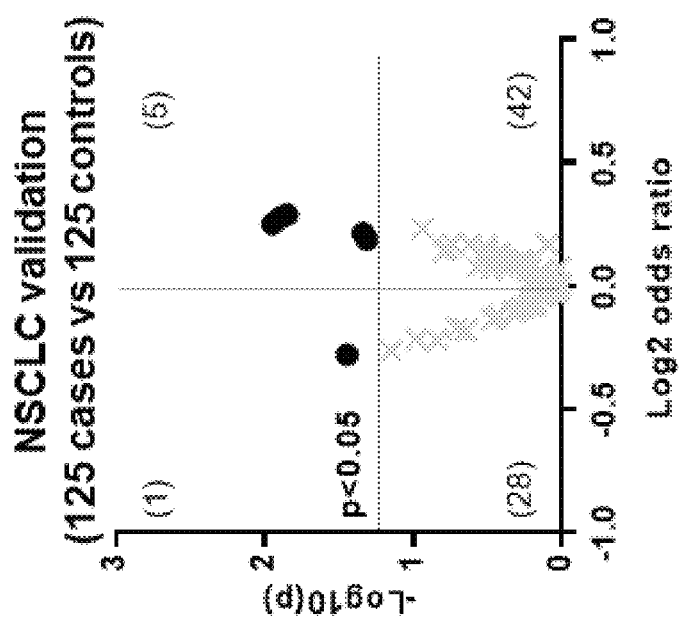

We recently concluded a study in which we identified B cells as the immune population with the largest increase in content when comparing NSCLC tumor immune cell content to that identified in non-adjacent lung tissue (FIGS. 5A, 5B and 5G). Cancer cells can produce unique epitopes to tumor-infiltrating lymphocytes through multiple mechanisms including altered antigen exposure via immunogenic cell death, defects in immune tolerance, inflammation, changes in protein expression levels or location, or altered protein structure. To explore this, flow cytometry of single cell suspensions from freshly dissociated NSCLC tumor yielded ~5% of CD45+ cells (leukocytes) as CD19+ B-cells. After CD19+ column purification, flow cytometry yielded>96% pure B-cells. After culturing B cells for 48 hours, the Ig-rich supernatant was removed, the B cells were lysed and IgG and IgM content of the combined supernatant and lysate (termed B cell extract) determined (FIGS. 5C-5D and 5H-5I). The extract was incubated on a HuProt® array that contains ~17,000 proteins expressed in yeast. After washing, bound IgG and IgM were simultaneously detected. An analysis of 10 lung tumors (7 ADCA, 3 SCCA), 10 matched plasma, and 10 control plasma from benign nodules on HuProt® arrays showed an average of 105 autoantibodies present per lung tumor sample and of these, 45 autoantibodies to specified proteins were found in >50% of the samples (i.e., autoantibodies to 45 proteins showed at least 50% sensitivity) and 9 showed at least 80% sensitivity. One of these was found in all tumors but was not present in any benign sample while several more had ≥70% specificity in these 10 samples. We narrowed down the list of 45 autoantibodies to 13 with ≥50% sensitivity and >70% specificity to examine further (FIGS. 5E and 5H). Consistent with their utility, 10 of the 13 were increased in cases on the antibody array we probed looking for autoantibody-antigen complexes (N=20) (FIG. 5F). To determine if these free autoantibodies were also present in these samples in complex with their autoantigens, we made a targeted antibody array and found 11 of these 13 were also present as autoantibody-antigen complexes. Five of the 13 maintained significant increases (p<0.05) when we probed on the Fred Hutch LCEDPC set (N=250) (FIG. 5I). A combination of 4 autoantibodies could detect malignant nodules with an AUC=0.74, which increased to an AUC=0.78 in a sub-cohort of indeterminate pulmonary nodules (FIG. 5J) (21). Combining this 4-marker panel with any of 3 published nodule prediction models (Brock, Mayo, or Gould) showed statistically significant improved identification of indeterminate malignant nodules compared to any model alone (FIGS. 5J-5K). It is contemplated that a related autoantibody discovery strategy can be employed by subjecting SCLC case/control plasma to HuProt® arrays in order to comprehensively identify SCLC specific circulating antibodies which can be transferred to our antibody platform and validated in independent cohorts.

Figure 6:
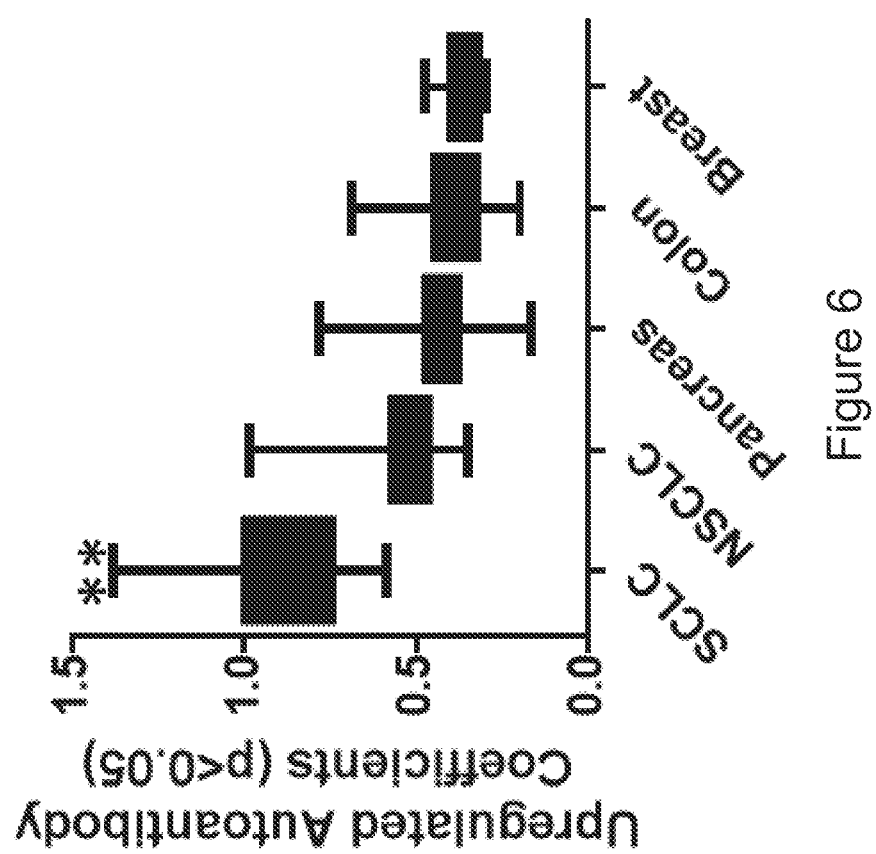
FIG. 6 IgG antigen-complexed autoantibodies is significantly higher in SCLC compared to other cancer types. The mean coefficient signal of upregulated (p<0.05) IgG autoantibodies in SCLC is significantly higher (**p<0.0001, one-way ANOVA) than any other cancer type analyzed on our antibody arrays.

FIG. 6 illustrates signal of upregulated IgG antigen-complexed autoantibodies is significantly higher in SCLC compared to other cancer types. Since data from the National Lung Screening Trial (NLST) does not support the use of CT screening of SCLC early detection (28), novel approaches must be considered. SCLC has a unique cell of origin, the pulmonary neuroendocrine cell (PNEC), which represents just 0.4% of lung airway cells, but accounts for nearly 15% of lung cancers (30, 31). Likely as a function of its unique cell of origin, antibodies against CNS antigens are encountered in SCLC patients, which occasionally give rise to paraneoplastic syndromes (PNS) (32). This serves as a key proof of concept that specific autoantibodies exist in some SCLC patients that can be leveraged for diagnostic purposes. Although numerous cancer histologic types can be affected by PNS, lung cancer is by far the most likely to be implicated (33). Some of these syndromes involve the secretion of biologically active hormones, such as the case with the syndrome of inappropriate anti-diuretic hormone (SIADH) and hypercalcemia induced by parathyroid related protein. Both of these syndromes are associated with lung squamous cell carcinoma in addition to SCLC; however, the antibody associated PNS affect SCLC approximately 10-fold more than any other cancer type. SCLC accounts for about 50% of the limbic encephalitis cases, with breast cancer (8%) and testis cancer (20%) also representing important subsets. The other CNS PNS are almost entirely comprised of SCLC cases (34). The most common PNS, Lambert-Eaton myasthenic syndrome (LEMS) affects nearly 1% of all SCLC patients, much greater than any other cancer type. Cancer-associated retinopathy (CAR) is almost exclusively associated with SCLC, with other subtypes still case-reportable. Consistent with these reports, data disclosed herein clearly shows that plasma autoantibody-antigen complexes are an order of magnitude higher in SCLC than it is in NSCLC, pancreatic cancer, breast cancer, and colon cancer (FIG. 6). The scientific rationale for the disclosed methods and systems is based on these findings: that tumor-specific autoantibodies are more common in SCLC than in any other cancer type and that the presence of known and not-yet identified tumor-specific antigen-antibody complexes and free autoantibody can be utilized to identify the presence of SCLC prior to clinical detection.

Autoantibodies Distinguish SCLC Cases from Controls

We have acquired three sample sets totaling N=98 SCLC cases and N=143 matched controls where we sequentially discovered and validated autoantibody-antigen complexes. When we subjected the CHS pre-diagnostic specimens (N=34) to our antibody array and probed for autoantibody-antigen complexes, we were able to identify 24 IgG and 102 IgM markers that were significantly up-regulated at $p<0.05$ (FIG. 7A). We carried forward 19 IgG and 66 upregulated IgM autoantibodies and tested their expression in the Fred Hutch SCLC diagnostic cohort (N=52). 13/19 IgG markers (68% $p<0.0001$) and 14/66 IgM markers (21.2% $p<0.02$) validated in this second cohort (FIG. 7B). In a third cohort from Vanderbilt (N=155) 8/13 (61.5% $p<0.004$) IgG autoantibodies and 11/13 (84.6% $p<0.03$) IgM autoantibodies were validated (FIG. 7C). Thirteen validated autoantibodies are listed in Table 2A.

TABLE 2A

Autoantibody Markers.
Table 2A. Autoantibody Antigen-Complex Markers in SCLC Cohorts

| Gene | UniProt Accession | GenBank Protein Accession | CHS | | | | | FH | | | | |
|---|---|---|---|---|---|---|---|---|---|---|---|---|
| | | | coef | p value | AUC | Spec | Sens | coef | p value | AUC | Spec | Sens |
| GPLD1 | P80108 | AAH20748; CAC14844; EAW55451; P80108; XP_016866243; EAW55450; AAH07614; AAH93645; AAI12002; AAA36444; EAW55448; AAG16627; AAA36445; XP_011512811; XP_016866242; ; CAC87068; NP_001494; EAW55449 | 0.77 | 0.05 | 0.689 | 0.71 | 0.65 | 1.33 | 9.28E−06 | 0.866 | 0.84 | 0.92 |
| PTPRU | Q92729 | EAX07652; BAG52941; XP_016855484; AAC51938; XP_016855482; NP_573439; AAB07074; BAD92092; AAI46656; ; Q92729; CAA65832; XP_006710332; XP_016855481; XP_016855483; CAA65016; NP_573438; EAX07650; EAX07651; NP_005695; CCQ43332; AAB51343; NP_001181930 | 0.69 | 0.03 | 0.713 | 0.71 | 0.71 | 0.91 | 0.001 | 0.797 | 0.77 | 0.77 |
| NUDT5 | Q9UKK9 | ; EAW86320; CAG33476; NP_001308576; NP_054861; EAW86322; AAF25479; EAW86321; | 0.87 | 0.01 | 0.74 | 0.59 | 0.88 | 1.68 | 4.70E−07 | 0.914 | 0.80 | 0.92 |

TABLE 2A-continued

Autoantibody Markers.
Table 2A. Autoantibody Antigen-Complex Markers in SCLC Cohorts

| Gene | UniProt Accession | GenBank Protein Accession | CHS | | | | | FH | | | | |
|---|---|---|---|---|---|---|---|---|---|---|---|---|
| | | | coef | p value | AUC | Spec | Sens | coef | p value | AUC | Spec | Sens |
| INHA | P05111 | AAF29079; BAF83820; NP_001308577; Q9UKK9; AAF06734; AAH00025 EAW70774; ACI28454; AAH06391; CAA01158; CAA28040; AAP35600; AAA59166; AAA59167; ; P05111; NP_002182 | 0.83 | 0.03 | 0.713 | 0.59 | 0.76 | 4.48 | 1.37E−18 | 0.999 | 0.96 | 1.00 |
| INHBC | P55103 | EAW97011; BAG37366; NP_005529; ; P55103; AAI30325; AAI30327 | 0.71 | 0.03 | 0.737 | 0.76 | 0.71 | 1.99 | 8.11E−10 | 0.986 | 0.92 | 1.00 |
| ANAPC2 | Q9UJX6 | BAG58931; F05751; AAH01579; Q9UJX6; AAH32503; NP_037498; AAH09487; EAW88361; BAA92644; BAG57788 | 0.99 | 0.01 | 0.743 | 0.47 | 1.00 | 1.59 | 2.91E−07 | 0.899 | 0.79 | 1.00 |
| PLD3 | Q8IV08 | EAW56954; EAW56956; XP_005258761; EAW56951; AAH00553; AAH36327; AAH96820; XP_005258766; EAW56957; XP_005258764; EAW56953; EAW56955; Q8IV08; AAB16799; XP_016882037; NP_036400; ; EAW56958; XP_005258767; XP_011524995; XP_016882035; NP_001278240; EAW56950; EAW56952; CAD57504; EAW56959; XP_011524994; BAG57127; XP_005258765; XP_006723185; XP_016882036; XP_016882038; NP_001026866 | 0.75 | 0.03 | 0.757 | 0.81 | 0.76 | 1.80 | 6.93E−09 | 0.95 | 0.96 | 0.88 |
| PTEN | P60484 | AAD13528; AMQ76358; EAW50172; AAC51182; AAD38372; CCF23296; ADM26755; ADM26756; | 0.97 | 0.03 | 0.689 | 0.65 | 0.71 | 2.46 | 1.66E−12 | 0.979 | 1.00 | 0.92 |

TABLE 2A-continued

Autoantibody Markers.
Table 2A. Autoantibody Antigen-Complex Markers in SCLC Cohorts

| Gene | UniProt Accession | GenBank Protein Accession | CHS | | | | | FH | | | | |
|---|---|---|---|---|---|---|---|---|---|---|---|---|
| | | | coef | p value | AUC | Spec | Sens | coef | p value | AUC | Spec | Sens |
| | | AEZ67429; AEZ67430; AMQ76357; CCV19970; DAA64601; NP_001291646; ADM26753; AEZ67432; AEZ67435; AEZ67436; AEZ67437; CAG29302; AHW56562; NP_001291647; AAC08699; AEZ67438; CDI44160; EAW50173; ADZ48535; ARB02560; ADM26759; AEZ67434; AMQ76359; CCV66764; P60484; AAC51183; NP_000305; AAY57327; ADM26754; AEZ67431; BAA24090; EAW50174; EAW50175; AAH05821; AAB66902; ; ADM26749; AEZ67433; BAG36351 | | | | | | | | | | |
| CTSB | P07858 | AAL99369; EAW65631; EAW65632; CAI46053; NP_680093; EAW65633; CAA77178; XP_006716308; XP_016868588; EAW65634; BAG52127; BAG59411; XP_016868586; P07858; BAG52477; XP_011542114; XP_016868590; EAW65630; EAW65635; XP_006716307; XP_016868587; XP_016868589; ; AAL99368; NP_680090; EAW65636; BAF82928; AAH95408; AAC37547; AAA52125; NP_001899; NP_680092; BAG53460; BAG60046; AAH10240; | 0.83 | 0.01 | 0.744 | 0.65 | 0.82 | 1.93 | 3.53E−09 | 0.975 | 1.00 | 0.88 |

TABLE 2A-continued

Autoantibody Markers.
Table 2A. Autoantibody Antigen-Complex Markers in SCLC Cohorts

| Gene | UniProt Accession | GenBank Protein Accession | CHS | | | | | FH | | | | |
|---|---|---|---|---|---|---|---|---|---|---|---|---|
| | | | coef | p value | AUC | Spec | Sens | coef | p value | AUC | Spec | Sens |
| SSRP1 | Q08945 | AAA52129; NP_001304166; NP_680091 CCQ43203; EAW73734; XP_016873669; AAH05116; NP_003137; Q08945; AAA58660; ; BAD92369; EAW73735; AAH91486; XP_016873670 | 0.82 | 0.03 | 0.699 | 0.81 | 0.65 | 1.57 | 3.16E−08 | 0.953 | 0.88 | 0.92 |
| MMP15 | P51511 | ; AAP35361; EAW82966; P51511; BAA13071; CAA88373; NP_002419; EAW82965; AAH55428; ABJ53423; BAA22225; AAH36495 | 0.94 | 0.03 | 0.702 | 1.00 | 0.44 | 1.60 | 1.62E−07 | 0.925 | 0.84 | 0.96 |
| B3GNT6 | Q6ZMB0 | BAB88882; BAD18819; BAG36432; ; AAI03909; AAI03910; BAC87028; AAI03911; EAW75013; AAH25357; NP_619651; Q6ZMB0; BAF85462 | 0.94 | 0.03 | 0.709 | 0.47 | 0.88 | 1.86 | 4.46E−06 | 0.897 | 0.84 | 0.92 |
| ACP1 | P24666 | CAA76416; NP_004291; AAB59628; BAF82623; AAI06012; AAP35800; AAB59355; AAC52067; EAX01115; EAX01116; AAH07422; AAY14958; EAX01111; BAD93075; AAB27085; NP_001035739; EAX01112; P24666; AEE61174; AAB59354; NP_009030; ; EAX01113; EAX01114; BAF84550 | 1.16 | 0.05 | 0.671 | 0.71 | 0.59 | 1.73 | 9.64E−07 | 0.891 | 0.77 | 0.77 |

We were able to identify several 2-marker combinations displaying perfect 100% sensitivity and specificity in this study (see Table 2B, below).

TABLE 2B

SCLC 2-marker combinations.
Table 2B. AUCs of 2-autoantibody combination in FH Cohort

| | | Marker 1 | | | Marker 2 | | | |
|---|---|---|---|---|---|---|---|---|
| AUC | Antigen | UniProt Accession Number | GenBank Protein Accession Number | Isotype | Antigen | Isotype | UniProt Accession Number | GenBank Protein Accession Number |
| 1 | CRMP5 | Q9BPU6 | ; AAK16830; CAT03392; CAD28503; EAX00668; Q9BPU6; EAX00667; AAY14652; NP_064519; CAR95653; AAF80348; AAP35517; AAX93268; CAB95124; AAH02874; NP_001240652; NP_001240653 | IgG | Ma_PNMA1 | IgG | Q8ND90 | CAG33393; NP_006020; AAN05100; BAF83669; CAD38995; Q8ND90; EAW81126; AAH39577 |
| 1 | CRMP5 | Q9BPU6 | ; AAK16830; CAT03392; CAD28503; EAX00668; Q9BPU6; EAX00667; AAY14652; NP_064519; CAR95653; AAF80348; AAP35517; AAX93268; CAB95124; AAH02874; NP_001240652; NP_001240653 | IgG | Ta_PNMA2 | IgG | Q9UL42 | BAG51501; AAH47515; AAF05626; EAW63575; BAA74906; NP_009188; AAH36489; AAD02098; AAH62301; XP_011542667; AAF05625; ; Q9UL42 |
| 1 | Ma_PNMA1 | Q8ND90 | CAG33393; NP_006020; ; AAN05100; BAF83669; CAD38995; Q8ND90; EAW81126; AAH39577 | IgG | Ta_PNMA2 | IgG | Q9UL42 | BAG51501; AAH47515; AAF05626; EAW63575; BAA74906; NP_009188; AAH36489; AAD02098; AAH62301; XP_011542667; AAF05625; ; Q9UL42 |
| 1 | Ma_PNMA1 | Q8ND90 | CAG33393; NP_006020; ; AAN05100; BAF83669; CAD38995; Q8ND90; EAW81126; AAH39577 | IgG | Yo_CDR1 | IgG | P51861 | ; AAA51962; NP_004056; AAI13473; P51861; AAI13475; AAA52472 |
| 1 | Ma_PNMA1 | Q8ND90 | CAG33393; NP_006020; ; AAN05100; BAF83669; CAD38995; Q8ND90; EAW81126; AAH39577 | IgG | Sox | IgG | O00570 | CAA73847; NP_005977; EAX09158; ; O00570 |
| 1 | Ma_PNMA1 | Q8ND90 | CAG33393; NP_006020; ; AAN05100; BAF83669; CAD38995; | IgG | GABA-b | IgG | Q9UBS5;; O75899 | AQY76821; EAX03206; AAC98508; EAX03212; Q9UBS5; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| | | | Q8ND90;<br>EAW81126;<br>AAH39577 | | | | | BAD92027;<br>EAX03207;<br>CAA12359;<br>CAA12360;<br>BAF82880;<br>XP_006715110;<br>XP_016866165;<br>EAX03208;<br>CAA09940;<br>BAD97339;<br>AAH50532;<br>AQY76820;<br>EAX03205;<br>BAG35233;<br>XP_011512755;<br>NP_068703;<br>AQY76819;<br>AQY76823;<br>AQY76824;<br>AQY76825;<br>CAA09031;<br>EAX03211;<br>AAH42598;<br>AQY76827;<br>BAC05730;<br>EAX03209;<br>EAX03210;<br>CAA09939;<br>CAA09980; ;<br>AQY76822;<br>AQY76826;<br>CAA21453;<br>CAA21454;<br>CAI79356;<br>AAG23962;<br>CAA09941;<br>AAH41332;<br>XP_005249039;<br>XP_011512757;<br>NP_001305982;<br>NP_001461;<br>NP_068704;;<br>EAW58889;<br>EAW58890;<br>EAW58891;<br>O75899;<br>AAD03336;<br>AAD30389;<br>CAI79357;<br>XP_005252373;<br>XP_016870821; ;<br>BAA34793;<br>AAC99345;<br>AAH35071;<br>NP_005449;<br>AAC63228;<br>AFF59483;<br>XP_016870820;<br>AAD45867;<br>CAA09942 |
| 1 | Ma_PNMA1 | Q8ND90 | CAG33393;<br>NP_006020; ;<br>AAN05100;<br>BAF83669;<br>CAD38995;<br>Q8ND90;<br>EAW81126;<br>AAH39577 | IgG | GAD65 | IgG | Q05329 | EAW86101;<br>EAW86104;<br>EAW86103;<br>CAB62572;<br>AAA62367; ;<br>Q05329;<br>AAH29517;<br>AAA58491;<br>EAW86102;<br>NP_000809;<br>AAP88040;<br>NP_001127838;<br>AAI26328;<br>AAI26330;<br>BAC86947 |

TABLE 2B-continued

SCLC 2-marker combinations.
Table 2B. AUCs of 2-autoantibody combination in FH Cohort

| | | Marker 1 | | | Marker 2 | | |
|---|---|---|---|---|---|---|---|
| 1 | Ma_PNMA1 | Q8ND90 | CAG33393; NP_006020; ; AAN05100; BAF83669; CAD38995; Q8ND90; EAW81126; AAH39577 | IgG | CRMP5 | IgM | Q9BPU6 | ; AAK16830; CAT03392; CAD28503; EAX00668; Q9BPU6; EAX00667; AAY14652; NP_064519; CAR95653; AAF80348; AAP35517; AAX93268; CAB95124; AAH02874; NP_001240652; NP_001240653 |
| 1 | Ma_PNMA1 | Q8ND90 | CAG33393; NP_006020; ; AAN05100; BAF83669; CAD38995; Q8ND90; EAW81126; AAH39577 | IgG | Ma_PNMA1 | IgM | Q8ND90 | CAG33393; NP_006020; ; AAN05100; BAF83669; CAD38995; Q8ND90; EAW81126; AAH39577 |
| 1 | Ma_PNMA1 | Q8ND90 | CAG33393; NP_006020; ; AAN05100; BAF83669; CAD38995; Q8ND90; EAW81126; AAH39577 | IgG | Ta_PNMA2 | IgM | Q9UL42 | BAG51501; AAH47515; AAF05626; EAW63575; BAA74906; NP_009188; AAH36489; AAD02098; AAH62301; XP_011542667; AAF05625; ; Q9UL42 |
| 1 | Ma_PNMA1 | Q8ND90 | CAG33393; NP_006020; ; AAN05100; BAF83669; CAD38995; Q8ND90; EAW81126; AAH39577 | IgG | Yo_CDR1 | IgM | P51861 | ; AAA51962; NP_004056; AAI13473; P51861; AAI13475; AAA52472 |
| 1 | Ma_PNMA1 | Q8ND90 | CAG33393; NP_006020; ; AAN05100; BAF83669; CAD38995; Q8ND90; EAW81126; AAH39577 | IgG | Sox | IgM | O00570 | CAA73847; NP_005977; EAX09158; ; O00570 |
| 1 | Ma_PNMA1 | Q8ND90 | CAG33393; NP_006020; ; AAN05100; BAF83669; CAD38995; Q8ND90; EAW81126; AAH39577 | IgG | GABA-b | IgM | Q9UBS5; ; O75899 | AQY76821; EAX03206; AAC98508; EAX03212; Q9UBS5; BAD92027; EAX03207; CAA12359; CAA12360; BAF82880; XP_006715110; XP_016866165; EAX03208; CAA09940; BAD97339; AAH50532; AQY76820; EAX03205; BAG35233; XP_011512755; NP_068703; AQY76819; AQY76823; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| | | | | | | | | AQY76824; AQY76825; CAA09031; EAX03211; AAH42598; AQY76827; BAC05730; EAX03209; EAX03210; CAA09939; CAA09980; ; AQY76822; AQY76826; CAA21453; CAA21454; CAI79356; AAG23962; CAA09941; AAH41332; XP_005249039; XP_011512757; NP_001305982; NP_001461; NP_068704;; EAW58889; EAW58890; EAW58891; O75899; AAD03336; AAD30389; CAI79357; XP_005252373; XP_016870821; ; BAA34793; AAC99345; AAH35071; NP_005449; AAC63228; AFF59483; XP_016870820; AAD45867; CAA09942 |
| 1 | Ma_PNMA1 | Q8ND90 | CAG33393; NP_006020; ; AAN05100; BAF83669; CAD38995; Q8ND90; EAW81126; AAH39577 | IgG | GAD65 | IgM | Q05329 | EAW86101; EAW86104; EAW86103; CAB62572; AAA62367; ; Q05329; AAH29517; AAA58491; EAW86102; NP_000809; AAP88040; NP_001127838; AAI26328; AAI26330; BAC86947 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | Yo_CDR1 | IgG | P51861 | AAA51962; NP_004056; AAI13473; P51861; AAI13475; AAA52472 |
| 1 | Ta_PNMA2 | Q9UL42 | BAG51501; AAH47515; AAF05626; EAW63575; BAA74906; NP_009188; | IgG | Sox | IgG | O00570 | CAA73847; NP_005977; EAX09158; ; O00570 |

TABLE 2B-continued

SCLC 2-marker combinations.
Table 2B. AUCs of 2-autoantibody combination in FH Cohort

| | Marker 1 | | | | | | Marker 2 | |
|---|---|---|---|---|---|---|---|---|
| 1 | Ma_PNMA1 | Q8ND90 | AAH36489; AAD02098; AAH62301; XP_011542667; AAF05625; ; Q9UL42 CAG33393; NP_006020; ; AAN05100; BAF83669; CAD38995; Q8ND90; EAW81126; AAH39577 | IgG | GABA-b | IgM | Q9UBS5;; O75899 | AQY76821; EAX03206; AAC98508; EAX03212; Q9UBS5; BAD92027; EAX03207; CAA12359; CAA12360; BAF82880; XP_006715110; XP_016866165; EAX03208; CAA09940; BAD97339; AAH50532; AQY76820; EAX03205; BAG35233; XP_011512755; NP_068703; AQY76819; AQY76823; AQY76824; AQY76825; CAA09031; EAX03211; AAH42598; AQY76827; BAC05730; EAX03209; EAX03210; CAA09939; CAA09980; ; AQY76822; AQY76826; CAA21453; CAA21454; CAI79356; AAG23962; CAA09941; AAH41332; XP_005249039; XP_011512757; NP_001305982; NP_001461; NP_068704;; EAW58889; EAW58890; EAW58891; O75899; AAD03336; AAD30389; CAI79357; XP_005252373; XP_016870821; ; BAA34793; AAC99345; AAH35071; NP_005449; AAC63228; AFF59483; XP_016870820; AAD45867; CAA09942 |
| 1 | Ma_PNMA1 | Q8ND90 | CAG33393; NP_006020; ; AAN05100; BAF83669; | IgG | GAD65 | IgM | Q05329 | EAW86101; EAW86104; EAW86103; CAB62572; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| | | | CAD38995; Q8ND90; EAW81126; AAH39577 | | | | | AAA62367; ; Q05329; AAH29517; AAA58491; EAW86102; NP_000809; AAP88040; NP_001127838; AAI26328; AAI26330; BAC86947 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | Yo_CDR1 | IgG | P51861 | AAA51962; NP_004056; AAI13473; P51861; AAI13475; AAA52472 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | Sox | IgG | O00570 | CAA73847; NP_005977; EAX09158; ; O00570 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | GABA-b | IgG | Q9UBS5;; O75899 | AQY76821; EAX03206; AAC98508; EAX03212; Q9UBS5; BAD92027; EAX03207; CAA12359; CAA12360; BAF82880; XP_006715110; XP_016866165; EAX03208; CAA09940; BAD97339; AAH50532; AQY76820; EAX03205; BAG35233; XP_011512755; NP_068703; AQY76819; AQY76823; AQY76824; AQY76825; CAA09031; EAX03211; AAH42598; AQY76827; BAC05730; EAX03209; EAX03210; CAA09939; CAA09980; ; AQY76822; AQY76826; CAA21453; CAA21454; CAI79356; AAG23962; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| | | | | | | | | CAA09941; AAH41332; XP_005249039; XP_011512757; NP_001305982; NP_001461; NP_068704 EAW58889; EAW58890; EAW58891; O75899; AAD03336; AAD30389; CAI79357; XP_005252373; XP_016870821; ; BAA34793; AAC99345; AAH35071; NP_005449; AAC63228; AFF59483; XP_016870820; AAD45867; CAA09942 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | GAD65 | IgG | Q05329 | EAW86101; EAW86104; EAW86103; CAB62572; AAA62367; ; Q05329; AAH29517; AAA58491; EAW86102; NP_000809; AAP88040; NP_001127838; AAI26328; AAI26330; BAC86947 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | CRMP5 | IgM | Q9BPU6 | ; AAK16830; CAT03392; CAD28503; EAX00668; Q9BPU6; EAX00667; AAY14652; NP_064519; CAR95653; AAF80348; AAP35517; AAX93268; CAB95124; AAH02874; NP_001240652; NP_001240653 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | Ma_PNMA1 | IgM | Q8ND90 | CAG33393; NP_006020; ; AAN05100; BAF83669; CAD38995; Q8ND90; EAW81126; AAH39577 |
| 1 | Ta_PNMA2 | Q9UL42 | BAG51501; AAH47515; AAF05626; EAW63575; BAA74906; NP_009188; AAH36489; | IgG | Ta_PNMA2 | IgM | Q9UL42 | BAG51501; AAH47515; AAF05626; EAW63575; BAA74906; NP_009188; AAH36489; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| 1 | Ta_PNMA2 | Q9UL42 | AAD02098; AAH62301; XP_011542667; AAF05625; ; Q9UL42 BAG51501; AAH47515; AAF05626; EAW63575; BAA74906; NP_009188; AAH36489; | IgG | Yo_CDR1 | IgM | P51861 | AAD02098; AAH62301; XP_011542667; AAF05625;; Q9UL42 ; AAA51962; NP_004056; AAI13473; P51861; AAI13475; AAA52472 |
| 1 | Ta_PNMA2 | Q9UL42 | AAD02098; AAH62301; XP_011542667; AAF05625; ; Q9UL42 BAG51501; AAH47515; AAF05626; EAW63575; BAA74906; NP_009188; AAH36489; AAD02098; AAH62301; XP_011542667; AAF05625; ; Q9UL42 | IgG | Sox | IgM | O00570 | CAA73847; NP_005977; EAX09158; ; O00570 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | GABA-b | IgM | Q9UBS5;; O75899 | AQY76821; EAX03206; AAC98508; EAX03212; Q9UBS5; BAD92027; EAX03207; CAA12359; CAA12360; BAF82880; XP_006715110; XP_016866165; EAX03208; CAA09940; BAD97339; AAH50532; AQY76820; EAX03205; BAG35233; XP_011512755; NP_068703; AQY76819; AQY76823; AQY76824; AQY76825; CAA09031; EAX03211; AAH42598; AQY76827; BAC05730; EAX03209; EAX03210; CAA09939; CAA09980; ; AQY76822; AQY76826; CAA21453; CAA21454; CAI79356; AAG23962; CAA09941; AAH41332; XP_005249039; XP_011512757; NP_001305982; NP_001461; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| | | | | | | | | NP_068704;; EAW58889; EAW58890; EAW58891; O75899; AAD03336; AAD30389; CAI79357; XP_005252373; XP_016870821; ; BAA34793; AAC99345; AAH35071; NP_005449; AAC63228; AFF59483; XP_016870820; AAD45867; CAA09942 |
| 1 | Ta_PNMA2 | Q9UL42 | BAG51501; AAH47515; AAF05626; EAW63575; BAA74906; NP_009188; AAH36489; AAD02098; AAH62301; XP_011542667; AAF05625; ; Q9UL42 | IgG | GAD65 | IgM | Q05329 | EAW86101; EAW86104; EAW86103; CAB62572; AAA62367; ; Q05329; AAH29517; AAA58491; EAW86102; NP_000809; AAP88040; NP_001127838; AAI26328; AAI26330; BAC86947 |

| AUC | Isotype | Antigen | UniProt Accession Number | GenBank Protein Accession Number | Isotype | Antigen | UniProt Accession Number | GenBank Protein Accession Number |
|---|---|---|---|---|---|---|---|---|
| 1 | IgG | GPLD1 | P80108 | AAH20748; CAC14844; EAW55451; P80108; XP_016866243; EAW55450; AAH07614; AAH93645; AAI12002; AAA36444; EAW55448; AAG16627; AAA36445; XP_011512811; XP_016866242; ; CAC87068; NP_001494; EAW55449 | IgG | INHA | P05111 | EAW70774; ACI28454; AAH06391; CAA01158; CAA28040; AAP35600; AAA59166; AAA59167; ; P05111; NP_002182 |
| 1 | IgG | PTPRU | Q92729 | EAX07652; BAG52941; XP_016855484; AAC51938; XP_016855482; NP_573439; AAB07074; BAD92092; AAI46656; ; Q92729; CAA65832; XP_006710332; XP_016855481; XP_016855483; CAA65016; NP_573438; EAX07650; | IgG | INHA | P05111 | EAW70774; ACI28454; AAH06391; CAA01158; CAA28040; AAP35600; AAA59166; AAA59167; ; P05111; NP_002182 |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| 1 | IgG | NUDT5 | Q9UKK9 | EAX07651; NP_005695; CCQ43332; AAB51343; NP_001181930; EAW86320; CAG33476; NP_001308576; NP_054861; EAW86322; AAF25479; EAW86321; AAF29079; BAF83820; NP_001308577; Q9UKK9; AAF06734; AAH00025 | IgG | INHA | P05111 | EAW70774; ACI28454; AAH06391; CAA01158; CAA28040; AAP35600; AAA59166; AAA59167; ; P05111; NP_002182 |
| 1 | IgG | INHA | P05111 | EAW70774; ACI28454; AAH06391; CAA01158; CAA28040; AAP35600; AAA59166; AAA59167; ; P05111; NP_002182 | IgG | INHBC | P55103 | EAW97011; BAG37366; NP_005529; ; P55103; AAI30325; AAI30327 |
| 1 | IgG | INHA | P05111 | EAW70774; ACI28454; AAH06391; CAA01158; CAA28040; AAP35600; AAA59166; AAA59167; ; P05111; NP_002182 | IgG | ANAPC2 | Q9UJX6 | BAG58931; ; AAF05751; AAH01579; Q9UJX6; AAH32503; NP_037498; AAH09487; EAW88361; BAA92644; BAG57788 |
| 1 | IgG | INHA | P05111 | EAW70774; ACI28454; AAH06391; CAA01158; CAA28040; AAP35600; AAA59166; AAA59167; ; P05111; NP_002182 | IgG | PLD3 | Q8IV08 | EAW56954; EAW56956; XP_005258761; EAW56951; AAH00553; AAH36327; AAH96820; XP_005258766; EAW56957; XP_005258764; EAW56953; EAW56955; Q8IV08; AAB16799; XP_016882037; NP_036400; ; EAW56958; XP_005258767; XP_011524995; XP_016882035; NP_001278240; EAW56950; EAW56952; CAD57504; EAW56959; XP_011524994; BAG57127; XP_005258765; XP_006723185; XP_016882036; XP_016882038; NP_001026866 |
| 1 | IgG | INHA | P05111 | EAW70774; ACI28454; AAH06391; CAA01158; CAA28040; | IgG | PTEN | P60484 | AAD13528; AMQ76358; EAW50172; AAC51182; AAD38372; |

TABLE 2B-continued

SCLC 2-marker combinations.
Table 2B. AUCs of 2-autoantibody combination in FH Cohort

| | Marker 1 | | | | | Marker 2 | | | |
|---|---|---|---|---|---|---|---|---|---|
| | | | | AAP35600;<br>AAA59166;<br>AAA59167; ;<br>P05111;<br>NP_002182 | | | | CCF23296;<br>ADM26755;<br>ADM26756;<br>AEZ67429;<br>AEZ67430;<br>AMQ76357;<br>CCV19970;<br>DAA64601;<br>NP_001291646;<br>ADM26753;<br>AEZ67432;<br>AEZ67435;<br>AEZ67436;<br>AEZ67437;<br>CAG29302;<br>AHW56562;<br>NP_001291647;<br>AAC08699;<br>AEZ67438;<br>CDI44160;<br>EAW50173;<br>ADZ48535;<br>ARB02560;<br>ADM26759;<br>AEZ67434;<br>AMQ76359;<br>CCV66764;<br>P60484;<br>AAC51183;<br>NP_000305;<br>AAY57327;<br>ADM26754;<br>AEZ67431;<br>BAA24090;<br>EAW50174;<br>EAW50175;<br>AAH05821;<br>AAB66902;<br>ADM26749; ;<br>AEZ67433;<br>BAG36351 |
| 1 | IgG | INHA | P05111 | EAW70774;<br>ACI28454;<br>AAH06391;<br>CAA01158;<br>CAA28040;<br>AAP35600;<br>AAA59166;<br>AAA59167; ;<br>P05111;<br>NP_002182 | IgG | CTSB | P07858 | AAL99369;<br>EAW65631;<br>EAW65632;<br>CAI46053;<br>NP_680093;<br>EAW65633;<br>CAA77178;<br>XP_006716308;<br>XP_016868588;<br>EAW65634;<br>BAG52127;<br>BAG59411;<br>XP_016868586;<br>P07858;<br>BAG52477;<br>XP_011542114;<br>XP_016868590;<br>EAW65630;<br>EAW65635;<br>XP_006716307;<br>XP_016868587;<br>XP_016868589; ;<br>AAL99368;<br>NP_680090;<br>EAW65636;<br>BAF82928;<br>AAH95408;<br>AAC37547;<br>AAA52125;<br>NP_001899;<br>NP_680092;<br>BAG53460;<br>BAG60046;<br>AAH10240; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| 1 | IgG | INHA | P05111 | EAW70774; ACI28454; AAH06391; CAA01158; CAA28040; AAP35600; AAA59166; AAA59167; ; P05111; NP_002182 | IgG | SSRP1 | Q08945 | AAA52129; NP_001304166; NP_680091 CCQ43203; EAW73734; XP_016873669; AAH05116; NP_003137; Q08945; AAA58660; ; BAD92369; EAW73735; AAH91486; XP_016873670 |
| 1 | IgG | INHA | P05111 | EAW70774; ACI28454; AAH06391; CAA01158; CAA28040; AAP35600; AAA59166; AAA59167; ; P05111; NP_002182 | IgG | MMP15 | P51511 | ; AAP35361; EAW82966; P51511; BAA13071; CAA88373; NP_002419; EAW82965; AAH55428; ABJ53423; BAA22225; AAH36495 |
| 1 | IgG | INHA | P05111 | EAW70774; ACI28454; AAH06391; CAA01158; CAA28040; AAP35600; AAA59166; AAA59167; ; P05111; NP_002182 | IgG | B3GNT6 | Q6ZMB0 | BAB88882; BAD18819; BAG36432; ; AAI03909; AAI03910; BAC87028; AAI03911; EAW75013; AAH25357; NP_619651; Q6ZMB0; BAF85462 |
| 1 | IgG | INHA | P05111 | EAW70774; ACI28454; AAH06391; CAA01158; CAA28040; AAP35600; AAA59166; AAA59167; ; P05111; NP_002182 | IgG | ACP1 | P24666 | CAA76416; NP_004291; AAB59628; BAF82623; AAI06012; AAP35800; AAB59355; AAC52067; EAX01115; EAX01116; AAH07422; AAY14958; EAX01111; BAD93075; AAB27085; NP_001035739; EAX01112; P24666; AEE61174; AAB59354; NP_009030; ; EAX01113; EAX01114; BAF84550 |
| 1 | IgG | INHA | P05111 | EAW70774; ACI28454; AAH06391; CAA01158; CAA28040; AAP35600; AAA59166; AAA59167; ; P05111; NP_002182 | IgM | NLRP7 | Q8WX94 | AAL69963; XP_006723138; EAW72313; BAG63894; DAA01246; ; NP_996611; BAG60806; XP_006723139; XP_011524898; XP_011524903; EAW72315; EAW72316; AAO18158; AAI09125; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| 1 | IgG | INHA | P05111 | EAW70774; ACI28454; AAH06391; CAA01158; CAA28040; AAP35600; AAA59166; AAA59167; ; P05111; NP_002182 | IgM | CDH5 | P33151 | AAI09126; XP_011524901; EAW72314; Q8WX94; NP_001120727; NP_631915 AAI17521; P33151; BAG62180; BAG62074; ; BAD93145; AAH96364; XP_011521103; BAA87418; CAA42468; AAH96363; AAH96365; EAW83009; BAG62052; AAB41796; CAA56306; NP_001786 |
| 1 | IgG | INHA | P05111 | EAW70774; ACI28454; AAH06391; CAA01158; CAA28040; AAP35600; AAA59166; AAA59167; ; P05111; NP_002182 | IgM | HSPG2 | P98160 | AAB95116; P98160; AAI09205; AAA52700; XP_016856611; NP_001278789; EAW94994; EAW94995; EAW94996; CAA44373; CAC18534; EAW94997; BAD93088; XP_011539620; XP_016856609; NP_005520; AAL79552; AAB21121; ; AAA52699; XP_016856610 |
| 1 | IgG | INHA | P05111 | EAW70774; ACI28454; AAH06391; CAA01158; CAA28040; AAP35600; AAA59166; AAA59167; ; P05111; NP_002182 | IgM | SPINK1 | P00995 | ABH06584; AAA36521; CAA68697; P00995; ; AAG00531; NP_001341895; ABH06583; EAW61817; NP_003113; AAH25790; AAA36522 |
| 1 | IgG | INHA | P05111 | EAW70774; ACI28454; AAH06391; CAA01158; CAA28040; AAP35600; AAA59166; AAA59167; ; P05111; NP_002182 | IgM | CD34 | P28906 | CAJ01226; EAW93459; AAN15135; BAF85719; BAG57638; BAG62486; AAH39146; AAB25223; BAE46748; AAA03181; NP_001764; AAA03659; CAD98000; ; P28906; AAF14634; AAM82157; AAB25222; EAW93458; BAF84218; NP_001020280 |
| 1 | IgG | INHA | P05111 | EAW70774; ACI28454; | IgM | MAPRE1 | Q15691 | AAI06069; AAC09471; |

TABLE 2B-continued

SCLC 2-marker combinations.
Table 2B. AUCs of 2-autoantibody combination in FH Cohort

| | Marker 1 | | | | Marker 2 | | | |
|---|---|---|---|---|---|---|---|---|
| | | | | AAH06391; CAA01158; CAA28040; AAP35600; AAA59166; AAA59167; ; P05111; NP_002182 | | | | EAW76349; BAG59745; AAI28443; NP_036457; ; Q15691; AAI09282; EAW76348; BAG35484; XP_011526998 |
| 1 | IgG | INHA | P05111 | EAW70774; ACI28454; AAH06391; CAA01158; CAA28040; AAP35600; AAA59166; AAA59167; ; P05111; NP_002182 | IgM | NADSYN1 | Q6IA69 | BAC65148; Q6IA69; EAW74792; BAB14034; CAG33567; BAA91722; BAG53556; AAH03638; AAH03666; NP_060631; ; EAW74793 |
| 1 | IgG | INHA | P05111 | EAW70774; ACI28454; AAH06391; CAA01158; CAA28040; AAP35600; AAA59166; AAA59167; ; P05111; NP_002182 | IgM | SPINT2 | O43291 | ; BAA25024; AAV38918; AAC02781; EAW56766; AAB84031; AAV38919; CAG28532; NP_001159575; EAW56767; AAH11951; O43291; BAG59653; CAE06264; AAH11955; BAF84221; AAH12868; NP_066925; AAH07705; AAV38920; AEE61093; AAH01668 |
| 1 | IgG | INHA | P05111 | EAW70774; ACI28454; AAH06391; CAA01158; CAA28040; AAP35600; AAA59166; AAA59167; ; P05111; NP_002182 | IgM | CA9 | Q16790 | CBL94025; CAB82444; NP_001207; ; Q16790; ABL67717; ALQ33410; ALQ33411; EAW58359; CAA47315; AAH14950 |
| 1 | IgG | INHA | P05111 | EAW70774; ACI28454; AAH06391; CAA01158; CAA28040; AAP35600; AAA59166; AAA59167; ; P05111; NP_002182 | IgM | HIF1A | Q16665 | ; AAF20139; AAG43026; BAG35314; EAW80807; EAW80808; AAF20140; BAG59438; NP_001521; AAF20149; BAG65259; ACN88547; AAC68568; BAB70608; BAI49183; BAM28632; BAG61496; EAW80806; AAP88778; AAC50152; BAG65167; AAC51210; NP_001230013; NP_851397; EAW80809; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| 1 | IgG | INHA | P05111 | EAW70774; ACI28454; AAH06391; CAA01158; CAA28040; AAP35600; AAA59166; AAA59167; ; P05111; NP_002182 | IgM | TFRC | P02786 | Q16665; AAH12527 AAH01188; CAD97930; NP_001121620; NP_001300895; NP_003225; EAW53670; EAW53672; AAF04564; EAW53671; EAW53673; AAA61153; BAF84412; BAD92491; CAA25527; ABF47088; P02786; NP_001300894; ; BAH11872 |
| 1 | IgG | INHA | P05111 | EAW70774; ACI28454; AAH06391; CAA01158; CAA28040; AAP35600; AAA59166; AAA59167; ; P05111; NP_002182 | IgM | CDH23 | Q9H251 | BAB47441; AAG48303; CAB59256; AAT72162; AAI08255; XP_011538346; EAW54429; BAB61902; AAG27034; AAT72166; AAH65284; AAI39904; XP_006718003; NP_001165403; NP_001165405; NP_443068; AAT72165; AAI36977; XP_011538348; XP_011538351; XP_011538353; NP_001165404; EAW54428; AAH11570; AAI36978; XP_006718005; XP_011538345; XP_011538354; XP_016871995; NP_001165406; NP_001165407; ; EAW54432; BAC04231; AAH32581; XP_011538350; XP_016871988; XP_016871997; NP_001165401; NP_071407; EAW54430; AAQ88980; XP_011538341; XP_011538344; XP_016871990; XP_016871992; XP_016871994; NP_001165402; CCQ43681; EAW54427; BAB84986; XP_011538349; XP_016871989; XP_016871991; XP_016871993; EAW54426; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| 1 | IgG | INHA | P05111 | EAW70774; ACI28454; AAH06391; CAA01158; CAA28040; AAP35600; AAA59166; AAA59167; ; P05111; NP_002182 | IgM | SLMO2 | Q9Y3B1 | EAW54431; Q9H251; AAT72161; XP_011538347; XP_016871996 Q9Y3B1; ; NP_057129; AAH13969; AAD34102; NP_001243332; EAW75443; BAG60414; AAH10649; EAW75442; BAA92114 |
| 1 | IgG | INHA | P05111 | EAW70774; ACI28454; AAH06391; CAA01158; CAA28040; AAP35600; AAA59166; AAA59167; ; P05111; NP_002182 | IgM | GRAP2 | O75791 | AAC69273; AAF60319; NP_001278755; EAW60357; EAW60360; AAF31758; AAD41782; BAH14008; CAG46647; AAD13027; CAA09757; BAH13929; XP_006724439; EAW60356; BAH13978; NP_001278753; NP_001278754; NP_001278757; O75791; AAD04926; AAL58573; AAH26002; CAG30384; NP_004801; ; CAG38761; EAW60358; EAW60359; EAW60361; AAF60320; BAH13944; BAH13969; BAG35685; AAH25692; CAA77021 |
| 1 | IgG | INHBC | P55103 | EAW97011; BAG37366; NP_005529; ; P55103; AAI30325; AAI30327 | IgG | B3GNT6 | Q6ZMB0 | BAB88882; BAD18819; BAG36432; ; AAI03909; AAI03910; BAC87028; AAI03911; EAW75013; AAH25357; NP_619651; Q6ZMB0; BAF85462 |
| 1 | IgG | INHBC | P55103 | EAW97011; BAG37366; NP_005529; ; P55103; AAI30325; AAI30327 | IgG | ACP1 | P24666 | CAA76416; NP_004291; AAB59628; BAF82623; AAI06012; AAP35800; AAB59355; AAC52067; EAX01115; EAX01116; AAH07422; AAY14958; EAX01111; BAD93075; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| 1 | IgG | INHBC | P55103 | EAW97011; BAG37366; NP_005529; ; P55103; AAI30325; AAI30327 | IgM | SPINT2 | O43291 | AAB27085; NP_001035739; EAX01112; P24666; AEE61174; AAB59354; NP_009030; ; EAX01113; EAX01114; BAF84550 ; BAA25024; AAV38918; AAC02781; EAW56766; AAB84031; AAV38919; CAG28532; NP_001159575; EAW56767; AAH11951; O43291; BAG59653; CAE06264; AAH11955; BAF84221; AAH12868; NP_066925; AAH07705; AAV38920; AEE61093; AAH01668 |
| 1 | IgG | CTSB | P07858 | AAL99369; EAW65631; EAW65632; CAI46053; NP_680093; EAW65633; CAA77178; XP_006716308; XP_016868588; EAW65634; BAG52127; BAG59411; XP_016868586; P07858; BAG52477; XP_011542114; XP_016868590; EAW65630; EAW65635; XP_006716307; XP_016868587; XP_016868589; ; AAL99368; NP_680090; EAW65636; BAF82928; AAH95408; AAC37547; AAA52125; NP_001899; NP_680092; BAG53460; BAG60046; AAH10240; AAA52129; NP_001304166; NP_680091 | IgG | ACP1 | P24666 | CAA76416; NP_004291; AAB59628; BAF82623; AAI06012; AAP35800; AAB59355; AAC52067; EAX01115; EAX01116; AAH07422; AAY14958; EAX01111; BAD93075; AAB27085; NP_001035739; EAX01112; P24666; AEE61174; AAB59354; NP_009030; ; EAX01113; EAX01114; BAF84550 |
| 1 | IgG | CTSB | P07858 | AAL99369; EAW65631; EAW65632; CAI46053; NP_680093; EAW65633; CAA77178; | IgM | HSPG2 | P98160 | AAB95116; P98160; AAI09205; AAA52700; XP_016856611; NP_001278789; EAW94994; |

TABLE 2B-continued

SCLC 2-marker combinations.
Table 2B. AUCs of 2-autoantibody combination in FH Cohort

| | | Marker 1 | | | | Marker 2 | | |
|---|---|---|---|---|---|---|---|---|
| | | | | XP_006716308; XP_016868588; EAW65634; BAG52127; BAG59411; XP_016868586; P07858; BAG52477; XP_011542114; XP_016868590; EAW65630; EAW65635; XP_006716307; XP_016868587; XP_016868589; ; AAL99368; NP_680090; EAW65636; BAF82928; AAH95408; AAC37547; AAA52125; NP_001899; NP_680092; BAG53460; BAG60046; AAH10240; AAA52129; NP_001304166; NP_680091 | | | | EAW94995; EAW94996; CAA44373; CAC18534; EAW94997; BAD93088; XP_011539620; XP_016856609; NP_005520; AAL79552; AAB21121; ; AAA52699; XP_016856610 |
| 1 | IgG | CTSB | P07858 | AAL99369; EAW65631; EAW65632; CAI46053; NP_680093; EAW65633; CAA77178; XP_006716308; χP_016868588; EAW65634; BAG52127; BAG59411; XP_016868586; P07858; BAG52477; XP_011542114; XP_016868590; EAW65630; EAW65635; XP_006716307; XP_016868587; XP_016868589; ; AAL99368; NP_680090; EAW65636; BAF82928; AAH95408; AAC37547; AAA52125; NP_001899; NP_680092; BAG53460; BAG60046; AAH10240; AAA52129; NP_001304166; NP_680091 | IgM | NADSYN1 | Q6IA69 | BAC65148; Q6IA69; EAW74792; BAB14034; CAG33567; BAA91722; BAG53556; AAH03638; AAH03666; NP_060631; ; EAW74793 |
| 1 | IgG | MMP15 | P51511 | ; AAP35361; EAW82966; P51511; BAA13071; CAA88373; NP_002419; EAW82965; AAH55428; | IgG | ACP1 | P24666 | CAA76416; NP_004291; AAB59628; BAF82623; AAI06012; AAP35800; AAB59355; AAC52067; |

TABLE 2B-continued

SCLC 2-marker combinations.
Table 2B. AUCs of 2-autoantibody combination in FH Cohort

| Marker 1 | Marker 2 |
|---|---|
| ABJ53423; BAA22225; AAH36495 | EAX01115; EAX01116; AAH07422; AAY14958; EAX01111; BAD93075; AAB27085; NP_001035739; EAX01112; P24666; AEE61174; AAB59354; NP_009030; ; EAX01113; EAX01114; BAF84550 |

Since we have run these arrays on over 1,000 control specimens over the past several years for various studies, we queried our database to determine how frequently these markers are identified in control specimens and found that they are not (X/Y positive).

A unique feature of SCLC, which also serves as a proof of concept, is that autoantibodies targeting CNS antigens are frequently encountered in SCLC patients which occasionally give rise to PNS. Highlighting a key advantage to the disclosed autoantibody-antigen complex detection method, we can identify several PNS autoantibody-antigen complexes in the majority of our SCLC cases, while un-complexed autoantibodies (which are used clinically to diagnose PNS) are reportedly present in less than 20% of SCLC (32) (Table 2C).

TABLE 2C

Paraneoplastic syndrome-associated antibodies in SCLC

| Antibody | Syndrome | Approximate frequency of free autoantibody in SCLC patient without PNS | Correct call averages of autoantibody-antigen complexes at 92% NPV in FH and VB cohorts |
|---|---|---|---|
| Anti-CRMP | Encephalomyelitis | 10% | 50% |
| Anti-VGCC | Lambert-Eaton | 5% | 38% |
| Anti-SOX | Lambert-Eaton | 25-35% | 50% |
| Anti-GAD65 | Lambert-Eaton | 15% | 64% |
| Anti-Rc | CAR | 10-15% | 42% |

Additionally, we had added some of the PNS markers from Table 2A to our panel prior to running Fred Hutch specimens (the CHS specimens were analyzed earlier in the year) and found four markers capable of distinguishing SCLC case from control with perfect or nearly perfect sensitivity and specificity (Table 3, the top 7 entries are for IgG and the bottom 7 for IgM). Specifically, anti-Ma and anti-Ta displayed 100% sensitivity and specificity within the Fred Hutch cohort.

TABLE 3

Fred Hutch PNS Autoantibodies (N = 26)

| | AUC | Specificity | Sensitivity |
|---|---|---|---|
| IgG CRMP5 | 0.883 | 0.947368 | 0.785714 |
| IgG PNMA1 (Ma) | 1 | 1 | 1 |
| IgG PNMA2 (Ta) | 1 | 1 | 1 |
| IgG CDR2 (Yo) | 0.928 | 0.769231 | 1 |
| IgG Sox | 0.876 | 0.846154 | 0.846154 |
| IgG GABA.b | 0.627 | 0.538462 | 0.769231 |
| IgG GAD65 | 0.963 | 0.923077 | 0.884615 |
| IgM CRMP5 | 0.692 | 0.736842 | 0.642857 |
| IgM PNMA1 (Ma) | 0.635 | 0.538462 | 0.730769 |
| IgM PNMA2 (Ta) | 0.525 | 0.96 | 0.230769 |
| IgM CDR2 (Yo) | 0.642 | 0.538462 | 0.769231 |
| IgM Sox | 0.436 | 0.846154 | 0.230769 |
| IgM GABA.b | 0.781 | 0.653846 | 0.846154 |
| IgM GAD65 | 0.541 | 0.192308 | 1 |

We have not previously encountered autoantibody markers with this degree of performance in any other dataset of any cancer type. This unexpected result is based on the disclosed technique, as we are identifying autoantibody-antigen complexes, and not free circulating antibody (FIG. 2).

We also subjected the CHS SCLC specimens to the proteomic and glycomic probing strategies. We were able to identify 51 markers that were significantly up-regulated and 32 markers that were significantly down-regulated between cases and controls (Table 4). The glycomic analyses revealed 4 anti-SleX up-regulated markers and 34 anti-SleX down-regulated markers (Table 4). Anti-SleA studies also identified significantly different markers, 13 of which were up-regulated and 17 of which were down-regulated.

TABLE 4

Proteomic and Glycomic Biomarkers for SCLC

| Marker Type and Direction in SCLC Cases Compared to Controls | Gene Name | UniProt Accession | GenBank Protein Accession |
|---|---|---|---|
| Proteomic Up | PSENEN | Q9NZ42 | NP_758844; BAG35166; AAH09575; NP_001268461; Q9NZ42; AAF67646 |
| Proteomic Up | ERCC1 | P07992 | AAL56574; AAA35810; XP_016881950; AAH52813; XP_016881949; EAW57350; BAB62810; NP_001974; NP_973730; BAG52472; AAH08930; AAV38609; AAA52394; XP_016881952; XP_016881955; AAC16253; BAG37398; XP_005258692; XP_016881954; AAA52395; AAM34796; XP_005258693; NP_001159521; EAW57348; EAW57349; P07992; XP_005258691; XP_011524912; XP_016881951; XP_016881953; AAD14434; XP_005258694; XP_016881948 |
| Proteomic Up | PDIA3 | P30101 | BAG56782; AAC51518; EAW77236; CEO43495; AAH36000; AAH71878; AAC50331; CAA89996; BAA11928; CAK18760; CCD35251; EAW77234; EAW77235; P30101; BAG52144; ; BAA03759; ACF94491; BAG52151; AAH14433; ACI46022; NP_005304 |
| Proteomic Up | TIMP1 | P01033 | CAR95107; EAW59316; CAG28566; CAG46779; CAA26902; AAA75558; P01033; BAG52016; BAG58865; ; CAA00898; AAH00866; AAD14009; CAA26443; EAW59315; BAG34878; AAA52436; AAA63234; AAX47478; NP_003245; CBX47572; XP_016885255; BAA01913; CAS92765 |
| Proteomic Up | LPXN | O60711 | EAW73809; BAG36111; CAG38768; XP_011543690; BAG62693; XP_011543693; XP_016874068; NP_001137467; AAC16014; BAH12983; AAH19035; ; EAW73808; XP_011543695; O60711; BAG62583; XP_006718813; NP_001294880; XP_011543692; NP_004802; EAW73807; BAD96885; XP_011543696 |
| Proteomic Up | CTLA4 | P16410 | ADV60199; NP_005205; AAA52127; AAF02499; ADV60197; ADV60200; AAH74893; NP_001032720; AAL40932; ABG78999; EAW70354; AAL07473; AAH69566; AAB59385; ; ADV60198; AAV66331; AAY00166; P16410; BAG36473; AAH74842; AAD00698; AAA52773; AAK13084; ABC67470; AAO17066; AAX93176; ABG79000; CAY55959; AAL96664; AAH70162; ABG85285 |
| Proteomic Up | PSCD4 | Q9UIA0 | AAH41161; EAW60155; AAF28896; BAA92107; AAH17780; NP_001304953; ; BAG37529; EAW60154; BAB15718; XP_011528450; NP_037517; EAW60156; BAG65270; CAG30437; Q9UIA0; AAF15389; XP_011528449 |
| Proteomic Up | ORM1 | P02763 | BAH14578; AAI04819; CAA29229; BAG34972; NP_000598; AAI43315; AAA35515; CAA26397; EAW87416; P02763; AAH26238; AAI04821; AAV38593; ; BAA34292; AAI43314; ACJ13638 |
| Proteomic Up | AARS | P49588 | EAW51839; ; AAH11451; P49588; BAG61157; BAA06808; EAW51838; NP_001596; EAW51840; BAD96544 |
| Proteomic Up | TXN | P10599 | BAF82197; AAA74596; CAA38410; CAG28593; AAN33187; AEE61109; AAF86466; AAH03377; EAW59060; AAG34699; BAA05742; NP_003320; AAH54866; CAA54687; NP_001231867; AAC17430; AFH41799; ; EAW59059; P10599; AAF87085 |
| Proteomic Up | RANBP1 | P43487 | EAX02988; EAX02989; BAG56987; XP_016884379; BAG53504; EAX02991; EAX02993; XP_011528592; EAX02990; AEE61231; XP_011528591; EAX02992; BAH13377; CAG30442; XP_011528593; XP_016884380; NP_001265570; EAX02986; P43487; BAA07269; NP_002873; ; EAX02987; BAD97226; CAA58592; XP_016884381; NP_001265568; EAX02994; NP_001265569 |
| Proteomic Up | IL13 | P35225 | AAH96141; AAA36107; NP_001341922; AAA83738; AAB01681; CBX47445; EAW62326; CAA48823; NP_001341920; NP_001341921; NP_002179; AAH96139; AAH96140; AAH96138; CAA48824; P35225; ; AAK53823; EAW62327; AAC03535; EAW62324; EAW62325 |
| Proteomic Up | STK11 | Q15831 | AAB97833; AAF97257; EAW69538; EAW69540; XP_005259674; AAC39527; CAH59749; XP_011526511; BAD92790; AAG17221; AAH19334; ALQ33798; XP_005259675; AAC15742; AAB05809; AAH07981; ABR45718; ADD71158; ; NP_000446; EAW69539; Q15831; BAG37374; ALQ33797 |
| Proteomic Up | PHLPPL | Q6ZVD8 | EAW59226; AAH35267; AAI29984; ; BAC85924; EAW59225; Q6ZVD8; BAA76775; BAA91943; NP_001275932; AAI29928; NP_055835 |
| Proteomic Up | PPIE | Q9UNP9 | EAX07255; BAG52903; BAG36418; AAI07737; AAC00006; XP_016855540; NP_001306222; AAZ93379; XP_006710353; NP_001181936; BAG65464; XP_006710352; XP_016855541; AAD19906; BAF85783; ; EAX07256; Q9UNP9; AAC00007; AAH04898; NP_006103; AAD19907; AAH08451; NP_982281; XP_011538803 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| Proteomic Up | ENO2 | P09104 | CBN61368; NP_001966; EAW88710; AAB59554; AAH02745; AAA52388; CAA36215; EAW88709; P09104; CAG38819; AAB51320; BAH12015; BAG35316; ACJ13661; CAA32505; ; EAW88711; CAA31512; BAG54062; BAF83214; AAP36047 |
| Proteomic Up | LAMB1 | P07942 | EAL24388; EAW83423; AAA59485; EAW83424; AAA59482; AAA59486; P07942; AAH26018; AAS07514; BAG64534; XP_016867691; CCQ43174; AAI13456; NP_002282; AAA59487; XP_016867690 |
| Proteomic Up | IL17RA | Q96F46 | EAW57741; NP_001276834; CAL44890; NP_055154; ADY18334; ; CAV28582; AAB99730; CCB07364; EAW57739; EAW57738; Q96F46; AAH11624; CAJ86450; EAW57740 |
| Proteomic Up | TYR | P14679 | AAA61242; AGV39053; AGV39060; AGV39067; AGV39068; AGV39078; AGV39080; AGV39117; AGV39126; AGV39133; AGV39134; AGV39141; AGV39143; AGV39144; AGV39150; AGV39174; AGV39178; AGV39186; AGV39190; AGV39198; AGV39199; AGV39200; XP_011541272; AGV39064; AGV39073; AGV39074; AGV39075; AGV39098; AGV39107; AGV39112; AGV39125; AGV39128; AGV39129; AGV39130; AGV39138; AGV39142; AGV39145; AGV39152; AGV39153; AGV39204; AGV39207; EAW59357; P14679; BAM75356; NP_000363; AGV39065; AGV39100; AGV39103; AGV39106; AGV39121; AGV39146; AGV39149; AGV39155; AGV39158; AGV39161; AGV39177; AGV39197; AGV39203; AGV39208; BAM75358; AAA61241; ; AGV39062; AGV39085; AGV39093; AGV39105; AGV39116; AGV39120; AGV39131; AGV39140; AGV39154; AGV39210; EAW59356; AAH27179; AAB60319; AGV39056; AGV39072; AGV39079; AGV39081; AGV39097; AGV39115; AGV39118; AGV39124; AGV39137; AGV39147; AGV39148; AGV39157; AGV39182; AGV39196; AGV39201; AGV39202; AAA61244; AAK00805; AGV39055; AGV39059; AGV39063; AGV39066; AGV39069; AGV39076; AGV39088; AGV39101; AGV39109; AGV39110; AGV39114; AGV39136; AGV39139; AGV39179; AGV39180; AGV39183; AGV39189; AHZ44440; CAA34205; BAM75357; AAG38762; AGV39057; AGV39058; AGV39061; AGV39119; AGV39127; AGV39160; AGV39169; AGV39185; AGV39191; AGV39206; AAD13984; CAA68756; AAD13985; AGV39051; AGV39052; AGV39070; AGV39071; AGV39077; AGV39094; AGV39099; AGV39108; AGV39111; AGV39113; AGV39135; AGV39151; AGV39156; AGV39159; AGV39163; AGV39181; AGV39184; AGV39187; AGV39193; AGV39195; AGV39205; AGV39209; AAB37227 |
| Proteomic Up | GRIN2D | O15399 | XP_011525174; NP_000827; AAC15910; O15399; EAW52346; BAD92529 |
| Proteomic Up | ENPEP | Q07075 | CAP09202; CAP09197; CAP09200; CAP09201; AAA16876; XP_016863366; CAP09203; CAP09206; EAX06261; CAP09205; AAA35522; CCQ43158; CAP09199; CAP09204; Q07075; BAG36206; CAP09198; AAH94770; NP_001968; CAP09207 |
| Proteomic Up | NOTCH3 | Q9UM47 | ACL52278; CAA55955; AAB91371; AAC14346; AAC15789; AAC04897; EAW84466; XP_005259981; ; Q9UM47; BAD92684; NP_000426 |
| Proteomic Up | LGALS7 | P47929 | EAW56817; CAG33198; NP_002298; AAH61588; AAA86820; AAH42911; EAW56818; NP_001035972; CAD48636; AAH73743; AAA67899; P47929 |
| Proteomic Up | GDF11 | O95390 | AAF21630; NP_005802; ; AAF21631; EAW96831; O95390; EAW96830; AAC72852; CAD38427; XP_006719257 |
| Proteomic Up | CEACAM5 | P06731 | CAA79884; AAH34671; XP_016881634; XP_016881635; CAA44076; BAN83790; EAW57059; P06731; CAH18191; AAA51967; AAA62835; EAW57060; BAN83789; AAA51963; NP_001278413; AAA51964; AAA51972; NP_004354; AAB59513; CAG27582; CAA34474; XP_005258470; NP_001295327; ; BAD96821; AAA51968; XP_011524624 |
| Proteomic Up | RBL1 | P28749 | NP_001310210; NP_002886; AAD14290; AAH32247; AAA36397; XP_011527257; EAW76088; EAW76089; P28749; XP_011527260; NP_001310211; BAF83069; NP_899662; AAA02489; XP_006723905; XP_016883481 |
| Proteomic Up | CEP164 | Q9UPV0 | AAH00602; AAH54015; XP_016872856; XP_016872861; XP_016872866; XP_011540976; XP_016872859; XP_016872860; XP_016872862; XP_016872868; ; CAB56023; XP_005271510; XP_006718851; XP_011540992; XP_016872870; EAW67319; BAG64184; XP_016872869; XP_016872873; EAW67321; BAA83004; XP_005271513; XP_005271514; XP_016872855; XP_016872863; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | XP_016872867; Q9UPV0; BAC86384; BAH13870; XP_016872864; XP_016872865; XP_016872874; XP_016872875; NP_001258862; NP_055771; EAW67318; XP_016872857; XP_016872871; XP_016872872; CCQ43474; EAW67320; BAA91677; CAB70664; XP_006718857; XP_016872853; XP_016872854; XP_016872858 |
| Proteomic Up | CSRP1 | P21291 | EAW91371; AAH04265; CAH10559; ACF94473; ; AAV38327; NP_001180499; AAA58431; CDI44529; BAG63590; AAA35720; NP_004069; AAH32493; NP_001180501; P21291; BAD92993; BAF85742; CAH10496; EAW91370; ACV87179; BAG53741; BAD18652; BAF82822; BAG65246; NP_001180500 |
| Proteomic Up | EPHB6 | O15197 | AAD03058; XP_011514181; BAA21560; ABV55388; NP_001267724; EAW51902; AAI10607; XP_011514182; XP_011514183; EAL23775; XP_011514184; XP_006715944; EAW51901; AAI10608; ; EAW51903; O15197; NP_001267723; NP_004436; AAP20939; EAW51900 |
| Proteomic Up | CTSC | P53634 | AFK75980; AFK76003; AFK76008; AAQ08887; BAG34864; AAI09387; AAI13851; AAI13898; AFK75978; AFK75979; AFK75986; AFK75989; AFK75990; AFK75992; AFK75997; AFK75998; AFK76029; EAW59364; AAL48195; AAI00893; AAI00894; AFK75981; AFK75987; AFK75995; AFK75999; AFK76007; AFK76011; AFK76023; CAA60671; AFK75988; AFK76001; AFK76006; AFK76012; AFK76016; AFK76025; AFK76026; AFK76028; EAW59363; AAI10072; NP_001107645; AFK75983; AFK76013; AFK76027; AAL48192; BAD96758; BAF84806; AAH54028; AAI00895; CAD97897; AFK75976; AFK75977; AFK75984; AFK75996; AFK76017; P53634; AAL48191; NP_001805; NP_680475; AAC51341; AFK75982; AFK75985; AFK75993; AFK76002; AFK76005; AFK76009; AFK76010; AFK76014; AFK76024; AAQ08888; AAI00892; ; AFK75991; AFK75994; AFK76000; AFK76004; AFK76015; AFK76018; AFK76019; AFK76020; AFK76021; AFK76022; BAG58920 |
| Proteomic Up | IL12RB2 | Q99665 | AAT45456; EAX06499; AAI04773; XP_011539686; Q99665; AAB36675; NP_001245145; AAI04775; XP_005270884; XP_011539685; NP_001306162; ; EAX06500; BAG61833; XP_016856691; BAH14896; AAI43250; XP_006710680; NP_001245144; BAG57715; XP_016856692; NP_001245143; XP_005270882; XP_005270885; XP_016856693; NP_001550 |
| Proteomic Up | PPP2R4 | Q15257 | CAB77602; EAW87883; BAG64070; NP_821067; EAW87878; BAD96508; XP_011517138; XP_016870377; CAB77601; XP_011517137; NP_001180326; NP_821070; AAF24143; EAW87877; EAW87884; EAW87885; CAA60163; EAW87881; XP_011517139; BAG56817; XP_011517140; NP_001258761; ; EAW87876; BAG59687; BAG63436; CAH18670; NP_066954; CAB77603; EAW87879; EAW87880; EAW87882; Q15257; AAH02545; AAH11605; AAV38922; CAA51873; XP_011517136; NP_821068 |
| Proteomic Up | IL10 | P22301 | AAI04253; AAI04254; CAG46825; AAL06594; CAA51942; AAA63207; AAA80104; AAC03534; ACE95684; ; AAK19173; ACV30066; CAG46790; ABB01008; EAW93524; AAK38162; NP_000563; P22301; CAA55201; CAA82914; ACE95685 |
| Proteomic Up | CCR2 | P41597 | AGC02842; P41597; AAB57791; AGC02846; EAW64761; AAA19120; ; ABW17217; AGC02843; AGC02847; EAW64760; AAI36397; XP_011532371; AGC02849; AGC02850; NP_001116513; AAC51636; AGC02848; CAD88094; EAW64762; AAH95540; BAA06253; AAB57792; AAC51637; AAN16400; AGC02851; BAF85374; BAF85609; CAA64835; ABW17216; AGC02844; AGC02845; AAH74751; AAI26453; AAA19119; NP_001116868 |
| Proteomic Up | HLADR | P01903 | ARB08430; ARB08434; ARB08447; CAA23783; CAP40293; BAG35943; CAG33294; AAA59787; CAA23782; CAA23787; AAV74560; AHW47952; ARB08429; ARB08431; ARB08432; ARB08442; ARB08444; EAX03629; BAH13427; AAA36283; NP_061984; ARB08428; ARB08433; ARB08437; ARB08441; ARB08443; ARB08445; ARB08446; AAH32350; AAA36302; AAV74559; AHW47969; ARB08439; CAA25076; EAX03631; BAG62899; AAA59783; ARB08435; ARB08438; P01903; BAG59560; AAA36272; AAA36275; AAA59785; AAA36301; AHW47918; ARB08440; CAB06609; CAP40292; EAX03630; BAG62726; AAO23887; AHW47935; ARB08436; AAH71659; ; BAG65256 |
| Proteomic Up | CCSP2 | Q5GFL6 | ; XP_016871668; Q5GFL6; XP_011538056; XP_016871667; BAC87116; AAT77225; AAI28589; XP_011538059; NP_001258975; CAD60276; NP_001307733; AAT77226; BAC85505; XP_016871669; EAW49475; CAE83814; XP_016871666; XP_016871670 |
| Proteomic Up | ILK | Q13418 | EAW68688; AAH01554; XP_005252962; ; BAH12404; NP_001014794; NP_001265371; Q13418; BAD92653; BAH11516; NP_001265370; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | NP_004508; AAF74449; XP_011518367; XP_016873161; CAB99253; CAG28601; EAW68690; AAC16892; EAW68689; CAH18077; ACJ13679; XP_005252961; NP_001014795 |
| Proteomic Up | SERPIND1 | P05546 | EAX02941; P05546; ; AAA36185; CAG30459; AAA52642; AAA52641; NP_000176; EAX02942; CAA27218; BAG36878; AAH35028 |
| Proteomic Up | CASP3 | P42574 | NP_001341708; CAC88866; NP_001341706; CBX53864; EAX04676; CAI46084; AAA65015; AAA74929; NP_001341711; NP_001341712; ; EAX04674; AAH16926; AAB60355; NP_001341709; NP_001341710; NP_004337; NP_116786; AAO25654; CAG17895; CAV28500; CBX53863; EAX04673; P42574; BAF84026; NP_001341707; EAX04675; XP_011530603; NP_001341713 |
| Proteomic Up | CCSP1 | Q8WUJ3 | Q8WUJ3; AAG41059; BAD02451; EAW99111; AAU06219; CDI30208; AAH20256; ; AAU06220; AAU06221; BAA86513; NP_001280233; CAB94391; NP_001280227; NP_061159 |
| Proteomic Up | USH1c | Q9Y6N9 | EAW68433; AAC18048; BAB15040; DAA00086; ALQ33957; BAA81740; XP_011518134; XP_011518136; XP_016872563; BAA81739; BAF83477; ALQ33956; NP_005700; Q9Y6N9; AAH16057; XP_016872562; NP_001284693; EAW68431; EAW68432; EAW68434; BAG62565; XP_016872561; XP_016872564; NP_710142; ; AAC18049 |
| Proteomic Up | PLA12 | G0Y0V0 | AAB50262; AAC82596; NP_057856 |
| Proteomic Up | NID1 | P14543 | CCQ43182; P14543; BAD92685; EAW70039; AAA57261; EAW70041; AAA59932; XP_011542497; AAH45606; CAA57709; NP_002499; EAW70040; BAG59717 |
| Proteomic Up | RIPK2 | O43353 | BAH13484; AAS94254; AAC24561; AAQ89173; AAH04553; XP_005251149; AAC27722; ALQ33896; ALQ33895; NP_003812; AAC34970; BAG52085; EAW91655; EAW91656; O43353; AAC25668; AAQ89172; AAS75586; XP_011515659 |
| Proteomic Up | KDM5B | Q9UGL1 | EAW91432; BAG51084; BAG53706; EAW91435; CAB61368; CAB61375; CAB61395; XP_011507393; XP_011507394; Q9UGL1; BAA34803; BAG51090; XP_011507392; EAW91433; CAB63108; EAW91434; CAB43532; XP_011507390; NP_001300971; NP_001334520; AAD16061; BAG50904; AAQ82849; CAB70847; NP_006609 |
| Proteomic Up | DPP7 | Q9UHL4 | BAG60548; BAD93024; XP_011516902; EAW88349; Q9UHL4; BAG57135; AAF12747; AAH16961; XP_016870141; AAH11907; XP_005266132; XP_011516901; XP_016870140; BAF84801; XP_006717146; NP_037511 |
| Proteomic Up | TMPRSS11E | Q9UL52 | NP_054777; ; AAF04328; AAQ89376; BAG36587; XP_011530198; AAY40995; Q9UL52; BAF85476; AAI13413; EAX05573; AAY41025; AAI13415 |
| Proteomic Up | MAP3K8 | P41279 | P41279; FAA00321; XP_016871196; XP_016871201; EAW86004; EAW86005; EAW86006; EAW86007; AAI04834; NP_001231063; NP_005195; BAD92776; AAI13567; XP_016871197; CAG47079; BAA03387; XP_016871203; NP_001307890; AAP45053; BAF83009; CAA78512; XP_016871200; XP_016871198; BAG36102; XP_016871199; XP_016871202 |
| Proteomic Up | ETV6 | P41212 | CAA84815; XP_011518910; AAB39882; XP_011518909; XP_016874479; AAB17135; P41212; ALQ33508; AAB17016; AAC50690; CAJ57643; AAA19786; AAB17134; ALQ33507; XP_011518911; XP_011518913; XP_011518914; XP_016874480; AAB39862; EAW96240; BAF82130; AAH43399; NP_001978 |
| Proteomic Up | CDH5 | P33151 | AAI17521; P33151; BAG62180; BAG62074; BAD93145; AAH96364; XP_011521103; BAA87418; CAA42468; AAH96363; AAH96365; EAW83009; BAG62052; AAB41796; CAA56306; NP_001786 |
| Proteomic Up | CSNK1G2 | P78368 | AAC26983; BAG70092; XP_005259556; XP_005259557; XP_016881787; EAW69426; EAW69431; AAG01997; AAH18693; XP_016881786; EAW69427; XP_005259555; XP_005259558; EAW69429; EAW69430; BAG70224; AAC00212; AAH18699; AAH20972; EAW69428; P78368; AAP88924; AAB88627; NP_001310 |
| Proteomic Up | MALT1 | Q9UDY8 | BAA83099; Q9UDY8; AAG38589; XP_011524096; BAF84075; CAB70725; NP_006776; EAW63079; AAD38507; AAH30143; NP_776216; EAW63078 |
| Proteomic Up | TAL1 | P17542 | AAA36599; CAA41478; AAB19683; NP_001277332; CAA41477; CDL93504; NP_001277334; XP_016857676; XP_016857677; NP_001274276; CAA41476; EAX06875; P17542; CAA36246; XP_016857681; CAB72254; EAX06876; EAX06877; XP_005271217; XP_016857680; NP_001277335; AAA36600; ; NP_003180; CAB72103; XP_016857678; XP_016857679; XP_016857682; NP_001277333 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| Proteomic Up | PPARA | Q07869 | CAD55571; CAQ09267; EAW73402; BAH02281; CAQ09265; EAW73404; CAG33716; ABY73535; XP_005261713; XP_006724333; NP_001001928; ABI52419; ABI52420; ABI52421; BAF82510; AAO89524; AAA36468; CAA68898; XP_011528545; XP_011528547; ABI52422; CAQ09266; Q07869; AAO89523; CAG30433; XP_011528546; EAW73403; AAO89526; ACD12656; CAA76112; ABI52417; CAI22450; CBX54356; AAO89522; XP_006724332; XP_011528542; XP_016884329; NP_005027; ; AAO13489; ABI52418; AAO89521; AAO89525; ADZ17373; AAB32649; XP_011528541; XP_011528543; XP_016884328; BAG34887; XP_005261712; XP_011528544 |
| Proteomic Up | LRG1 | P02750 | BAG64800; NP_443204; EAW69211; P02750; BAG37106; AAH34389; AAH70198; BAD38644; AAK95527; BAG51312 |
| Proteomic Down | AXIN1 | O15169 | ALQ33873; XP_016879232; XP_016879234; XP_016879235; XP_016879237; AAK61224; O15169; ALQ33872; XP_011520984; XP_011520988; NP_003493; NP_851393; EAW85835; AAH17447; EAW85836; BAD92113; XP_011520985; CAI95589; CAI95590; CAQ09649; XP_011520986; AAH44648; XP_016879233; XP_016879236; AAC51624; ALQ33871 |
| Proteomic Down | CAT | P04040 | ; AAA16651; AAI12218; AAS37679; AAK29181; EAW68170; P04040; AAB59522; CAA27721; EAW68171; BAF84274; BAG37746; AAH27300; AOP17813; BAG63070; NP_001743; AAI12220; AAI10399; CAA27717 |
| Proteomic Down | LRP6 | O75581 | EAW96253; XP_006719141; CCF76957; ; BAG51971; NP_002327; CDM49020; AAI26406; XP_016874793; AAC33006; AAD21410; BAG52027; AAI17137; O75581; XP_011518973; BAD92920; AAI43726 |
| Proteomic Down | IL4 | P05112 | ADD60204; ADN03411; AAH67515; NP_000580; NP_001341919; ADN03418; CAA29925; ADN03412; ADN03415; CAJ75955; CBL86566; EAW62322; AAC03537; CAP72493; AAA59149; AAA59150; ADN03410; ADN03416; ADN03422; AAH70123; CAA57444; ADN03408; ADN03414; CBX32734; AGM38212; ; AAK71324; ADN03419; CAV32874; BAD89396; AAH66277; ADN03413; ADN03417; ADN03420; ADN03423; NP_758858; ADN03409; ADN03421; EAW62323; P05112; AAH67514; ABM53124 |
| Proteomic Down | S100A8 | P05109 | P05109; AAH05928; CAA68390; ; NP_001306126; NP_001306130; AAA36327; BAF84017; CAA29580; NP_002955; NP_001306127; CAA01001; EAW53330; EAW53331; AAP36042; NP_001306125; CAG28602 |
| Proteomic Down | Cx44 | P17302 | P17302; BAD97009; CAG46461; BAG57837; BAG59841; AAD37802; EAW48178; BAG35246; AAH26329; BAG60109; BAG60112; NP_000156; BAG58393; CAA37122; ; AAA52131 |
| Proteomic Down | IL24 | Q13007 | AAL34146; Q13007; ; AAP35820; AAO67513; AAA91780; XP_016855610; AAG41401; CAJ18816; EAW93518; NP_001172086; NP_006841; AAK52589; AAV52801; CAJ98561; AAV52800; XP_011507403; EAW93519; NP_001172085; NP_001172087; CAY39296; CAY86021; AAH09681 |
| Proteomic Down | HSPB1 | P04792 | AAA62175; EAW71803; AAH00510; AAH12768; ACI46015; AAB20722; AAH14920; CAA34498; AAH12292; AAV38691; ABC88475; NP_001531; CDM22284; BAG59449; BAG34835; CAG38728; P04792; BAB17232; AAH73768; CAG28542; AAB51056; CAA38016 |
| Proteomic Down | ZYX | Q15942 | EAW51849; AAH08743; EAL23788; CAA65050; AAS07459; NP_001010972; EAW51850; BAG61089; CAA64447; NP_003452; BAH14598; AAH10031; ; CBX47470; BAG61030; AAH02323; AAH09360; AAH17183; EAW51848; EAW51851; BAG63647; CAG33712; AAA78902; CBX47471; Q15942; XP_011514871; XP_016868076 |
| Proteomic Down | BCL3 | P20749 | BAH12275; AAH64993; EAW57291; NP_005169; P20749; AAA51816; AAC51348; XP_011525502; XP_011525500; XP_016882598; AAA51815; ; XP_011525499; XP_016882599 |
| Proteomic Down | IFNAR1 | P17181 | EAX09838; BAD96532; AFN73228; EAX09839; AFN73226; AFN73227; ; CAA42992; P17181; AAH21825; AFN73229; NP_000620; EAX09837; BAD96490; AAT49100; BAG60345; AAA52730; XP_005261021; BAG35516; AAH02590; XP_011527854 |
| Proteomic Down | SMAD5 | Q99717 | AAD20799; AAD20801; AAB95090; XP_016864959; BAG36195; ; AAD20803; AAB92396; AAB66353; AAD20800; AAD20802; Q99717; AAH09682; NP_001001419; NP_001001420; CAG33705; CAH18219; CAH18303; EAW62194; EAW62196; AAC50791; EAW62195; AAB72180; NP_005894 |
| Proteomic Down | LGALS3BP | Q08380 | AAH02403; ALQ33622; EAW89546; BAG58382; EAW89544; Q08380; CAA55699; AAA36193; EAW89543; EAW89545; BAG62653; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| Proteomic Down | SEPT9* | Q9UHD8 | NP_005558; BAG51600; BAG56725; BAG62970; AAH02998; AAH15761; ALQ33623 EAW89463; CAC42221; AAH21192; AAP35879; NP_001280627; EAW89461; EAW89464; AAD39749; BAH13140; XP_011522509; NP_001106966; NP_001280625; EAW89468; AAG27922; CAC42225; AAI28417; ALQ33996; NP_001106965; EAW89462; EAW89466; EAW89467; Q9UHD8; BAB14057; BAF83057; BAH14844; ALQ33997; XP_005257019; XP_006721707; NP_001106963; NP_001106968; NP_006631; BAG62029; BAG64494; BAG65036; AAI14551; XP_016879520; NP_001106964; NP_001280624; EAW89465; AAF23374; CAC42224; BAG51732; CAB45728; NP_001280626; ; AAH54004; XP_006721706; XP_011522506; NP_001106967; BAA76835; AAG27919; AAF23373; CAC42222; CAC42223; BAG62031; XP_011522508; XP_011522510; XP_016879521 |
| Proteomic Down | MARCO | Q9UEW3 | BAG59558; AQN67651; AAC08800; XP_016860660; AAX88875; AAD41064; CAD36112; EAW95207; BAG62941; BAG35958; XP_011510384; NP_006761; Q9UEW3; AAH16004; XP_011510385 |
| Proteomic Down | PF4 | P02776 | AAI12094; AAY41003; AAA60066; EAX05694; AAH93965; CAG28605; AAK29643; NP_002610; P02776; XP_005265753 |
| Proteomic Down | THBS4 | P35443 | BAH13818; XP_016865287; AAS66982; XP_016865288; XP_016865289; NP_001293142; P35443; CAA79635; NP_003239; BAG36356; NP_001293143; EAW95841; AAH50456; NP_001293141 |
| Proteomic Down | NOS3 | P29474 | ABB79840; XP_016867721; AAA36365; EAL24494; BAH13275; AAH69465; ABB79839; NP_001153583; ; AAA36374; AAL07497; EAW54069; AAK83389; BAG37648; AAH63294; AAA36372; XP_016867723; P29474; AFX88321; AAD14336; XP_006716065; NP_001153582; ABY87544; NP_000594; AAM74944; BAF85617; BAH13779; XP_016867722; NP_001153581; CDI44688; AFX88322; CAA53950; BAD97356; ABB79838; AFX88320; AAA36364 |
| Proteomic Down | CHRDL1 | Q9BU40 | EAX02655; NP_001137454; NP_660277; ; EAX02657; AAU25841; XP_005262278; XP_016885448; Q9BU40; BAG52508; NP_001137453; XP_005262279; XP_005262280; EAX02656; BAG59955; BAD92785; BAF85795; AAH02909; XP_005262281; NP_001137455 |
| Proteomic Down | GRB2 | P62993 | AAC72075; ABY87532; P62993; AAG44485; BAG52262; AAM21073; BAG37940; CAG46740; AAA58448; ; EAW89271; AAH00631; NP_002077; NP_987102; AGC09591; AAG27442; BAB14923; EAW89272; AAC37549; EAW89270; AAQ13606; CAG29359; CAA44664 |
| Proteomic Down | CXCL11 | O14625 | AAD10206; CAB69205; O14625; NP_005400; ; CAB51859; AAH12532; NP_001289052; EAX05774; AAC39775; AAC51845; CAA75510; AAK52900; AAH05292; AAB17374; AAD38327; AAI10987; AAP35433; AAD38867 |
| Proteomic Down | SPARC | P09486 | P09486; AAA60570; NP_003109; EAW61667; NP_001296373; EAW61672; BAG61416; BAG37963; AAH08011; CAG33080; CAA68724; ; AAH72457; AAA60993; EAW61668; EAW61670; AAH04974; EAW61669; EAW61671; BAA05747; NP_001296372; AAS50152 |
| Proteomic Down | PHB | P35232 | AAH13401; AAB21614; NP_001268425; NP_002625; ; EAW94681; CAL48156; BAF83455; BAG35532; AAP36079; P35232; ACS44653; EAW94680; AAO18340; BAG63609; AAS88903; AAH95460; CAG46507; XP_016880251; XP_016880252; NP_001268426; ACI46033; NP_001268644; AAA86691; BAD96901 |
| Proteomic Down | ATP6V1G1 | O75348 | NP_004879; AAH08452; EAW87424; CAG33252; EAW87425; CAG47033; O75348; AAC39868 |
| Proteomic Down | CSF2 | P04141 | AAC08707; AAA52578; NP_000749; CBH19850; AAI14000; AAA52122; AAA98768; CAA26822; EAW62353; P04141; AAU21240; AAI13925; CAL40350; AJC19278; AAM44054; AAA52121; CBX47495; AAK51563; AAI08725 |
| Proteomic Down | CTTN | Q14247 | XP_016872801; EAW74766; Q14247; XP_006718510; XP_006718511; EAW74770; AAH33889; NP_001171669; NP_005222; NP_612632; BAF83786; BAG65370; EAW74767; EAW74769; AAH08799; CEF49523; AAA58455; BAD06416; EAW74768; BAG52416; BAD96333 |
| Proteomic Down | A2M | P01023 | XP_006719119; NP_000005; CAA48670; BAD92851; ; AAK38109; CCO13665; CAH18188; NP_001334354; EAW88590; AAH40071; CAA77774; AAT02228; AAA51552; NP_001334352; AAK38110; NP_001334353; P01023; AAH26246; AAA51551 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| Proteomic Down | GABARAP | O95166 | AAD32455; BAG35138; CAH10737; AAD47641; CAG47031; EAW90238; BAB21549; ; AAG09694; AAI06749; AEZ06293; NP_009209; O95166; CAG33324; EAW90234; AAD02337; AAI06750 |
| Proteomic Down | ALDOB | P05062 | NP_000026; BAA00125; EAW58951; EAW58952; CAA25072; P05062; AAH29399; CAA25572; BAF83484; AAA51691; ; CAA26526 |
| Proteomic Down | NCOR1 | O75376 | EAX04496; XP_005256925; XP_005256930; XP_011522388; XP_016880886; XP_016880902; XP_016880906; XP_016880909; NP_001177369; EAX04494; O75376; AAO32942; XP_005256923; XP_005256932; XP_016880887; XP_016880888; BAA83818; BAG58687; AAH58511; XP_005256929; XP_006721665; XP_006721667; XP_011522387; XP_016880895; XP_016880897; EAX04493; EAX04495; AAO32941; CAB70854; AAH50594; XP_011522386; XP_016880908; NP_001177367; NP_006302; BAA83819; AAP97166; XP_005256928; XP_011522385; XP_016880890; XP_016880900; XP_016880901; XP_016880903;; AAH56862; AAH68996; AAI67431; XP_016880889; XP_016880892; XP_016880905; XP_016880907; EAX04492; AAC33550; AAO32940; XP_005256931; XP_006721664; XP_006721666; XP_016880885; XP_016880891; XP_016880893; XP_016880894; XP_016880904; BAA82999; BAG63960; AAH26028; AAI07773; AAI42649; XP_016880896; XP_016880898; XP_016880899 |
| Proteomic Down | CCNB1 | P14635 | BAF82120; CAO99273; AAD14154; AAK27418; AAK27425; AAH06510; AAP88038; CBX86318; AAK27417; NP_001341773; AAD14818; EAW51306; AAK27420; AAK27424; AAV38930; P14635; AAK27419; AAK27421; AAK27422; AAK27423; NP_001341774; NP_114172 |
| Proteomic Down | AXIN1 | O15169 | ALQ33873; XP_016879232; XP_016879234; XP_016879235; XP_016879237; AAK61224; O15169; ALQ33872; XP_011520984; XP_011520988; NP_003493; NP_851393; EAW85835; AAH17447; ; EAW85836; BAD92113; XP_011520985; CAI95589; CAI95590; CAQ09649; XP_011520986; AAH44648; XP_016879233; XP_016879236; AAC51624; ALQ33871 |
| Proteomic Down | PEPD | P12955 | AAH28295; AAA60064; CAG46470; P12955; BAG56678; BAF83445; BAF83470; AEE61049; BAF84250; NP_001159528; AAH15027; AAP35338; NP_001159529; NP_000276; BAG57802; AAH04305 |
| Proteomic Down | CALR | P27797 | AMR60715; AMR60716; AMR60721; EAW84330; BAG65301; ACI46003; AAA36582; AMR60718; AMR60722; EAW84331; P27797; BAD96780; AAP36116; AAA51916; AMR60712; CCD35250; CEO43494; NP_004334; AMR60709; ; AMR60711; AMR60720; CAK18761; CRH09108; AAL13126; AAB51176; AMR60706; AMR60707; BAG58223; AAH07911; AAH20493; AMR60705; AMR60708; AMR60710; EAW84332; BAG70222; AMR60713; AMR60714; AMR60717; AMR60719; AAH02500; CAG33351 |
| Proteomic Down | MAPK14 | Q16539 | EAX03867; EAX03870; XP_016865791; NP_001306; CIW96073; BAB85654; XP_011512612; XP_016865789; AGC09599; EAX03869; EAX03873; AAH00092; AAA57456; ABY87549; CAA80919; EAX03871; EAX03872; Q16539; BAF84398; AAP35579; XP_016865793; NP_620583; AAC50329; AAF36770; AAH31574; CAG38743; ACI00233; AAA57455; XP_016865788; NP_620581; NP_620582; ; XP_016865792; EAX03868; BAG64467; ACI00234; XP_006715061; XP_016865790 |
| Proteomic Down | PTPRC | P08575 | AAM12758; AAS46930; AAS46962; EAW91301; AAS75254; AAI27658; ; AAS46922; CBU83087; AAH17863; XP_006711537; AAS46946; BAG61807; CAA68269; CAA68669; XP_006711536; EAW91300; XP_006711535; NP_563578; BAF84820; AAH14239; AAI21087; AAD15274; AAS46938; EAW91302; AAD15275; AAG26082; AAS46954; CBU30438; EAW91303; P08575; AAI21088; NP_001254727; AAA59497; BAG64565; AAI27657; AAI48258; NP_002829 |
| Proteomic Down | PTBP1 | P26599 | EAW61155; XP_005259654; NP_114368; EAW61156; EAW61157; EAW61158; BAD92147; AAH13694; CAA46444; CAA47386; EAW61154; AAH02397; CAA43056;; AAC99798; EAW61152; AAP35465; AAH04383; CAA46443; NP_002810; NP_114367; CAA43973; EAW61153; P26599; XP_005259655 |
| Proteomic Down | PPP2CA | P67775 | EAW62268; BAG70054; AAH19275; AAH31696; BAG51913; CAA31176; AAA36466; EAW62269; BAG70179; ; BAG53493; AAH02657; CAG33698; AAB38019; NP_002706; P67775; AAH00400; NP_001341948 |
| Proteomic Down | LTBP1 | Q14766 | AAY14953; EAX00435; XP_011531163; NP_996826; ; AAY15036; EAX00437; BAG61269; BAH14362; XP_005264374; XP_011531164; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | NP_001159738; AAA96327; AAF08252; AAF08253; AAY24260; XP_005264375; EAX00439; BAG64043; AAI44129; XP_016859598; NP_001159736; Q14766; BAD92038; AAM03124; XP_011531160; XP_011531161; XP_016859597; EAX00438; BAG61750; XP_011531155; XP_011531159; XP_011531162; EAX00436; AAI30290; AAA61160; XP_011531157; XP_011531158; XP_016859599; NP_000618; BAG60329; NP_001159737 |
| Proteomic Down | APOBEC3F | Q8IUX4 | AAZ38720; EAW60289; AEA39617; XP_016884131; BAG57929; AAH38808; NP_001006667; XP_016884132; ; EAW60288; Q8IUX4; AGI04218; CAG30281; NP_660341; XP_011528296 |
| Proteomic Down | ERG | P11308 | AAB65763; NP_891548; CDL93500; CDL93501; CDM55455; CDM55456; AAA35811; AJT59682; XP_016883776; NP_001129626; NP_001278320; NP_004440; AAA52398; ASY97863; CDI44159; EAX09679; P11308; AAB65762; AAP41719; XP_011527788; NP_001230361; ; ASY97862; CDM55454; BAG62127; BAG64546; AAH40168; AAB29724; XP_016883777; NP_001230357; CCV19969; EAX09680; BAG60145; XP_011527789; NP_001129627; NP_001230358; AAB37717; CAD79711; CDM55453; BAG62837; BAG65437; AAP41720; XP_016883778; NP_001317954 |
| SLEA Down | PPP2CA | P67775 | EAW62268; BAG70054; AAH19275; AAH31696; BAG51913; CAA31176; AAA36466; EAW62269; BAG70179; ; BAG53493; AAH02657; CAG33698; AAB38019; NP_002706; P67775; AAH00400; NP_001341948 |
| SLEA Down | FETUB | Q9UGM5 | BAA78341; AAR22508; NP_055190; CAB62538; EAW78185; EAW78186; AAQ10515; XP_011510983; XP_011510984; NP_1295006; AAH74734; XP_011510985; ; BAH14069; CAC24999; BAG37713; AAH69670; AAH69820; Q9UGM5; AAR22507; AAI14617; XP_005247408; NP_001295008 |
| SLEA Down | CD44 | P16070 | BAH30705; EAW68149; BAG65282; AAM50041; AAH04372; AAH67348; AAB13627; AAB13628; EAW68148; EAW68151; CAD89965; AAA36138; CAA47271; XP_005253290; XP_011518789; XP_011518790; AAB13622; AAB13625; BAH57879; EAW68153; CAB61878; AAA35674; XP_005253288; XP_011518784; XP_011518786; NP_001001391; CBX54346; EAW68152; AAB27918; XP_005253297; XP_006718451; XP_011518787; XP_011518791; NP_000601; NP_001001389; NP_001189486; AAB30429; AAD14279; ABW75083; EAW68146; EAW68154; EAW68155; P16070; AAC70782; BAG60121; AAA51950; XP_005253289; XP_011518788; NP_001001392; NP_001189484; AAB13623; ARX77882; BAH57528; CDM22272; EAW68144; EAW68145; EAW68147; ACI46596; AAD14389; AAA82949; AAD00766; XP_005253292; XP_005253295; XP_005253296; XP_011518785; NP_001001390; AAB13624; AAB13626; BAH57527; BAF83113; AAH52287; BAA05813; ABQ59315; CAA44602; XP_005253291; XP_006718453; XP_016874072; XP_016874074; NP_001189485; BAH57857; EAW68150; AAM50040; AAB27917; AAB27919; CAA38951; CAA39404; CAA40133; XP_016874073 |
| SLEA Down | LASP1 | Q14847 | BAG58436; CAA57833; ; EAW60543; BAG57861; EAW60545; BAF82536; BAG58846; AAH12460; NP_006139; EAW60544; AAH07560; Q14847; NP_001258537 |
| SLEA Down | C5orf4 | Q96IV6 | EAW61630; AAH04506; XP_006714816; XP_016864454; XP_016864455; CCQ42941; BAG58453; BAG62567; EAW61629; Q96IV6; XP_005268415; NP_115761; AAF22611; EAW61631; AAH07216 |
| SLEA Down | CLDN12 | P56749 | BAG35384; AAH36754; AAH68532; CAG38501; AAP22363; EAW76876; CAB60617; CAD35081; CAB66704; NP_001172002; NP_036261; EAW76877; EAL24163; NP_001172001; ; P56749 |
| SLEA Down | ADAM7 | Q9H2U9 | AAG43987; AAH43207; BAF85181; NP_003808; ; Q9H2U9; AAH58037; EAW63606; AAC36742; XP_016869432 |
| SLEA Down | BCL2 | P10415 | API71152; API71157; API71160; API71168; API71170; CAR95112; AAA35591; NP_000624; API71147; API71153; EAW63138; AAH27258; AAA51814; ; API71164; AAD14111; API71156; API71159; API71162; API71163; API71165; CDM22285; EAW63136; ABX60202; XP_016881406; API71149; API71151; API71161; API71169; CCA94580; CDM22286; NP_000648; AAO26045; API71150; API71155; CAR95111; AAL02169; API71166; API71167; EAW63139; AAA51813; API71154; API71158; API71171; EAW63137; P10415; CAA29778; XP_011524437 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| SLEA Down | VNN1 | O95497 | BAF83114; AAH96268; EAW48020; AAH96266; AAF21453; NP_004657; O95497; AAH96267; AAY88742; CAA10568; BAG36929; AAH96265 |
| SLEA Down | CLDN6 | P56747 | EAW85432; EAW85431; AAH08934; BAG52111; AAK02013; AAQ88844; CAI72055; P56747; AAP36063; CAB56533; NP_067018 |
| SLEA Down | RNF39 | Q9H2S5 | AQY77079; AAG40629; AAG40630; NP_739575; EAX03255; AQY77080; AQY77082; XP_016866815; AQY77083; AQY77085; AQY77086; BAB63333; AAG40628; BAC54920; EAX03256; Q9H2S5; NP_079512; AQY77081; AQY77084; BAE78602; XP_016866814; AQY77078 |
| SLEA Down | RGS14 | O43566 | AAM12650; AAH14094; XP_005265852; NP_006471; EAW85011; AAB92613; BAG53582; XP_005265851; EAW85013; AAY26402; EAW85012; O43566; BAC85600; AAB92614 |
| SLEA Down | POLG2 | Q9UHN1 | ADP91697; ADP91707; ADP91709; ADP91713; ADP91721; ADP91722; EAW94204; Q9UHN1; NP_009146; ADP91695; ADP91700; ADP91702; ADP91708; ADP91711; ADP91712; ADP91716; ADP91719; ADP91720; ADP91723; ADP91727; ADP91729; AAD56640; ADP91694; ADP91698; ADP91730; ADP91731; AAD50382; AAD56542; ADP91705; ADP91710; ADP91718; XP_006721714; ADP91703; ADP91717; ADP91728; AAC51321; ADP91732; AAH00913; ADP91701; ADP91704; ADP91706; ADP91715; ; ADP91696; ADP91699; ADP91714; ADP91724; ADP91725; ADP91726; ADP91733; AAH09194; XP_016879561 |
| SLEA Down | PTGFRN | Q9P2B2 | EAW56663; BAA92674; AAH98142; AAI39719; NP_065173; BAB20271; BAC11104; AAI14521; AAI52455; ; Q9P2B2; EAW56662; XP_016857363 |
| SLEA Down | FAM48A | Q8NEM7 | Q8NEM7; XP_005266514; XP_016876146; NP_060039; EAX08582; EAX08583; EAX08584; EAX08585; AAQ15220; AAH01145; XP_005266511; XP_005266513; XP_016876145; NP_001265409; CAB62207; XP_005266518; XP_005266524; ; AAD40550; AAL38587; XP_005266508; XP_005266517; XP_016876143; NP_001265411; EAX08586; BAG51343; XP_005266506; XP_005266519; XP_016876148; NP_001014308; NP_001265410; XP_005266504; XP_005266512; XP_005266515; XP_016876142; XP_016876147; BAG65097; AAH30686; XP_005266521; XP_005266522; XP_016876144; XP_016876149; XP_016876150; BAF85065 |
| SLEA Down | NPAS4 | Q8IUM7 | AAI05002; XP_016873026; BAC04271; AAI05004; NP_849195; BAC04738; XP_016873028; BAC19830; AAI43631; EAW74525; Q8IUM7; XP_016873027; NP_001305733 |
| SLEA Down | RPLP2 | P05387 | CAG47044; CAG47008; AAH05354; AAH62314; EAX02394; P05387; AAH05920; AAH07573; BAG34894; BAA05777; BAB79475; EAX02393; NP_000995; AAA36472 |
| SLEA Up | TTR | P02766 | AAA73473; NP_000362; AAA60018; AAB36045; AAL92041; AAL92042; EAX01264; EAX01265; AAA60012; BAG34987; AAA36784; AAP35853; BAA00059; AAD45014; ACJ13724; AAA98771; AAD14098; EAX01266; P02766; ADU87635; AAA60013; AAD14937; AAL92043; AAH05310; AAH20791; CAA42087; CAG33189; ABI63351; AAA60011; AAA61181 |
| SLEA Up | FOXO1 | Q12778 | AAP36123; XP_011533310; NP_002006; ; XP_011533312; AAC39591; AAA03629; AAH21981; AAH70065; EAX08627; Q12778 |
| SLEA Up | VWF | P04275 | AAA61294; CCQ25771; EAW88817; BAG60382; NP_000543; AAB59458; EAW88815; EAW88816; BAG62791; AAA61293; AAA65940; CAA26503; AEY75227; EAW88814; P04275; CDI44165; CAA27765; CAA29985; BAG59985; CAA27972; BAF84811; AAH22258; AAB39987; ; AAA61295; CBX54458; EAW88818; AAB59512 |
| SLEA Up | MUC16 | Q8WXI7 | BAG54742; BAG54743; AAL65133; XP_016882975; Q8WXI7; AAK74120; XP_016882977; XP_016882981; BAB14899; CAP17281; XP_016882978; XP_016882982; XP_016882985; XP_016882986; XP_016882989; ; BAC87568; XP_016882979; NP_078966; XP_016882976; XP_016882980; XP_016882983; XP_016882984; XP_016882987; XP_016882988; XP_016882990 |
| SLEA Up | UCHL3 | P15374 | AEE61131; NP_001257881; CCQ43344; EAW80543; EAW80546; P15374; BAG36417; XP_011533515; XP_016876214; XP_016876215; CCQ43343; EAW80542; EAW80547; AAH18125; AAV38166; CAG33136; ; AAG80545; AAA36791; XP_011533514; XP_011533516; NP_005993; EAW80544; XP_016876216 |
| SLEA Up | CD71 | P02786 | AAH01188; CAD97930; NP_001121620; NP_001300895; NP_003225; EAW53670; EAW53672; AAF04564; EAW53671; EAW53673; AAA61153; BAF84412; BAD92491; CAA25527; ABF47088; P02786; NP_001300894; ; BAH11872 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| SLEA Up | USP8 | P40818 | BAA06225; XP_016878207; XP_016878208; NP_001122082; EAW77399; XP_006720825; XP_016878210; XP_016878211; BAF85089; EAW77401; EAW77402; EAW77400; P40818; AAH15545; XP_006720824; AAH26954; AAH38801; XP_016878209; BAG59120; BAG62288; AAH51345; AAI10591; CAD97662; XP_011520495; NP_001269978; ; BAG52415; NP_005145 |
| SLEA Up | YES1 | P07947 | ; XP_016881449; EAX01709; BAG36767; AAA35735; XP_005258196; EAX01710; NP_005424; CCQ43321; P07947; AAH48960 |
| SLEA Up | RECQL4 | O94761 | BAA86899; XP_016869490; EAW82070; BAA74453; AAH11602; AAH13277; NP_004251; XP_016869480; XP_016869483; XP_016869484; XP_016869489; XP_016869482; XP_016869487; ; O94761; XP_016869481; XP_016869485; XP_011515686; XP_016869486; AAZ85145; EAW82071; AHN60090; XP_016869488 |
| SLEA Up | CCNE1 | P24864 | P24864; BAF84238; AEF32520; AHC02488; NP_001309190; AAA83269; AAM54043; CAA64688; XP_011525742; NP_001309188; CAA64687; AAH35498; AKJ51805; NP_001229; NP_001309191; AHC02489; |
| SLEA Up | HLA-A | P01891 | AAA03603; AAA59613; AAA84994; AAA98118; AAA98727; AAB60653; AAB87051; AAB87060; AAB87423; AAB87425; AAC14104; AAC72736; AAD00912; AAD02208; AAD22271; AAD38681; AAD39980; AAD48507; AAD53402; AAF03239; AAF04849; AAG10040; AAK49190; AAK52487; AAK52516; AAK58590; AAK94510; AAL32021; AAL33641; AAL35387; AAM78538; AAN01238; AAN01241; AAO17717; AAO49823; AAP21777; AAP32699; AAP49445; AAT35595; AAT41623; AAW83823; AAX94767; AAZ15017; ABA29233; ABC79293; ABC79296; ABD75333; ABD93917; ABF54964; ABF67610; ABG91056; ABK97608; ABL67641; ABL98038; ABL98041; ABM97536; ABP02054; ABP88249; ABQ45970; ABQ45971; ABR08288; ABU86839; ABU96767; ABW38317; ABW38319; ABX60509; ABY21176; ABY26525; ACA35000; ACA35004; ACA51866; ACD49990; ACF95805; ACH56947; ACH57398; ACI15740; ACI26702; ACJ53924; ACJ71689; ACJ71691; ACL51723; ACL99858; ACN76763; ACN76770; ACN81181; ACN81184; ACN81188; ACN81204; ACN81209; ACN81214; ACN81234; ACN81240; ACN89870; ACN89875; ACN91032; ACN91038; ACN91039; ACO44530; ACO44543; ACO44548; ACO44551; ACO44552; ACO44553; ACO44554; ACO44565; ACO44602; ACO44608; ACO44627; ACO44632; ACO44635; ACO48410; ACO48415; ACO48417; ACO58646; ACO87716; ACP27869; ACP27872; ACQ99524; ACR54304; ACR54311; ACR54328; ACR55724; ACR55731; ACR55732; ACS12733; ACS12734; ACS27555; ACS27564; ACS27571; ACS27576; ACS27689; ACS36355; ACS36365; ACS36384; ACS36385; ACS36396; ACT76259; ACT76260; ACT79395; ACT83688; ACU02130; ACU02136; ACU02144; ACU02163; ACU02170; ACU02198; ACU27243; ACU27251; ACU29568; ACU29573; ACU78156; ACU78157; ACU78163; ACU78169; ACV40691; ACV52060; ACV52062; ACV89432; ACV89434; ACV95338; ACX42600; ACX42612; ACX50458; ACX55002; ACX81370; ACZ56418; ACZ65011; ADB81928; ADB81931; ADC32155; ADC32182; ADC32234; ADC32240; ADC32241; ADC32245; ADC32246; ADC32260; ADC79893; ADC79906; ADC79930; ADC79936; ADC79940; ADC79951; ADC79963; ADC81010; ADC81012; ADC81013; ADC81014; ADC81025; ADC81027; ADC81035; ADC81043; ADC81045; ADC81059; ADC81077; ADC81080; ADC81081; ADC81082; ADD14008; ADD97837; ADD97839; ADD97840; ADD97845; ADE58586; ADE58597; ADE58606; ADE58628; ADE58630; ADE58646; ADE58651; ADE62147; ADE72803; ADE72804; ADE72829; ADE72840; ADE72850; ADE72856; ADE72860; ADE72863; ADE72868; ADE73014; ADE73015; ADE73018; ADE73022; ADE73026; ADE73027; ADE73028; ADE73053; ADE73106; ADE73117; ADE73193; ADE73236; ADE73288; ADE73300; ADE73343; ADE73347; ADE73355; ADE73465; ADE73471; ADE73495; ADE73540; ADE73608; ADE73609; ADE73612; ADE73659; ADE73666; ADE73777; ADE73781; ADE73787; ADE73801; ADE73812; ADI95501; ADI95505; ADM72723; ADM72725; ADM72741; ADN86006; ADN92578; ADN92579; ADN92583; ADN92593; ADN92595; ADQ55907; ADQ55908; ADR72653; ADW24256; ADW24259; ADW24284; ADX21062; ADZ31209; ADZ38939; ADZ73071; ADZ73077; ADZ73080; ADZ73085; AEA49769; AEA49775; AEA49790; AEA49801; AEB26702; AEF13098; AEF13103; AEF13110; AEF13787; AEF13807; AEF13808; AEF13816; AEF13827; AEF13829; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AEF13831; AEI00960; AEI00965; AEI00968; AEI00974; AEI30760; AEI30769; AEI59543; AEI59549; AEI59559; AEJ90498; AEK67314; AEK94818; AEK94884; AEK94886; AEK94911; AEK94912; AEK94913; AEK94919; AEK94974; AEK94981; AEK95021; AEK95022; AEK95032; AEK95104; AEK95290; AEK95305; AEK95345; AEK95490; AEK95493; AEK95499; AEK95504; AEK95508; AEK95517; AEK95529; AEK95714; AEK95721; AEK95734; AEK95763; AEK95767; AEK95770; AEK95775; AEK95789; AEK95803; AEK95804; AEK95806; AEK95817; AEK95823; AEK95829; AEK95846; AEK95851; AEK95860; AEK95861; AEK95870; AEK95874; AEK95877; AEK95879; AEK95892; AEK95893; AEP39698; AEQ26027; AER92532; AET98769; AEU10176; AEV23222; AEV42056; AEW23007; AEW23011; AEW23013; AEW23016; AEW23055; AEW23057; AEW90659; AFA42426; AFA42444; AFA42457; AFA42461; AFA42470; AFA42472; AFA42535; AFA42579; AFA42631; AFA42697; AFA42746; AFC95812; AFD23760; AFD23770; AFD36921; AFD36955; AFD36958; AFD36988; AFD61652; AFD61657; AFD62790; AFD62797; AFE48715; AFE88961; AFH66652; AFH66662; AFH78045; AFH78048; AFH78050; AFH78052; AFH78057; AFI14686; AFI57823; AFJ44813; AFK08514; AFK08515; AFK76448; AFK87751; AFK87752; AFK87776; AFL91483; AFM44677; AFM44702; AFM55924; AFN88140; AFP43712; AFP72372; AFU81189; AFU81190; AFU93083; AFV73985; AFV73991; AFV73997; AFV74006; AFV74055; AFV74056; AFV74072; AFV99140; AFX84018; AFX84022; AFZ93938; AFZ93963; AFZ93973; AFZ94386; AFZ94457; AFZ94463; AFZ94490; AFZ94549; AFZ94585; AGC82236; AGD91923; AGG56510; AGG56517; AGG79785; AGG79878; AGG79893; AGG79961; AGG79992; AGG80016; AGH39910; AGH58089; AGH62645; AGI48702; AGJ52182; AGJ52188; AGJ84086; AGJ84087; AGJ95107; AGK44346; AGL09213; AGL73113; AGL73117; AGL93364; AGN74859; AG006070; AGQ03749; AGQ03753; AGQ03758; AGT37254; AGT79675; AGZ87478; AGZ87482; AGZ87508; AGZ87523; AGZ87534; AGZ87537; AGZ87552; AGZ87563; AGZ87567; AGZ87569; AGZ87570; AGZ87571; AGZ87576; AGZ87582; AGZ87591; AGZ87592; AGZ87609; AGZ87610; AGZ92790; AGZ92792; AGZ92800; AGZ92802; AGZ92813; AGZ92825; AGZ92844; AGZ92846; AGZ92848; AGZ92850; AGZ95029; AHA49735; AHF20808; AHF71344; AH185959; AHN92455; AHV90562; AHY61466; AHY61491; AHY61502; AHY61519; AHY61523; AHY61555; AHY61560; AHY61562; AHY61580; AHY61583; AHY61584; AHY61591; AHY61621; AHY61627; AHY81345; AHY81356; AHY81364; AHY81379; AHY81386; AHY81391; AHY81405; AHY81409; AHY81424; AHY81430; AHY81442; AHY81457; AHY81458; AHY81477; AHY81498; AHY81505; AHY81520; AHY81527; AHY81538; AHY81547; AHY81558; AHY81562; AHY81565; AHZ30688; AHZ30689; AHZ30693; AHZ30698; AHZ30700; AHZ30739; AHZ30744; AHZ30758; AHZ30770; AHZ30806; AHZ30809; AIE39132; AIE39134; AIE39147; AIE39155; AIE39171; AIN41814; AIN41815; AIN41827; AIN41830; AIN41835; AIN41854; AIN41858; AIN41859; AIX94090; AIX94098; AIX94115; AIX94120; AIX94131; AIY63475; AJ143017; AJ143025; AJ143029; AJ143036; AJ143059; AJ143074; AKA93888; AKA93892; AKK23738; AKK75093; AKO90352; ALD83653; ALP46214; ALT08035; ALY06086; AMK47898; AMP83988; BAC02897; BAD20748; BAD29714; BAD30023; BAD99518; BAE48523; BAF37072; BAG15909; BAI50006; BAI59699; BAI66259; BAI66263; BAJ25761; BAJ46510; BAK53227; BAN62611; BAO02310; CAA06807; CAA61854; CAA73073; CAA96532; CAB64340; CAD20188; CAD22452; CAD30043; CAD60933; CAD61024; CAD61338; CAD87772; CAD92641; CAE01416; CAE46482; CAF06506; CAG23922; CAG27088; CAG28694; CAI45286; CAJ09236; CAJ34946; CAJ70623; CAL48952; CAL59517; CAL85627; CAM12538; CAN89177; CAO78190; CAO85640; CAO98726; CAQ37790; CAQ68183; CAV31552; CBL59219; CBL59222; CBL59225; CBL59251; CBM42056; CBM43070; CBN86245; CBW44087; CBW44120; CBX19696; CBX19772; CBX19773; CBX25642; CBY83775; CBY89318; CBZ46994; CCA61008; CCA62424; CCB78844; CCB78847; CCB78851; CCB78854; CCB78860; CCB78863; CCB78864; CCB78879; CCB78881; CCB78889; CCB78890; CCB78891; CCB78902; CCB78970; CCB78976; CCB78982; CCB78983; CCD33126; CCH75804; CCJ51909; CCK73125; CDF59527; CDF59528; CDF63774; CDF63777; CDI48076; CDJ26751; CDM99291; CDO19445; CDO33930; CDO33931; CDO33936; CDO33938; CDO33949; CDO67969; CDO67974; CDO67978; CDP32916; CDQ37741; CDQ51637; CDQ51659; CDQ51671; CDW91874; CDX10189; CEF48054; CEG29843; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CRG63508; CU125654; CUS06604; CUT08916; CUV66676; CUV66681; CUV66688; CUV66689; CUV66694; CUV66702; CUV66709; CUV66733; CUV66753; CUV66756; CUV66757; CUV66773; CUV66780; CUV66785; CUV66790; CUV66796; CUV66799; CUV66801; CUV66803; CUV66809; CUX90945; CUX90951; CUX90953; CUX90965; CUX90967; CUX90988; CUX90999; EAX03240; P01891; P05534; P16188; P16190; P30512; SAL89098; SAP17550; BAD92354; BAG35940; AAV53343; AAV53344; BAA08783; CDG23669; AAA17889; AAA59637; AAA59603; AAA59606; AAB38491; CAA41022; CAA43872; CAB38057; CAA81644; AAB70275; AAC17178; AAC18859; AAC24825; AAD02205; AAD02207; AAD02210; AAD02224; AAD02225; AAD28171; AAD30272; AAD33849; AAD33894; AAD45690; AAD56941; AAF03241; AAF59927; AAK32955; AAK38635; AAM77796; AAN64246; AAO47730; AAP44396; AAT44890; AAW65995; AAW81981; AAW81983; AAX18628; AAX73212; ABB00701; ABB43072; ABC79295; ABC79297; ABD93913; ABF93214; ABI54281; ABI63914; ABI78963; ABJ90453; ABK60080; ABK97607; ABL09833; ABO61519; ABP01670; ABQ96855; ABR08286; ABR08291; ABR68010; ABS18720; ABU62816; ABU86830; ABV53970; ABV66222; ABY21169; ABY21688; ABY64666; ABZ89503; ACA34998; ACA34999; ACA35001; ACA35003; ACA51037; ACD62376; ACE63267; ACE88695; ACF54638; ACI22945; ACJ05911; ACJ09051; ACJ71684; ACL34371; ACN76767; ACN76769; ACN76772; ACN81186; ACN81187; ACN81199; ACN81206; ACN81215; ACN81230; ACN81231; ACN89841; ACN89876; ACN91029; ACN91030; ACO44536; ACO44556; ACO44557; ACO44559; ACO44561; ACO44563; ACO44564; ACO44578; ACO44582; ACO44583; ACO44591; ACO44593; ACO44600; ACO44604; ACO44617; ACO44618; ACO44628; ACO48405; ACO48412; ACO87720; ACO87726; ACO87730; ACP40976; ACR54303; ACR54306; ACR54308; ACR54315; ACR54325; ACR54326; ACR55712; ACR55713; ACR55715; ACR55729; ACR55730; ACS12746; ACS27552; ACS27557; ACS27575; ACS27578; ACS27579; ACS27688; ACS36352; ACS36354; ACS36357; ACS36378; ACS36382; ACS36406; ACS36408; ACT76256; ACT76261; ACT83690; ACT83693; ACT83697; ACU02148; ACU02157; ACU02165; ACU02167; ACU02172; ACU02204; ACU29572; ACU29575; ACU78131; ACU78161; ACU78167; ACU78172; ACU78178; ACV40702; ACV89442; ACV89445; ACX42593; ACX42615; ACX42619; ACX81361; ACX81371; ACZ04957; ACZ73426; ADB25042; ADB81927; ADB81929; ADC32156; ADC32163; ADC32238; ADC32252; ADC32253; ADC32258; ADC32259; ADC32265; ADC79910; ADC79943; ADC79953; ADC81015; ADC81053; ADC81060; ADC81062; ADD17359; ADD97830; ADE58580; ADE58617; ADE58625; ADE58627; ADE58634; ADE58638; ADE58639; ADE58645; ADE58655; ADE72798; ADE72808; ADE72811; ADE72812; ADE72823; ADE72826; ADE72844; ADE73011; ADE73012; ADE73037; ADE73038; ADE73055; ADE73109; ADE73229; ADE73234; ADE73346; ADE73352; ADE73356; ADE73454; ADE73467; ADE73491; ADE73500; ADE73597; ADE73607; ADE73611; ADE73614; ADE73769; ADE73802; ADE73804; ADE73809; ADE73811; ADF58787; ADG34823; ADI75500; ADI75501; ADI95498; ADJ67215; ADM72711; ADM72716; ADN87366; ADN92574; ADN92581; ADN92590; ADN92598; ADN92601; ADN92603; ADP09051; ADP09052; ADQ48107; ADQ48110; ADQ55899; ADQ86004; ADW24278; ADW24280; ADW24293; ADZ73062; ADZ73078; ADZ73087; AEA49770; AEA49772; AEA49778; AEA49786; AEA49793; AEA49795; AEA49802; AEA49807; AEA49812; AEA50948; AEA51187; AEC33253; AEF13114; AEF13795; AEF13809; AEF13819; AEF13835; AEF13841; AEI00993; AEI17784; AEI30758; AEI30761; AEI30766; AEI30770; AEI30772; AEI30781; AEI59542; AEI59545; AEI59550; AEI98740; AEJ22068; AEJ22071; AEJ87203; AEK67316; AEK86202; AEK94822; AEK94824; AEK94829; AEK94887; AEK94922; AEK94975; AEK95020; AEK95028; AEK95297; AEK95307; AEK95342; AEK95349; AEK95483; AEK95502; AEK95515; AEK95516; AEK95712; AEK95723; AEK95731; AEK95766; AEK95793; AEK95837; AEK95839; AEK95843; AEK95844; AEK95867; AEK95887; AEK95890; AEK95896; AEK95906; AEK95910; AEP16360; AEP17321; AEP17323; AEQ28961; AER23868; AER92531; AEU10166; AEW23054; AEW23061; AEW23067; AEW90664; AEY80132; AFA42475; AFA42499; AFA42515; AFA42518; AFA42532; AFA42537; AFA42577; AFA42629; AFA42696; AFA42700; AFA42706; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AFA42744; AFA42745; AFA42747; AFC91649; AFD23751; AFD23753; AFD23757; AFD23772; AFD36893; AFD36895; AFD36919; AFD36968; AFD36979; AFD36981; AFD62771; AFD62783; AFD97748; AFE48706; AFE48708; AFH66638; AFH66651; AFH66658; AFH78040; AFH78047; AFH78054; AFH88380; AFI25182; AFI25185; AFJ44805; AFJ44807; AFJ79206; AFK08506; AFK08512; AFK08513; AFK24405; AFK24408; AFK24417; AFK64699; AFK64712; AFK64717; AFK76449; AFM44680; AFM44692; AFM44696; AFM77784; AFM77786; AFM77788; AFN66535; AFN89847; AFO62998; AFP43705; AFP43707; AFP72373; AFR69124; AFR69127; AFS64118; AFS64119; AFT82614; AFU81194; AFU93084; AFU93838; AFV73993; AFV73999; AFV74005; AFV74013; AFV74019; AFV74050; AFV74069; AFX62381; AFX84021; AFX95920; AFZ93937; AFZ93943; AFZ93944; AFZ93974; AFZ94387; AFZ94388; AFZ94392; AFZ94397; AFZ94398; AFZ94461; AFZ94485; AFZ94489; AFZ94491; AFZ94561; AFZ94582; AGC82235; AGD80268; AGE97322; AGG68829; AGG68831; AGG79669; AGG79701; AGG79722; AGG79724; AGG79726; AGG79802; AGG79925; AGG79989; AGH25493; AGH58092; AGJ52180; AGK44310; AGK44313; AGK44314; AGK44345; AGK44380; AGL07600; AGL09214; AGL73111; AGO32831; AGO86844; AGQ03754; AGQ03762; AGS42401; AGV54900; AGV68803; AGZ87471; AGZ87485; AGZ87499; AGZ87504; AGZ87509; AGZ87513; AGZ87519; AGZ87543; AGZ87549; AGZ87550; AGZ87559; AGZ87560; AGZ87561; AGZ87578; AGZ87583; AGZ87588; AGZ87589; AGZ87595; AGZ87596; AGZ87597; AGZ92789; AGZ92791; AGZ92794; AGZ92801; AGZ92808; AGZ92811; AGZ92812; AGZ92818; AGZ92823; AGZ92827; AGZ92831; AGZ92843; AHA11844; AHA49738; AHF52841; AHF71338; AHF71346; AHG52865; AHG52867; AHI42990; AHN92454; AHN92458; AHN92460; AHY61451; AHY61464; AHY61487; AHY61504; AHY61527; AHY61531; AHY61559; AHY61577; AHY61578; AHY61582; AHY61592; AHY61606; AHY61623; AHY61626; AHY81363; AHY81381; AHY81383; AHY81396; AHY81407; AHY81417; AHY81429; AHY81437; AHY81445; AHY81451; AHY81455; AHY81460; AHY81462; AHY81464; AHY81467; AHY81468; AHY81469; AHY81475; AHY81476; AHY81480; AHY81485; AHY81488; AHY81492; AHY81493; AHY81499; AHY81508; AHY81522; AHY81533; AHY81539; AHY81540; AHY81546; AHY81550; AHY81552; AHY81555; AHY81556; AHZ30687; AHZ30692; AHZ30694; AHZ30701; AHZ30716; AHZ30718; AHZ30719; AHZ30727; AHZ30734; AHZ30738; AHZ30745; AHZ30746; AHZ30748; AHZ30751; AHZ30754; AHZ30756; AHZ30757; AHZ30760; AHZ30764; AHZ30779; AHZ30780; AHZ30786; AHZ30789; AHZ30807; AIA66931; AIA98431; AIC77109; AIE39126; AIE39131; AIE39141; AIE39144; AIE39146; AIE39148; AIE39154; AIE39157; AIE39168; AIN41805; AIN41806; AIN41808; AIN41824; AIN41840; AIN41846; AIN41856; AIX94092; AIX94097; AIX94104; AIX94118; AIX94130; AIY25917; AJI43006; AJI43007; AJI43012; AJI43015; AJI43016; AJI43018; AJI43049; AJI43058; AJI43060; AJI43062; AJI43065; AJI43069; AJI43076; AJI43080; AJM87486; AKA93870; AKA93883; AKA93899; AKA93903; AKP49082; AKU19359; ALA65388; ALD83649; ALF37830; ALG04358; ALG76662; ALH21895; ALM96678; ALN39129; ALO24306; ALP46209; ALP46213; ALS46615; ALT08036; AMB21151; AMP83989; AMR70862; AMR70865; AMR70870; AMR70926; AMR70929; AMR70989; ANG08799; BAA84645; BAB71760; BAD19045; BAE78598; BAE87033; BAG12800; BAG12801; BAG30710; BAG30812; BAI50007; BAI52764; BAI52915; BAI66261; BAI66267; BAN04714; BAN59832; BAN59844; CAA39243; CAB41999; CAB43110; CAB57318; CAB96870; CAB96998; CAC00689; CAC36395; CAC37336; CAC44382; CAD24477; CAD44640; CAD48117; CAD61867; CAD66674; CAE22481; CAE45179; CAG38621; CAH25490; CAJ01785; CAJ21345; CAJ41178; CAJ66086; CAL59518; CAM12704; CAM90933; CAP58182; CAQ68182; CAX48969; CBL59231; CBL59234; CBL59243; CBM41441; CBM42058; CBW44094; CBW44118; CBW47476; CBW69643; CBW94250; CBX19695; CBX19704; CBX19705; CBX19706; CBX19817; CBX24358; CBX87026; CBX87027; CBX87028; CCA61234; CCB78843; CCB78846; CCB78857; CCB78858; CCB78861; CCB78880; CCB78884; CCB78895; CCB78912; CCB78951; CCB78965; CCB78966; CCB78977; CCC15080; CCC15144; CCF17390; CCF23461; CCF78535; CCH57804; CCK33017; CCL98004; CCM43937; CCV02677; CCW36800; CDF63775; CDK41204; CDO33933; CDO33934; CDO67976; CDQ51631; CDQ51636; CDQ51667; CDR19365; CDX47509; CEE15325; CEF48094; CEG29829; CEO43662; CEP28081; CQR91471; CUV66662; CUV66668; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CUV66675; CUV66677; CUV66678; CUV66686; CUV66712; CUV66723; CUV66731; CUV66748; CUV66755; CUV66775; CUV66791; CUV66792; CUV66797; CUV66800; CUV66805; CUV66807; CUX90949; CUX90954; CUX90955; CUX90962; CUX90964; CUX90973; CUX90980; CUX90984; CUX90990; CUX91007; EAX03244; P30453; SAP17543; CAA04647; CAC27416; BAA05549; BAA07530; BAA11935; BAA11936; ABC55710; ABC55714; AAA59600; AAA59599; CAA26297; CAA69599; CAA80612; AAA03604; AAA36218; AAA76608; AAB02120; AAB16923; AAB87057; AAC06320; AAC18858; AAD02206; AAD23437; AAD28168; AAD33739; AAD33859; AAD33865; AAF03242; AAF25960; AAF64506; AAF70298; AAF73063; AAF78045; AAG21403; AAL10675; AAL10684; AAL87131; AAP32698; AAP88042; AAQ67705; AAQ72733; AAR28200; AAS48457; AAW22618; AAW58069; AAW63722; AAW66599; AAW81982; AAX18627; AAY23009; AAY85375; ABB00702; AAZ32762; ABB00703; ABC74568; ABC79294; ABD62871; ABD62872; ABE00934; ABE27974; ABF71073; ABF71714; ABG43098; ABI64161; ABK60079; ABL98043; ABN45878; ABN51227; ABO86192; ABQ45967; ABQ96854; ABU86832; ABU86841; ABW86960; ABY26534; ABY64662; ABZ89499; ACA34992; ACA34995; ACA51867; ACA79968; ACB45596; ACG49999; ACH56946; ACI22667; ACI22947; ACI43208; ACJ06427; ACJ24536; ACJ31783; ACJ71677; ACJ71688; ACJ71692; ACL51037; ACL51727; ACN76766; ACN76771; ACN76774; ACN76776; ACN81182; ACN81196; ACN81211; ACN81235; ACN81237; ACN91031; ACO40325; ACO44524; ACO44525; ACO44527; ACO44531; ACO44535; ACO44542; ACO44550; ACO44560; ACO44573; ACO44576; ACO44580; ACO44581; ACO44585; ACO44597; ACO44599; ACO44601; ACO44609; ACO44621; ACO44633; ACO44643; ACO48411; ACO87714; ACO87725; ACO87727; ACO90214; ACP27988; ACP27989; ACP40975; ACQ99525; ACR25161; ACR54307; ACR54329; ACR55721; ACS12740; ACS12754; ACS12757; ACS27547; ACS27573; ACS27687; ACS36349; ACS36351; ACS36356; ACS36371; ACS36374; ACS36391; ACS36394; ACS36403; ACS36405; ACT76255; ACT83687; ACT99993; ACT99994; ACU02132; ACU02135; ACU02138; ACU02140; ACU02143; ACU02152; ACU02159; ACU02166; ACU02168; ACU02173; ACU29562; ACU78164; ACU78171; ACU78188; ACV30340; ACV40698; ACV52061; ACV66341; ACV89433; ACV92041; ACV92042; ACX42604; ACX42607; ACX50456; ACX71598; ACX71838; ACZ56419; ACZ56420; ACZ56423; ADB25044; ADC32160; ADC32183; ADC32231; ADC32239; ADC32263; ADC32264; ADC45399; ADC45438; ADC79891; ADC79915; ADC79917; ADC79920; ADC79925; ADC79926; ADC79934; ADC79944; ADC79950; ADC81026; ADC81040; ADC81041; ADC81042; ADC81047; ADC81052; ADC81055; ADC81068; ADC81075; ADC81083; ADD17360; ADD23525; ADD97841; ADE42864; ADE58592; ADE58593; ADE58600; ADE58611; ADE58615; ADE58641; ADE58642; ADE58653; ADE58656; ADE72805; ADE72820; ADE72821; ADE72824; ADE72827; ADE72834; ADE72838; ADE72848; ADE72851; ADE72858; ADE73003; ADE73004; ADE73107; ADE73113; ADE73293; ADE73349; ADE73353; ADE73468; ADE73494; ADE73496; ADE73539; ADE73542; ADE73596; ADE73661; ADE73776; ADE73783; ADE73786; ADE73795; ADE73798; ADE80888; ADE80889; ADH04230; ADI95496; ADI95503; ADJ54141; ADM72715; ADM72717; ADM72721; ADM72735; ADN87360; ADN87367; ADN92575; ADN92589; ADN92597; ADN92599; ADN92606; ADP09050; ADQ12886; ADQ48106; ADQ55909; ADQ55912; ADW24255; ADW24265; ADW24271; ADW24273; ADX94775; ADZ31204; ADZ38938; ADZ38946; ADZ73065; ADZ73079; ADZ73082; ADZ73086; AEA49774; AEA49783; AEA49811; AEB65790; AEF13090; AEF13091; AEF13092; AEF13111; AEF13784; AEF13798; AEF13802; AEF13820; AEF13825; AEG64621; AEI00952; AEI00959; AEI00963; AEI00971; AEI00983; AEI00985; AEI00987; AEI59556; AEI91788; AEI98729; AEJ90502; AEJ90504; AEK32811; AEK67312; AEK94826; AEK94916; AEK94918; AEK95023; AEK95033; AEK95035; AEK95291; AEK95302; AEK95303; AEK95346; AEK95350; AEK95496; AEK95523; AEK95525; AEK95711; AEK95738; AEK95749; AEK95753; AEK95773; AEK95794; AEK95805; AEK95809; AEK95838; AEK95842; AEK95853; AEK95859; AEK95862; AEK95901; AEP17317; AER92533; AEU10178; AEU10180; AEV23664; AEW23014; AEW23017; AEW23018; AEW90652; AEW90655; AFA42428; AFA42500; AFA42575; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AFA42583; AFA42634; AFA42636; AFA42742; AFD23764; AFD23768; AFD23773; AFD23776; AFD23778; AFD23778; AFD36894; AFD36896; AFD36918; AFD36967; AFD62784; AFD62787; AFD62789; AFD62792; AFE48716; AFH66634; AFH66635; AFH66647; AFH66649; AFH66650; AFH66657; AFH78049; AFH89646; AFI57820; AFJ04126; AFJ44773; AFK08516; AFK24403; AFK64686; AFK64690; AFK64691; AFK87761; AFM44683; AFM44685; AFM44693; AFM44700; AFM56240; AFM56243; AFM77791; AFN61284; AFN88136; AFN89844; AFP20869; AFP58879; AFU81191; AFV73990; AFV73996; AFV74007; AFV74047; AFV74067; AFV74071; AFX84020; AFX84023; AFZ93931; AFZ93932; AFZ93935; AFZ93939; AFZ93962; AFZ94381; AFZ94459; AFZ94487; AFZ94493; AFZ94552; AFZ94555; AFZ94557; AGC51043; AGG11861; AGG68826; AGG79703; AGG79737; AGG79782; AGG79787; AGG79887; AGG79891; AGG80009; AGG80014; AGH39852; AGH58091; AGI02598; AGI65159; AGJ95110; AGK44308; AGK44312; AGL73110; AGQ03760; AGU13630; AGU13633; AGZ87481; AGZ87487; AGZ87490; AGZ87492; AGZ87506; AGZ87522; AGZ87532; AGZ87536; AGZ87564; AGZ87581; AGZ87586; AGZ87593; AGZ87602; AGZ87605; AGZ87606; AGZ92814; AGZ92820; AGZ92821; AGZ92830; AGZ92842; AGZ92845; AHA44502; AHA49734; AHA49737; AHJ80989; AHN92459; AHN92461; AHV90273; AHW45891; AHY61459; AHY61467; AHY61469; AHY61473; AHY61476; AHY61477; AHY61483; AHY61497; AHY61539; AHY61543; AHY61544; AHY61551; AHY61568; AHY61572; AHY61573; AHY61586; AHY61603; AHY81346; AHY81358; AHY81359; AHY81366; AHY81368; AHY81370; AHY81374; AHY81375; AHY81390; AHY81392; AHY81395; AHY81399; AHY81406; AHY81433; AHY81440; AHY81452; AHY81456; AHY81461; AHY81471; AHY81497; AHY81501; AHY81503; AHY81523; AHY81526; AHY81543; AHY81544; AHZ30697; AHZ30720; AHZ30728; AHZ30736; AHZ30737; AHZ30747; AHZ30755; AHZ30759; AHZ30762; AHZ30769; AHZ30784; AHZ30785; AHZ30792; AHZ30794; AHZ30796; AHZ30812; AIA66933; AIB52375; AIB55777; AIB55786; AIE39143; AIE39166; AIE39176; AII80554; AIK28511; AIN41810; AIN41828; AIN41837; AIN41843; AIN41844; AIN41857; AIN41861; AIX09858; AIX94086; AIX94117; AIX94125; AIX94127; AIX94132; AIY26931; AJA90812; AJI43002; AJI43005; AJI43019; AJI43026; AJI43035; AJI43043; AJI43047; AJI43048; AJI43054; AJI43055; AJI43057; AJI43067; AJI43077; AKA93875; AKA93885; AKG95443; AKJ75507; AKL83124; ALA10821; ALA65386; ALG76651; ALH21902; ALO23540; ALS55299; AMB21152; AMD39525; AME17705; AMO26192; AMR70308; AMR70988; BAD36754; BAD77818; BAD77942; BAD95617; BAD95618; BAE48524; BAE78473; BAE93145; BAH09092; BAH23561; BAH85290; BAI59696; BAI59698; BAI66260; BAI66262; BAI66266; BAJ25762; BAJ83600; BAK53479; BAM28631; BAN59784; BAN59838; CAB09723; CAB42000; CAB57306; CAB65738; CAC06086; CAC27518; CAD26949; CAD45178; CAD45434; CAD66673; CAD79469; CAD79470; CAF18417; CAF33344; CAG27089; CAH59953; CAI26292; CAI96181; CAJ43230; CAJ70701; CAJ84550; CAL18290; CAL69123; CAL80737; CAM34677; CAN89495; CAQ16345; CAR66114; CAR94521; CAX33835; CAZ66352; CAZ66354; CAZ66355; CAZ66356; CBB38510; CBH26012; CBI61642; CBJ18094; CBL86580; CBM41039; CBN72525; CBW31642; CBW44121; CBW47474; CBW94246; CBX36124; CBY93684; CBZ39250; CCB78840; CCB78841; CCB78856; CCB78870; CCB78877; CCB78892; CCB78901; CCB78904; CCB78907; CCB78954; CCB78960; CCB78978; CCB78979; CCC55552; CCD04083; CCF23448; CCG14227; CCH27328; CCM12467; CCN97890; CCW36807; CDJ79535; CDJ79538; CDK41189; CDK41200; CDL72710; CDM99289; CDO67965; CDO67977; CDQ51630; CDQ51655; CDQ51664; CDQ51673; CDR98157; CDX10186; CDX10188; CEF52522; CEH11576; CQR91467; CQR91470; CTQ48003; CTQ48004; CUH74625; CU125653; CUR70744; CUV66666; CUV66669; CUV66670; CUV66687; CUV66695; CUV66707; CUV66714; CUV66729; CUV66734; CUV66736; CUV66742; CUV66752; CUV66754; CUV66774; CUV66778; CUW00372; CUW00373; CUW00374; CUW01267; CUX90940; CUX90943; CUX90956; CUX90960; CUX90970; CUX90971; CUX90987; CUX91003; CUX91009; CUX91010; CVK15079; CZQ50133; P04439; P30443; P30455; P30459; Q09160; SAL89094; AAB66704; AAD05568; AAF25781; AAG27626; CAA04643; BAG62841; AAH08611; BAA03279; AAA80569; AAB60406; AAB08574; CAA43873; CAA43880; CAA66389; AAA59612; AAA59838; AAA59839; AAA65449; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AAB48628; AAB50149; AAB70278; AAB82079; AAB87048; AAB87054; AAB87058; AAB92550; AAC28559; AAD09489; AAD28170; AAD34010; AAD39981; AAD44708; AAD45369; AAD48505; AAD53014; AAF19525; AAF34685; AAF61965; AAK49189; AAL01996; AAL10676; AAL38666; AAM77210; AAP49444; AAP49446; AAP55807; AAQ96777; AAR07615; AAR28202; AAS75118; AAT41625; AAT44889; AAW30168; AAZ28909; AAZ28919; AAZ75663; ABB00704; ABB00707; ABB13527; ABC79298; ABD64774; ABF18978; ABF58776; ABK63711; ABM92294; ABO14984; ABO87673; ABP57138; ABP73295; ABQ08748; ABQ08750; ABQ45961; ABQ45966; ABR21559; ABS18722; ABS85167; ABU86834; ABU86835; ABU86836; ABU86840; ABU86844; ABV66224; ACA28730; ACA28732; ACE76868; ACF24760; ACF95802; ACH73187; ACI43211; ACJ71678; ACJ71679; ACL51721; ACM24226; ACN76768; ACN81185; ACN81190; ACN81192; ACN81202; ACN81213; ACN81242; ACN89869; ACN91037; ACO44529; ACO44534; ACO44537; ACO44545; ACO44547; ACO44570; ACO44572; ACO44592; ACO44595; ACO44603; ACO44606; ACO44613; ACO44614; ACO44630; ACO44636; ACO44637; ACO44642; ACO48406; ACO48418; ACO48420; ACP27992; ACR54310; ACR54316; ACR54318; ACR54330; ACR54331; ACR55734; ACS27554; ACS27570; ACS27572; ACS36362; ACS36381; ACS36387; ACS36390; ACS36393; ACS36395; ACS36399; ACS36400; ACS36404; ACT64610; ACT76258; ACT79396; ACT79397; ACT83686; ACT83699; ACU00666; ACU02131; ACU02151; ACU02153; ACU02160; ACU02171; ACU02175; ACU02176; ACU27249; ACU27250; ACU27253; ACU78159; ACU78175; ACV40689; ACV40700; ACV89431; ACV89439; ACV89443; ACV92040; ACX42592; ACX42597; ACX42599; ACX42605; ACX42613; ACX50455; ACX71599; ACX81362; ACX81363; ACX81367; ACX81369; ACY41034; ACZ56422; ACZ64210; ADB27768; ADB55625; ADB81930; ADC32159; ADC32162; ADC32181; ADC32184; ADC32185; ADC32233; ADC32235; ADC32244; ADC32249; ADC32255; ADC32256; ADC79896; ADC79900; ADC79916; ADC79923; ADC79927; ADC79937; ADC79945; ADC79948; ADC79955; ADC79966; ADC79967; ADC81007; ADC81020; ADC81029; ADC81033; ADC81044; ADC81046; ADC81072; ADC81076; ADD97829; ADD97831; ADD97834; ADD97836; ADD97842; ADD97843; ADD97844; ADE18745; ADE58582; ADE58585; ADE58594; ADE58595; ADE58598; ADE58599; ADE58602; ADE58613; ADE58626; ADE58631; ADE58649; ADE72797; ADE72801; ADE72806; ADE72809; ADE72815; ADE72817; ADE72818; ADE72841; ADE72852; ADE72865; ADE72866; ADE73029; ADE73034; ADE73056; ADE73108; ADE73232; ADE73235; ADE73265; ADE73266; ADE73267; ADE73357; ADE73466; ADE73545; ADE73601; ADE73657; ADE73772; ADE73774; ADI95499; ADI95502; ADJ67225; ADM52299; ADM72714; ADM72742; ADN92604; ADP09053; ADQ48103; ADQ55910; ADT71648; ADW24267; ADW24268; ADW24276; ADW24288; ADZ05619; ADZ05621; ADZ73066; ADZ73070; ADZ73084; AEA49771; AEA49780; AEA49782; AEA49792; AEA49799; AEA49808; AEF13106; AEF13108; AEF13790; AEF13794; AEF13815; AEF13838; AEF13842; AEI00945; AEI00953; AEI00964; AEI00969; AEI30773; AEI30775; AEI30778; AEI30780; AEI59541; AEJ22075; AEJ90499; AEK67315; AEK94821; AEK94830; AEK94980; AEK95025; AEK95289; AEK95300; AEK95301; AEK95306; AEK95495; AEK95503; AEK95719; AEK95727; AEK95736; AEK95750; AEK95786; AEK95792; AEK95797; AEK95798; AEK95818; AEK95822; AEK95828; AEK95835; AEK95845; AEK95852; AEK95856; AEK95857; AEK95883; AEK95885; AEK95898; AEP17316; AEP17319; AEP17320; AER92535; AEU10167; AEU10181; AEW23008; AEW23020; AEW23052; AEW23065; AEW23066; AEW23068; AEW90661; AEW90662; AEX25776; AEY80133; AFA42425; AFA42471; AFA42502; AFA42538; AFA42578; AFA42698; AFA42737; AFA42739; AFA42740; AFA42749; AFD23749; AFD23761; AFD23774; AFD23777; AFD36922; AFD36925; AFD36969; AFD61653; AFD62775; AFE48718; AFE48720; AFE88965; AFH66645; AFH66646; AFH66655; AFH66659; AFH78034; AFH78036; AFH78038; AFH78055; AFI55464; AFI57821; AFI57824; AFJ04127; AFK08500; AFK08507; AFK08511; AFK24410; AFK24416; AFK24418; AFK49810; AFK64688; AFK64695; AFK64698; AFK76447; AFK87750; AFL91481; AFM44669; AFM44670; AFM44672; AFM44675; AFM44681; AFM44686; AFM44688; AFM44698; AFN61285; AFN88127; AFN88131; AFN88132; AFN88135; AFN89848; AFT82612; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AFU93836; AFV73995; AFV74011; AFV74012; AFV74017; AFV74018; AFV74051; AFV74070; AFV74680; AFW99834; AFX62377; AFX62378; AFX84019; AFZ93928; AFZ94389; AFZ94488; AFZ94556; AFZ94583; AFZ94617; AFZ94618; AGD80567; AGE97320; AGE97321; AGG56509; AGG68830; AGG79670; AGG79786; AGG79803; AGG79873; AGG79928; AGG79991; AGG80017; AGH58093; AGH70373; AGJ52189; AGJ84085; AGJ84088; AGJ95111; AGK44350; AGL07597; AGL73108; AGL73115; AGL73116; AGM53430; AGQ03757; AGS38344; AGU13640; AGU38489; AGX13923; AGZ87468; AGZ87470; AGZ87483; AGZ87486; AGZ87488; AGZ87491; AGZ87493; AGZ87500; AGZ87503; AGZ87507; AGZ87514; AGZ87516; AGZ87517; AGZ87533; AGZ87542; AGZ87572; AGZ87573; AGZ87587; AGZ87600; AGZ87607; AGZ92806; AGZ92819; AGZ92826; AGZ92851; AGZ95028; AHA49716; AHA49717; AHF71342; AHN52943; AHY61470; AHY61471; AHY61484; AHY61493; AHY61494; AHY61505; AHY61530; AHY61533; AHY61535; AHY61536; AHY61542; AHY61550; AHY61556; AHY61561; AHY61576; AHY61581; AHY61587; AHY61595; AHY61602; AHY61614; AHY61616; AHY81360; AHY81361; AHY81382; AHY81385; AHY81389; AHY81397; AHY81400; AHY81402; AHY81412; AHY81419; AHY81422; AHY81423; AHY81463; AHY81472; AHY81478; AHY81479; AHY81489; AHY81504; AHY81507; AHY81516; AHY81534; AHY81541; AHY81548; AHY81549; AHY81559; AHY81566; AHZ30715; AHZ30717; AHZ30722; AHZ30730; AHZ30743; AHZ30776; AHZ30778; AHZ30783; AHZ30798; AHZ30801; AHZ30808; AHZ30811; AID53086; AIE39136; AIE39139; AIE39150; AIE39158; AIE39162; AIE39165; AIE39170; AIE39174; AII80553; AIN41802; AIN41813; AIN41820; AIN41822; AIN41825; AIN41832; AIN41848; AIN41849; AIN41850; AIN41860; AIV00670; AIX94096; AIX94102; AIX94110; AIX94122; AJA90814; AJI43003; AJI43020; AJI43033; AJI43034; AJI43038; AJI43045; AJI43051; AJI43063; AJI43081; AKA93873; AKA93877; AKA93878; AKA93881; AKA93904; AKE47352; AKJ66245; ALJ77678; AMO26194; AMR93990; ANG08796; BAA84643; BAD00981; BAD30024; BAD77941; BAD77943; BAD98466; BAF46392; BAK53480; BAM28627; BAM28629; BAM72630; BAN59790; BAN59808; BAN59814; BAN62612; CAA73072; CAB07989; CAB41636; CAB43622; CAB56605; CAC27241; CAD23134; CAD30042; CAD44950; CAD45435; CAD61025; CAE53175; CAG24006; CAI34859; CAI39219; CAI84068; CAJ32464; CAJ66087; CAL34150; CAL80735; CAM28531; CAM98059; CAN85194; CAN89497; CAO98862; CAP58181; CAP60755; CAU70302; CAZ66353; CAZ66358; CAZ90644; CAZ90645; CBA35167; CBH20089; CBL51955; CBL59232; CBL59249; CBL59250; CBM41440; CBW44117; CBW44119; CBW47472; CBW69639; CBW69644; CBX19770; CBX19816; CBY83773; CCB78849; CCB78866; CCB78868; CCB78869; CCB78871; CCB78876; CCB78878; CCB78887; CCB78914; CCB78953; CCB78963; CCB78972; CCB78981; CCE73899; CCF03534; CCG14175; CCK73123; CCQ18709; CCW03265; CDF63776; CDH35264; CDI30154; CDI43893; CDK13052; CDK41171; CDM87252; CDN39948; CDO33940; CDO67967; CDO67968; CDQ51660; CDQ51669; CDQ51670; CDQ51679; CDQ51680; CDQ51681; CDR98158; CEF48045; CEN31973; CQR91465; CRG63509; CUU97276; CUV03801; CUV66679; CUV66680; CUV66690; CUV66696; CUV66699; CUV66706; CUV66717; CUV66724; CUV66726; CUV66740; CUV66746; CUV66760; CUV66763; CUV66766; CUV66767; CUV66779; CUX90977; CUX90979; CUX90996; CUX91015; EAX03242; EAX03245; P10316; P30450; SAI78371; SAI78377; SAL89097; AAD02067; CAA04209; CAB56838; BAC86217; AAO20854; AAH19236; BAA03280; BAA03282; BAA04119; ABC55713; AFH41801; AAB59614; AAA59598; AAB47873; AAA59653; AAA73518; AAA87572; CAA31503; CAA73716; AAA59615; AAA76609; AAB70277; AAB82080; AAB82081; AAC14103; AAC26020; AAC79721; AAD22269; AAD22272; AAD27539; AAD33737; AAD34883; AAF04848; AAF05535; AAF23125; AAF29553; AAF66709; AAF73068; AAF73862; AAG01872; AAG16251; AAG27627; AAG38635; AAG42276; AAG49321; AAK09376; AAK49188; AAK52517; AAK58591; AAL09700; AAL55399; AAN52398; AAN64244; AAP94631; AAQ72734; AAT35596; AAW21338; AAW81710; AAX07135; AAX58630; AAZ28911; AAZ40332; AAZ66805; ABA29234; ABB00705; ABB00706; ABF54961; ABL98210; ABM98423; ABO87665; ABP57139; ABP96833; ABQ01715; ABQ45965; ABS18723; ABS18724; ABS29696; ABU86831; ABW21689; ACA34990; ACA34997; ACB45878; ACB98185; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ACE60612; ACF19761; ACG59279; ACI15742; ACI43212; ACJ71686; ACJ71693; ACK44105; ACL34370; ACL51724; ACN76765; ACN81176; ACN81179; ACN81180; ACN81200; ACN81232; ACN81236; ACN81238; ACN81239; ACN89874; ACO44523; ACO44526; ACO44544; ACO44549; ACO44571; ACO44610; ACO44615; ACO44616; ACO44619; ACO44620; ACO44622; ACO44626; ACO44629; ACO44639; ACO48404; ACO48407; ACO87722; ACO87731; ACP27866; ACP27870; ACP27995; ACQ99523; ACR23346; ACR25159; ACR54309; ACR54314; ACR54317; ACR54319; ACR54321; ACR54327; ACR55725; ACR55727; ACR55733; ACS27556; ACS27558; ACS27560; ACS27561; ACS27678; ACS36353; ACS36358; ACS36360; ACS36366; ACS36377; ACS36401; ACS36402; ACT34382; ACT64611; ACT83696; ACT97163; ACU02133; ACU02147; ACU02154; ACU02196; ACU27248; ACU27255; ACU29574; ACU29580; ACU29582; ACU29584; ACU46619; ACU78162; ACU78170; ACU78173; ACU78190; ACV40688; ACV40695; ACV40696; ACV87226; ACV89446; ACX42596; ACX42602; ACX42617; ACX50454; ACX81360; ACZ04959; ADC32157; ADC32186; ADC32237; ADC32254; ADC32261; ADC45434; ADC79892; ADC79898; ADC79913; ADC79921; ADC79922; ADC79931; ADC79933; ADC79935; ADC79939; ADC79954; ADC79958; ADC81019; ADC81021; ADC81030; ADC81036; ADC81048; ADC81051; ADC81054; ADC81056; ADC81057; ADC81061; ADC81064; ADC81069; ADD71847; ADD97827; ADD97846; ADE58574; ADE58576; ADE58588; ADE58590; ADE58601; ADE58614; ADE58632; ADE58640; ADE58650; ADE72828; ADE72830; ADE72837; ADE72864; ADE73013; ADE73016; ADE73019; ADE73023; ADE73025; ADE73031; ADE73100; ADE73102; ADE73105; ADE73114; ADE73115; ADE73264; ADE73294; ADE73359; ADE73450; ADE73455; ADE73490; ADE73493; ADE73598; ADE73600; ADE73602; ADE73603; ADE73655; ADE73663; ADE73665; ADE73667; ADE73768; ADE73780; ADE73788; ADE73793; ADE73796; ADE73797; ADE73810; ADE80887; ADI24376; ADI56258; ADI95504; ADM26765; ADM72712; ADM72730; ADM72737; ADN87365; ADN87369; ADN92586; ADN92605; ADW24257; ADW24262; ADW24264; ADW24269; ADW24277; ADW24279; ADX86747; ADZ31205; ADZ31207; ADZ31208; ADZ38940; ADZ73067; AEA49784; AEA49785; AEA; |
| SLEA UP | HLA-B | P30488 | AAA52657; AAA52659; AAA52664; AAA59620; AAB00197; AAB02607; AAB06739; AAB07700; AAB48493; AAB49760; AAB50151; AAB51453; AAB62223; AAB67809; AAB67816; AAB67818; AAB70250; AAB70281; AAB70282; AAB70295; AAB82056; AAB84035; AAB87726; AAB96792; AAC07913; AAC08026; AAC14124; AAC17712; AAC18388; AAC18816; AAC33187; AAC67567; AAC67570; AAD14426; AAD19591; AAD23392; AAD23461; AAD27537; AAD28165; AAD28166; AAD28167; AAD51743; AAD51748; AAD55793; AAF19426; AAF32321; AAF36681; AAF70328; AAF89550; AAF97850; AAG01821; AAG42279; AAG42280; AAK07653; AAK07654; AAK31806; AAK38401; AAK57737; AAK69671; AAK94505; AAK94512; AAK97443; AAK97445; AAL18232; AAL59421; AAN16457; AAO18660; AAO21940; AAO21942; AAQ16164; AAT11511; AAT35594; AAU89133; AAV91504; AAW88384; AAX56911; AAX73223; AAX73224; AAY26573; AAY96636; AAZ15022; ABA07958; ABA07959; ABA29237; ABB51135; ABD64574; ABE27965; ABE27970; ABF18980; ABF60560; ABF93211; ABH03381; ABH03570; ABI26620; ABI95095; ABJ90454; ABK33465; ABL63749; ABM92296; ABM92298; ABN11363; ABN51218; ABP87680; ABS59404; ABU63662; ABU96080; ACA28733; ACB45466; ACD01090; ACD87747; ACI45411; ACJ71680; ACK37875; ACL34365; ACL34366; ACM68929; ACM90164; ACN12930; ACN12948; ACN38392; ACN76608; ACN76612; ACN81074; ACN81087; ACN81111; ACN81118; ACN81122; ACN81123; ACN81126; ACN81156; ACN81160; ACN81161; ACN81164; ACN81171; ACN81223; ACN81271; ACN81272; ACN81273; ACN89863; ACN91041; ACO70684; ACO70688; ACO70697; ACO70702; ACO70706; ACO70707; ACO70722; ACO70730; ACO70749; ACO70753; ACO70754; ACO82431; ACO82442; ACO82448; ACO82476; ACO82514; ACO82529; ACO90078; ACO91532; ACO91533; ACO91543; ACO91546; ACO91556; ACO94130; ACO94140; ACO94152; ACO94154; ACO94155; ACO94159; ACP27885; ACP27891; ACP27893; ACP27896; ACP27901; ACP27906; ACP27964; ACP27966; ACP27970; ACP27980; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ACR54337; ACR54344; ACR81567; ACR83851; ACS27583; ACS27587; ACS27679; ACS31817; ACS37225; ACT64594; ACT64608; ACT64621; ACT76265; ACU00002; ACU01992; ACU02083; ACU02096; ACU02098; ACU02099; ACU02100; ACU02101; ACU02105; ACU02106; ACU02109; ACU02177; ACU02191; ACU27264; ACU27268; ACU29552; ACU46617; ACV30331; ACV31935; ACV31965; ACV40713; ACV40717; ACV92045; ACV92049; ACX42627; ACX42629; ACX42634; ACX81377; ACX81380; ACY09097; ACZ26469; ACZ54646; ACZ54648; ACZ54665; ACZ54666; ADB27758; ADC32147; ADD10596; ADD97859; ADE58670; ADE58671; ADE73084; ADE73120; ADE73126; ADE73132; ADE73134; ADE73195; ADE73198; ADE73222; ADE73226; ADE73302; ADE73369; ADE73373; ADE73501; ADE73515; ADE73560; ADE73562; ADE73620; ADE73623; ADE73625; ADE73680; ADE73686; ADE73691; ADF58790; ADJ56363; ADJ67223; ADK88901; ADM16682; ADM72744; ADM72756; ADN92672; ADN94472; ADQ48113; ADQ48123; ADQ48126; ADQ55924; ADU18062; ADU18065; ADU18072; ADU18075; ADV71253; ADW24301; ADW24331; ADX97430; ADZ38952; ADZ38955; ADZ73098; ADZ73110; ADZ73111; AEA51190; AEB21055; AEB66065; AEB66069; AEB66079; AEB66080; AEB66091; AEB66094; AEB66095; AEC47992; AEF12652; AEF13124; AEF13867; AEF13873; AEF13883; AEH95527; AEI01003; AEI01021; AEI01052; AEI30799; AEI30800; AEI59573; AEI59586; AEJ87202; AEJ87319; AEK94831; AEK94995; AEK95057; AEK95108; AEK95109; AEK95114; AEK95152; AEK95315; AEK95353; AEK95464; AEK95470; AEK95479; AEK95533; AEK95544; AEK95547; AEK95560; AEK95571; AEK95912; AEK95914; AEK95922; AEK95966; AEK95986; AEK95996; AEK96009; AEK96013; AEK96071; AEK96075; AEK96081; AEK96093; AEK96094; AER25321; AER92538; AET21249; AEU10148; AEU43542; AEW23031; AEW23037; AEW23074; AEW46916; AEY80121; AEY80127; AFA42553; AFA42586; AFA42659; AFA42751; AFA42756; AFA43494; AFD36903; AFD36916; AFD36917; AFE48752; AFH88385; AFI57825; AFJ04136; AFJ04143; AFK08606; AFK24431; AFK24437; AFK27532; AFM44706; AFN88151; AFN89850; AFP43721; AFP87507; AFQ37291; AFQ62727; AFR69130; AFS64122; AFU93073; AFV73989; AFV74025; AFV74046; AFV74078; AFV74081; AFV74083; AFV74085; AFX62386; AFX84025; AFZ93958; AFZ94402; AFZ94407; AFZ94498; AFZ94502; AFZ94527; AFZ94539; AFZ94540; AGE97340; AGG79727; AGG79794; AGG79894; AGG79898; AGG79963; AGG79966; AGK07563; AGK38318; AGK44322; AGK44377; AGL34716; AGL34724; AGL73123; AGM48499; AGO86845; AGT79701; AGT79703; AGT79704; AGU13623; AGU13631; AGU13634; AGU13639; AGW47691; AGZ87638; AGZ87639; AGZ87651; AHA37284; AHA37285; AHA37293; AHA37295; AHA37298; AHA37313; AHA53624; AHA53626; AHA53634; AHA53635; AHA90554; AHA90559; AHA92980; AHA92981; AHA92986; AHA92987; AHA92989; AHA92991; AHA92995; AHA93014; AHG52854; AHG52856; AHG52868; AHG54852; AHM24912; AHN52941; AHX83048; AHX83056; AHY61651; AHY61685; AHY61687; AHY61693; AHY61700; AHY61701; AHY61733; AHY61747; AHY61754; AHY61763; AHY61767; AHY61773; AHY61774; AHY61793; AHY61795; AHY61798; AHY61805; AHY61813; AHY61819; AHY81572; AHY81596; AHY81603; AHY81606; AHY81611; AHY81625; AHY81634; AHY81638; AHY81678; AHY81692; AHZ30852; AHZ30873; AHZ30875; AHZ30877; AHZ30882; AHZ30886; AIA10258; AIB06694; AIC77119; AIE39181; AIE39183; AIE39193; AIE39199; AIE39205; AIE39209; AIE39220; AIK19711; AIN41876; AIN41881; AIN41883; AIN41905; AIN41928; AIX09860; AIX94145; AIX94151; AIX94173; AJG01750; AJI43107; AJI43119; AJI43146; AJM93393; ALA11181; ALD83654; ALH21889; ALL98853; ALS55305; ALS87624; ALT55323; ALZ40818; AMC30598; AMH87644; AMO26197; AMO26201; AMR70991; AMR70992; AMS35084; ANG08653; ANG08654; ANG08657; ANG08663; ANG08678; ANG08682; ANG08703; ANG08706; ANG08713; ANG08719; ANG08724; ANG08726; ANG08742; ANG08746; BAA82678; BAA84113; BAB64902; BAB64906; BAB71761; BAD29715; BAD29719; BAD82816; BAF36836; BAF37802; BAF46253; BAG30816; BAG30944; BAG31991; BAH11161; BAJ83598; BAJ83632; BAK52278; BAN59797; BAO73032; BAU45194; CAA08965; CAA10726; CAA39244; CAA58070; CAA58086; CAA58090; CAA58097; CAA71137; CAA77102; CAA77194; CAA77242; CAB40714; CAB44775; CAB56342; CAB57307; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CAB86196; CAB91090; CAB98266; CAC00639; CAC03611; CAC10402; CAC15501; CAC17137; CAC17463; CAC33441; CAC34573; CAC34836; CAC38391; CAC38393; CAC41989; CAD10399; CAD10408; CAD43055; CAD43721; CAD48120; CAD54119; CAD55950; CAD67713; CAD68158; CAD68985; CAD79563; CAD89002; CAD89532; CAE30300; CAE54963; CAG24074; CAG26751; CAG33759; CAG44444; CAH04149; CAH23707; CAH61728; CAH61735; CAH61742; CAH61751; CAH61771; CAH61776; CAH61777; CAH61779; CAH61780; CAH61784; CAH89320; CAI39231; CAI54297; CAI91563; CAI94608; CAJ18634; CAJ31317; CAJ76277; CAJ80804; CAJ84020; CAJ85742; CAJ85743; CAJ85792; CAJ90723; CAK02793; CAK22320; CAL85405; CAM33242; CAM35493; CAM54065; CAN89176; CAN89606; CAO00139; CAP62365; CAP66397; CAQ17034; CAQ17036; CAQ77248; CAZ66362; CBG37836; CBH41119; CBJ05864; CBL87045; CBL94703; CBM41445; CBN82207; CBW44096; CBW44101; CBX36122; CBZ05557; CBZ47000; CCA61266; CCA63180; CCA63200; CCA63208; CCA63224; CCA63266; CCA63272; CCA63290; CCA63315; CCA63328; CCA64020; CCB84713; CCB84715; CCB84719; CCC33057; CCD32994; CCF23450; CCH03682; CCH22527; CCI61548; CCK73128; CCK73129; CCK73130; CCO56212; CCO56216; CCV19550; CCW03241; CCW36810; CCX35396; CCX39670; CCX39696; CDG32166; CDG43873; CDH35267; CDN33433; CDO33948; CDQ51703; CDX10183; CEO86997; CEO87026; CFW94257; CUX07554; CVK15080; CVK15082; CZF95219; EAX03385; SAL89105; SAP17547; AAF01052; BAG36634; BAA03277; BAA08821; ABC59614; AAA59694; AAA56835; AAA56834; AAA96733; AAC41941; AAA69724; AAL40073; AAA53258; AAA57145; AAA59641; AAA59630; AAA59684; AAA19926; AAB06829; AAB60357; AAB60359; AAA75321; AAC35422; AAC50447; AAB80796; CAA62035; CAA70199; CAA70261; CAA80366; XP_011512859; ; AAA59616; AAA59666; AAB07699; AAB47480; AAB62541; AAB66705; AAB69444; AAB70283; AAB70284; AAB70298; AAB84307; AAB96791; AAC14580; AAC33189; AAD13298; AAD14427; AAD16176; AAD22265; AAD23393; AAD23460; AAD38675; AAD38676; AAD46382; AAF00932; AAF08610; AAF19424; AAF20156; AAF24484; AAF24857; AAF59417; AAF81600; AAF81601; AAF89609; AAF97847; AAF97852; AAG01820; AAG02198; AAK66765; AAK97441; AAL10678; AAL10683; AAL18236; AAL18241; AAL31360; AAL58574; AAL62464; AAM89239; AAN05037; AAP70484; AAQ13834; AAR15394; AAT74665; AAU88210; AAV54588; AAX18629; AAX18630; AAX34394; AAX59047; AAY25028; AAY26571; AAY85374; AAZ28920; AAZ28932; AAZ67357; AAZ67358; AAZ95952; ABA07957; ABA08413; ABC55316; ABC61960; ABD62870; ABD64575; ABD64578; ABE27966; ABG23665; ABH03572; ABH85354; ABJ52524; ABJ55656; ABK96991; ABL98119; ABN15022; ABN49619; ABO10496; ABO93325; ABQ09223; ABQ09226; ABQ23499; ABS89174; ABS89175; ABW38321; ABW38323; ABY64664; ACB45469; ACB45471; ACB46958; ACC93940; ACD01074; ACD01083; ACD01086; ACM17889; ACN12928; ACN56333; ACN56337; ACN76583; ACN76586; ACN76597; ACN76603; ACN76613; ACN81065; ACN81068; ACN81077; ACN81085; ACN81091; ACN81095; ACN81112; ACN81114; ACN81125; ACN81136; ACN81138; ACN81151; ACN81154; ACN81170; ACN81244; ACN81247; ACN81250; ACN81253; ACN81278; ACN81280; ACN89838; ACN89839; ACN91040; ACO58651; ACO70683; ACO70689; ACO70695; ACO70698; ACO70716; ACO70727; ACO70728; ACO70744; ACO70745; ACO70748; ACO70760; ACO82435; ACO82450; ACO82457; ACO82474; ACO82480; ACO82522; ACO82530; ACO91514; ACO91519; ACO91520; ACO91523; ACO91544; ACO94123; ACO94135; ACO94150; ACO94153; ACP27880; ACP27888; ACP27889; ACP27899; ACP27903; ACP27907; ACR38911; ACR54333; ACS27582; ACS27592; ACS31816; ACS31819; ACS37215; ACS37234; ACS37235; ACT21196; ACT63864; ACT64591; ACT64603; ACT76266; ACT79387; ACT99999; ACU00005; ACU02042; ACU02043; ACU02050; ACU02052; ACU02058; ACU02062; ACU02077; ACU02081; ACU02090; ACU02108; ACU02180; ACU02206; ACU27279; ACU27282; ACU29548; ACU29560; ACV30330; ACV31933; ACV31942; ACV40715; ACV40718; ACV89348; ACV91888; ACY09096; ACY24447; ACZ04963; ACZ04965; ACZ04967; ADB27762; ADB55617; ADC32148; ADC81084; ADD10590; ADD10790; ADD10793; ADE58659; ADE58661; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ADE58662; ADE72869; ADE72870; ADE73062; ADE73067; ADE73072; ADE73073; ADE73078; ADE73121; ADE73218; ADE73316; ADE73375; ADE73377; ADE73386; ADE73475; ADE73505; ADE73516; ADE73567; ADE73571; ADE73619; ADE73627; ADE73673; ADE73755; ADE73820; ADI24355; ADM72755; ADN92636; ADN92638; ADN92649; ADO22684; ADQ48115; ADQ48116; ADQ48118; ADQ48119; ADQ55922; ADU18060; ADU18061; ADU18073; ADV71244; ADV71251; ADW24298; ADW24308; ADW24327; ADW24328; ADZ05623; ADZ38949; ADZ73108; ADZ73117; ADZ73118; ADZ73119; ADZ73121; AEA49740; AEA49746; AEA49750; AEA49752; AEA49872; AEA49875; AEA50947; AEB21054; AEB65791; AEB66061; AEB66096; AEF13851; AEF13852; AEF13881; AEI00996; AEI01028; AEI01032; AEI01037; AEI01050; AEI30786; AEI30796; AEI59569; AEI59576; AEI59585; AEI98732; AEJ22086; AEJ22088; AEJ87325; AEJ90515; AEJ90517; AEK67319; AEK94927; AEK94935; AEK94938; AEK95013; AEK95121; AEK95469; AEK95539; AEK95574; AEK95587; AEK95919; AEK95929; AEK95931; AEK95951; AEK95970; AEK95974; AEK96001; AEK96042; AEK96045; AEK96063; AEK96065; AEK96087; AEK96096; AEK96103; AEK96106; AEP27188; AEV45764; AEW23032; AEW23035; AEW23079; AEY80123; AFA42546; AFA42549; AFA42597; AFA42710; AFD23802; AFD23804; AFD36902; AFD36930; AFD36960; AFD36962; AFD36998; AFD64703; AFD64710; AFH78067; AFH78078; AFK24423; AFK87769; AFL91485; AFM91112; AFN88155; AFN88156; AFP43719; AFP73454; AFQ62718; AFQ62721; AFQ62725; AFQ62735; AFR69135; AFV73987; AFV73994; AFV74032; AFV74040; AFV74080; AFV74094; AFW98275; AFX62385; AFX62388; AFX84024; AFX84027; AFZ93947; AFZ93959; AFZ93966; AFZ94400; AFZ94411; AFZ94468; AFZ94496; AGB06225; AGE97332; AGG56514; AGG68843; AGG79674; AGG79708; AGG79747; AGG79780; AGG79935; AGI02597; AGI37645; AGI48704; AGJ52185; AGK07564; AGK38447; AGK44362; AGK44366; AGK44369; AGK44378; AGK44384; AGL73125; AGL73133; AGL93380; AGM48500; AGM53426; AGO28197; AGQ03747; AGS42402; AGT79702; AGU13614; AGZ87615; AGZ87621; AGZ87625; AGZ87632; AGZ87634; AGZ87636; AGZ87645; AGZ87649; AGZ87652; AHA37287; AHA37319; AHA44854; AHA46394; AHA53621; AHA90549; AHA90565; AHA92985; AHA92999; AHA93009; AHA93012; AHA93029; AHF71354; AHG52842; AHG54850; AHM24915; AHN65173; AHX83053; AHY61638; AHY61644; AHY61660; AHY61668; AHY61677; AHY61679; AHY61683; AHY61697; AHY61707; AHY61748; AHY61752; AHY61753; AHY61788; AHY81574; AHY81623; AHY81648; AHY81652; AHY81656; AHY81657; AHY81663; AHY81709; AHZ30826; AHZ30829; AHZ30832; AHZ30845; AHZ30860; AHZ30865; AHZ30870; AHZ30876; AHZ30888; AHZ30896; AHZ30903; AIB06697; AIC77112; AIC77124; AIE39196; AIE39227; AIL88458; AIN41869; AIN41871; AIN41892; AIN41895; AIN41902; AIN41916; AIN41918; AIQ80895; AIX09859; AIX94157; AIX94161; AIY26929; AJI43082; AJI43097; AJI43099; AJI43108; AJI43117; AJI76868; AKA93914; AKA93915; AKA93916; AKA93917; AKA93927; AKA93929; AKA93933; AKH87437; ALA10822; ALD83651; ALG76652; ALG76660; ALH21900; ALH21906; ALO24301; ALS87656; ALT45948; ALZ40836; AMB37048; AME17692; AML03226; AMR70985; ANG08651; ANG08655; ANG08658; ANG08662; ANG08667; ANG08674; ANG08729; ANG08732; ANG08741; ANG08744; ANG08747; BAA22205; BAA23588; BAA88572; BAB62097; BAC02740; BAD13378; BAD29720; BAD30027; BAD99583; BAE93429; BAG30941; BAG30945; BAG30956; BAG31389; BAG32143; BAH85286; BAH85287; BAI48381; BAJ78303; BAJ83602; BAL72668; BAL72727; BAL72730; BAL72732; BAM24701; BAN59779; BAN59815; BAN59821; BAO02311; BAT51026; CAA07578; CAA58078; CAA58080; CAA58082; CAA58092; CAA64228; CAA76681; CAB37943; CAB42825; CAB50864; CAB69069; CAB72096; CAC08201; CAC11131; CAC12838; CAC12864; CAC12874; CAC17462; CAC21498; CAC27238; CAC29021; CAC29240; CAC33891; CAC41988; CAC87878; CAD11988; CAD12426; CAD42656; CAD42873; CAD45438; CAD45442; CAD47824; CAD47825; CAD47828; CAD48118; CAD48121; CAD55949; CAD60653; CAD79567; CAD88897; CAD89529; CAE01414; CAE22451; CAE30299; CAE45007; CAE46109; CAE55199; CAF05628; CAG15346; CAG25514; CAG25773; CAG44552; CAH61731; CAH61755; CAH61759; CAH61765; CAH68435; CAI39218; CAI54296; CAI54298; CAI56420; CAI59269; CAI78825; CAI91545; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CAJ01383; CAJ18324; CAJ27509; CAJ27510; CAJ30029; CAJ30030; CAJ31083; CAJ76276; CAJ83997; CAL30081; CAM12256; CAM34698; CAM54069; CA000631; CAP09889; CAP46845; CAP46862; CAQ37792; CAQ55956; CAQ65001; CAX33860; CAY86113; CAZ64216; CAZ66363; CAZ90646; CBG40701; CBK62708; CBL88502; CBL88503; CBX02937; CBX25643; CBX25644; CBX25673; CBX45565; CBX55581; CBZ05558; CBZ41208; CCA63188; CCA63196; CCA63217; CCA63229; CCA63267; CCA63278; CCA63283; CCA94559; CCB84711; CCB84716; CCD31480; CCF55431; CCG14230; CCG58704; CCH27331; CCI69287; CCK33881; CCM12468; CCW03238; CCW43248; CCX39630; CDF59530; CDI43895; CDI48078; CDI48079; CDK41172; CDO33945; CDO58209; CDQ51632; CDQ51638; CDQ51677; CDQ51705; CEF48120; CEJ95860; CEO86994; CEO86995; CEO86996; CEO86998; CEO87003; CEO87004; CEO87016; CEO87019; CEO87030; CEO87034; CEO90880; CQR91443; CRK76916; CUH74624; CUT08905; CUU97278; CUU97283; CUU97286; CUU97317; CZF95220; CZS63623; P03989; P10319; P30475; Q29836; Q29940; SAI78381; SAL89112; SAL89120; AAF27539; AAL26324; AAL30414; CAA11468; BAG64567; CAM98308; AAG02001; AAM50088; BAA08822; BAA08826; BAA08827; BAA08829; BAA12868; ABC59615; AAA59621; AAA18249; AAA56837; AAC37548; AAA65639; AAC41980; AAL77533; AAL40070; AAL40071; AAA59665; AAA59647; AAA59608; AAA03687; AAA61268; AAA58628; AAD13875; AAA87396; AAB60349; AAB60360; AAC32741; AAC50392; AAB61773; AAC35423; AAA81336; AAB18369; AAC31793; CAA62864; CAA65327; CAA78849; AAA59644; AAB00144; AAB07726; AAB39106; AAB51452; AAB51454; AAB65424; AAB66706; AAB66707; AAB67810; AAB67817; AAB67821; AAB70280; AAC18817; AAC25920; AAC29503; AAC32199; AAC32561; AAC32997; AAC35939; AAC35940; AAC35941; AAC79719; AAD19590; AAD22267; AAD23458; AAD50969; AAD51971; AAF00934; AAF08606; AAF08608; AAF09480; AAF17097; AAF20813; AAF36714; AAF67340; AAF73065; AAF78090; AAF85974; AAF97848; AAF97851; AAF97853; AAF97854; AAG42274; AAG42278; AAG42281; AAG53946; AAK50429; AAL04501; AAL18234; AAL40076; AAL93257; AAN64245; AAO37684; AAR07617; AAS75119; AAT27439; AAT40957; AAT99913; AAV84071; AAV85897; AAV85899; AAV85901; AAW62302; AAW81707; AAW81709; AAW83824; AAW88317; AAX58628; AAY26572; AAY59439; AAZ15021; AAZ15025; AAZ20629; AAZ28916; AAZ67360; AAZ95953; ABA60115; ABB00288; ABB55456; ABC55315; ABC61959; ABC61961; ABC61965; ABD64572; ABD75758; ABE27967; ABF93213; ABG38307; ABK20869; ABK97605; ABL84351; ABM53026; ABM53027; ABM69180; ABM97534; ABR22623; ABS59405; ABY21170; ABY85895; ACA51865; ACB20807; ACB20808; ACC97176; ACC97179; ACC97182; ACD63063; ACK99599; ACK99600; ACN12942; ACN12946; ACN29617; ACN38393; ACN56328; ACN76594; ACN81069; ACN81078; ACN81131; ACN81141; ACN81158; ACN81163; ACN81248; ACN81257; ACN81259; ACN81277; ACN81279; ACN91043; ACO70692; ACO70693; ACO70725; ACO70726; ACO70732; ACO70734; ACO70738; ACO82434; ACO82441; ACO82443; ACO82459; ACO82475; ACO82477; ACO82479; ACO82493; ACO82495; ACO82506; ACO82509; ACO82516; ACO82525; ACO82535; ACO91529; ACO91530; ACO91541; ACO91559; ACO94131; ACO94136; ACO94138; ACO94149; ACP27892; ACP27904; ACP27960; ACP27972; ACP27978; ACR38914; ACR54356; ACR81568; ACR81574; ACS27584; ACS31814; ACS37213; ACS37217; ACS37226; ACS92458; ACT64596; ACT64618; ACT64619; ACT65992; ACT76263; ACT76684; ACT79388; ACT79392; ACT83712; ACT83715; ACU02070; ACU02071; ACU02082; ACU02086; ACU02089; ACU02093; ACU02189; ACU02220; ACU27261; ACU27262; ACU27281; ACU29547; ACU29556; ACV31931; ACV40710; ACV89457; ACV92043; ACV92046; ACX42620; ACX42626; ACX42643; ACX81372; ACX81381; ACX81383; ACZ04964; ACZ54663; ACZ54668; ACZ54672; ADB81936; ADC79835; ADD10782; ADD71855; ADD83055; ADE58658; ADE58667; ADE58668; ADE58674; ADE73063; ADE73092; ADE73093; ADE73124; ADE73194; ADE73277; ADE73308; ADE73381; ADE73400; ADE73510; ADE73559; ADE73617; ADE73626; ADE73628; ADE73690; ADE73752; ADE73817; ADE73821; ADF58789; ADF83884; ADI24371; ADJ67227; ADM72743; ADM72760; ADN92645; ADN92648; ADN92669; ADN92674; ADU18064; ADU18068; ADU18071; ADV71246; ADZ38953; ADZ73094; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ADZ73096; ADZ73114; ADZ73125; AEA48886; AEA48984; AEA49731; AEA49759; AEB66062; AEB66066; AEB66067; AEB66068; AEB66092; AEE39324; AEF12647; AEF12648; AEF13121; AEF13871; AEF13876; AEF13888; AEI00994; AEI01011; AEI01023; AEI01047; AEI30797; AEI30798; AEI59563; AEI59564; AEI59588; AEI70713; AEI98731; AEJ10022; AEK94931; AEK94941; AEK95062; AEK95115; AEK95127; AEK95129; AEK95132; AEK95144; AEK95147; AEK95321; AEK95357; AEK95466; AEK95478; AEK95540; AEK95541; AEK95556; AEK95561; AEK95583; AEK95584; AEK95586; AEK95589; AEK95594; AEK95917; AEK95981; AEK95999; AEK96014; AEK96017; AEK96025; AEK96083; AEK96092; AEK96100; AEK96107; AEO22186; AEP17329; AEP17330; AEU10142; AEV53354; AEW23027; AEW23028; AEW23034; AEW23038; AEW68006; AEW90675; AEY80122; AFA41740; AFA42476; AFA42482; AFA42555; AFA42592; AFA42649; AFA42664; AFA42711; AFD23788; AFD23796; AFD36899; AFD36906; AFD36936; AFD36996; AFD64693; AFD64713; AFE88967; AFH78063; AFH78069; AFH78071; AFH78082; AFI57832; AFJ04145; AFJ44774; AFJ44775; AFK08521; AFK24429; AFK24435; AFK64708; AFK87767; AFM77796; AFN88145; AFO66770; AFO66771; AFO70113; AFQ62722; AFQ90207; AFR54425; AFU93074; AFU93841; AFV74023; AFV74038; AFV74084; AFV74093; AFV74674; AFZ93956; AFZ93957; AFZ94399; AFZ94500; AFZ94591; AFZ94592; AGD99114; AGG68840; AGG79683; AGG79685; AGG79743; AGG79744; AGG79795; AGG80026; AGH25494; AGK44368; AGM20578; AGN74857; AGO59961; AGX13896; AGX13904; AGZ87618; AGZ87619; AGZ87620; AGZ87622; AGZ87628; AGZ87629; AGZ87644; AGZ87654; AGZ87663; AGZ87664; AGZ87671; AGZ87683; AHA37274; AHA37279; AHA37282; AHA37307; AHA37317; AHA46396; AHA46398; AHA46400; AHA46405; AHA92979; AHA92988; AHA93007; AHF52839; AHF52846; AHF71353; AHH92856; AHK23752; AHY61634; AHY61637; AHY61658; AHY61686; AHY61722; AHY61769; AHY61777; AHY61781; AHY61809; AHY81590; AHY81594; AHY81629; AHY81681; AHY81683; AHY81698; AHY81703; AHZ30816; AHZ30833; AHZ30834; AHZ30840; AHZ30855; AHZ30869; AHZ30871; AHZ30878; AHZ30887; AHZ30891; AHZ30904; AHZ62763; AIB06696; AIC77106; AIC77114; AIC77123; AIE39185; AIE39216; AIN40495; AIN41863; AIN41866; AIN41868; AIN41901; AIN41922; AIQ78392; AIX94135; AIX94142; AIX94144; AIX94155; AJA90832; AJI43101; AJI43115; AJI43116; AKA93911; AKA93919; AKE47355; AKK23740; AKN09957; AKQ99119; ALA65381; ALA65382; ALL25695; ALO23538; ALT08033; ALT31486; AMB37049; AMD16555; AML03224; AML81031; AMO26202; AMQ81183; AMR70923; AMR70927; AMR70986; AMR70987; ANG08665; ANG08670; ANG08680; ANG08688; ANG08692; ANG08698; ANG08716; ANG08720; ANG08730; ANG08745; BAA07944; BAB18306; BAC02738; BAC02741; BAC11811; BAC54941; BAD27528; BAD29717; BAD30026; BAE78655; BAE93256; BAE95334; BAF63624; BAG30916; BAG30917; BAG30947; BAH48247; BAH85285; BAI52765; BAI52850; BAI52963; BAI66042; BAI66045; BAJ25766; BAL72729; BAM24700; BAN51778; BAN63380; CAA06616; CAA10754; CAA27302; CAA58088; CAA58099; CAA74916; CAA76612; CAA94390; CAB37940; CAB40715; CAB43478; CAB83041; CAB86194; CAB92313; CAB98264; CAC01694; CAC07211; CAC12861; CAC12862; CAC12866; CAC12876; CAC24484; CAC33440; CAC33892; CAC38066; CAC38763; CAC87132; CAD10406; CAD10413; CAD10414; CAD12423; CAD12425; CAD22131; CAD22132; CAD22133; CAD43056; CAD43645; CAD47829; CAD79562; CAD79566; CAD87773; CAD90011; CAD91416; CAD92861; CAE12197; CAE30458; CAE45177; CAE46176; CAG44445; CAH55767; CAH61726; CAH61729; CAH61730; CAH61734; CAH61738; CAH61743; CAH61744; CAH61762; CAI29181; CAI46274; CAI46900; CAI79093; CAI94663; CAJ01770; CAJ18327; CAJ29287; CAJ30031; CAJ38413; CAJ77418; CAJ80870; CAJ91096; CAL36609; CAL47252; CAM33395; CAM33599; CAM84027; CAN84677; CAO94504; CAP17405; CAP58275; CAQ35181; CAR67866; CAT99520; CAX12624; CBI71169; CBK52926; CBX19707; CBX36120; CBX45600; CBY83777; CCA28517; CCA63174; CCA63176; CCA63177; CCA63187; CCA63195; CCA63203; CCA63212; CCA63223; CCA63225; CCA63227; CCA63270; CCA63271; CCA63279; CCA63288; CCB84714; CCG14229; CCH57811; CCI55631; CCI61354; CCO56210; CCV19548; CDH92860; CDH97909; CDI27938; CDI44685; CDI48080; CDK41191; CDL74822; CDO58211; CDR89236; CDX10187; CEE15327; CEF48040; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CEH24664; CEO86990; CEO87001; CEO87005; CEO87009; CEO87017; CEO87024; CTP93520; CUR70741; CUR70746; CUU97281; CUU97282; CUU97287; CUU97288; CUX07549; CUX91848; CZF95218; CZT32967; CZT32968; EAX03384; EAX03386; P30480; P30483; P30491; P30498; SAL89101; SAL89114; AAD50968; AAL30412; AAL30413; CAA05834; CAB88037; BAG54016; BAF83259; AAO34409; CDH93737; AAA36217; AAC37572; AAL77528; AAC41979; AAL77530; AAL77532; AAL77531; AAA61297; AAA60305; AAA50577; AAA03719; AAA92997; AAA19925; AAA75592; AAB40632; AAB41720; AAB39257; CAA59215; CAA62036; CAA73901; AAA52658; AAA52661; AAA59627; AAA59662; AAA59664; AAA65040; AAA74045; AAA97481; AAB03576; AAB50143; AAB50146; AAB50417; AAB50419; AAB62540; AAB67807; AAB67811; AAB67812; AAB70286; AAB82333; AAB96793; AAC26002; AAC32568; AAC32570; AAC32821; AAC35937; AAD02035; AAD22273; AAD23459; AAD26151; AAD28786; AAD30276; AAD46385; AAD51744; AAF04579; AAF05596; AAF20814; AAF26413; AAF29556; AAF73067; AAF78047; AAF78080; AAF89555; AAF97855; AAF97856; AAG01819; AAG10154; AAG27470; AAG31646; AAG40883; AAG42271; AAG42282; AAK31805; AAK57725; AAK57734; AAK94506; AAK94508; AAK94513; AAL08024; AAL18233; AAP55803; AAQ13832; AAQ55467; AAQ75375; AAR15889; AAR87010; AAT74662; AAT74664; AAT74666; AAU06587; AAV54589; AAV85898; AAW65334; AAW66600; AAX63419; AAZ15020; AAZ28913; AAZ28914; AAZ73722; ABB52626; ABC84218; ABD93918; ABE27968; ABF60563; ABG37693; ABG66731; ABH03576; ABI64162; ABI74453; ABI96691; ABJ09708; ABK20870; ABL98036; ABM67084; ABN42643; ABN51224; ABO14986; ABO69698; ABP51958; ABQ08745; ABQ09222; ABQ09225; ABQ16592; ABQ23496; ABR24118; ABW38025; ABW38324; ABY85892; ACA48229; ACB05659; ACB13199; ACB45464; ACC97172; ACD01073; ACD01088; ACD63062; ACF20359; ACF75465; ACF77152; ACH61853; ACI04546; ACI43064; ACJ09137; ACK37874; ACK99604; ACK99607; ACL51023; ACM17888; ACM17892; ACM24221; ACN12939; ACN12950; ACN29616; ACN56338; ACN58389; ACN76580; ACN76582; ACN76599; ACN81073; ACN81092; ACN81135; ACN81148; ACN81243; ACN81251; ACN81263; ACN81270; ACN81274; ACN81281; ACN81282; ACN89837; ACN96127; ACO35692; ACO70680; ACO70694; ACO70709; ACO82436; ACO82461; ACO82491; ACO82496; ACO82500; ACO82517; ACO82518; ACO82532; ACO91540; ACO94124; ACO94134; ACP27882; ACP27886; ACP27900; ACP27902; ACP27979; ACP27985; ACR38910; ACR54339; ACR54340; ACR54355; ACS27676; ACS31815; ACS37219; ACS37228; ACS37230; ACT64617; ACT64625; ACT83701; ACT83710; ACU01987; ACU01991; ACU02040; ACU02059; ACU02087; ACU02091; ACU02094; ACU02104; ACU02182; ACU02208; ACU02211; ACU02213; ACU02218; ACU27257; ACU27267; ACU27273; ACU29553; ACU29554; ACU29555; ACU31097; ACU68588; ACU86977; ACV31937; ACV31941; ACV31945; ACV40705; ACV89471; ACX34101; ACX42635; ACX42637; ACX81384; ACY24885; ACZ54652; ACZ54655; ACZ54660; ACZ54667; ACZ73427; ADB25053; ADB55622; ADB81937; ADC79836; ADC81085; ADD10588; ADD10595; ADD10784; ADD97858; ADE58663; ADE58677; ADE73060; ADE73082; ADE73086; ADE73130; ADE73139; ADE73142; ADE73225; ADE73274; ADE73287; ADE73306; ADE73310; ADE73312; ADE73364; ADE73368; ADE73476; ADE73478; ADE73479; ADE73683; ADE73685; ADE73819; ADI24372; ADI25073; ADI75497; ADJ67216; ADN92654; ADN92670; ADN93294; ADP09055; ADQ48124; ADQ55918; ADU18063; ADU18506; ADW24302; ADW24304; ADW24315; ADW24321; ADZ73099; ADZ73113; ADZ73115; ADZ73128; AEA49768; AEB65805; AEB65806; AEB66057; AEB66070; AEF13115; AEF13858; AEF13866; AEF13869; AEI01005; AEI01014; AEI01033; AEI30790; AEI30793; AEI30794; AEI59572; AEJ08641; AEJ87204; AEJ87332; AEJ88778; AEJ90505; AEJ90516; AEK94900; AEK94929; AEK94934; AEK94937; AEK94940; AEK94942; AEK94943; AEK95063; AEK95112; AEK95134; AEK95148; AEK95308; AEK95311; AEK95324; AEK95458; AEK95460; AEK95472; AEK95545; AEK95563; AEK95916; AEK95927; AEK95935; AEK95939; AEK95963; AEK95977; AEK96026; AEK96032; AEK96068; AEK96073; AEK96076; AEK96078; AEK96090; AEK96101; AEK96102; AEL16987; AEP16443; AEP17325; AER92536; AET21250; AET98767; AEW23026; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AEW23033; AEW90668; AEW90669; AEW90670; AEW90671; AEW90676; AEW90680; AEY77525; AEZ49178; AFA42545; AFA42647; AFA42712; AFD23781; AFD23793; AFD36934; AFD36995; AFD64690; AFD64698; AFJ04138; AFJ04141; AFJ04146; AFJ44772; AFJ44782; AFJ44783; AFJ44784; AFJ44799; AFK24419; AFK24422; AFK24439; AFK64706; AFK64710; AFL91486; AFM44703; AFM44708; AFM55928; AFP43715; AFP43722; AFP54195; AFP73451; AFP99303; AFQ55484; AFQ55488; AFQ55493; AFQ62733; AFQ62737; AFR68835; AFU73593; AFU81205; AFU93844; AFV74041; AFV74076; AFV74088; AFV74097; AFX62389; AFX84026; AFZ93949; AFZ93968; AFZ94495; AFZ94497; AFZ94499; AFZ94534; AFZ94538; AFZ94621; AGC54625; AGC95095; AGC95096; AGE97329; AGG56511; AGG79672; AGG79673; AGG79777; AGG79790; AGG79791; AGG79806; AGG79929; AGG79933; AGG79936; AGG79941; AGI05710; AGI65158; AGJ84090; AGK38319; AGK44315; AGL34710; AGL34712; AGL34717; AGL34720; AGL34722; AGL34723; AGL73118; AGL73128; AGM48494; AGT51198; AGT79696; AGW18229; AGX13891; AGZ87617; AGZ87633; AGZ87637; AGZ87640; AGZ87655; AGZ87659; AGZ87665; AGZ87673; AGZ87674; AGZ87677; AHA37311; AHA37312; AHA37318; AHA37325; AHA46401; AHA46406; AHA53631; AHA90551; AHA90555; AHA90578; AHA92982; AHA92984; AHA92996; AHA92997; AHA93005; AHA93011; AHA93030; AHC92620; AHF71348; AHG54853; AHL39252; AHW68478; AHX83047; AHY61654; AHY61663; AHY61666; AHY61678; AHY61694; AHY61714; AHY61724; AHY61751; AHY61764; AHY61782; AHY61802; AHY61815; AHY61822; AHY81576; AHY81578; AHY81587; AHY81598; AHY81600; AHY81622; AHY81644; AHY81650; AHY81667; AHY81668; AHY81670; AHY81675; AHY81695; AHZ30819; AHZ30823; AHZ30850; AHZ30874; AHZ30900; AHZ30914; AIE39180; AIE39184; AIE39203; AIE39207; AIE39212; AIE39229; AII80552; AIN41873; AIN41874; AIN41893; AIN41929; AIN41931; AIQ80896; AIX94149; AIX94160; AIX94165; AJI43093; AJI43102; AJI43110; AJI43113; AJI43118; AJI43123; AJI43127; AKA93937; AKA93939; AKE14221; AKG62086; AKG95444; AKH87441; AKO84202; ALG76650; ALG76663; ALH21907; ALO23537; ALP73448; ALS55306; ALZ40817; ALZ40828; AMD11595; AMH86043; AML03225; AMP83990; AMS25592; AMX81295; ANG08644; ANG08648; ANG08650; ANG08656; ANG08659; ANG08661; ANG08666; ANG08668; ANG08671; ANG08672; ANG08689; ANG08691; ANG08699; ANG08731; ANG08734; ANG08737; BAA82676; BAA84114; BAC02739; BAC11810; BAD13377; BAD27530; BAD30030; BAD77940; BAD95616; BAD95811; BAD95812; BAD98467; BAE78632; BAF32753; BAF56918; BAG30815; BAG31387; BAG32146; BAH11162; BAH85289; BAI66043; BAL72663; BAM15777; BAN59809; BAN59833; BAN63382; BAP82420; CAA10522; CAA58085; CAA58091; CAA64227; CAA75059; CAA76682; CAA77103; CAB38945; CAB50865; CAB71933; CAB71937; CAB94227; CAC05371; CAC12837; CAC12869; CAC12870; CAC12875; CAC15502; CAC16172; CAC18875; CAC35468; CAC38863; CAC87136; CAD10396; CAD10410; CAD10411; CAD10412; CAD11989; CAD43181; CAD43182; CAD43184; CAD45441; CAD47826; CAD79443; CAD79474; CAD79564; CAD79565; CAD91417; CAE02643; CAE22466; CAE22467; CAE22484; CAE45171; CAE47421; CAE51940; CAE82735; CAE82737; CAE82739; CAG25673; CAH04148; CAH61752; CAH61753; CAH61754; CAH61760; CAH61763; CAH61766; CAJ28576; CAJ85944; CAL36608; CAL90886; CAM34699; CAO00836; CAO85638; CAO85722; CAP20081; CAQ17035; CBW44100; CBW44125; CBW44127; CBW47478; CBW69645; CBX19710; CBX36121; CBZ05559; CBZ47172; CCA63179; CCA63183; CCA63184; CCA63185; CCA63198; CCA63205; CCA63226; CCA63256; CCA63274; CCA63287; CCA63292; CCA63317; CCB63202; CCB84718; CCB84721; CCF23269; CCH35762; CCJ27668; CCJ70647; CCK73127; CCM12470; CCN79819; CCW03232; CCW03236; CCW36811; CCX39681; CDI48083; CDK41190; CDL93446; CDN39815; CDQ51675; CEE15326; CEF48038; CEF48056; CEF48090; CEH11577; CEO86987; CEO86993; CEO87006; CEO87018; CEO87023; CEO87025; CEO87027; CQR75221; CQR91444; CRF45622; CTP93680; CUR44395; CUW00369; P18463; P18464; P18465; P30460; P30462; P30466; P30479; P30492; P30493; SAI83281; SAL89102; SAL89121; SAL89122; AAC17467; AAB81828; AAC42275; BAF84915; AAS79490; BAA08823; BAA08828; AAA73509; AAB59484; AAL77535; AAA59607; AAA03690; AAA03688; AAA59634; AAA17373; AAF70855; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AAA91229; AAB19242; AAB70114; AAB16919; CAA43875; CAA45785; CAA53566; CAA58317; AAA02950; AAA59667; AAA59682; AAA74046; AAB03574; AAB18131; AAB29305; AAB39108; AAB50145; AAB61335; AAB67808; AAB67813; AAB67814; AAB67824; AAB67827; AAB67828; AAB70287; AAB70294; AAB80722; AAB82057; AAB82304; AAB82306; AAB87723; AAB94028; AAC14582; AAC14881; AAC18391; AAC25779; AAC25780; AAC26783; AAC32560; AAC32562; AAC32572; AAC33188; AAC35938; AAC41923; AAC79720; AAD02034; AAD22266; AAD23395; AAD27536; AAD28172; AAD31431; AAD38677; AAD46386; AAD48506; AAD51746; AAF05898; AAF19393; AAF19425; AAF19428; AAF21438; AAF26305; AAF26751; AAF36715; AAF70329; AAF73066; AAF76144; AAF78083; AAG27466; AAK51092; AAK57736; AAL04500; AAL10679; AAL11335; AAL59419; AAL73385; AAL77051; AAL84755; AAL87224; AAM14398; AAM16153; AAM95705; AAP23305; AAQ55468; AAT74663; AAT99914; AAV36001; AAV54590; AAV54591; AAW47400; AAW71782; AAX22231; AAX56910; AAX63418; AAY40252; AAY57924; AAZ15018; AAZ15024; AAZ23041; AAZ67359; AAZ95590; ABA39797; ABB51651; ABC61958; ABC61963; ABC94580; ABD93914; ABE27964; ABF58778; ABF60561; ABF74595; ABJ99998; ABK51451; ABK90988; ABK96978; ABL73204; ABL98037; ABM97420; ABN49618; ABN51221; ABN51230; ABP57140; ABU94839; ABW38327; ABW38328; ABY64663; ACA51863; ACA79907; ACB45462; ACB56574; ACC97177; ACC97178; ACD63061; ACG55682; ACH57397; ACH57402; ACJ04569; ACL51028; ACL97991; ACL98163; ACM17887; ACM17890; ACN12943; ACN56330; ACN76591; ACN76595; ACN76600; ACN76604; ACN76611; ACN81066; |
| SLEA Up | HLA-C | P30508 | ; AAA59648; AAA59670; AAB03583; AAB03623; AAB66710; AAB66711; AAC17719; AAC17725; AAC17737; AAF19427; AAF65514; AAG42272; AAG49322; AAK31618; AAL87225; AAN33107; AAO49822; AAP30863; AAR06668; AAR15147; AAR87009; AAR99590; AAT65966; AAW88385; AAX18631; AAX94769; ABB52622; ABB52623; ABD60574; ABE00936; ABG43100; ABR31792; ABS29298; ABV58993; ABW21685; ABW86961; ABY74344; ACE63274; ACE63275; ACF54630; ACL34372; ACL37146; ACL98474; ACM78893; ACM78896; ACM78902; ACM78916; ACM78931; ACM78932; ACM78937; ACM78941; ACN24631; ACN81046; ACN81048; ACN81050; ACN81055; ACN81056; ACN81063; ACN81286; ACN81292; ACN89850; ACN89857; ACN89858; ACN91016; ACN91025; ACN91027; ACN97202; ACO90079; ACO90083; ACP27913; ACP27944; ACP27956; ACR54368; ACR54378; ACR54383; ACR54391; ACR54393; ACR78562; ACR78564; ACS12735; ACS27603; ACS27607; ACS27628; ACS27633; ACS27638; ACS27662; ACS27668; ACS27694; ACS36190; ACS36192; ACS36194; ACS36202; ACS36419; ACS36435; ACS36440; ACS36453; ACS36454; ACS36464; ACS36472; ACT76247; ACT76254; ACT83720; ACU01995; ACU01997; ACU01999; ACU02003; ACU02012; ACU02018; ACU02116; ACU02120; ACU27291; ACU27292; ACU27294; ACU27309; ACU27312; ACU27315; ACU29590; ACU29591; ACU50938; ACU50945; ACU50947; ACU78141; ACV03835; ACV30334; ACV40724; ACV40726; ACV40736; ACV40738; ACV40741; ACV89476; ACV92057; ACX42656; ACX42668; ACX53677; ACX81408; ADB80083; ADB91969; ADC32130; ADC32131; ADC32132; ADC32136; ADC32139; ADC32166; ADC32178; ADC32179; ADC32190; ADC32206; ADC32224; ADC45460; ADC45470; ADC45480; ADC45483; ADC79685; ADC79844; ADC79850; ADC79868; ADC79870; ADC79881; ADC79983; ADC79986; ADC79994; ADC79999; ADC80000; ADC80006; ADC80016; ADC80019; ADC80035; ADC80039; ADC80041; ADC80066; ADC80069; ADD10599; ADD71850; ADE58708; ADE58734; ADE58743; ADE72879; ADE72904; ADE72910; ADE72912; ADE72933; ADE72946; ADE72949; ADE72977; ADE72982; ADE72988; ADE73040; ADE73147; ADE73155; ADE73160; ADE73183; ADE73206; ADE73215; ADE73245; ADE73250; ADE73257; ADE73321; ADE73332; ADE73404; ADE73424; ADE73458; ADE73459; ADE73483; ADE73487; ADE73488; ADE73520; ADE73533; ADE73535; ADE73574; ADE73584; ADE73630; ADE73714; ADE73731; ADE73733; ADE73738; ADE73828; ADE73830; ADE73834; ADI24370; ADM72761; ADM72769; ADM72772; ADM72781; ADN92613; ADN92615; ADN92616; ADU18056; ADU18057; ADV78237; ADV78582; ADZ05543; ADZ05558; ADZ05566; ADZ05568; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ADZ38968; ADZ73132; ADZ73136; ADZ73142; ADZ73147; ADZ73154; AEA49826; AEA49827; AEB91581; AEF13134; AEF13900; AEF13902; AEF13904; AEF13907; AEF13925; AEF13933; AEF13945; AEF13956; AEI01059; AEI01062; AEI01063; AEI01067; AEI01068; AEI30805; AEI30815; AEI30826; AEI58954; AEI58958; AEI59603; AEI59606; AEJ22102; AEJ22103; AEJ90524; AEK67334; AEK67337; AEK67338; AEK67343; AEK67351; AEK94845; AEK94890; AEK94894; AEK94951; AEK94952; AEK94954; AEK94955; AEK94960; AEK95014; AEK95068; AEK95072; AEK95078; AEK95083; AEK95084; AEK95087; AEK95088; AEK95093; AEK95157; AEK95167; AEK95169; AEK95180; AEK95192; AEK95193; AEK95331; AEK95369; AEK95390; AEK95392; AEK95403; AEK95404; AEK95405; AEK95412; AEK95416; AEK95417; AEK95421; AEK95425; AEK95427; AEK95428; AEK95439; AEK95442; AEK95447; AEK95453; AEK95456; AEK95598; AEK95607; AEK95612; AEK95615; AEK95620; AEK95622; AEK95630; AEK95632; AEK95645; AEK95650; AEK95698; AEK95699; AEK95704; AEK95706; AEK95710; AEK96112; AEK96120; AEK96122; AEK96123; AEK96130; AEK96144; AEK96146; AEK96153; AEK96159; AEK96170; AEK96171; AEK96186; AEK96188; AEK96205; AEK96207; AEK96224; AEK96228; AEK96253; AEK96266; AEK96294; AEK96307; AET21253; AET21254; AEW23046; AEW23051; AEW23094; AEW23095; AEW23098; AEW90701; AFA41746; AFA41753; AFA42443; AFA42510; AFA42565; AFA42604; AFA42609; AFA42612; AFA42615; AFA42667; AFA42670; AFA42677; AFA42728; AFA42762; AFA42772; AFD23815; AFD23818; AFD23842; AFD23843; AFD23852; AFD36911; AFD36912; AFD36953; AFD36976; AFD37005; AFD64715; AFD64716; AFD64718; AFD64726; AFD64730; AFD64733; AFD64740; AFD64743; AFE48726; AFE48742; AFE48743; AFE83588; AFE88959; AFG26503; AFL91490; AFM35817; AFM77808; AFM77809; AFM77813; AFM77815; AFM77817; AFM77818; AFN88161; AFN88162; AFN88164; AFN88175; AFQ62760; AFQ62761; AFQ62765; AFQ62770; AFU93090; AFU93092; AFU93094; AFU93095; AFU93096; AFZ93990; AFZ94012; AFZ94025; AFZ94031; AFZ94032; AFZ94036; AFZ94040; AFZ94051; AFZ94053; AFZ94057; AFZ94060; AFZ94080; AFZ94083; AFZ94084; AFZ94103; AFZ94104; AFZ94115; AFZ94117; AFZ94119; AFZ94121; AFZ94129; AFZ94130; AFZ94134; AFZ94136; AFZ94143; AFZ94146; AFZ94149; AFZ94150; AFZ94162; AFZ94168; AFZ94208; AFZ94212; AFZ94219; AFZ94222; AFZ94230; AFZ94239; AFZ94241; AFZ94246; AFZ94414; AFZ94418; AFZ94439; AFZ94443; AFZ94446; AFZ94471; AFZ94513; AFZ94517; AFZ94519; AFZ94545; AFZ94594; AFZ94600; AGC22563; AGG40972; AGG79687; AGG79713; AGG79813; AGG79905; AGG79999; AGI48710; AGK44329; AGK44332; AGL09219; AGL73134; AGL73136; AGL73144; AGL93374; AGM48501; AGM48504; AGQ16892; AGQ16895; AGQ16905; AGQ16919; AGQ16923; AGQ16937; AGQ16939; AGQ16944; AGQ16977; AGQ16979; AGQ16987; AGS13720; AGV53072; AGX13915; AGZ87701; AGZ87709; AGZ87713; AGZ87730; AGZ87743; AGZ87747; AGZ87763; AGZ87765; AGZ87779; AGZ87780; AGZ87782; AGZ87802; AGZ87809; AGZ87813; AGZ87826; AHA46414; AHA46416; AHA46436; AHA53645; AHA53648; AHA53649; AHA80969; AHA90714; AHA90725; AHA90741; AHA90749; AHA90765; AHA90773; AHA90774; AHA90784; AHA90796; AHA90800; AHA90801; AHA93023; AHC08481; AHF52847; AHG52873; AHL20279; AHY61830; AHY61831; AHY61841; AHY61852; AHY61857; AHY61878; AHY61890; AHY61900; AHY61909; AHY61911; AHY61918; AHY61936; AHY61937; AHY61942; AHY61949; AHY61958; AHY61963; AHY61991; AHY62006; AHY81714; AHY81726; AHY81732; AHY81738; AHY81744; AHY81752; AHY81762; AHY81764; AHY81771; AHY81783; AHY81785; AHY81788; AHY81794; AHY81809; AHY81812; AHY81820; AHY81832; AHY81833; AHY81836; AHZ30938; AHZ30943; AHZ30945; AHZ30950; AHZ30967; AHZ30989; AHZ30996; AHZ31005; AHZ31014; AIB55780; AIE39250; AIE39267; AIE39278; AIE39284; AIE39291; AIE39292; AIN41953; AIN41964; AIN41981; AIN41984; AIR95105; AIX94181; AIX94186; AIX94192; AIX94194; AIX94197; AIX94199; AIX94206; AIX94207; AIX94211; AJA90819; AJA90821; AJI43152; AJI43154; AJI43160; AJI43161; AJI43162; AJI43167; AJI43170; AJI43173; AJI43182; AJI43210; AJI43214; AJI43221; AJI43225; AJW76731; AJW76741; AKA93944; AKA93947; AKA93971; AKA93981; AKA93985; AKJ66248; AKP18566; ALL98858; ALM26180; ALO24303; ALO24304; ALZ40825; AMD11594; AMD16554; AMR70859; AMR70924; AMR74920; ANG08617; ANG08629; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ANG08630; ANG08640; BAB63310; BAE76022; BAJ12111; BAJ39877; BAJ83635; BAK82020; BAK82023; BAL41374; BAL41376; BAL41478; BAL41479; BAN59816; BAN59834; BAN60467; BAO02314; CAA75756; CAB44356; CAB71800; CAC11132; CAC79613; CAD12428; CAD12436; CAD12437; CAD12801; CAD47856; CAD90009; CAE22465; CAE84101; CAF33342; CAH40829; CAI48027; CAJ97443; CAK02799; CAL33985; CAM23859; CAM23874; CAQ51272; CAQ60108; CBK13146; CBL88505; CBV65829; CBW44114; CBW47475; CBW52907; CBX19684; CBX19688; CBX19689; CBX24359; CBX25670; CBX36126; CBX36133; CBX45593; CBY83776; CCB84260; CCB84264; CCB84271; CCB84272; CCB84283; CCB84304; CCB84306; CCB84307; CCB84337; CCB84340; CCB84347; CCB84350; CCB84394; CCB84397; CCB84402; CCB84409; CCB84420; CCB84425; CCD28284; CCD31403; CCH23040; CCH57805; CCH57810; CCO56208; CDG23682; CDG23683; CDK41193; CDO33942; CDO67986; CDQ51634; CDQ51650; CDQ51653; CDQ51678; CDQ51694; CDQ51699; CEF48046; CEF48058; CEF48075; CEG29916; CEP25294; CEP25308; CEP25312; CEP25317; CEP25332; CEP25338; CQR75219; CRK76920; CTQ34887; CUH82789; CUI25656; CUU97107; CUU97108; CUU97118; CUU97130; CUU97161; CUU97169; CUU97171; CUU97178; CUU97194; CUU97197; CUU97211; CUU97216; CUU97244; CUU97246; CUU97249; CUU97250; CUU97254; CUU97296; CUU97301; CUV03804; CUX91021; CUX91028; CUX91041; CUX91053; CUX91849; EAX03376; P30508; Q29960; BAA32615; CBJ19438; AFH75432; AAA52666; AAA36235; AAA57258; AAA59685; AAA59686; CAA50210; CAA65986; CAA86839; AAA81371; AAB03581; AAB03624; AAB48516; AAB70288; AAC17716; AAC17721; AAC17722; AAF33239; AAK69510; AAM14725; AAM44831; AAM91947; AAO73564; AAR10880; AAT39989; AAT46360; AAU14145; AAW21339; AAX98239; AAZ28915; AAZ28917; ABB16354; ABB55457; ABC47332; ABC59292; ABD64576; ABJ52522; ABN79858; ACA51861; ACC86064; ACF54637; ACF95806; ACG50686; ACI62420; ACK77783; ACM78904; ACM78913; ACM78923; ACM78925; ACM78927; ACM78928; ACM78938; ACM78942; ACN24627; ACN24630; ACN24632; ACN81044; ACN81057; ACN81217; ACN81222; ACN81287; ACN81288; ACN89847; ACN91012; ACN91013; ACN91015; ACN91022; ACN91023; ACN97192; ACO06754; ACP27909; ACP27916; ACP27954; ACQ76715; ACR54361; ACR54385; ACR54390; ACR78567; ACS12741; ACS12748; ACS12749; ACS16070; ACS27606; ACS27635; ACS27640; ACS27656; ACS27658; ACS27659; ACS27700; ACS36182; ACS36203; ACS36423; ACS36424; ACS36445; ACS36457; ACS36460; ACS36462; ACS36469; ACS36474; ACS93143; ACT76249; ACT76253; ACT79367; ACT79380; ACT79384; ACT83722; ACT83724; ACU02031; ACU02032; ACU02125; ACU27284; ACU27295; ACU27314; ACU50930; ACU50940; ACU50941; ACU50948; ACV40733; ACV40742; ACV89473; ACV91114; ACV91117; ACV91124; ACV92060; ACX42654; ACX81397; ACX81400; ACX81407; ACX94082; ADB80078; ADB81945; ADB81946; ADC32140; ADC32188; ADC32193; ADC32195; ADC32200; ADC32203; ADC32204; ADC32217; ADC32220; ADC45456; ADC45466; ADC45467; ADC45476; ADC79848; ADC79859; ADC79863; ADC79880; ADC79973; ADC79976; ADC79984; ADC79991; ADC80008; ADC80013; ADC80014; ADC80021; ADC80052; ADC80054; ADC80056; ADC80059; ADC80063; ADD10604; ADD97863; ADE58700; ADE58701; ADE58704; ADE58705; ADE58706; ADE58709; ADE58715; ADE58716; ADE58719; ADE58721; ADE58733; ADE58737; ADE58747; ADE58753; ADE72889; ADE72891; ADE72893; ADE72903; ADE72905; ADE72922; ADE72942; ADE72969; ADE72981; ADE72995; ADE73039; ADE73041; ADE73048; ADE73149; ADE73161; ADE73174; ADE73238; ADE73240; ADE73249; ADE73269; ADE73336; ADE73394; ADE73413; ADE73422; ADE73486; ADE73518; ADE73523; ADE73529; ADE73583; ADE73585; ADE73587; ADE73633; ADE73637; ADE73694; ADE73704; ADE73707; ADE73709; ADE73734; ADE73740; ADE73743; ADE73745; ADE73746; ADE73833; ADH04229; ADI24365; ADI24369; ADM72779; ADM72782; ADM72788; ADM72789; ADN92618; ADQ55904; ADU18051; ADU18500; ADX97429; ADZ05538; ADZ05541; ADZ05548; ADZ05553; ADZ05564; ADZ31189; ADZ73150; ADZ73153; ADZ73157; AEA49816; AEA49831; AEA49836; AEA49838; AEA49841; AEB21065; AEB21069; AEB26707; AEB65788; AEF13147; AEF13898; AEF13903; AEF13911; AEF13951; AEF13958; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AEF13959; AEF13964; AEH41458; AEI01065; AEI01070; AEI30804; AEI30816; AEI30825; AEI58955; AEI59596; AEI59607; AEI87646; AEJ87317; AEJ87330; AEJ90523; AEK94834; AEK94949; AEK94957; AEK95011; AEK95016; AEK95017; AEK95019; AEK95096; AEK95174; AEK95175; AEK95182; AEK95184; AEK95203; AEK95207; AEK95360; AEK95364; AEK95375; AEK95376; AEK95398; AEK95434; AEK95437; AEK95445; AEK95454; AEK95455; AEK95609; AEK95610; AEK95613; AEK95621; AEK95625; AEK95633; AEK95637; AEK95642; AEK95659; AEK95672; AEK95688; AEK95701; AEK95705; AEK95707; AEK96111; AEK96124; AEK96125; AEK96133; AEK96147; AEK96190; AEK96198; AEK96199; AEK96202; AEK96216; AEK96226; AEK96237; AEK96238; AEK96242; AEK96278; AEP39695; AEP39697; AER28318; AEW22797; AEW23084; AEW23091; AEW23092; AEW23102; AEW90683; AEW90691; AEW90693; AEY80116; AFA41752; AFA42062; AFA42520; AFA42558; AFA42559; AFA42567; AFA42610; AFA42680; AFA42770; AFC90105; AFD23820; AFD23821; AFD23828; AFD23829; AFD23846; AFD23848; AFD23856; AFD29103; AFD36908; AFD36943; AFD36972; AFD36975; AFD37007; AFD37010; AFD64720; AFD64724; AFD64728; AFD64738; AFE48732; AFI25177; AFI25183; AFM36912; AFM55925; AFM55927; AFN88167; AFP43726; AFP43727; AFQ55482; AFQ62738; AFQ62745; AFQ62752; AFQ62757; AFQ90213; AFQ90221; AFQ90235; AFU93086; AFU93091; AFX62394; AFX62399; AFZ93991; AFZ93992; AFZ94003; AFZ94004; AFZ94008; AFZ94019; AFZ94023; AFZ94030; AFZ94033; AFZ94034; AFZ94038; AFZ94039; AFZ94072; AFZ94095; AFZ94106; AFZ94108; AFZ94122; AFZ94132; AFZ94135; AFZ94140; AFZ94178; AFZ94185; AFZ94187; AFZ94191; AFZ94196; AFZ94199; AFZ94201; AFZ94204; AFZ94207; AFZ94215; AFZ94224; AFZ94424; AFZ94425; AFZ94427; AFZ94444; AFZ94447; AFZ94509; AFZ94512; AFZ94516; AFZ94518; AFZ94542; AGG79686; AGG79690; AGG79882; AGG79904; AGG79906; AGG79907; AGG79967; AGG79971; AGI48711; AGJ84093; AGJ84097; AGK07570; AGK07574; AGK30599; AGL93365; AGL93370; AGL93371; AGL93373; AGM48497; AGM48498; AGO86846; AGQ16893; AGQ16902; AGQ16914; AGQ16920; AGQ16921; AGQ16931; AGQ16932; AGQ16940; AGQ16945; AGQ16954; AGQ16974; AGQ16996; AGW17263; AGW52119; AGZ87684; AGZ87685; AGZ87704; AGZ87708; AGZ87712; AGZ87715; AGZ87717; AGZ87739; AGZ87751; AGZ87755; AGZ87760; AGZ87781; AGZ87785; AGZ87794; AGZ87798; AGZ87815; AGZ87819; AHA46421; AHA46432; AHA53657; AHA53669; AHA53679; AHA80968; AHA90712; AHA90718; AHA90720; AHA90734; AHA90789; AHA90790; AHA93038; AHA93039; AHA93054; AHA93057; AHA93062; AHG52860; AHG52872; AHG52874; AHG52878; AHG52880; AHW85474; AHY61835; AHY61854; AHY61858; AHY61859; AHY61864; AHY61868; AHY61895; AHY61905; AHY61910; AHY61923; AHY61939; AHY61943; AHY61947; AHY61959; AHY61966; AHY61972; AHY61974; AHY61984; AHY61987; AHY61988; AHY61989; AHY62000; AHY81719; AHY81734; AHY81746; AHY81747; AHY81760; AHY81763; AHY81784; AHY81800; AHY81822; AHY81831; AHZ30933; AHZ30956; AHZ30975; AHZ30985; AHZ30987; AHZ30991; AHZ31004; AHZ31006; AHZ31007; AHZ31018; AHZ31028; AIB52374; AIE39248; AIE39258; AIK22438; AIN41939; AIN41947; AIN41950; AIN41982; AIN41986; AIN41990; AIN41993; AIR74892; AIW39916; AIX94180; AIX94183; AIX94201; AIX94209; AIX94217; AIX94219; AJA90820; AJI43153; AJI43158; AJI43171; AJI43178; AJI43184; AJI43188; AJI43191; AJI43192; AJI43203; AJI43226; AJW76740; AJW76742; AKA93943; AKA93948; AKA93956; AKA93976; AKA93977; AKA93980; AKA93982; AKA93984; AKA93987; ALH21913; ALL98857; ALS87621; AMK47896; AMR70925; ANG08627; ANG08636; BAE76021; BAG12757; BAJ12110; BAJ12116; BAJ12118; BAK82022; BAL41480; BAM29372; BAM29373; BAM29375; BAM29376; BAN59780; BAR79274; CAB02408; CAB02409; CAB37945; CAB53538; CAB65546; CAB71936; CAB71939; CAD12430; CAD12432; CAD12438; CAE84103; CAE92338; CAF32228; CAI40345; CAL48261; CAM23865; CAM23873; CAM90595; CAO00839; CAO78196; CAO91744; CAP60756; CAP66396; CAQ76695; CAQ77245; CAQ77246; CAR31393; CAR97780; CAX16733; CAX30810; CBI12486; CBJ55212; CBM42642; CBN86244; CBW38077; CBW44108; CBW44115; CBW46373; CBW47559; CBW52906; CBX02939; CBX19685; CBX36134; CCB84273; CCB84275; CCB84293; CCB84296; CCB84302; CCB84305; CCB84308; CCB84315; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CCB84336; CCB84343; CCB84344; CCB84359; CCB84362; CCB84380; CCB84393; CCB84412; CCC54374; CCD31402; CCD31404; CCF23446; CCH26300; CCH63458; CCL98003; CCN80305; CCP37718; CCQ71727; CCV02681; CCW36812; CDI48084; CDK13049; CDN40102; CDO67983; CDO67988; CDQ51645; CDQ51646; CDQ51647; CDQ51691; CEF48069; CEF48070; CEF48076; CEF48093; CEF48103; CEF48116; CEH11580; CEP25299; CEP25304; CEP25321; CEP25325; CEP25328; CEP25335; CEP25337; CEP25339; CEP25355; CEP25358; CEP25359; CEQ43511; CUU67666; CUU97102; CUU97123; CUU97137; CUU97140; CUU97144; CUU97160; CUU97167; CUU97186; CUU97192; CUU97199; CUU97204; CUU97205; CUU97210; CUU97213; CUU97218; CUU97220; CUU97223; CUU97228; CUU97236; CUU97256; CUU97257; CUU97264; CUU97267; CUU97275; CUU97292; CUU97295; CUU97297; CUU97304; CUX91035; CUX91043; CUX91050; P30499; Q07000; SAI78373; SAL89125; SAP35401; CAA09341; AAH07814; AAH08457; BAA08625; BAA11747; AAA52665; AAA59847; AAA53259; CAA41427; CAA48029; CAA57634; CAA65401; CAA68035; CAA71531; AAA59669; AAA81370; AAB70291; AAC17714; AAD21014; AAD52687; AAD53513; AAF04638; AAF29567; AAK07655; AAK31619; AAL49978; AAN10166; AAQ72735; AAR19102; AAR28679; AAT41622; ABD62875; ABG81862; ABG91051; ABI99472; ABO77641; ACA28734; ACF54634; ACF54635; ACF54636; ACF95804; ACF95810; ACI62421; ACM78934; ACM78936; ACN81043; ACN81052; ACN81054; ACN81172; ACN81219; ACN81220; ACN81295; ACN81297; ACN89859; ACN97198; ACO40493; ACO58590; ACO58644; ACO90082; ACO90084; ACP27910; ACP27917; ACP27953; ACR54363; ACR54374; ACR54376; ACR54380; ACR54381; ACR54395; ACS12736; ACS27620; ACS27627; ACS27629; ACS27630; ACS27639; ACS27664; ACS27666; ACS27692; ACS27693; ACS27695; ACS27702; ACS36191; ACS36201; ACS36206; ACS36414; ACS36415; ACS36417; ACS36420; ACS36443; ACS36448; ACT66300; ACT76682; ACT79366; ACT79371; ACT79377; ACT79379; ACT83089; ACT83719; ACU02008; ACU02011; ACU02019; ACU02035; ACU02119; ACU02122; ACU27287; ACU27304; ACU27305; ACU27306; ACU27308; ACU27313; ACU29586; ACU29587; ACU29588; ACU29589; ACU29599; ACU29600; ACU50928; ACU50939; ACU78145; ACU78153; ACU86978; ACV40737; ACV40743; ACV40746; ACV89474; ACV92055; ACX42647; ACX42650; ACX42660; ACX42662; ACX42669; ACX50448; ACX81389; ACX81396; ACX81405; ADB25036; ADB25037; ADB27759; ADB80084; ADB80086; ADB80087; ADB81942; ADB91968; ADC32129; ADC32133; ADC32189; ADC32191; ADC32198; ADC32215; ADC45457; ADC45475; ADC79686; ADC79839; ADC79853; ADC79860; ADC79865; ADC79869; ADC79871; ADC79873; ADC79877; ADC79878; ADC79974; ADC79989; ADC79993; ADC80002; ADC80032; ADC80037; ADC80047; ADC80049; ADC80061; ADD97868; ADD97869; ADE58698; ADE58702; ADE58729; ADE58740; ADE72884; ADE72900; ADE72914; ADE72923; ADE72925; ADE72927; ADE72937; ADE72943; ADE72944; ADE72957; ADE72968; ADE72973; ADE72983; ADE73051; ADE73148; ADE73170; ADE73172; ADE73178; ADE73179; ADE73200; ADE73204; ADE73209; ADE73242; ADE73243; ADE73255; ADE73327; ADE73328; ADE73334; ADE73389; ADE73393; ADE73396; ADE73407; ADE73460; ADE73522; ADE73525; ADE73527; ADE73638; ADE73706; ADE73716; ADE73730; ADE73744; ADE73838; ADI24378; ADM47606; ADM72771; ADM72773; ADM72776; ADM72780; ADM72785; ADN92612; ADN92625; ADQ55896; ADQ55915; ADT71649; ADU17379; ADU18050; ADU18489; ADU18492; ADU18496; ADZ05539; ADZ05551; ADZ05561; ADZ31192; ADZ38959; ADZ73139; ADZ73140; ADZ73158; ADZ98840; AEA49842; AEA49846; AEA49847; AEB21068; AEB65783; AEE39322; AEF13131; AEF13145; AEF13899; AEF13913; AEF13920; AEF13928; AEF13929; AEF13954; AEF13960; AEF13961; AEF32518; AEI01060; AEI01073; AEI01075; AEI01077; AEI30809; AEI30819; AEI30823; AEI30828; AEI58957; AEI59601; AEI59605; AEI87639; AEJ22094; AEJ22096; AEJ22100; AEJ87320; AEK67333; AEK67336; AEK94836; AEK94841; AEK94843; AEK94891; AEK94946; AEK94947; AEK94948; AEK95006; AEK95071; AEK95074; AEK95082; AEK95085; AEK95090; AEK95092; AEK95094; AEK95170; AEK95173; AEK95195; AEK95197; AEK95212; AEK95370; AEK95378; AEK95389; AEK95410; AEK95424; AEK95426; AEK95443; AEK95446; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AEK95623; AEK95644; AEK95646; AEK95651; AEK95661; AEK95666; AEK95673; AEK95674; AEK95675; AEK95679; AEK95685; AEK95689; AEK95691; AEK95692; AEK95708; AEK96115; AEK96126; AEK96149; AEK96158; AEK96168; AEK96176; AEK96203; AEK96212; AEK96213; AEK96215; AEK96229; AEK96230; AEK96247; AEK96267; AEK96269; AEK96270; AEK96271; AEK96275; AEK96276; AEK96277; AEK96280; AEK96284; AEK96285; AEK96288; AEK96291; AEL87268; AE045080; AEW23042; AEW23049; AEW23085; AEW90684; AEW90687; AEW90688; AEW90692; AEW90697; AEW90703; AEY80111; AEY80117; AEY80119; AFA41747; AFA41755; AFA42460; AFA42490; AFA42560; AFA42598; AFA42607; AFA42669; AFA42678; AFA42681; AFA42685; AFA42725; AFA42730; AFA42771; AFA42774; AFD23807; AFD23814; AFD23824; AFD23831; AFD23835; AFD23837; AFD23849; AFD23854; AFD36942; AFD36950; AFD36952; AFD37003; AFD37004; AFD37009; AFD37013; AFD64729; AFD64735; AFE48741; AFI25180; AFM77804; AFM77805; AFM77820; AFM77823; AFM77826; AFN88176; AFP73457; AFQ62751; AFQ62755; AFQ62756; AFQ90214; AFQ90219; AFQ90223; AFQ90227; AFQ90233; AFQ90234; AFU93093; AFU93104; AFU93106; AFV35204; AFV74672; AFZ93993; AFZ93998; AFZ94017; AFZ94021; AFZ94022; AFZ94024; AFZ94027; AFZ94052; AFZ94055; AFZ94062; AFZ94067; AFZ94075; AFZ94085; AFZ94097; AFZ94111; AFZ94145; AFZ94151; AFZ94152; AFZ94161; AFZ94175; AFZ94176; AFZ94183; AFZ94200; AFZ94210; AFZ94213; AFZ94214; AFZ94232; AFZ94234; AFZ94245; AFZ94428; AFZ94431; AFZ94432; AFZ94436; AFZ94438; AFZ94440; AFZ94470; AFZ94503; AFZ94504; AFZ94508; AFZ94510; AFZ94511; AFZ94522; AFZ94547; AFZ94595; AFZ94596; AFZ94598; AFZ94599; AGC51042; AGE97346; AGG79677; AGG79679; AGG79688; AGG79696; AGG79697; AGG79716; AGG79943; AGG79975; AGK07572; AGK07575; AGK44358; AGL73135; AGL73147; AGL93368; AGL93376; AGM48495; AGM48496; AGN74858; AGQ16899; AGQ16900; AGQ16922; AGQ16941; AGQ16953; AGQ16963; AGQ16965; AGQ16968; AGQ16971; AGQ16972; AGQ16983; AGQ16984; AGQ16993; AGQ16995; AGV08317; AGX13911; AGX13913; AGX13918; AGZ87693; AGZ87694; AGZ87698; AGZ87700; AGZ87722; AGZ87732; AGZ87734; AGZ87738; AGZ87742; AGZ87746; AGZ87766; AGZ87767; AGZ87773; AGZ87776; AGZ87778; AGZ87804; AGZ87808; AGZ87811; AGZ87820; AGZ87822; AGZ87830; AHA46435; AHA53638; AHA53651; AHA53653; AHA53654; AHA53676; AHA80972; AHA90557; AHA90715; AHA90729; AHA90740; AHA90742; AHA90757; AHA90758; AHA90772; AHA90776; AHA90783; AHA90792; AHA90795; AHA90797; AHA90799; AHA93026; AHA93036; AHA93045; AHA93048; AHA93055; AHA93061; AHA93067; AHC53643; AHG52871; AHG52877; AHY61842; AHY61846; AHY61850; AHY61851; AHY61853; AHY61879; AHY61884; AHY61886; AHY61904; AHY61917; AHY61932; AHY61945; AHY61952; AHY61954; AHY61973; AHY61975; AHY61982; AHY61985; AHY62003; AHY62004; AHY81716; AHY81718; AHY81721; AHY81741; AHY81759; AHY81765; AHY81768; AHY81773; AHY81779; AHY81796; AHY81802; AHY81818; AHY81823; AHY81826; AHZ30934; AHZ30937; AHZ30944; AHZ30947; AHZ30953; AHZ30957; AHZ30960; AHZ30973; AHZ30976; AHZ30982; AHZ30990; AHZ30993; AHZ31008; AHZ31012; AHZ31021; AIE39246; AIE39247; AIE39274; AIE39282; AIE39296; AIN41946; AIN41948; AIN41951; AIN41955; AIN41958; AIN41979; AIN41985; AIN41998; AIX94185; AIX94188; AIX94223; AIX94224; AJA90822; AJI43155; AJI43166; AJI43169; AJI43198; AJI43200; AJI43204; AJI43209; AJI43216; AJI43217; AJI43220; AJI43223; AJI43229; AJI43230; AJW76732; AJW76735; AKA93952; AKA93959; AKA93960; AKA93972; AKH87443; AKH87446; ALF62714; ALL25869; ALT55321; ALZ40821; AMY16456; ANG08606; ANG08611; ANG08612; ANG08614; ANG08615; ANG08618; ANG08619; ANG08620; ANG08633; ANG08642; ANG56533; BAF96505; BAJ12112; BAK82021; BAN59828; BAS02390; BAU51805; CAA76197; CAA76614; CAB02077; CAB65545; CAB65548; CAD12429; CAD12433; CAD29450; CAD45557; CAD47827; CAD56468; CAD59685; CAD70711; CAD90010; CAE30287; CAE30456; CAF32229; CAG26753; CAH65480; CAI29271; CAK12752; CAM23866; CAN89179; CAO00835; CAP17410; CAP72284; CAQ35180; CAQ35182; CAR31339; CAR81649; CAX20348; CAZ66350; CBA11527; CBG92451; CBL87902; CBM41836; CBM42645; CBW44105; CBW54814; CBX19376; CBX19686; CBX19687; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CBX19691; CBX32752; CBX36127; CBX45592; CBZ05562; CBZ41141; CCB84257; CCB84278; CCB84279; CCB84291; CCB84295; CCB84297; CCB84300; CCB84309; CCB84334; CCB84346; CCB84354; CCB84363; CCB84368; CCB84371; CCB84377; CCB84385; CCB84389; CCB84401; CCB84403; CCB84405; CCB84407; CCB84414; CCB84418; CCB84428; CCB84430; CCB84438; CCB84439; CCD28283; CCD66661; CCF23166; CCF23445; CCF72066; CCG28538; CCG58320; CCH27332; CCJ65512; CCL97791; CCN97891; CCV02680; CDG23678; CDI30221; CDK13051; CDN65461; CDO33941; CDO58213; CDO67702; CDO67714; CDQ51692; CDQ51696; CDQ51701; CEF48071; CEF48081; CEF48083; CEF48084; CEF48087; CEF48109; CEF48111; CEP25297; CEP25331; CEP25334; CEP25340; CEP25344; CEP25347; CEP25354; CEP25357; CUU97113; CUU97117; CUU97119; CUU97133; CUU97154; CUU97165; CUU97175; CUU97184; CUU97188; CUU97196; CUU97215; CUU97224; CUU97233; CUU97237; CUU97241; CUU97243; CUU97259; CUU97263; CUU97294; CUU97305; CUX91020; CUX91032; CUX91036; CUX91039; EAX03379; P30504; Q29865; SAI78374; SAI78376; SAL89123; SLI54175; BAG65328; BAA19535; BAA19536; AAA59656; AAA59703; AAA59704; AAA59705; AAA88088; AAA92995; AAA17674; CAA50209; AAA59700; AAB03578; AAB48495; AAB70290; AAB70292; AAC05205; AAC17710; AAC17717; AAC17724; AAD48066; AAF04743; AAF64391; AAO24136; AAP84346; AAV39503; AAX18632; AAZ53372; ABC61964; ABC61966; ABD62869; ABD65644; ABH03035; ABH10663; ABI55240; ABK97602; ABM64722; ABO14989; ABO31936; ABR58850; ABV68908; ABY64665; ABZ89497; ACD63075; ACE63276; ACF54631; ACF54632; ACG61385; ACL37148; ACM78895; ACM78898; ACM78900; ACM78901; ACM78903; ACM78924; ACM78935; ACM78943; ACN24622; ACN24633; ACN81045; ACN81051; ACN81058; ACN81221; ACN81289; ACN89840; ACN91000; ACN91017; ACN91021; ACN91024; ACN97191; ACN97193; ACN97194; ACN97197; ACO37270; ACO58589; ACO90086; ACP27912; ACP27921; ACP27937; ACP27947; ACR54366; ACR54389; ACR54400; ACS12744; ACS12751; ACS27613; ACS27614; ACS27617; ACS27621; ACS27653; ACS36186; ACS36196; ACS36198; ACS36205; ACS36207; ACS36426; ACS36427; ACS36434; ACS36439; ACS36441; ACS36442; ACS36463; ACS36465; ACS36470; ACT76245; ACT79375; ACT79383; ACT79394; ACT79973; ACT83090; ACT83721; ACU02001; ACU02002; ACU02004; ACU02013; ACU02021; ACU02030; ACU02118; ACU02124; ACU02129; ACU27286; ACU27307; ACU27311; ACU29594; ACU33856; ACU43582; ACU50927; ACU50929; ACU78140; ACU78149; ACV40722; ACV40744; ACV40745; ACV89472; ACV89477; ACV89481; ACV91115; ACV91118; ACV91119; ACV91120; ACX42649; ACX42652; ACX42653; ACX42655; ACX42661; ACX42663; ACX42665; ACX42666; ACX81394; ADB27761; ADB55628; ADB80076; ADB80077; ADB80090; ADB81947; ADB81951; ADB91966; ADC29456; ADC32175; ADC32197; ADC32207; ADC32209; ADC32210; ADC32223; ADC45454; ADC45462; ADC45479; ADC45485; ADC79842; ADC79843; ADC79852; ADC79882; ADC79887; ADC79888; ADC79975; ADC79977; ADC79981; ADC80001; ADC80003; ADC80005; ADC80007; ADC80023; ADC80025; ADC80044; ADC80051; ADC80053; ADC80060; ADC80064; ADC80067; ADD10600; ADD10601; ADD10602; ADD97866; ADD97871; ADE58699; ADE58710; ADE58714; ADE58725; ADE58728; ADE58731; ADE58736; ADE58742; ADE58746; ADE58749; ADE58750; ADE72878; ADE72886; ADE72888; ADE72890; ADE72907; ADE72915; ADE72917; ADE72921; ADE72932; ADE72935; ADE72939; ADE72941; ADE72952; ADE72959; ADE72962; ADE72965; ADE72967; ADE72971; ADE72976; ADE72984; ADE72989; ADE73000; ADE73042; ADE73043; ADE73046; ADE73047; ADE73052; ADE73150; ADE73151; ADE73166; ADE73201; ADE73213; ADE73319; ADE73320; ADE73322; ADE73388; ADE73395; ADE73399; ADE73405; ADE73406; ADE73524; ADE73579; ADE73631; ADE73634; ADE73635; ADE73695; ADE73699; ADE73701; ADE73713; ADE73718; ADE73719; ADE73739; ADE73832; ADF58788; ADI75492; ADI75496; ADM47607; ADM72763; ADM72765; ADN87361; ADN92609; ADN92622; ADN92626; ADU18055; ADU18490; ADV71255; ADV78584; ADX94777; ADZ05544; ADZ05546; ADZ05547; ADZ05549; ADZ31199; ADZ38961; ADZ38965; ADZ38966; ADZ73141; ADZ73143; ADZ73149; ADZ73151; AEA49818; AEA49820; AEA49829; AEA49837; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | AEA49843; AEA49845; AEF13136; AEF13138; AEF13142; AEF13146; AEF13906; AEF13910; AEF13914; AEF13931; AEF13938; AEF13942; AEF13948; AEF13949; AEI01074; AEI30811; AEI58959; AEI59593; AEI59608; AEI59609; AEI87638; AEJ22097; AEJ90525; AEJ90526; AEJ90528; AEK67339; AEK94837; AEK94840; AEK94963; AEK95018; AEK95073; AEK95076; AEK95095; AEK95156; AEK95162; AEK95171; AEK95187; AEK95326; AEK95396; AEK95419; AEK95432; AEK95441; AEK95457; AEK95599; AEK95600; AEK95629; AEK95658; AEK95665; AEK95676; AEK95677; AEK95682; AEK95683; AEK95696; AEK95700; AEK96119; AEK96127; AEK96131; AEK96136; AEK96141; AEK96143; AEK96152; AEK96156; AEK96161; AEK96172; AEK96200; AEK96210; AEK96222; AEK96233; AEK96234; AEK96251; AEK96257; AEK96258; AEK96261; AEK96262; AEK96292; AEU43543; AEW90686; AEW90689; AEW90694; AEW90699; AEW90702; AEY80115; AFA42434; AFA42439; AFA42441; AFA42450; AFA42487; AFA42489; AFA42504; AFA42505; AFA42508; AFA42566; AFA42603; AFA42668; AFA42672; AFA42675; AFA42724; AFA42732; AFA42769; AFD23806; AFD23808; AFD23812; AFD23813; AFD23819; AFD23823; AFD23825; AFD23832; AFD23836; AFD23840; AFD23851; AFD23858; AFD23859; AFD36913; AFD36944; AFD36971; AFD37000; AFD64725; AFD64739; AFD64742; AFE48727; AFE48735; AFE48737; AFE88898; AFM77816; AFM77819; AFN88158; AFN88173; AFN88177; AFO66764; AFO66766; AFP73458; AFQ62741; AFQ62749; AFQ62766; AFQ62767; AFQ90220; AFQ90231; AFU93103; AFU93855; AFV35203; AFV74671; AFX62396; AFX62401; AFZ93987; AFZ93999; AFZ94001; AFZ94043; AFZ94056; AFZ94068; AFZ94071; AFZ94087; AFZ94091; AFZ94098; AFZ94099; AFZ94102; AFZ94126; AFZ94139; AFZ94153; AFZ94160; AFZ94163; AFZ94167; AFZ94171; AFZ94172; AFZ94173; AFZ94179; AFZ94194; AFZ94195; AFZ94205; AFZ94211; AFZ94216; AFZ94244; AFZ94445; AFZ94505; AFZ94521; AFZ94544; AFZ94546; AFZ94626; AGE97344; AGG68835; AGG79750; AGG79775; AGG79776; AGG79912; AGG79914; AGG79942; AGG80000; AGK07568; AGK07571; AGK44323; AGK44325; AGK44327; AGL09218; AGL73139; AGL73145; AGL93379; AGM48502; AGO64290; AGO64291; AGQ16894; AGQ16897; AGQ16909; AGQ16929; AGQ16935; AGQ16938; AGQ16946; AGQ16949; AGQ16951; AGQ16957; AGQ16964; AGQ16967; AGQ16970; AGQ16973; AGQ16975; AGQ16989; AGT79678; AGU99986; AGV08372; AGX13912; AGX13917; AGX13919; AGZ87691; AGZ87699; AGZ87710; AGZ87720; AGZ87728; AGZ87735; AGZ87736; AGZ87737; AGZ87741; AGZ87748; AGZ87758; AGZ87771; AGZ87772; AGZ87788; AGZ87792; AGZ87795; AGZ87805; AGZ87829; AGZ95032; AHA46415; AHA46418; AHA46419; AHA46422; AHA46441; AHA50095; AHA53640; AHA53647; AHA53652; AHA53667; AHA53671; AHA53672; AHA53677; AHA53680; AHA80967; AHA80970; AHA80973; AHA90710; AHA90732; AHA90735; AHA90744; AHA90746; AHA90747; AHA90781; AHA90786; AHA90788; AHA90793; AHA93022; AHA93027; AHA93034; AHA93037; AHA93042; AHA93058; AHA93065; AHG52876; AHG52879; AHG52881; AHK05785; AHY61828; AHY61837; AHY61838; AHY61849; AHY61856; AHY61866; AHY61869; AHY61873; AHY61877; AHY61893; AHY61897; AHY61899; AHY61931; AHY61935; AHY61969; AHY61970; AHY61976; AHY61992; AHY61997; AHY81715; AHY81727; AHY81733; AHY81743; AHY81745; AHY81757; AHY81761; AHY81766; AHY81772; AHY81776; AHY81778; AHY81795; AHY81810; AHY81811; AHY81816; AHY81824; AHY81827; AHY81835; AHZ30955; AHZ30958; AHZ30962; AHZ30974; AHZ30977; AHZ30979; AHZ30984; AHZ30994; AHZ30995; AHZ30999; AHZ31001; AHZ31009; AHZ31023; AIB55782; AIE39238; AIE39239; AIE39241; AIE39243; AIE39252; AIE39254; AIE39261; AIE39265; AIE39269; AIE39270; AIE39273; AIE39275; AIE39285; AIE39289; AIN41943; AIN41944; AIN41962; AIN41963; AIN41973; AIN41988; AIN41989; AIQ78393; AIX94179; AIX94184; AIX94189; AIX94198; AIX94204; AJI43164; AJI43174; AJI43176; AJI43189; AJI43195; AJI43197; AJI43205; AJI43228; AJI43233; AJW76729; AJW76744; AKA93953; AKA93954; AKJ66250; ALZ40823; AMB73108; AMC30594; AMD39523; AMO26196; AMR74919; ANG08604; ANG08609; ANG08625; ANG08631; ANG08638; BAD77815; BAD77817; BAJ78306; BAN59786; BAN59792; BAN59798; BAN59804; BAN59840; CAA05125; CAA25190; CAA75755; CAB71935; CAC01936; CAC05372; CAC12745; CAD29451; CAD44641; CAD45440; CAD70710; CAD90008; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | CAE22463; CAE84097; CAE85468; CAE92337; CAF33343; CAH17687; CAH65479; CAJ32665; CAJ55681; CAJ55741; CAL91416; CAL92190; CAM23862; CAM23864; CAM28533; CAN89496; CAO00838; CAO99143; CAR82587; CAR97781; CAX44302; CAZ66347; CAZ86765; CAZ91489; CBA18267; CBJ19218; CBL93952; CBW38079; CBW38447; CBW44106; CBW44109; CBW47473; CBX19681; CBX36131; CBX45595; CBZ05561; CCA63067; CCA94503; CCB84256; CCB84258; CCB84263; CCB84280; CCB84286; CCB84292; CCB84299; CCB84316; CCB84335; CCB84342; CCB84348; CCB84353; CCB84383; CCB84398; CCB84413; CCB84415; CCB84422; CCB84429; CCB84431; CCB84432; CCB84433; CCC15088; CCH57807; CCJ65511; CCK33882; CCN79818; CCP29692; CCQ71728; CDG23680; CDK41198; CDN33434; CDO58212; CDQ37740; CDQ51635; CDQ51649; CDQ51652; CDQ51690; CDQ51693; CED53875; CEF48050; CEF48064; CEF48098; CEO90881; CEP25293; CEP25295; CEP25302; CEP25305; CEP25309; CEP25345; CEP25349; CQR91447; CRL92732; CUU97115; CUU97122; CUU97131; CUU97135; CUU97139; CUU97202; CUU97222; CUU97225; CUU97248; CUU97260; CUU97266; CUU97268; CUU97270; CUU97271; CUU97272; CUU97302; CUX07555; CUX91018; CUX91019; CUX91026; CUX91033; CUX91042; CUX91048; CUX91844; CUX91852; EAX03382; SAI78372; AAM76870; AAL03994; CAD29433; BAG62842; AAH10542; BAA07531; BAA89793; BAA32610; BAA32613; CDP32880; AAA59699; AAA88089; AAD14147; CAA53783; AAA74583; AAB03587; AAC14579; AAC16245; AAC27626; AAD38674; AAD51331; AAD51747; AAF04581; AAG40881; AAK07656; AAR08453; AAR15062; AAR19086; ABB52621; ABD62874; ABD62877; ABI64159; ABK97603; ABS56982; ACA28736; ACA79905; ACF95809; ACG61386; ACL37143; ACL37145; ACM78914; ACM78929; ACM90848; ACN22289; ACN24624; ACN24634; ACN81049; ACN81059; ACN81060; ACN81173; ACN81285; ACN89853; ACN90998; ACN91005; ACN91009; ACN91010; ACN91011; ACN91014; ACN91018; ACN91020; ACN91026; ACN97190; ACN97195; ACN97201; ACO88011; ACO90085; ACP27946; ACP27955; ACR54377; ACR54379; ACR54392; ACR54396; ACR78565; ACR78566; ACS12752; ACS27602; ACS27604; ACS27610; ACS27615; ACS27616; ACS27618; ACS27625; ACS27641; ACS27646; ACS27657; ACS27661; ACS27665; ACS27672; ACS27696; ACS27698; ACS27699; ACS27701; ACS36181; ACS36412; ACS36429; ACS36432; ACS36446; ACS36450; ACS36459; ACT68330; ACT76683; ACT79368; ACT79372; ACT79381; ACU02022; ACU02033; ACU02034; ACU27269; ACU27283; ACU27285; ACU27288; ACU27298; ACU29592; ACU50932; ACU50933; ACU50934; ACU50936; ACU78147; ACU78154; ACU78155; ACV30333; ACV30335; ACV40735; ACV40740; ACV40748; ACV89483; ACV91116; ACV91121; ACV91123; ACX29956; ACX42657; ACX81385; ACX81386; ACX81391; ACX81393; ACX81395; ADB25049; ADB27763; ADB80082; ADB80089; ADB80093; ADB81943; ADB81948; ADB81949; ADB91967; ADC32127; |
| SLEX Down | PPP2CA | P67775 | EAW62268; BAG70054; AAH19275; AAH31696; BAG51913; CAA31176; AAA36466; EAW62269; BAG70179; ; BAG53493; AAH02657; CAG33698; AAB38019; NP_002706; P67775; AAH00400; NP_001341948 |
| SLEX Down | SRGAP2 | O75044 | CAH73674; O75044; AAI44344; BAA32301; BAG56851; BAG57406; AAI32875; XP_011507656; XP_016856327; ; CAH73675; XP_011507657; BAG50836; XP_016856328; NP_056141; CAH73676; AAI32873; AQN67656; XP_005277567; XP_016856329; EAW93550; XP_005277568; XP_005277571; XP_005277572; XP_011507661; NP_001164108; XP_011507658; XP_016856330; NP_001287881; BAH12200 |
| SLEX Down | SHH | Q15465 | BAA34689; AAS01990; ADL14518; NP_001297391; AAB67604; Q15465; XP_011514782; ; AAA62179; EAL23913; AAQ87879; EAX04543; XP_011514781; NP_000184 |
| SLEX Down | FETUB | Q9UGM5 | BAA78341; AAR22508; NP_055190; CAB62538; EAW78185; EAW78186; AAQ10515; XP_011510983; XP_011510984; NP_001295006; AAH74734; XP_011510985; ; BAH14069; CAC24999; BAG37713; AAH69670; AAH69820; Q9UGM5; AAR22507; AAI14617; XP_005247408; NP_001295008 |
| SLEX Down | CHST1 | O43916 | AAH28235; BAA24840; AAH22567; AAC28776; AAP88041; EAW68038; AAD19878; EAW68034; ; EAW68037; EAW68036; EAW68039; EAW68035; O43916; XP_006718419; XP_016873948; NP_003645 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| SLEX Down | CYR61 | O00622 | AAH09199; CAB10848; EAW73197; ; AAG59863; AAR05446; EAW73196; O00622; BAG58373; CAA72167; EAW73198; AAB84227; BAD97105; AAH01271; CAG38757; AAH16952; AAB58319; AAF21597; AAB61240; CAA72802; NP_001545; BAG37152; CAB09804 |
| SLEX Down | CLDN12 | P56749 | BAG35384; AAH36754; AAH68532; CAG38501; AAP22363; EAW76876; CAB60617; CAD35081; CAB66704; NP_001172002; NP_036261; EAW76877; EAL24163; NP_001172001; ; P56749 |
| SLEX Down | INHBE | P58166 | CAF86622; ; P58166; BAC11521; NP_113667; EAW97012; AAN03682; AAH05161 |
| SLEX Down | LASP1 | Q14847 | BAG58436; CAA57833; ; EAW60543; BAG57861; EAW60545; BAF82536; BAG58846; AAH12460; NP_006139; EAW60544; AAH07560; Q14847; NP_001258537 |
| SLEX Down | EGFR | P00533 | AAA63171; AAC50796; AAC50797; AAG35787; AAS07524; AFK93471; AFK93472; CAA29668; CAA34902; CBK51924; CCO75437; BAH11869; AAT97979; ADL28125; AAA52371; NP_001333827; NP_958439; AAG35789; AFK93476; BAF79636; BAF80003; BAF80004; CAJ55813; CEF34368; AAG43240; ADN43066; NP_001333829; NP_958440; AAC50798; AAS83109; ART34941; BAL41217; CBK51923; EAW50963; AAH94761; ADZ75461; ADY76965; NP_001333826; ; AAC50804; CBK51921; CBK51922; P00533; ABQ66238; CAA25282; NP_958441; AAA52370; AAC50799; AFK93475; AFK93478; AIE16170; AIE16171; ART34939; ART34943; ART34944; AAT97978; AAI18666; AAZ66620; AAG35790; AAG43243; AFK93474; ART92273; BAE15958; CCO13722; CCO75439; CCV20014; EAW50964; EAW50965; BAD92679; BAF83041; AAC50802; CAA25240; NP_005219; AAG35786; AAG35788; AAG43245; AFK93473; AFK93477; ART34942; ART34945; BAL40868; EAW50962; AAB53063; NP_001333870; AAC50800; AAC50801; AAC50803; AAG43244; ART34940; CAM91181; CAV33298; AAK01080; AAT52212; AAI28420; ABQ66237; NP_001333828 |
| SLEX Down | FAM48A | Q0D2Q4 | Q8NEM7; XP_005266514; XP_016876146; NP_060039; EAX08582; EAX08583; EAX08584; EAX08585; AAQ15220; AAH01145; XP_005266511; XP_005266513; XP_016876145; NP_001265409; CAB62207; XP_005266518; XP_005266524; ; AAD40550; AAL38587; XP_005266508; XP_005266517; XP_016876143; NP_001265411; EAX08586; BAG51343; XP_005266506; XP_005266519; XP_016876148; NP_001014308; NP_001265410; XP_005266504; XP_005266512; XP_005266515; XP_016876142; XP_016876147; BAG65097; AAH30686; XP_005266521; XP_005266522; XP_016876144; XP_016876149; XP_016876150; BAF85065 |
| SLEX Down | RGS14 | O43566 | AAM12650; AAH14094; XP_005265852; NP_006471; EAW85011; AAB92613; BAG53582; XP_005265851; EAW85013; AAY26402; EAW85012; O43566; BAC85600; AAB92614 |
| SLEX Down | BRCA1 | P38398 | AAC37594; AAZ16492; AAZ79408; AAZ79409; ABA29214; ABA29220; ABA29229; ABB87060; ABB87066; AFU88804; AIC83545; AIC83546; AIC83547; AIC83548; AIC83550; AIC83552; AIC83554; AIC83574; AIC83575; AIC83579; AIY34492; AKE50579; AKG51646; AKR15646; AMO12813; EAW60923; EAW60940; AAH72418; AAI15038; AEQ98814; NP_009225; ; AAF97939; AAM18220; AAZ05886; AAZ79407; ABB87058; ABB87063; ABB87070; ABB87071; AFU88805; AIC83541; AIC83556; AIC83557; AKE50580; AKJ80194; AMO12815; AMO12816; AMO12821; AOG75862; CCD57770; CCD57771; EAW60925; EAW60929; EAW60932; EAW60935; AAH62429; AAI06746; AAA73985; AAB08105; AAB34725; AAM18223; ABA29217; ABB87057; ABB87067; ABB87068; ABB87069; AFU88803; AFU88807; AIC83540; AIC83542; AIC83551; AIC83580; AIC83581; AKE50577; AKQ62934; AKQ62935; AKR15645; ALF35866; CAA70003; CCD57768; CCD57772; CCD57773; AAU93634; AKG51648; AAC00049; AAM18221; AAN61423; AAN61425; AAZ79406; AAZ79410; ABB87062; ABB87074; AIC83572; AKE50578; AKG51645; ALO20344; AMO12814; AMO12819; CCD57769; CCD57774; EAW60934; EAW60942; AAB61673; BAH14571; AAH85615; ABC59810; AAP12647; ABA29223; ABB87059; ABB87061; ABF14462; ACR33809; AIC83549; AIC83555; AIC83571; AIC83576; AIC83582; AKE50581; AKG51644; AKJ84699; ALO20343; ALY05710; ALY05711; EAW60924; NP_009230; AAM18218; AAM18219; AAM18225; AAN10167; AAP70031; ABA29211; ABA29226; ABB87064; ABB87077; ABB87079; AFU88802; AIC83558; AIC83559; ALO20345; AMO12818; AMO12820; EAW60922; EAW60933; EAW60939; P38398; AAQ92977; AAI06747; |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| | | | ABC59811; AKG51647; AAM18222; AAM18226; AAN61424; AAU21564; AAU21565; ABA29208; ABB87053; ABB87054; ABB87055; ABB87056; ABB87072; ABB87075; ABB87076; ABB87078; AFU88808; AFU88809; AIC83539; AIC83553; AIC83577; AIC83578; AKE50575; ALD10297; AMO12812; AMO12817; ATE47047; EAW60927; EAW60928; EAW60930; EAW60936; EAW60941; ABC88652; NP_009228; NP_009231; AAM18224; AAN71744; AAU21563; ABB87065; ABB87073; AFU88806; AIC83544; AIC83573; AKE50574; AKE50576; AKQ62933; EAW60926; EAW60931; EAW60937; EAW60938; BAK64160; AAH30969; NP_009229 |
| SLEX Down | ADAM7 | Q9H2U9 | AAG43987; AAH43207; BAF85181; NP_003808; ; Q9H2U9; AAH58037; EAW63606; AAC36742; XP_016869432 |
| SLEX Down | CEACAM6 | P40199 | CDM55345; AAH05008; AAA51739; AAA59909; CAG27583; CDM22277; P40199; AAA59908; EAW57061; ; AAA51971; AAA59907; AAA59915; XP_011525292; BAG35441; NP_002474; AAP88776 |
| SLEX Down | VNN1 | O95497 | BAF83114; AAH96268; ; EAW48020; AAH96266; AAF21453; NP_004657; O95497; AAH96267; AAY88742; CAA10568; BAG36929; AAH96265 |
| SLEX Down | CASP9 | P55211 | AAP35557; XP_011540575; NP_001264983; NP_127463; BAA87905; ; BAF84769; AAV33129; XP_005246071; AAO21133; EAW51731; P55211; BAF84800; AAH02452; NP_001220; BAA82697; EAW51730; BAG64715; AAC50776; BAD92384; AAD12248; AAD13615; CAH03131; BAA78780; AAH06463; AAC50640 |
| SLEX Down | CUL2 | Q13617 | BAG53007; AAC51190; XP_011518045; BAH11667; AEE61248; NP_001185706; EAW85924; EAW85928; EAW85926; BAH13294; NP_001185707; EAW85922; AAD23581; AAI10902; XP_011518047; NP_001185708; NP_003582; ; EAW85925; Q13617; NP_001311305; EAW85927; AAH09591; XP_011518049; AAC50545; XP_011518046; NP_001311304 |
| SLEX Down | TLX2 | O43763 | ; O43763; BAA83463; AAH06356; EAW99630; BAJ84026; NP_057254 |
| SLEX Down | CSNK1A1 | P48729 | AAG17246; BAG57180; AAC41760; AAH07246; AAH08717; CAA56710; NP_001258670; CAG47002; NP_001883; EAW61767; AAV38632; ACF94482; ; EAW61769; EAW61774; AAF69665; AAL60204; BAG57435; BAG58018; AAH21971; AAV38633; NP_001258671; EAW61771; EAW61772; EAW61773; EAW61776; EAW61768; EAW61775; AAH25371; AAY84562; NP_001020276; EAW61770; P48729; BAG64751 |
| SLEX Down | DDEF1 | Q9ULH1 | CBX47524; AAH20631; XP_016868958; CAD97831; XP_006716626; NP_001234925; BAA86563; AAI37136; XP_006716628; XP_006716629; XP_011515355; ; EAW92131; XP_005250982; EAW92130; AAF67666; XP_006716627; XP_016868956; XP_016868957; CCQ43599; Q9ULH1; XP_011515354; NP_060952 |
| SLEX Down | CLDN6 | P56747 | EAW85432; EAW85431; AAH08934;; BAG52111; AAK02013; AAQ88844; CAI72055; P56747; AAP36063; CAB56533; NP_067018 |
| SLEX Down | TMEFF2 | Q9UIK5 | CCQ43534; AAH08973; NP_001292074; AAX88893; AAY14874; AAG49452; BAG37769; BAG51979; BAD96411; CAG33671; AAF91397; BAA90820; XP_011509192; XP_016859228; NP_057276; AAG49451; Q9UIK5; AAD55776; XP_016859229; NP_001292063; ; AAQ89266; CAH05705; EAX10831; BAA87897; CAR82354; EAX10832; BAC11030; CAB75654; AAZ43216 |
| SLEX Down | NPAS4 | Q8IUM7 | ; AAI05002; XP_016873026; BAC04271; AAI05004; NP_849195; BAC04738; XP_016873028; BAC19830; AAI43631; EAW74525; Q8IUM7; XP_016873027; NP_001305733 |
| SLEX Down | TCEB3 | Q14241 | ; Q14241; AAA75492; EAW95070; EAW95071; BAG35905; AAO15305; AAH02883; NP_003189 |
| SLEX Down | APOE | P02649 | AAG27089; AAL82810; AFS60672; ALQ33371; BAA96080; CAA63051; AAD02505; EAW57306; NP_001289618; ; ACN81314; ADK26133; BAG37412; ALQ33368; AAB59546; ALQ33370; CAA94806; NP_000032; NP_001289620; AAB59397; P02649; AAH03557; ALQ33369; AAB59518; CAA25017; NP_001289617; NP_001289619 |
| SLEX Down | PTMS | P20962 | AAH17025; AAI28230; ; EAW88742; NP_002815; AAA61185; NP_001317262; XP_011519289; CAA73913; P20962 |
| SLEX Down | PSMB9 | P28065 | CAA78700; AAC60646; AHW47978; EAX03654; AQY77063; CAA47024; P28065; AHW47961; EAX03653; CAA44603; AHW47927; AQY77059; AAH65513; CAG46457; AAC50154; NP_002791; AHW47944; AQY77061; AQY77062; AQY77060; BAG64224; ; CAA60784 |
| SLEX Down | RPLP2 | P05387 | CAG47044; CAG47008; AAH05354; AAH62314; EAX02394; P05387; AAH05920; AAH07573; BAG34894; BAA05777; ; BAB79475; EAX02393; NP_000995; AAA36472 |

TABLE 4-continued

Proteomic and Glycomic Biomarkers for SCLC

| Marker Type and Direction in SCLC Cases Compared to Controls | Gene Name | UniProt Accession | GenBank Protein Accession |
|---|---|---|---|
| SLEX Down | CFL2 | Q9Y281 | AAF64498; AAD31280; AAD31281; AAH22876; NP_068733; AAM10495; AAF97934; EAW65908; XP_011534665; ; Q9Y281; BAG36842; EAW65912; AAH11444; AAH22364; EAW65910; EAW65911; NP_001230574; NP_619579 |
| SLEX Down | CLASP1 | Q7Z460 | EAW95253; XP_011509150; XP_016859147; XP_016859151; XP_016859152; XP_016859174; XP_016859176; XP_016859177; NP_001135746; NP_056097; CAC35156; XP_006712446; XP_016859154; XP_016859158; XP_016859166; XP_016859167; XP_016859169; XP_016859170; XP_016859173; Q7Z460; XP_006712440; XP_006712444; XP_006712445; XP_011509151; XP_016859153; XP_016859168; XP_016859175; XP_016859178; XP_016859179; ; AAQ15051; BAH11926; AAH32563; AAI32724; CAH18421; XP_016859148; XP_016859156; XP_016859165; BAH13003; CAI46251; XP_016859155; XP_016859159; XP_016859163; XP_016859172; NP_001135745; EAW95255; BAH13560; XP_016859160; XP_016859161; XP_016859180; AAX88872; EAW95254; BAA31597; BAH12576; BAH13694; AAI44108; ABB13627; XP_016859162; XP_016859164; XP_016859171; EAW95252; BAH12531; AAR07949; AAI12941; XP_006712448; XP_016859146; XP_016859149; XP_016859150; XP_016859157; NP_001193980 |
| SLEX Down | ADAMTS4 | O75173 | O75173; BAA31663; AAD41494; NP_001307265; EAW52627; AAH63293; AAL02262; BAF84262; AAQ89245; ; NP_005090; ABC88384 |
| SLEX Down | PCSK9 | Q8NBP7 | CDM55691; BAC11572; CDM55545; ABV59216; ACN81318; BAG57260; ; EAX06660; BAC85910; NP_777596; CAC38896; Q8NBP7; BAG59894; CAC60361; AAV67948; CDI44158 |
| SLEX Up | WNT4 | P56705 | AAK50427; AAK51699; XP_011539899; NP_110388; AAG38658;; EAW95010; XP_011539901; CAI38644; AAH57781; XP_011539900; AAQ89306; AAV38928; AAK25765; P56705; BAC23080; BAG58821 |
| SLEX Up | ANG | P03950 | NP_001091046; CDG31911; CAG28561; ; AAA51678; AAL67712; AAH20704; AAH62698; ACI45236; AAL67710; AAL67714; AAL67711; AAL67713; EAW66450; EAW66451; P03950; BAG36701; AAH54880; NP_001136 |
| SLEX Up | CTGF | P29279 | AAK60506; AAK60507; CAS92743; EAW48038; AAV38597; CAG46534; P29279; CAA55544; BAG37644; CAG46559; ; AAZ29611; ADL14512; CAA63267; EAW48039; AAH87839; BAG52518; AAQ95223; AAV38598; AAA75378; BAG54167; AAK60505; CBX51740; BAF83573; AAS55639; AAA91279; NP_001892 |
| SLEX Up | RECQL4 | O94761 | BAA86899; XP_016869490; EAW82070; BAA74453; AAH11602; AAH13277; NP_004251; XP_016869480; XP_016869483; XP_016869484; XP_016869489; XP_016869482; XP_016869487; ; O94761; XP_016869481; XP_016869485; XP_011515686; XP_016869486; AAZ85145; EAW82071; AHN60090; XP_016869488 |

Discovery of Autoantibody, Proteomic, and Glycomic Plasma Markers for SCLC Early Detection When diagnosed at limited stage, SCLC carries a much better prognosis than when diagnosed at extensive stage. The low-dose CT screening protocols that have proven effective for NSCLC have not displayed benefit in SCLC. This is likely a result of the aggressive nature of SCLC, such that annual imaging is not sufficient. We would argue that diagnostic methods capable of identifying SCLC at the microscopic stage, prior to clinical detection, would be necessary to reliably identify limited stage SCLC. Our strategy leverages two key molecular features unique to SCLC to achieve our goals. These are: 1) expression of CNS proteins by neuroendocrine cells that could be either directly identified in plasma (proteomic markers) or for which there would exist an autoantibody-antigen complex that could be detected in plasma (autoantibody markers) and 2) SCLC produced carbohydrate modified (glycomic marker) proteins amenable to detection in plasma. Thus, we argue that the amplification present in the immune system and widespread glycosylation "mistakes" could allow detection of even small tumors. There will be two components to these discovery studies. Initially, performed an unbiased screen on human SCLC plasma specimens using HuProt Arrays to comprehensively identify additional SCLC specific antibodies. Subsequently novel, small format antibody arrays were fabricated that include all of the candidates identified in the HuProt Arrays, PNS-related antibodies (including but not limited to those listed in Table 1A), and candidate proteomic and glycomic markers identified on large format arrays studies of CHS specimens. The entire discovery dataset of N=43 SCLC cases and controls were subjected to this array to develop a SCLC hybrid plasma marker panel.

Conditions

Cohorts. All studies proposed are performed on a discovery dataset of N=43 SCLC cases and controls (matched on age, sex, and smoking history (pack-years and current/former/never status)). N=26 of these cases originate from the Fred Hutch LCEDPC cohort and the other N=17 are from the CHS. Only markers with high performance in both cohorts are considered for additional study.

Unbiased SCLC specific antibody detection using HuProt Arrays. HuProt Arrays contain>17,000 recombinant proteins expressed in yeast. These arrays were used to detect circulating free antibody (not autoantibody-antigen complexes). To accomplish this, 2 µl of undepleted human plasma is diluted to 80 µl and incubated on the array for 1.5 h according to manufacturer's directions. After washing, incubation with Alexa Fluor 647-goat anti-human IgG (Jackson Labs) will be performed. These secondary antibodies are highly cross absorbed against other species and will not detect any other IgG species. After washing and scanning, data analysis was performed with the manufacturer-supplied software, ProtoArray Prospector.

Fabrication and incubation of arrays. Triplicate features of each antibody are printed onto Schott Nexterion H slides using a Genetix Q-Array 2 microarray platform. Antibodies are covalently linked via a reactive NHS-ester bound to a 3-D gel polymer coated on the glass slide. Printed arrays have good shelf life (we have seen no deterioration up to 5 years of storage at −80° C. under vacuum). The antibodies printed on these arrays contain all candidates from proteomic, glycomic, and autoantibody-antigen complexes, candidates from the HuProt arrays, control markers, and additional markers for the purposes of normalization.

Detection of differences in protein levels in cases vs. controls. In order to utilize less dye and effectively increase the concentration of less abundant proteins, we deplete albumin and IgG using a Sigma ProtIA spin column and concentrate the sample with a Microcon 10 k cut-off filter. 8-10 Proteins (200 µg) from case or control plasma are labeled with the fluorophore Cy5 (NHS-Cy5) and compete with protein from a reference plasma protein pool labeled with NHS-Cy3. Thus, the total amount of any protein bound to an arrayed antibody will only affect signal strength, not the ratio of Cy5/Cy3 assuming no preferential affinity of any antibody for either dye (controlled for by labeling the same sample with both dyes). The relative abundance of the protein in the case and control samples determines the relative fluorescence signal and since we use the same reference throughout a study, values are comparable between experiments allowing calculation of the relative difference between case and control.

Detection of differences in cancer specific-protein glycosylation levels in cases vs. controls. Most current clinical cancer biomarkers are glycoproteins (e.g., CA125, CA15-3, PSA and CEA for ovarian, breast, prostate and colon cancer, respectively) or cancer specific carbohydrate structures (e.g., CA19-9 which recognizes sialyl Lewis A for pancreas cancer). Cancer specific changes in glycosylation can occur due to defects in the complex glycosylation process caused during carcinogenesis and, in particular, sialyl-Lewis structures often result (sialyl-Lewis A, X, Tn). To detect the presence of cancer-specific glycosylation changes, 10 µl of undepleted human plasma is diluted to 80 µl and incubated on the array. After washing, Cy3 labeled anti-sialyl Lewis A (i.e., the CA19.9 antigen) antibody and Cy-5 labeled anti-sialyl Lewis X antibodies detect the presence of these cancer specific carbohydrate modifications. Incubation of the array with only secondary antibodies (i.e., no plasma) yields essentially no background signal from interaction with carbohydrate from >87% of the arrayed antibodies and only low signal from the remaining that can be subtracted out as background.

Detection of differences in cancer specific protein-autoantibody plasma levels in cases vs. controls. To detect the presence of autoantibody-antigen complexes, 2 µl of undepleted human plasma is diluted to 80 µl and incubated on the array as described above. After washing, human bound autoantibody-antigen complexes are detected with Alexa Fluor 546-goat anti-human IgG and Alexa Fluor 647-goat anti-human IgM (Jackson Labs, both highly cross absorbed). The secondary antibodies are highly specific and background levels from secondary antibodies alone (no plasma added) yield essentially no signal for >95% of the spots.

Array analysis, normalization, reproducibility, variability, and consistency. Array data contains a format identical to two-channel gene expression arrays and analysis proceeds analogously. The array image is scanned using a GenePix 4000B (Axon Instruments) scanner. The numerical data processed by Genepix Pro 6.0 is imported to Limma 2.4.11 (Linear Models for Micro Array, a Bioconductor R package) for background adjustment and normalization using loess methods (on print-tip, plate and antibody type). For proteomic analysis, the red (R) and green (G) intensities for each spot are corrected using the "subtract" method and M (log 2R-log 2G) and A ((log 2R+log 2G)/2) values are calculated and normalized. The M=log(median value of replicates) are used in each array for all antibodies. We estimate the marginal significance of each feature separately, controlling for operator and batch effects and their interaction effects using logistic regression; We predict Y=case status from batch, and operator (each as linear terms), their interaction, and M. The p-value corresponding to the coefficient of M is converted into false discovery rates (FDR). For glycosylation and autoantibody analysis cases and controls red and green spot intensities are analyzed separately for sialyl Lewis X and A or IgG and IgM specific autoantibody content.

We identified GAD65 autoantibody-antigen complexes in 88% of the Fred Hutch cohort. We also generated similar results using this format for PNMA1 (100%), PNMA2 (100%), and CRMP5 (78%). The nature of these relationships is determined by assaying for free antibody and autoantibody-antigen complexes alike.

ii. Refinement and Validation of Hybrid Plasma Marker Panel for SCLC Early Detection It is essential that biomarker panels be refined and validated in independent datasets. It is also essential that biomarker panels ultimately be transferred to formats that can be performed at most institutions. We will refine our preliminary biomarker panel in a total of N=131 SCLC plasma and matched controls from the PLCO, NLST, and WHI cohorts. These studies will be performed using the same small format arrays disclosed herein. This will enable us to adjust the biomarker panel if the performance characteristics of one of the primary candidates should falter, or if the performance characteristics of one of the secondary candidates should outperform its preliminary tests. Following the analysis of these assays, we will "fix" a rule, meaning that we will determine a final panel of biomarkers (likely 4-7 markers total), transfer these antibodies to the Luminex platform (to enhance translational value), and validate the final hybrid marker panel on a dataset of N=102 plasma specimens and matched controls.

Cohorts. The refinement studies will be performed using SCLC plasma specimens and matched controls (age, sex, race, smoking consumption) from the PLCO (N=38), WHI (N=70), and NLST (N=23) (see Table 4). The validation assay will be performed on N=102 SCLC plasma specimens and matched controls.

Refinement (pre-validation) of hybrid plasma marker panel. The small format arrays described above will be used for refinement or pre-validation of the preliminary hybrid marker panel. The probing strategies and analytical techniques will be identical to those described above.

Transfer of hybrid plasma marker panel to Luminex platform. Given the limited available volumes of these samples, coupled with our need to validate multiple candidates, we are employing Luminex assays for our validation studies because they provide the reliability and specificity of an ELISA assay but with significantly reduced volume requirements and the ability to multiplex assays. For this assay, we covalently link the antibody from the array that bound the specified biomarker to a color-coded BioPlex COOH beads according to the method disclosed in Gut, 2018 March; 67(3):473-484 (doi: 10.1136/gutjnl-2016-312794. Epub 2016 Nov. 7.) which is hereby incorporated by reference in its entirety. Instead of linking the plasma proteins to Cy3 or Cy5 as we would for array proteomics, we link them to biotin according to manufacturer's instructions using a Pierce EZ-link Sulfo-NHS-biotinylation kit. The BioPlex beads for each analyte are added to the diluted plasma sample, washed and Phycoerythrin (PE)-conjugated streptavidin is added, washed and signals are read on a dual-laser flow-based BioRad BioPlex detection instrument. One laser identifies the bead while the second determines the magnitude of the PE-derived signal.

Figure 8:
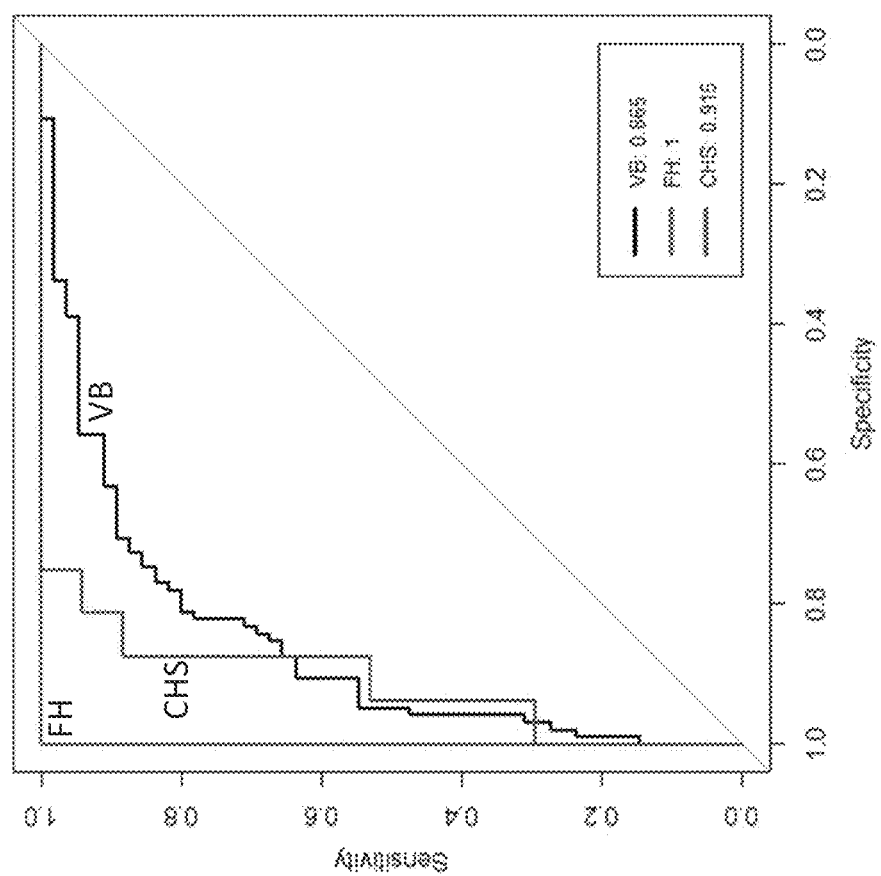
FIG. 8 is a ROC graph illustrating 4 autoantibody panel in 3 independent SCLC cohorts. A panel of 4 validated autoantibodies-antigen complexes (NLRP7-IgM, TFRC-IgM, PLD3-IgG, TIMP2-IgG) performed well in each study with an AUC of 0.915 in CHS (53% sensitivity at 90% specificity), 1.0 in Fred Hutch (100% sensitivity at 90% specificity) and 0.866 in Vanderbilt (64% sensitivity at 90% specificity).
Figure 9:
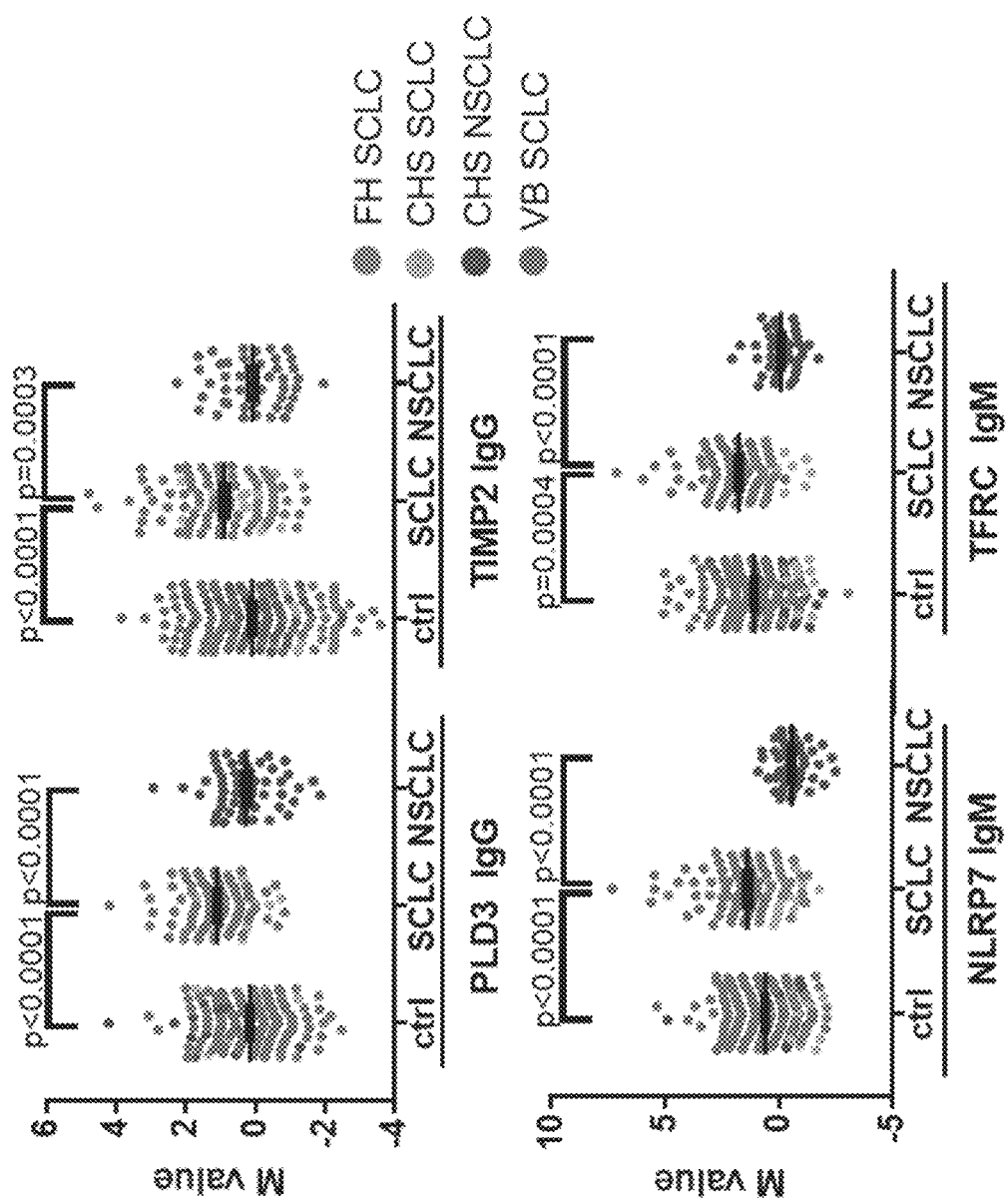
FIG. 9 Panel autoantibodies are specific for SCLC. We have evidence that each autoantibody-antigen complex in our initial 4 marker panel is specific for SCLC as none of these autoantibodies are upregulated in NSCLC samples from a CHS cohort (FIG. 9, N=59).
Figure 10:
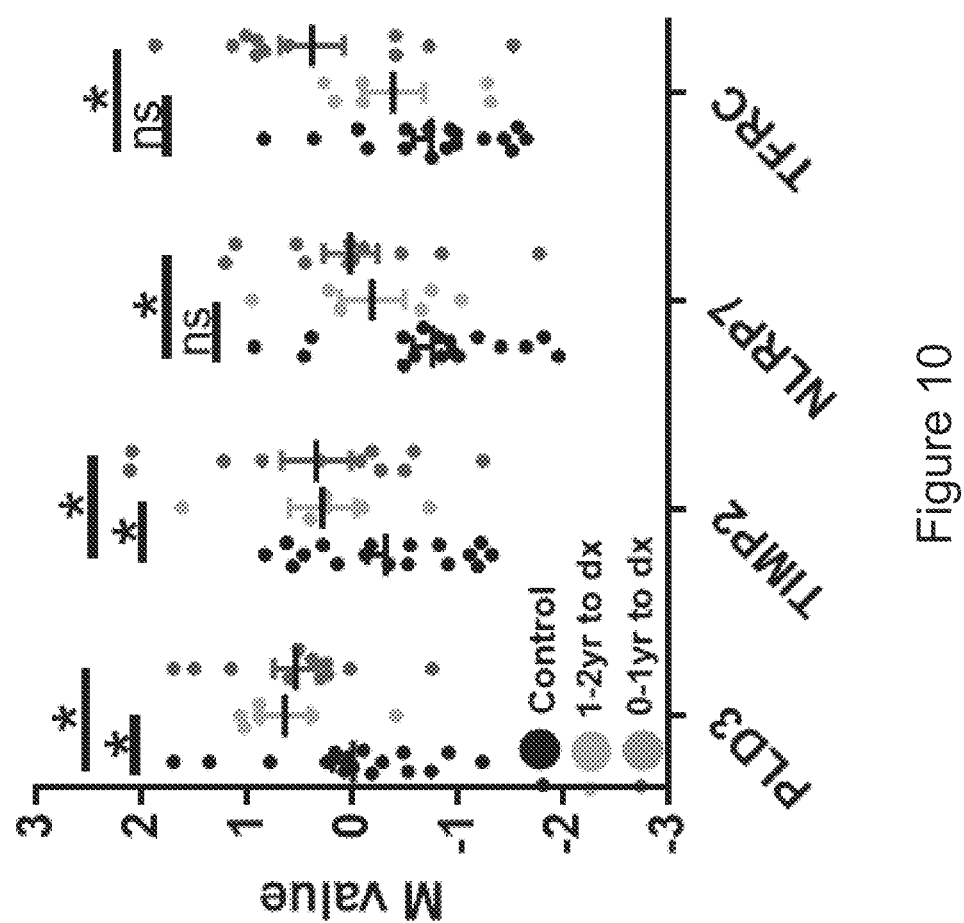

Validation. The final SCLC hybrid plasma marker early detection panel will be validated using N=102 specimens and matched controls on the Luminex platform (described above). The performance of the final panel will be expressed as cumulative sensitivity, specificity, positive predictive value, negative predictive value, and AUC value. We will achieve an AUC of at least 0.9. It is contemplated that gender specific panels may be developed. FIG. 8 illustrates the results of a 4 autoantibody panel in 3 independent SCLC cohorts. A panel of 4 validated autoantibodies-antigen complexes (NLRP7-IgM, TFRC-IgM, PLD3-IgG, TIMP2-IgG) performed well in each study with an AUC of 0.915 in CHS (53% sensitivity at 90% specificity), 1.0 in Fred Hutch (100% sensitivity at 90% specificity) and 0.866 in Vanderbilt (64% sensitivity at 90% specificity). Further, FIG. 9 illustrates that the panel autoantibodies are specific for SCLC. Evidence is provided that each autoantibody-antigen complex in the initial 4 marker panel is specific for SCLC as none of these autoantibodies are upregulated in NSCLC samples from a CHS cohort (N=59). FIG. 10 provides evidence that the disclosed SCLC panel FIG. 10 demonstrates SCLC panel autoantibodies are upregulated over 1 year prior to diagnosis. The CHS specimens (N=17) we utilized to generate preliminary data were drawn either 0-1 or 1-2 years prior to diagnosis. We re-analyzed the data from FIG. 8 as a function of the time of blood draw. The data show that most of the markers were similarly effective when the plasma was drawn 1-2 years prior to diagnosis as when drawn less than one year prior to diagnosis. These data support the hypothesis that autoantibody-antigen complex markers will prove effective at least 2 years prior to clinical diagnosis.

Figure 11:
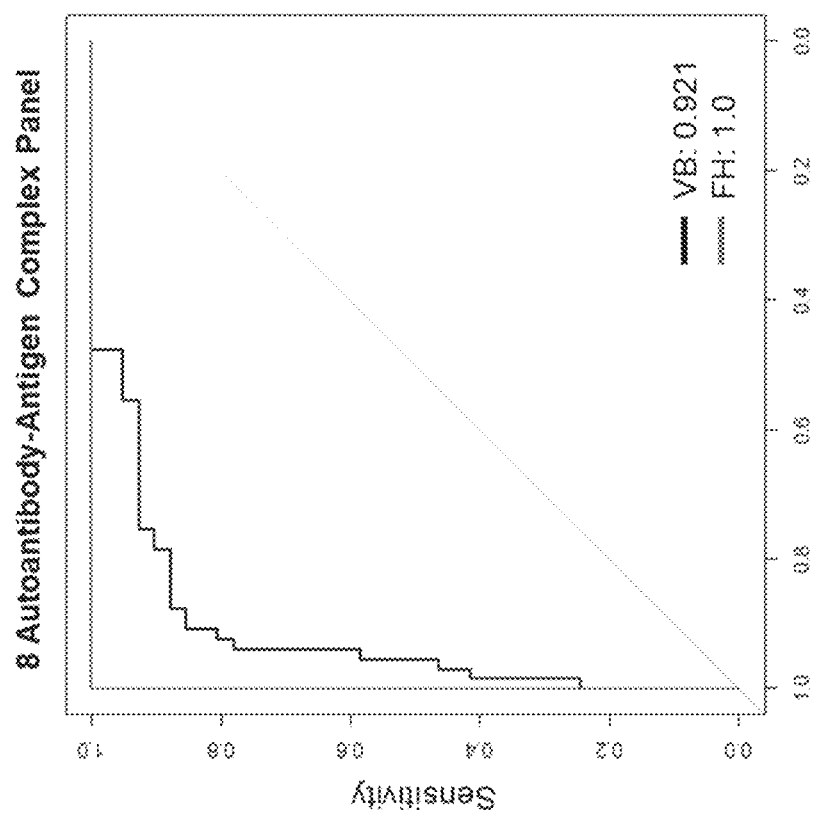
FIG. 11 ROC graph of 8 autoantibody panel in 2 independent SCLC cohorts. When 4 upregulated PNS autoantibodies (GABAb-IgG, GAD65-IgG, HU-IgG, RC-IgG) were added to an existing 4-autoantibody panel, the accuracy of SCLC detection was further increased with an AUC of 1.0 in Fred Hutch (100% sensitivity at 100% specificity) and 0.921 (85% sensitivity at 90% specificity) in the Vanderbilt SCLC cohort. Sample sets of this size are prone to overfitting so performance might be expected to diminish when tested in larger datasets. However, autoantibody markers with this degree of performance in any other dataset of any cancer have not been encountered (12, 16-19, 35). Furthermore, the sensitivity of PNS related markers are much higher than previously reported (for the few that have been looked at in SCLC cohorts). It is believed that these surprising results are due to the disclosed technique of identifying autoantibody-antigen complexes and not free circulating antibody, which appears to not be as abundant.

FIG. 11 is a ROC graph of 8 autoantibody panel in 2 independent SCLC cohorts. When 4 upregulated PNS autoantibodies (GABAb-IgG, GAD65-IgG, HU-IgG, RC-IgG) were added to an existing 4-autoantibody panel, the accuracy of SCLC detection was further increased with an AUC of 1.0 in Fred Hutch (100% sensitivity at 100% specificity) and 0.921 (85% sensitivity at 90% specificity) in the Vanderbilt SCLC cohort. Sample sets of this size are prone to overfitting so performance might be expected to diminish when tested in larger datasets. However, autoantibody markers with this degree of performance in any other dataset of any cancer have not been encountered (12, 16-19, 35). Furthermore, the sensitivity of PNS related markers are much higher than previously reported (for the few that have been looked at in SCLC cohorts). It is believed that these surprising results are due to the disclosed technique of identifying autoantibody-antigen complexes and not free circulating antibody, which appears to not be as abundant.

REFERENCES CITED IN EXAMPLE 1

1. States D J, Omenn G S, Blackwell T W, Fermin D, Eng J, Speicher D W, Hanash S M. Challenges in deriving high-confidence protein identifications from data gathered by a HUPO plasma proteome collaborative study. Nat Biotechnol. 2006; 24(3):333-8. PubMed PMID: 16525410.
2. Wingren C, Borrebaeck C A. Antibody-based microarrays. Methods Mol Biol. 2009; 509:57-84. Epub 2009/02/13. PubMed PMID: 19212715.
3. Angenendt P, Glokler J, Murphy D, Lehrach H, Cahill D J. Toward optimized antibody microarrays: a comparison of current microarray support materials. Anal Biochem. 2002; 309(2):253-60. PubMed PMID: 12413459.
4. Bereczki E, Gonda S, Csont T, Korpos E, Zvara A, Ferdinandy P, Santha M. Overexpression of biglycan in the heart of transgenic mice: an antibody microarray study. Journal of proteome research. 2007; 6(2):854-61. PubMed PMID: 17269742.
5. Haab B B, Dunham M J, Brown P O. Protein microarrays for highly parallel detection and quantitation of specific proteins and antibodies in complex solutions. Genome Biol. 2001; 2(2):RESEARCH0004. PubMed PMID: 11182887.
6. Haab B B. Antibody arrays in cancer research. Mol Cell Proteomics. 2005; 4(4):377-83. PubMed PMID: 15671041.
7. Chari S T, Leibson C L, Rabe K G, Ransom J, de Andrade M, Petersen G M. Probability of pancreatic cancer following diabetes: a population-based study. Gastroenterology. 2005; 129(2):504-11. PubMed PMID: 16083707.
8. Vazquez-Martin A, Colomer R, Menendez J A. Protein array technology to detect HER2 (erbB-2)-induced 'cytokine signature' in breast cancer. Eur J Cancer. 2007; 43(7):1117-24. PubMed PMID: 17379503.
9. Shafer M W, Mangold L, Partin A W, Haab B B. Antibody array profiling reveals serum TSP-1 as a marker to distinguish benign from malignant prostatic disease. Prostate. 2007; 67(3):255-67. PubMed PMID: 17192876.
10. Yue T, Goldstein I J, Hollingsworth M A, Kaul K, Brand R E, Haab B B. The prevalence and nature of glycan alterations on specific proteins in pancreatic cancer patients revealed using antibody-lectin sandwich arrays. Mol Cell Proteomics. 2009; 8(7):1697-707. Epub 2009/04/21. PubMed PMID: 19377061; PMCID: 2709194.
11. Yue T, Maupin K A, Fallon B, Li L, Partyka K, Anderson M A, Brenner D E, Kaul K, Zeh H, Moser A J, Simeone D M, Feng Z, Brand R E, Haab B B. Enhanced discrimination of malignant from benign pancreatic disease by measuring the C A 19-9 antigen on specific protein carriers. PLoS One. 2011; 6(12):e29180. Epub 2012/01/06. PubMed PMID: 22220206; PMCID: 3248411.
12. Loch C M, Ramirez A B, Liu Y, Sather C L, Delrow J J, Scholler N, Garvik B M, Urban N D, McIntosh M W, Lampe P D. Use of High Density Antibody Arrays to Validate and Discover Cancer Serum Biomarkers. Molecular Oncology. 2007; 1(3):313-20.
13. Rho J H, Lampe P D. High-throughput screening for native autoantigen-autoantibody complexes using antibody microarrays. J Proteome Res. 2013; 12(5):2311-20. Epub 2013/04/02. PubMed PMID: 23541305; PMCID: 3680356.
14. Rho J H, Mead J R, Wright W S, Brenner D E, Stave J W, Gildersleeve J C, Lampe P D. Discovery of sialyl Lewis A and Lewis X modified protein cancer biomarkers using high density antibody arrays. J Proteomics. 2014; 96:291-9. Epub 2013/11/05. PubMed PMID: 24185138.
15. Ramirez A B, Lampe P D. Discovery and validation of ovarian cancer biomarkers utilizing high density antibody microarrays. Cancer Biomarkers. 2011; 8(4-5):293-307. PubMed PMID: ISI:000296757900011.
16. Ramirez A B, Loch C M, Zhang Y, Liu Y, Wang X, Wayner E A, Sargent J, Sibani S, Mendoza E A, Eugene R, LaBaer J, Urban N, McIntosh M W, Lampe P D. Use of a single chain antibody library for ovarian cancer biomarker discovery. Mol Cell Proteomics. 2010; 9(7): 1449-60. Epub 2010/05/15. PubMed PMID: 20467042.
17. Li C I, Mirus J E, Zhang Y, Ramirez A B, Ladd J J, Prentice R L, McIntosh M W, Hanash S M, Lampe P D. Discovery and preliminary confirmation of novel early detection biomarkers for triple-negative breast cancer using preclinical plasma samples from the Women's Health Initiative observational study. Breast Cancer Res Treat. 2012; 135(2):611-8. Epub 2012/08/21. PubMed PMID: 22903690; PMCID: 3439142.
18. Minis J E, Zhang Y, Hollingsworth M A, Solan J L, Lampe P D, Hingorani S R. Spatiotemporal proteomic analyses during pancreas cancer progression identifies STK4 as a novel candidate biomarker for early stage disease. Mol Cell Proteomics. 2014; 13(12):3484-96. Epub 2014/09/17. PubMed PMID: 25225358.
19. Minis J E, Zhang Y, Li C I, Prentice R L, Solan J L, Hingorani S R, Lampe P D. Cross-species antibody microarray interrogation identifies a 3-protein panel of plasma biomarkers for the early detection of pancreas cancer. Clin Cancer Res. 2015; 21(7):1764-71.
20. Lambin P, Rios-Velazquez E, Leijenaar R, Carvalho S, van Stiphout R G, Granton P, Zegers C M, Gillies R, Boellard R, Dekker A, Aerts H I Radiomics: extracting more information from medical images using advanced feature analysis. Eur J Cancer. 2012; 48(4):441-6. PubMed PMID: 22257792; PMCID: PMC4533986.
21. Lastwika K J, Kargl J, Zhang Y, Zhu X, Lo E, Shelley D, Ladd J J, Wu W, Kinahan P, Pipavath S N J, Randolph T W, Shipley M, Lampe P D, Houghton A M. Tumor-Derived Autoantibodies Identify Malignant Pulmonary Nodules. Am J Respir Crit Care Med. 2018. Epub 2018/11/14. PubMed PMID: 30422669.
22. Yang L, Wang J, Li J, Zhang H, Guo S, Yan M, Zhu Z, Lan B, Ding Y, Xu M, Li W, Gu X, Qi C, Zhu H, Shao Z, Liu B, Tao S C. Identification of Serum Biomarkers for Gastric Cancer Diagnosis Using a Human Proteome Microarray. Molecular & cellular proteomics: MCP. 2016; 15(2):614-23. PubMed PMID: 26598640; PMCID: 4739676.
23. Bast R C, Jr., Feeney M, Lazarus H, Nadler L M, Colvin R B, Knapp R C. Reactivity of a monoclonal antibody with human ovarian carcinoma. J Clin Invest. 1981; 68(5):1331-7. PubMed PMID: 7028788.
24. McIntosh M W, Drescher C, Karlan B, Scholler N, Urban N, Hellstrom K E, Hellstrom I. Combining C A 125 and SMR serum markers for diagnosis and early detection of ovarian carcinoma. Gynecol Oncol. 2004; 95(1):9-15. PubMed PMID: 15385104.
25. Storey J D, Tibshirani R. SAM thresholding and false discovery rate for detecting differential gene expression in DNA microarrays. In: Parmigiani G, Garrett, E. S., Irizarry, R. A., and Zeger, S. L., editor. The Analysis of Gene Expression Data: Methods and Software. New York: Springer; 2003. p. 272-90.
26. Storey J D, Tibshirani R. Statistical significance for genomewide studies. Proceedings of the National Academy of Sciences of the United States of America. 2003; 100(16):9440-5. PubMed PMID: 12883005.
27. Kargl J, Busch S E, Yang G H, Kim K H, Hanke M L, Metz H E, Hubbard J J, Lee S M, Madtes D K, McIntosh M W, Houghton A M. Neutrophils dominate the immune cell composition in non-small cell lung cancer. Nat Commun. 2017; 8:14381. PubMed PMID: 28146145; PMCID: PMC5296654.
28. Thomas A, Pattanayak P, Szabo E, Pinsky P. Characteristics and Outcomes of Small Cell Lung Cancer Detected by C T Screening. Chest. 2018; 154(6):1284-90. Epub 2018/08/07. PubMed PMID: 30080997.
29. Gandhi L, Johnson B E. Paraneoplastic syndromes associated with small cell lung cancer. Journal of the National Comprehensive Cancer Network: JNCCN. 2006; 4(6):631-8. PubMed PMID: 16813730.
30. Semenova E A, Nagel R, Berns A. Origins, genetic landscape, and emerging therapies of small cell lung cancer. Genes & development. 2015; 29(14):1447-62. PubMed PMID: 26220992; PMCID: 4526731.
31. Song H, Yao E, Lin C, Gacayan R, Chen M H, Chuang P T. Functional characterization of pulmonary neuroendocrine cells in lung development, injury, and tumorigenesis. Proceedings of the National Academy of Sciences of the United States of America. 2012; 109(43):17531-6. PubMed PMID: 23047698; PMCID: 3491514.
32. Kazarian M, Laird-Offringa I A. Small-cell lung cancer-associated autoantibodies: potential applications to cancer diagnosis, early detection, and therapy. Molecular cancer. 2011; 10:33. PubMed PMID: 21450098; PMCID: 3080347.
33. Kanaji N, Watanabe N, Kita N, Bandoh S, Tadokoro A, Ishii T, Dobashi H, Matsunaga T. Paraneoplastic syndromes associated with lung cancer. World J Clin Oncol. 2014; 5(3):197-223. Epub 2014/08/13. PubMed PMID: 25114839; PMCID: PMC4127595.
34. Dalmau J, Rosenfeld M R. Paraneoplastic syndromes of the CNS. Lancet Neurol. 2008; 7(4):327-40. Epub 2008/03/15. PubMed PMID: 18339348; PMCID: PMC2367117.
35. Rho J H, Ladd J J, Li C I, Potter J D, Zhang Y, Shelley D, Shibata D, Coppola D, Yamada H, Toyoda H, Tada T, Kumada T, Brenner D E, Hanash S M, Lampe P D. Protein and glycomic plasma markers for early detection of adenoma and colon cancer. Gut. 2018; 67(3):473-84. PubMed PMID: 27821646.

Example 2

Identification and Potential Use of these Targets

As shown in Example 1 the disclosed novel platform is reproducible (mean CV 3.67%), efficient and reliable for high-throughput analysis of human plasma proteins for utility as biomarkers of disease (4-8). We utilized prediagnostic samples from the CHS (n=34) to discover SCLC specific markers and focused on 19 IgG and 66 IgM autoantibodies complexed with specific proteins (FIG. 12A). We then fabricated an array with these increased markers and tested the Fred Hutch SCLC cases/controls (N=52). 13/19 IgG markers (68%) and 14/66 IgM markers (21%) validated in the Fred Hutch cohort (FIG. 12B). In a third cohort from Vanderbilt (N=155) 8/13 (61.5% at p<0.004) IgG autoantibodies and 11/13 (84.6% at p<0.03) IgM autoantibodies validated (FIG. 12C). Moreover, most of these autoantibodies are not upregulated in NSCLC, colon cancer or pancreatic cancer further indicating their specificity for SCLC.

Additionally, we had added 10 other PNS markers to our panel prior to running Fred Hutch specimens and found four of these 10 autoantibodies markers capable of distinguishing SCLC case from control with perfect or nearly perfect sensitivity and specificity. We have not previously encountered autoantibody markers with this degree of performance in any other dataset of any cancer type. Furthermore, the sensitivity of PNS related markers are much higher than previously reported (for the few that have been looked at in SCLC cohorts) which we suspect is largely based on technique, as we identified autoantibody-antigen complexes, and while others only assayed free circulating antibody. When the top 6 autoantibodies are combined in a panel, they yield an AUC=0.901 in CHS, an AUC=1.0 in Fred Hutch and an AUC=0.905 in Vanderbilt cohorts. Additionally, analyzing the panel markers in the pre-diagnostic CHS dataset showed that the markers were similarly effective when the plasma was drawn 1-2 years prior to diagnosis as when drawn less than one year prior to diagnosis.

General Strategy and Screening Rationale

Lung cancer screening via CT for heavy smokers (>30 pack years) is now accepted to save lives and is paid for by insurance/Medicare. We envision that a blood sample could be taken during the screening process and tested for the 29 IgG or IgM autoantibodies that we have found to be specific for SCLC. If our robust autoantibody panel (i.e., 6 of the key markers) indicated a high-risk for SCLC, review or acquisition of diagnostic imaging would be appropriate. The fact that 10/29 of our validated autoantibody targets are reported to be expressed on the plasma membrane and contain transmembrane domains and 7/10 have low/no levels of protein expression in normal tissues can be exploited.

ImmunoPET:

If CT imaging is not informative as often is the case for SCLC, the most positive, SCLC tumor specific autoantibody candidate(s) identified by our blood screen is utilized to target a radiotracer (i.e., the antibody to the abundant, tumor-specific autoantigen would be tagged to allow immunoPET). The advantage with immunoPET includes the ability to identify small, centrally located tumors like SCLC that would not be seen with conventional CT.

CAR T-Cell Therapy:

In addition, the tumor-specific antigen targets identified by our autoantibody blood screen are translated into targets for CAR T-cells. The sequences for the antibody binding region(s) for the particular tumor specific antibody are initially engineered into standard $2^1$ generation chimeric antigen receptor (CAR) constructs. To circumvent potential toxicities associated with some of our targets, we will ultimately employ more novel strategies, such as tandem CAR constructs.

Figure 13A:
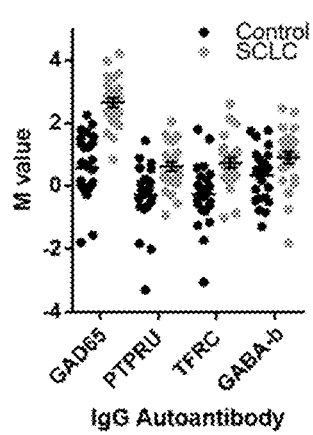
FIGS. 13A-13C are a graph and digital images demonstrating that auto antibody-antigen complexes are high in the white blood of SCLC patients and their corresponding proteins are expressed in SCLC PDX tumors and SCLC primary tumor biopsies.
Figure 13B:
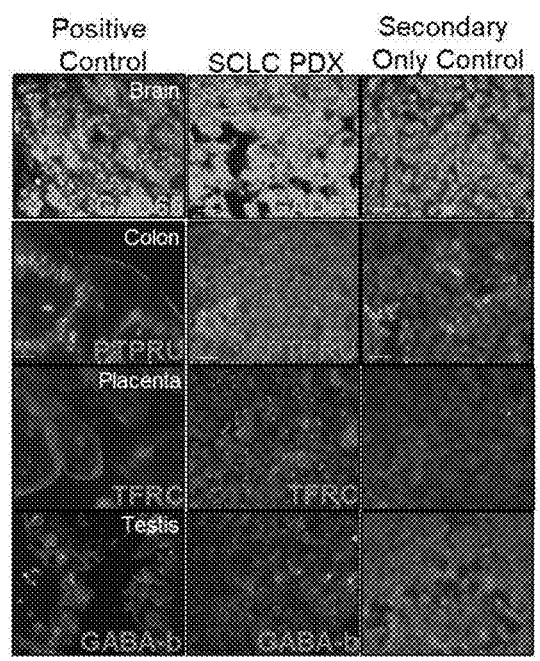

As an example, four of these validated targets, GAD65, PTPRU, TFRC and GABA-b were identified via our antibody array platform (FIG. 13A) as significantly higher (p<0.03) in SCLC verses healthy matched controls. We then probed 8 SCLC patient-derived xenografts (PDXs) for corresponding protein expression (FIG. 13B). We found strong expression of GAD65 in 8/8, PTPRU in 6/8, TFRC in 8/8 and GABA-b in 4/8 PDX tumors. To our knowledge, this is the first time PTPRU has been identified in SCLC. We have established expression of 10/10 transmembrane domain containing candidates in SCLC tumors via western blot and are now confirming membrane expression on PDX tumors.

Figure 13C:
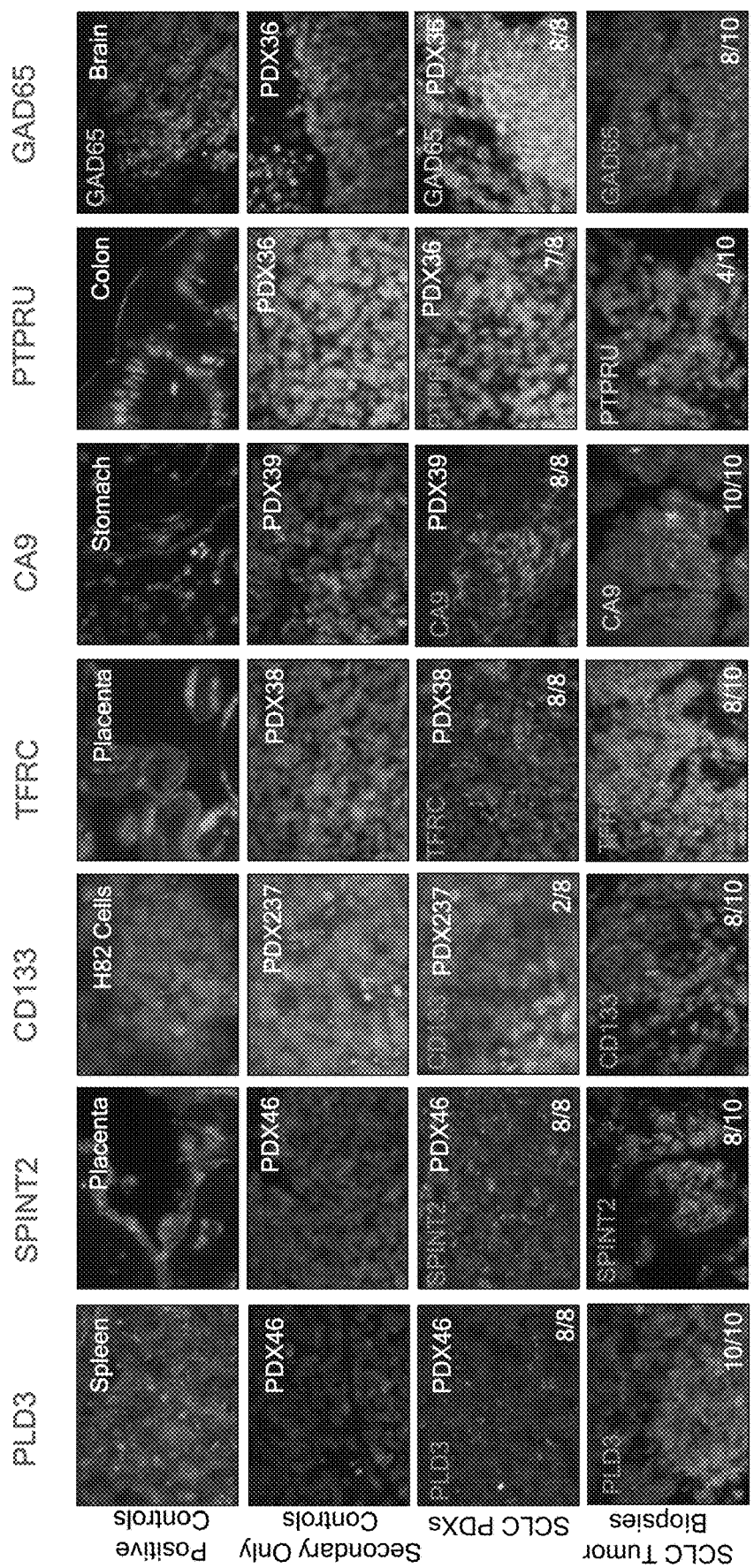

Additional data is included for validated targets PLD3, SPINT2, CD133, TFRC, CA9, PTPRU and GAD65 (FIG. 13C). It may be understood that there is some overlap between data shown at FIG. 13B and that shown at FIG. 13C. Specifically, validated targets PLD3, SPINT2, CD133, TFRC, CA9, PTPRU and GAD65 were developed into immunohistochemistry assays using normal human tissues (spleen, placenta, stomach, colon, brain) or an SCLC cell line (H82 cells) as positive controls (top row). Using these assays, 8 SCLC PDXs were probed and expression of the targets were found in the majority of PDXs examined (third row from top). Specifically, each of PLD3, SPINT2, TFRC, CA9, and GAD65 were found to be expressed in 8/8 PDXs examined CD133 was found to be expressed in 2/8 PDXs examined, and PTPRU was found to be expressed in 7/8 PDXs examined Secondary antibody-only controls (second row from top) show a lack of specific staining when a primary antibody is not included in the assay. Additionally, 10 SCLC primary tumor biopsies were assayed (fourth row from top), and a similar expression pattern to that of SCLC PDXs was found. Specifically, PLD3 and CA9 were found to be expressed in 10/10 primary tumor biopsies; SPINT2, CD133, TFRC and GAD65 were found to be expressed in 8/10 primary tumor biopsies; and PTPRU was found to be expressed in 4/10 primary tumor biopsies. This demonstrates that the antigen targets of the plasma-identified autoantibodies are expressed on the cell surface of SCLC tumors in vivo.

Summary:

Using a novel approach to discover autoantigen-autoantibody complexes, we have found tumor specific autoantigens. Screening patients with SCLC for these specific autoantigens could allow us to select one or more specific antibodies to these targets to specifically tailor diagnosis and treatment via immunoPET and for CAR T cell immunotherapy to the individual patient.

LITERATURE CITED IN EXAMPLE 2

1. Siegel R, Ma J, Zou Z, Jemal A. Cancer statistics, 2014. CA: a cancer journal for clinicians. 2014; 64(1):9-29. PubMed PMID: 24399786.
2. Lassen U, Osterlind K, Hansen M, Dombernowsky P, Bergman B, Hansen H H. Long-term survival in small-cell lung cancer: posttreatment characteristics in patients surviving 5 to 18+ years—an analysis of 1,714 consecutive patients. Journal of clinical oncology: official journal of the American Society of Clinical Oncology. 1995; 13(5):1215-20. PubMed PMID: 7738624.
3. National Lung Screening Trial Research T, Aberle D R, Adams A M, Berg C D, Black W C, Clapp J D, Fagerstrom R M, Gareen I F, Gatsonis C, Marcus P M, Sicks J D. Reduced lung-cancer mortality with low-dose computed tomographic screening. The New England journal of medicine. 2011; 365(5):395-409. PubMed PMID: 21714641; PMCID: 4356534.
4. Loch C M, Ramirez A B, Liu Y, Sather C L, Delrow J J, Scholler N, Garvik B M, Urban N D, McIntosh M W, Lampe P D. Use of High Density Antibody Arrays to Validate and Discover Cancer Serum Biomarkers. Molecular Oncology. 2007; 1(3):313-20.

5. Rho J H, Lampe P D. High-Throughput Screening for Native Autoantigen-Autoantibody Complexes Using Antibody Microarrays. Journal of proteome research. 2013; 12(5):2311-20. Epub 2013/04/02. PubMed PMID: 23541305.
6. Rho J H, Mead J R, Wright W S, Brenner D E, Stave J W, Gildersleeve J C, Lampe P D. Discovery of sialyl Lewis A and Lewis X modified protein cancer biomarkers using high density antibody arrays. Journal of Proteomics. 2014; 96:291-9. Epub 2013/11/05. PubMed PMID: 24185138.
7. Ramirez A B, Lampe P D. Discovery and validation of ovarian cancer biomarkers utilizing high density antibody microarrays. Cancer Biomark. 2011; 8(4-5):293-307. PubMed PMID: ISI:000296757900011.
8. Ramirez A B, Loch C M, Zhang Y, Liu Y, Wang X, Wayner E A, Sargent J, Sibani S, Mendoza E A, Eugene R, LaBaer J, Urban N, McIntosh M W, Lampe P D. Use of a single chain antibody library for ovarian cancer biomarker discovery. Mol Cell Proteomics. 2010; 9(7): 1449-60. Epub 2010/05/15. PubMed PMID: 20467042.
9. Lambin P, Rios-Velazquez E, Leijenaar R, Carvalho S, van Stiphout R G, Granton P, Zegers C M, Gillies R, Boellard R, Dekker A, Aerts H J. Radiomics: extracting more information from medical images using advanced feature analysis. Eur J Cancer. 2012; 48(4):441-6. PubMed PMID: 22257792; PMCID: PMC4533986.
10. Minis J E, Zhang Y, Hollingsworth M A, Solan J L, Lampe P D, Hingorani S R. Spatiotemporal proteomic analyses during pancreas cancer progression identifies STK4 as a novel candidate biomarker for early stage disease. Mol Cell Proteomics. 2014; 13(12):3484-96. Epub 2014/09/17. PubMed PMID: 25225358.
11. Minis J E, Zhang Y, Li C I, Prentice R L, Solan J L, Hingorani S R, Lampe P D. Cross-species antibody microarray interrogation identifies a 3-protein panel of plasma biomarkers for the early detection of pancreas cancer. Clin Cancer Res. 2015; 21(7):1764-71.
12. Lastwika K J, Kargl J, Zhang Y, Zhu X, Lo E, Shelley D, Ladd J J, Wu W, Kinahan P, Pipavath S N J, Randolph T W, Shipley M, Lampe P D, Houghton A M. Tumor-Derived Autoantibodies Identify Malignant Pulmonary Nodules. Am J Respir Crit Care Med. 2018. Epub 2018/11/14. PubMed PMID: 30422669. 29483136
13. Gandhi L, Johnson B E. Paraneoplastic syndromes associated with small cell lung cancer. Journal of the National Comprehensive Cancer Network: JNCCN. 2006; 4(6):631-8. PubMed PMID: 16813730.
14. Kazarian M, Laird-Offringa I A. Small-cell lung cancer-associated autoantibodies: potential applications to cancer diagnosis, early detection, and therapy. Molecular cancer. 2011; 10:33. PubMed PMID: 21450098; PMCID: 3080347.
15. Schiffman J D, Fisher P G, Gibbs P. Early detection of cancer: past, present, and future. American Society of Clinical Oncology educational book American Society of Clinical Oncology Meeting. 2015:57-65. PubMed PMID: 25993143.
16. Alvarado-Luna G, Morales-Espinosa D. Treatment for small cell lung cancer, where are we now?—a review. Translational lung cancer research. 2016; 5(1):26-38. PubMed PMID: 26958491; PMCID: 4758961.
17. Koletsis E N, Prokakis C, Karanikolas M, Apostolakis E, Dougenis D. Current role of surgery in small cell lung carcinoma. Journal of cardiothoracic surgery. 2009; 4:30. PubMed PMID: 19589150; PMCID: 2716318.
18. Drapkin B J, et al. Genomic and functional fidelity of small cell lung cancer patient-derived xenografts. Cancer Discovery. 2018. 8(5):600-615. PubMed PMID: 29483136.

Example 3

CD133 is Expressed on the Cell Surface of SCLC Tumors

Figure 14C:
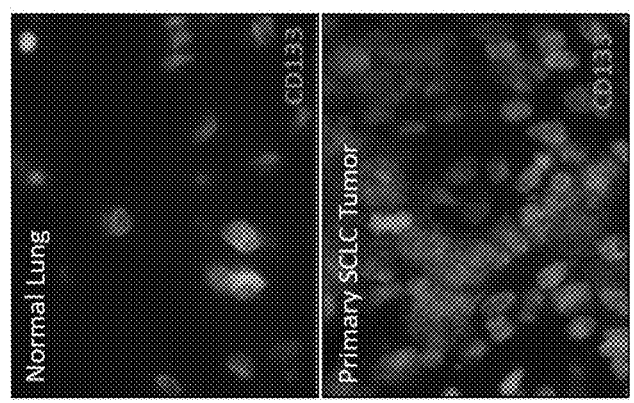
FIGS. 14A-14D depict graphs, digital images and plots showing that plasma autoantibody target CD133 is expressed on the cell surface of SCLC tumors and can be eliminated via CD133 targeting CAR T cells.
Figure 14B:
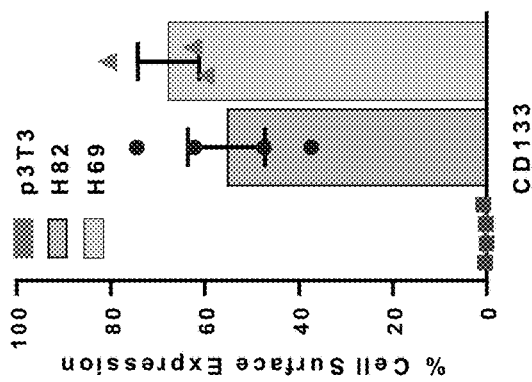
Figure 14A:
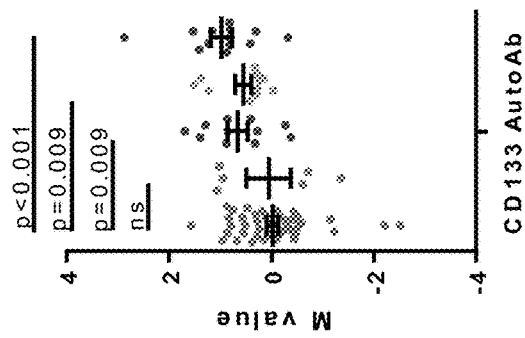

CD133 autoantibodies were analyzed as a function of the time of blood draw in the CHS (pre-diagnostic, 1-2 years prior to cancer diagnosis (dx), or less than 1 year prior to dx) and FHCRC (diagnostic, limited or extensive stage) (FIG. 14A). The results indicate that CD133 autoantibodies are significantly upregulated less than a year prior to diagnosis, and this upregulation is maintained independent of diagnostic stage. P values were derived from an unpaired t-test.

Two SCLC cell lines (H82 and H69) and a negative control fibroblast line (p3T3) were analyzed for cell surface CD133 expression by flow cytometry (FIG. 14B). The results indicate that both SCLC cell lines express extracellular CD133, but the 3T3 fibroblast line does not. Furthermore, CD133 expression was observed by fluorescent immunohistochemistry in primary SCLC tumor cells (FIG. 14C, bottom) but was not observed in normal lung cells (FIG. 14C, top).

Figure 14D:
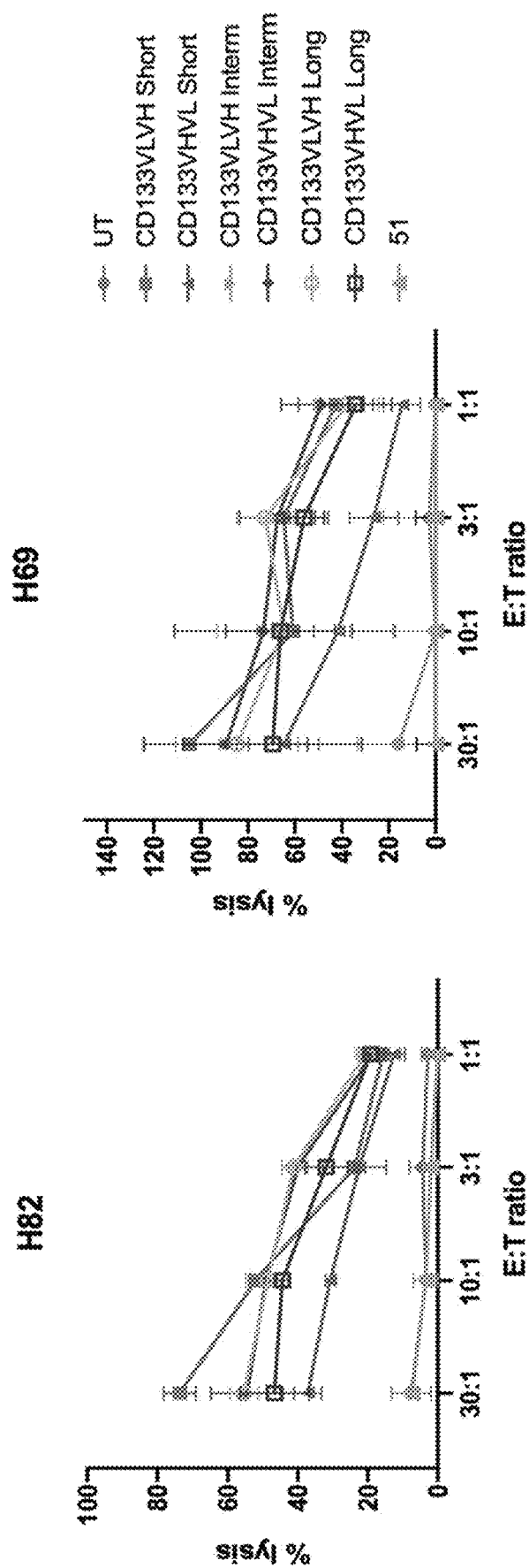

SCLC Tumor Cells Expressing CD133 can be Eliminated Via CD133 Targeting CAR T Cells Six different CAR T cell constructs were created with different variable light (VL) and variable heavy (VH) chain orders and linker sequence length (short, intermediate, or long). The constructs were transfected into human CD4+ and CD8+ T cells and killing efficiency (e.g., percent lysis) of an H82 SCLC cell line (FIG. 14D, left) and an H69 SCLC cell line (FIG. 14D, right) was examined as compared to untransfected (UT) T cells and an unrelated CAR T cell target not expressed in the SCLC cell lines (see "51" at FIG. 14D). The results indicate that at a 30:1 tumor (E) to T cell (T) ratio the CD133 CAR T cell constructs lysed 40-100% of SCLC tumor cells as measured by a chromium release assay, while controls lysed less than 20% of the SCLC tumor cells.

Summary:

Using a novel approach to discover autoantigen-autoantibody complexes, tumor specific autoantigens, one of which includes CD133, were found. Using CD133 as an example, the Example shows that screening patients for autoantibodies (e.g., CD133 autoantibodies) can allow for tailoring CAR T cell immunotherapy to the individual patient. This Example demonstrates that CAR T cell constructs specific for CD133 autoantigens can effectively lyse SCLC tumor cells as compared to T cells that do not contain the CAR T cell constructs, or T cells transfected with constructs that target an antigen not expressed on SCLC cell lines. The results indicate that screening patients for specific autoantigens and then tailoring diagnosis and treatment via techniques such as immunoPET and CAR T cell immunotherapy can be used for cancer treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating small cell lung cancer (SCLC) in a subject that has been diagnosed with limited stage SCLC, the method comprising administering to the subject a chemotherapy regimen or an immunotherapy regimen to the subject, wherein the subject has been diagnosed with limited stage SCLC by:
   (a) contacting a biological sample obtained from the subject with an array consisting essentially of antigens capable of specifically binding, respectively, to four autoantibodies, wherein the four autoantibodies are anti-GAD65 antibodies, anti-PTPRU antibodies, anti-TFRC antibodies, and anti-GABA-b antibodies;
   (b) detecting an amount of the four autoantibodies present in the biological sample when the autoantibodies bind to the antigens in the array; and
   (c) diagnosing limited stage SCLC in the subject when the amount of the four autoantibodies in the biological sample exceeds, respectively, a control amount.

2. The method of claim 1, wherein the control amount is an amount determined in a population of healthy individuals.

3. The method of claim 1, wherein the biological sample is a plasma sample.

4. The method of claim 1, wherein the immunotherapy regimen includes administration of a population of human T cells engineered to express a chimeric antigen receptor that binds an antigen selected from the group consisting of GAD65, PTPRU, TFRC, and GABA-b.

5. The method of claim 1, wherein the subject is a human.

6. The method of claim 5, wherein the subject is a smoker.

7. The method of claim 5, wherein the subject is a former smoker.

8. The method of claim 1, further comprising obtaining the biological sample from the subject.

9. A method of treating small cell lung cancer (SCLC) in a subject that has been diagnosed with limited stage SCLC, the method comprising administering to the subject a chemotherapy regimen or an immunotherapy regimen to the subject, wherein the subject has been diagnosed with limited stage SCLC by:
   (a) contacting a biological sample obtained from the subject with an array consisting essentially of antibodies capable of specifically binding, respectively, to four antigen-autoantibody complexes, wherein the four antigen-autoantibody complexes are a GAD65-autoantibody complex, a PTPRU-autoantibody complex, a TFRC-autoantibody complex, and a GABA-b-autoantibody complex;
   (b) detecting an amount of the four complexes present in the biological sample when the complexes bind to the antibodies in the array; and
   (c) diagnosing SCLC in the subject when the amount of the four complexes in the biological sample exceeds, respectively, a control amount.

10. The method of claim 9, wherein the control amount is an amount determined in a population of healthy individuals.

11. The method of claim 9, wherein the biological sample is a plasma sample.

12. The method of claim 9, wherein the immunotherapy regimen includes administration of a population of human T cells engineered to express a chimeric antigen receptor that binds an antigen selected from the group consisting of GAD65, PTPRU, TFRC, and GABA-b.

13. The method of claim 12, wherein the subject is a human.

14. The method of claim 13, wherein the subject is a smoker.

15. The method of claim 13, wherein the subject is a former smoker.

16. The method of claim 9, further comprising obtaining the biological sample from the subject.

17. A biomarker detection array for limited stage small cell lung cancer (SCLC) consisting essentially of:
   antibodies capable of specifically binding, respectively, to four antigen-autoantibody complexes, wherein the four antigen-autoantibody complexes are a GAD65-autoantibody complex, a PTPRU-autoantibody complex, a TFRC-autoantibody complex, and a GABA-b-autoantibody complex.

18. The array of claim 17, consisting of four antibodies, wherein the four antibodies bind, respectively, to an epitope from an antigen selected from a GAD65-autoantibody complex, a PTPRU-autoantibody complex, a TFRC-autoantibody complex, and a GABA-b-autoantibody complex.

* * * * *